US011498960B2

(12) United States Patent
Puffer et al.

(10) Patent No.: US 11,498,960 B2
(45) Date of Patent: Nov. 15, 2022

(54) POLYPEPTIDES THAT BIND COMPLEMENT COMPONENT C5 OR SERUM ALBUMIN AND FUSION PROTEINS THEREOF

(71) Applicant: Alexion Pharmaceuticals, Inc., New Haven, CT (US)

(72) Inventors: Bridget Puffer, South Weymouth, MA (US); Julian Chandler, Guilford, CT (US); Nimish Gera, Waltham, MA (US); Douglas L. Sheridan, Branford, CT (US); Siddharth Jindal, Hamden, CT (US); Paul P. Tamburini, Kensington, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 173 days.

(21) Appl. No.: 16/629,687

(22) PCT Filed: Jul. 11, 2018

(86) PCT No.: PCT/US2018/041661
§ 371 (c)(1),
(2) Date: Jan. 9, 2020

(87) PCT Pub. No.: WO2019/014360
PCT Pub. Date: Jan. 17, 2019

(65) Prior Publication Data
US 2020/0399351 A1 Dec. 24, 2020

Related U.S. Application Data

(60) Provisional application No. 62/531,215, filed on Jul. 11, 2017.

(51) Int. Cl.
*C07K 16/18* (2006.01)
*A61K 38/47* (2006.01)
*A61K 39/395* (2006.01)
*A61K 39/00* (2006.01)

(52) U.S. Cl.
CPC .............. *C07K 16/18* (2013.01); *A61K 38/47* (2013.01); *A61K 39/3955* (2013.01); *C12Y 302/01035* (2013.01); *A61K 2039/505* (2013.01); *C07K 2317/24* (2013.01); *C07K 2317/31* (2013.01); *C07K 2317/565* (2013.01); *C07K 2317/569* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 8,921,528 | B2 * | 12/2014 | Holt | ........................ | C07K 16/18 |
| | | | | | 530/389.3 |
| 9,079,949 | B1 * | 7/2015 | Andrien, Jr. | .............. | A61P 5/16 |

| 2006/0093599 | A1 | 5/2006 | Gazit-Bornstein et al. |
| 2011/0002931 | A1 | 1/2011 | Tamburini |
| 2011/0008340 | A1 | 1/2011 | Bansal |
| 2011/0064653 | A1 | 3/2011 | Hansen et al. |
| 2012/0301469 | A1 | 11/2012 | Depla et al. |
| 2013/0273052 | A1 | 10/2013 | Gies et al. |
| 2014/0212427 | A1 | 7/2014 | Song |
| 2015/0291686 | A1 | 10/2015 | Bansal |
| 2016/0122419 | A1 | 5/2016 | Bansal |
| 2019/0352381 | A1 | 11/2019 | Sheridan et al. |

FOREIGN PATENT DOCUMENTS

| CN | 1743009 A | 3/2006 |
| CO | 6731077 A2 | 8/2013 |
| EA | 012622 B1 | 10/2009 |
| EA | 201691764 A1 | 12/2016 |
| JP | 2015-508652 A | 3/2015 |
| JP | 2016-20345 A | 2/2016 |
| WO | WO-2007/056227 A2 | 5/2007 |
| WO | WO-2010/015608 A1 | 2/2010 |
| WO | WO-2010/151526 A1 | 12/2010 |
| WO | WO-2011/112850 A2 | 9/2011 |

(Continued)

OTHER PUBLICATIONS

Shibuya, Yuki et al. "Generation of camelid VHH bispecific constructs via in-cell intein-mediated protein trans-splicing." Protein engineering, design & selection : PEDS vol. 30,1 (2017): 15-21. doi:10.1093/protein/gzw057 (Year: 2017).*
Stryer, Biochemistry 4th, WH Freeman, New York. 1995 (Year: 1995).*
Colman, Peter M. Research in Immunology 145.1 (1994): 33-36 (Year: 1994).*
Ozen, Ahmet, et al. Nature immunology 22.2 (2021): 128-139 (Year: 2021).*
Pandey, Manoj K., et al. J Immunol May 1, 2021, 206 1 Supplement 64.01 (Year: 2021).*
Ghahroudi et al., FEBS Letters Sep. 15, 1997; 414(3): 521-526. (Year: 1997).*
Vincke, Cecile, et al. "General strategy to humanize a camelid single-domain antibody and identification of a universal humanized nanobody scaffold." Journal of Biological Chemistry 284.5 (2009): 3273-3284. (Year: 2009).*

(Continued)

*Primary Examiner* — Michael Szperka
*Assistant Examiner* — Lia E Taylor
(74) *Attorney, Agent, or Firm* — Clark & Elbing LLP

(57) ABSTRACT

The disclosure provides engineered polypeptides that specifically bind to human complement component C5 and/or serum albumin. The disclosure also provides fusion proteins comprising such engineered polypeptides, wherein such fusion proteins may be multivalent and multi-specific fusion proteins. The disclosure further provides nucleic acid molecules that encode such engineered polypeptides or fusion proteins, and methods of making such engineered polypeptides or fusion proteins. The disclosure further provides pharmaceutical compositions that comprise such engineered polypeptides or fusion proteins, and methods of treatment using such engineered polypeptides or fusion proteins.

14 Claims, 22 Drawing Sheets

Specification includes a Sequence Listing.

(56) References Cited

FOREIGN PATENT DOCUMENTS

| WO | WO-2013/093762 A1 | 6/2013 |
|---|---|---|
| WO | WO-2013/126006 A1 | 8/2013 |
| WO | WO-2015/028550 A1 | 3/2015 |
| WO | WO-2015/028558 A1 | 3/2015 |

OTHER PUBLICATIONS

Kipriyanov, Sergey M., and Fabrice Le Gall. "Generation and production of engineered antibodies." Molecular biotechnology 26.1 (2004): 39-60. (Year: 2004).*

Arbabi Ghahroudi, M. et al. "Selection and identification of single domain antibody fragments from camel heavy-chain antibodies." FEBS letters vol. 414,3 (1997): 521-6. doi:10.1016/s0014-5793(97)01062-4 (Year: 1997).*

Berglund, Magnus M., and Patrik Strömberg. "The clinical potential of Affibody-based inhibitors of C5 for therapeutic complement disruption." Expert review of proteomics 13.3 (2016): 241-243. (Year: 2016).*

Office Action for Colombian Patent Application No. NC2020/0000369, dated Sep. 14, 2021 (14 pages).

Extended European Search Report for European Patent Application No. 18744926.9 dated Jul. 10, 2020 (10 pages).

Harmsen et al. "Properties, production, and applications of camelid single-domain antibody fragments," Appl Microbiol Biotechnol. 77(1):13-22 (2007).

International Preliminary Report on Patentability for International Application No. PCT/US2018/015985, dated Jul. 30, 2019 (9 pages).

International Search Report and Written Opinion for International Application No. PCT/US2018/015985, dated Jun. 11, 2018 (16 pages).

International Search Report for International Application No. PCT/US2018/041661, dated Sep. 24, 2018 (5 pages).

Pedersen et al. "Recruitment of Properdin by Bi-Specific Nanobodies Activates the Alternative Pathway of Complement," Mol Immunol. 124:200-210 (2020).

Rother et al. "Discovery and development of the complement inhibitor eculizumab for the treatment of paroxysmal nocturnal hemoglobinuria," Nat Biotechnol. 25(11):1256-64 (2007) (10 pages).

Stork et al. "Biodistribution of a bispecific single-chain diabody and its half-life extended derivatives," J Biol Chem. 284(38):25612-9 (2009) (9 pages).

Tijink et al. "Improved Tumor Targeting of Anti-Epidermal Growth Factor Receptor Nanobodies Through Albumin Binding: Taking Advantage of Modular Nanobody Technology," Mol Cancer Ther. 7(8):2288-97 (2008).

Van Roy et al. "The preclinical pharmacology of the high affinity anti-IL-6R Nanobody® ALX-0061 supports its clinical development in rheumatoid arthritis," Arthritis Res Ther. 17:135 (2015) (16 pages).

Written Opinion for International Application No. PCT/US2018/041661, dated Sep. 24, 2018 (8 pages).

Office Action for Russian Patent Application No. 2020102910/10(004483) dated Dec. 2, 2021 (19 pages) (English language translation provided).

Office Action for Japanese Patent Application No. 2020-500686 dated Jun. 28, 2022 (9 pages).

* cited by examiner

SEQUENCE LISTING

<160> NUMBER OF SEQ ID NOS: 327

<210> SEQ ID NO 1
<211> LENGTH: 126
<212> TYPE: PRT
<213> ORGANISM: Artificial Sequence
<220> FEATURE:
<223> OTHER INFORMATION: Synthetic Construct

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Asn Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125
```

<210> SEQ ID NO 2
<211> LENGTH: 126
<212> TYPE: PRT
<213> ORGANISM: Artificial Sequence
<220> FEATURE:
<223> OTHER INFORMATION: Synthetic Construct

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125
```

<210> SEQ ID NO 3
<211> LENGTH: 126
<212> TYPE: PRT
<213> ORGANISM: Artificial Sequence
<220> FEATURE:
<223> OTHER INFORMATION: Synthetic Construct

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
                100                 105                 110

Tyr Asp Tyr Trp Gly Gln Gly Thr Leu Val Thr Val Ser Ser
            115                 120                 125
```

<210> SEQ ID NO 4
<211> LENGTH: 126
<212> TYPE: PRT
<213> ORGANISM: Artificial Sequence
<220> FEATURE:
<223> OTHER INFORMATION: Synthetic Construct

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Gly Leu Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Tyr Ile Tyr Ser Ser Met Arg Ser Asp Ser
                100                 105                 110

Tyr Asp Tyr Trp Gly Gln Gly Thr Leu Val Thr Val Ser Ser
            115                 120                 125
```

<210> SEQ ID NO 5
<211> LENGTH: 132
<212> TYPE: PRT
<213> ORGANISM: Artificial Sequence
<220> FEATURE:
<223> OTHER INFORMATION: Synthetic Construct

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
```

```
                50                  55                  60
Asp Ser Val Lys Gly Arg Phe Thr Ile Ser Arg Asp Asn Ala Lys Asp
 65                  70                  75                  80

Ser Leu Tyr Leu Gln Met Asn Ser Leu Arg Ala Glu Asp Thr Ala Val
                    85                  90                  95

Tyr Tyr Cys Ala Val Arg Thr Arg Arg Tyr Gly Ser Asn Leu Gly Glu
               100                 105                 110

Val Pro Gln Glu Asn Glu Tyr Gly Tyr Trp Gly Gln Gly Thr Leu Val
           115                 120                 125

Thr Val Ser Ser
        130

<210> SEQ ID NO 6
<211> LENGTH: 132
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
  1               5                  10                  15

Ser Leu Arg Leu Ser Cys Ala Ala Ser Gly Arg Thr Phe Ser Gly Ile
                 20                  25                  30

Leu Ser Pro Tyr Ala Val Gly Trp Phe Arg Gln Ala Pro Gly Lys Gly
             35                  40                  45

Leu Glu Phe Val Ser Thr Ile Thr Ser Gly Gly Ser Ala Ile Tyr Thr
         50                  55                  60

Asp Ser Val Lys Gly Arg Phe Thr Ile Ser Arg Asp Asn Ala Lys Asn
 65                  70                  75                  80

Thr Leu Tyr Leu Gln Met Asn Ser Leu Arg Ala Glu Asp Thr Ala Val
                    85                  90                  95

Tyr Tyr Cys Ala Val Arg Thr Arg Arg Tyr Gly Ser Asn Leu Gly Glu
               100                 105                 110

Val Pro Gln Glu Asn Glu Tyr Gly Tyr Trp Gly Gln Gly Thr Leu Val
           115                 120                 125

Thr Val Ser Ser
        130

<210> SEQ ID NO 7
<211> LENGTH: 132
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
  1               5                  10                  15

Ser Leu Arg Leu Ser Cys Ala Ala Ser Gly Arg Thr Phe Ser Gly Ile
                 20                  25                  30

Leu Ser Pro Tyr Ala Val Gly Trp Phe Arg Gln Ala Pro Gly Lys Gly
             35                  40                  45

Leu Glu Phe Val Ser Thr Ile Thr Ser Gly Gly Ser Ala Ile Tyr Thr
         50                  55                  60

Asp Ser Val Lys Gly Arg Phe Thr Ile Ser Arg Asp Asn Ala Lys Asn
 65                  70                  75                  80
```

```
Ser Val Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser
    130

<210> SEQ ID NO 8
<211> LENGTH: 132
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Gln Gly
        35                  40                  45

Leu Glu Phe Val Ala Thr Ile Thr Ser Gly Ser Ala Ile Tyr Thr
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser
    130

<210> SEQ ID NO 9
<211> LENGTH: 126
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg His Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110
```

Tyr Asp Tyr Trp Gly Gln Gly Thr Leu Val Thr Val Ser Ser
            115                 120                 125

<210> SEQ ID NO 10
<211> LENGTH: 126
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala His Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
            115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala His Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Asn Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
            115                 120                 125

<210> SEQ ID NO 12
<211> LENGTH: 126
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg His His Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Gly Arg Ala Phe Ser Asp Tyr Ala Met Ala
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic Construct

<400> SEQUENCE: 14

Gly Arg Thr Phe Ser Gly Ile Leu Ser Pro Tyr Ala Val Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Gly Arg His Phe Ser Asp Tyr Ala Met Ala
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Gly Arg Ala His Ser Asp Tyr Ala Met Ala
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Gly Arg His His Ser Asp Tyr Ala Met Ala
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct

<400> SEQUENCE: 18

Gly Ile Gly Trp Ser Gly Gly Asp Thr Leu Tyr Ala Asp Ser Val Arg
1               5                   10                  15

Gly

<210> SEQ ID NO 19
<211> LENGTH: 16
<212> TYPE: PRT
<213> ORGANISM: Artificial Sequence
<220> FEATURE:
<223> OTHER INFORMATION: Synthetic Construct

<400> SEQUENCE: 19

Thr Ile Thr Ser Gly Gly Ser Ala Ile Tyr Thr Asp Ser Val Lys Gly
1               5                   10                  15

<210> SEQ ID NO 20
<211> LENGTH: 19
<212> TYPE: PRT
<213> ORGANISM: Artificial Sequence
<220> FEATURE:
<223> OTHER INFORMATION: Synthetic Construct

<400> SEQUENCE: 20

Ala Ala Arg Gln Gly Gln Tyr Ile Tyr Ser Ser Met Arg Ser Asp Ser
1               5                   10                  15

Tyr Asp Tyr

<210> SEQ ID NO 21
<211> LENGTH: 22
<212> TYPE: PRT
<213> ORGANISM: Artificial Sequence
<220> FEATURE:
<223> OTHER INFORMATION: Synthetic Construct

<400> SEQUENCE: 21

Ala Val Arg Thr Arg Arg Tyr Gly Ser Asn Leu Gly Glu Val Pro Gln
1               5                   10                  15

Glu Asn Glu Tyr Gly Tyr
                20

<210> SEQ ID NO 22
<211> LENGTH: 127
<212> TYPE: PRT
<213> ORGANISM: Artificial Sequence
<220> FEATURE:
<223> OTHER INFORMATION: Synthetic Construct -continued

<400> SEQUENCE: 22

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Ser Asp
            20                  25                  30

Ala Ala Gly Trp Phe Arg Gln Ala Ser Gly Lys Glu Arg Glu Phe Val
        35                  40                  45

Ala Ser Ile Ser Trp Ser Gly Tyr Thr Tyr Tyr Ala Asp Ser Val
    50                  55                  60

Lys Gly Arg Phe Thr Ile Ser Ser Asp Asn Val Lys Asn Thr Val Tyr
65                  70                  75                  80

Leu Gln Met Asn Ser Leu Thr Pro Glu Asp Thr Ala Val Tyr Phe Cys
                85                  90                  95

Ala Thr Gly Asn Arg Tyr Ser Asp Tyr Arg Ile Ser Leu Val Thr Pro
            100                 105                 110

Ser Gln Tyr Glu Tyr Trp Gly Gln Gly Thr Leu Val Thr Val Ser
        115                 120                 125

<210> SEQ ID NO 23
<211> LENGTH: 124
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Glu Ser Gly Gly Gly Leu Val Gln Pro Gly Gly
1               5                   10                  15

Ser Leu Arg Leu Ser Cys Thr Gly Ser Gly His Ser Phe Ser Thr Tyr
            20                  25                  30

Thr Val Gly Trp Phe Arg Gln Ala Pro Gly Glu Glu Arg Lys Phe Val
        35                  40                  45

Ala Ser Ile Ser Trp Ser Gly Glu Val Thr Leu Tyr Gly Asp Ser Val
    50                  55                  60

Lys Gly Arg Phe Thr Ile Ser Arg Asp Asn Arg Lys Lys Thr Val Tyr
65                  70                  75                  80

Leu Gln Met His Ser Leu Lys Pro Glu Asp Ser Ala Ile Tyr Tyr Cys
                85                  90                  95

Ala Ala Lys Arg Gly Gly Arg Pro Thr Asp Ser Ser Asp Asp Tyr Phe
            100                 105                 110

Tyr Trp Gly Gln Gly Thr Gln Val Thr Val Ser Ser
        115                 120

<210> SEQ ID NO 24
<211> LENGTH: 123
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Asn Glu Ser Gly Gly Gly Met Val Gln Ala Gly Gly
1               5                   10                  15

Ser Leu Arg Leu Ser Cys Ala Ala Ser Gly Arg Thr Val Ser Asn Tyr
            20                  25                  30

Ala Ala Gly Trp Phe Arg Gln Ala Pro Gly Lys Glu Arg Glu Phe Val
        35                  40                  45

```
Ala Ala Ile Asn Trp Asn Lys Thr Thr Tyr Ala Asp Ser Val Lys
        50                  55                  60

Gly Arg Phe Ile Ile Ser Arg Glu Tyr Ala Lys Asn Thr Val Ala Leu
65                  70                  75                  80

Gln Met Asn Ser Leu Lys Pro Glu Asp Thr Ala Val Tyr Tyr Cys Ala
                85                  90                  95

Ala Val Phe Arg Ile Val Ala Pro Lys Thr Gln Tyr Glu Tyr Asp Tyr
                100                 105                 110

Trp Gly Gln Gly Thr Gln Val Thr Val Ser Ser
            115                 120

<210> SEQ ID NO 25
<211> LENGTH: 123
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Ile Glu Ser Gly Gly Gly Leu Val Gln Ala Gly Gly
1               5                   10                  15

Ser Leu Gly Leu Ser Cys Ala Ala Ser Gly Arg Pro Val Ser Asn Tyr
                20                  25                  30

Ala Ala Ala Trp Phe Arg Gln Ala Pro Gly Lys Glu Arg Glu Phe Val
            35                  40                  45

Ala Ala Ile Asn Trp Asn Lys Thr Ala Thr Tyr Ala Asp Ser Val Lys
        50                  55                  60

Gly Arg Phe Thr Ile Ser Arg Asp Asn Ala Lys Ser Thr Val Ala Leu
65                  70                  75                  80

Gln Met Asn Ser Leu Lys Pro Glu Asp Thr Ala Val Tyr Tyr Cys Ala
                85                  90                  95

Ala Val Phe Arg Val Val Ala Pro Lys Thr Gln Tyr Asp Tyr Asp Tyr
                100                 105                 110

Trp Gly Gln Gly Thr Gln Val Thr Val Ser Ser
            115                 120

<210> SEQ ID NO 26
<211> LENGTH: 123
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
                20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
```

```
                    100                 105                 110
Trp Gly Gln Gly Thr Leu Val Thr Val Ser Ser
            115                 120

<210> SEQ ID NO 27
<211> LENGTH: 123
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Ile Gly Trp Phe Arg Gln Ala Pro Gly Lys Ala Arg Glu Phe Val
        35                  40                  45

Ala Arg Val Ser Thr Ile Ala Gly Asp Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Ser Tyr Asn Val Arg Leu Val Thr Gly Glu Ala Asp Tyr
            100                 105                 110

Trp Gly Glu Gly Thr Gln Val Thr Val Ser Ser
            115                 120

<210> SEQ ID NO 28
<211> LENGTH: 123
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Ile Gly Trp Phe Arg Gln Ala Pro Gly Lys Ala Arg Glu Phe Val
        35                  40                  45

Ala Arg Val Ser Thr Ile Ala Gly Asp Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Ser Tyr Asn Val Arg Leu Gly Thr Gly Glu Ala Asp Tyr
            100                 105                 110

Trp Gly Glu Gly Thr Gln Val Thr Val Ser Ser
            115                 120

<210> SEQ ID NO 29
<211> LENGTH: 123
<212> TYPE: PRT
<213> ORGANISM: Artificial Sequence
<220> FEATURE:
```

<223> OTHER INFORMATION: Synthetic Construct

<400> SEQUENCE: 29

Glu Val Gln Leu Val Glu Ser Gly Gly Gly Leu Val Gln Ala Gly Asp
1               5                   10                  15

Ser Leu Arg Leu Ser Cys Ala Ala Ser Gly Phe Thr Phe Ser Asn Tyr
            20                  25                  30

Ala Ile Gly Trp Phe Arg Gln Ala Pro Gly Lys Ala Arg Glu Phe Val
        35                  40                  45

Ala Arg Val Ser Thr Ile Ala Gly Asp Thr Asp Tyr Ala Asn Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Glu Ser Tyr Asn Val Arg Leu Val Thr Gly Glu Ala Asp Tyr
            100                 105                 110

Trp Gly Glu Gly Thr Gln Val Thr Val Ser Ser
        115                 120

<210> SEQ ID NO 30
<211> LENGTH: 127
<212> TYPE: PRT
<213> ORGANISM: Artificial Sequence
<220> FEATURE:
<223> OTHER INFORMATION: Synthetic Construct

<400> SEQUENCE: 30

Gln Val Arg Leu Ala Glu Ser Gly Gly Gly Arg Val Gln Ala Gly Glu
1               5                   10                  15

Ser Leu Arg Leu Ser Cys Val Ala Ser Gly Arg Thr Phe Ser Asn Asp
            20                  25                  30

Ala Ala Gly Trp Phe Arg Glu Ala Ser Gly Lys Glu Arg Glu Phe Val
        35                  40                  45

Ala Ser Ile Ser Trp Ser Gly Asn Tyr Thr Tyr Tyr Ala Asp Ser Val
    50                  55                  60

Lys Gly Arg Phe Thr Ile Ser Glu Asp Asn Val Lys Asn Thr Val Tyr
65                  70                  75                  80

Leu Gln Met Thr Ser Leu Lys Pro Glu Asp Thr Ala Val Tyr Tyr Cys
                85                  90                  95

Ala Ala Gly Asn Arg Tyr Ser Asp Tyr Arg Ile Ser Leu Val Thr Pro
            100                 105                 110

Arg Leu Tyr Glu Tyr Trp Gly Gln Gly Thr Gln Val Thr Val Ser
        115                 120                 125

<210> SEQ ID NO 31
<211> LENGTH: 127
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Asp
            20                  25                  30

Ala Ala Gly Trp Phe Arg Gln Ala Ser Gly Lys Glu Arg Glu Phe Val

```
            35                  40                  45
Ala Ala Ile Ser Trp Ser Gly Asn Tyr Thr Tyr Ser Ala Asp Ser Val
        50                  55                  60

Lys Gly Arg Phe Thr Ile Ser Ser Asp Asn Val Lys Asn Thr Val Tyr
65                  70                  75                  80

Leu Gln Met Asn Ser Leu Lys Pro Glu Asp Thr Ala Val Tyr Leu Cys
                85                  90                  95

Ala Ala Gly Asn Arg Tyr Ser Asp Tyr Arg Ile Ser Leu Val Thr Pro
            100                 105                 110

Ser Gln Tyr Glu Tyr Trp Gly Gln Gly Thr Gln Val Thr Val Ser
        115                 120                 125

<210> SEQ ID NO 32
<211> LENGTH: 127
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Ser Asp
            20                  25                  30

Ala Ala Gly Trp Phe Arg Gln Ala Ser Gly Lys Glu Arg Glu Phe Val
        35                  40                  45

Ala Ser Ile Ser Trp Ser Gly Tyr Thr Tyr Tyr Ala Asp Ser Gly
    50                  55                  60

Thr Gly Arg Phe Thr Ile Ser Ser Asp Asn Val Lys Asn Thr Val Tyr
65                  70                  75                  80

Leu Gln Met Asn Ser Leu Thr Pro Glu Asp Thr Ala Val Tyr Phe Cys
                85                  90                  95

Ala Thr Gly Asn Arg Asp Ser Asp Tyr Arg Ile Ser Leu Val Thr Pro
            100                 105                 110

Ser Gln Tyr Glu Tyr Trp Gly Gln Gly Thr Gln Val Thr Val Ser
        115                 120                 125

<210> SEQ ID NO 33
<211> LENGTH: 127
<212> TYPE: PRT
<213> ORGANISM: Artificial Sequence
<220> FEATURE:
<223> OTHER INFORMATION: Synthetic Construct

<400> SEQUENCE: 33

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Ser Asp
            20                  25                  30

Ala Ala Gly Trp Phe Arg Gln Ala Ser Gly Lys Glu Arg Glu Phe Val
        35                  40                  45

Ala Ser Ile Ser Trp Ser Gly Tyr Thr Tyr Tyr Ala Asp Ser Gly
    50                  55                  60

Lys Gly Arg Phe Thr Ile Ser Ser Asp Asn Val Lys Asn Thr Val Tyr
65                  70                  75                  80

Leu Gln Met Asn Ser Leu Thr Pro Glu Asp Thr Ala Val Tyr Phe Cys
                85                  90                  95
```

Ala Thr Gly Asn Arg Tyr Ser Asp Tyr Arg Ile Ser Leu Val Thr Pro
            100                 105                 110

Ser Gln Tyr Asp Tyr Trp Gly Gln Gly Thr Gln Val Thr Val Ser
        115                 120                 125

<210> SEQ ID NO 34
<211> LENGTH: 127
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Ser Asp
            20                  25                  30

Ala Ala Gly Trp Phe Arg Gln Ala Ser Gly Lys Glu Arg Glu Phe Val
        35                  40                  45

Ala Ser Ile Ser Trp Ser Gly Gly Tyr Thr Tyr Tyr Ala Asp Ser Val
    50                  55                  60

Lys Gly Arg Phe Thr Ser Ser Asp Asn Val Lys Asn Thr Val Tyr
65                  70                  75                  80

Leu Gln Met Asn Ser Leu Thr Pro Glu Asp Thr Ala Val Tyr Phe Cys
                85                  90                  95

Ala Thr Val Asn Arg Tyr Ser Asp Tyr Arg Ile Ser Leu Val Thr Pro
            100                 105                 110

Ser Gln Tyr Glu Tyr Trp Gly Gln Gly Thr Gln Val Thr Val Ser
        115                 120                 125

<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

<400> SEQUENCE: 35

Gly Arg Thr Phe Gly Ser Asp Ala
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Gly His Ser Phe Ser Thr Tyr Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Gly Arg Thr Val Ser Asn Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Gly Arg Pro Val Ser Asn Tyr Ala
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Construct

<400> SEQUENCE: 39

Gly Arg Thr Phe Ser Ser Tyr Ala
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

Gly Phe Thr Phe Ser Asn Tyr Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct

<400> SEQUENCE: 41

Gly Arg Thr Phe Ser Asn Asp Ala
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

Gly Arg Thr Phe Ser Ser Asp Ala
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Construct

<400> SEQUENCE: 43

Gly Arg Thr Phe Gly Ser Asp Ala
1               5

```
<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

Ile Ser Trp Ser Gly Gly Tyr Thr
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic Construct

<400> SEQUENCE: 45

Ile Ser Trp Ser Gly Glu Val Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Construct

<400> SEQUENCE: 46

Ile Asn Trp Asn Lys Thr Thr Thr
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct

<400> SEQUENCE: 47

Ile Asn Trp Asn Lys Thr Ala Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Ile Asn Trp Gln Lys Thr Ala Thr
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Val Ser Thr Ile Ala Gly Asp Thr
1               5

<210> SEQ ID NO 50
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Ile Ser Trp Ser Gly Asn Tyr Thr
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Ile Ser Trp Ser Gly Gly Tyr Thr
1               5

<210> SEQ ID NO 52
<211> LENGTH: 21
<212> TYPE: PRT
<213> ORGANISM: Artificial Sequence
<220> FEATURE:
<223> OTHER INFORMATION: Synthetic Construct

<400> SEQUENCE: 52

Ala Thr Gly Asn Arg Tyr Ser Asp Tyr Arg Ile Ser Leu Val Thr Pro
1               5                   10                  15

Ser Gln Tyr Glu Tyr
            20

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Ala Ala Lys Arg Gly Gly Arg Pro Thr Asp Ser Ser Asp Asp Tyr Phe
1               5                   10                  15

Tyr

<210> SEQ ID NO 54
<211> LENGTH: 17
<212> TYPE: PRT
<213> ORGANISM: Artificial Sequence
<220> FEATURE:
<223> OTHER INFORMATION: Synthetic Construct

<400> SEQUENCE: 54

Ala Ala Val Phe Arg Ile Val Ala Pro Lys Thr Gln Tyr Glu Tyr Asp
1               5                   10                  15

Tyr

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct

<400> SEQUENCE: 55
```

```
Ala Ala Val Phe Arg Val Val Ala Pro Lys Thr Gln Tyr Asp Tyr Asp
1               5                   10                  15

Tyr

<210> SEQ ID NO 56
<211> LENGTH: 16
<212> TYPE: PRT
<213> ORGANISM: Artificial Sequence
<220> FEATURE:
<223> OTHER INFORMATION: Synthetic Construct

<400> SEQUENCE: 56

Ala Ala Asp Ser Tyr Asn Val Arg Leu Val Thr Gly Glu Ala Asp Tyr
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Synthetic Construct

<400> SEQUENCE: 57

Ala Ala Asp Ser Tyr Asn Val Arg Leu Gly Thr Gly Glu Ala Asp Tyr
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetic Construct

<400> SEQUENCE: 58

Ala Ala Glu Ser Tyr Asn Val Arg Leu Val Thr Gly Glu Ala Asp Tyr
1               5                   10                  15

<210> SEQ ID NO 59
<211> LENGTH: 21
<212> TYPE: PRT
<213> ORGANISM: Artificial Sequence
<220> FEATURE:
<223> OTHER INFORMATION: Synthetic Construct

<400> SEQUENCE: 59

Ala Ala Gly Asn Arg Tyr Ser Asp Tyr Arg Ile Ser Leu Val Thr Pro
1               5                   10                  15

Arg Leu Tyr Glu Tyr
            20

<210> SEQ ID NO 60
<211> LENGTH: 21
<212> TYPE: PRT
<213> ORGANISM: Artificial Sequence
<220> FEATURE:
<223> OTHER INFORMATION: Synthetic Construct

<400> SEQUENCE: 60

Ala Ala Gly Asn Arg Tyr Ser Asp Tyr Arg Ile Ser Leu Val Thr Pro
1               5                   10                  15

Ser Gln Tyr Glu Tyr
            20

<210> SEQ ID NO 61
```

```
<211> LENGTH: 21
<212> TYPE: PRT
<213> ORGANISM: Artificial Sequence
<220> FEATURE:
<223> OTHER INFORMATION: Synthetic Construct

<400> SEQUENCE: 61

Ala Thr Gly Asn Arg Asp Ser Asp Tyr Arg Ile Ser Leu Val Thr Pro
1               5                   10                  15

Ser Gln Tyr Glu Tyr
            20

<210> SEQ ID NO 62
<211> LENGTH: 21
<212> TYPE: PRT
<213> ORGANISM: Artificial Sequence
<220> FEATURE:
<223> OTHER INFORMATION: Synthetic Construct

<400> SEQUENCE: 62

Ala Thr Gly Asn Arg Tyr Ser Asp Tyr Arg Ile Ser Leu Val Thr Pro
1               5                   10                  15

Ser Gln Tyr Asp Tyr
            20

<210> SEQ ID NO 63
<211> LENGTH: 21
<212> TYPE: PRT
<213> ORGANISM: Artificial Sequence
<220> FEATURE:
<223> OTHER INFORMATION: Synthetic Construct

<400> SEQUENCE: 63

Ala Thr Val Asn Arg Tyr Ser Asp Tyr Arg Ile Ser Leu Val Thr Pro
1               5                   10                  15

Ser Gln Tyr Glu Tyr
            20

<210> SEQ ID NO 64
<211> LENGTH: 256
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly Gly
        115                 120                 125
```

```
Gly Ser Glu Val Gln Leu Val Glu Ser Gly Gly Leu Val Gln Pro
    130                 135                 140

Gly Gly Ser Leu Arg Leu Ser Cys Ala Ala Ser Gly Arg His Phe Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
                180                 185                 190

Ser Val Arg Gly Arg Phe Thr Ile Ser Arg Asp Asn Ala Lys Asn Thr
                195                 200                 205

Leu Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
225                 230                 235                 240

Asp Ser Tyr Asp Tyr Trp Gly Gln Gly Thr Leu Val Thr Val Ser Ser
                245                 250                 255
```

<210> SEQ ID NO 65
<211> LENGTH: 256
<212> TYPE: PRT
<213> ORGANISM: Artificial Sequence
<220> FEATURE:
<223> OTHER INFORMATION: Synthetic Construct

<400> SEQUENCE: 65

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Ala Ala Ser Gly Arg Ala His Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
                180                 185                 190

Ser Val Arg Gly Arg Phe Thr Ile Ser Arg Asp Asn Ala Lys Asn Thr
                195                 200                 205

Leu Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
225                 230                 235                 240
```

```
Asp Ser Tyr Asp Tyr Trp Gly Gln Gly Thr Leu Val Thr Val Ser Ser
            245                 250                 255

<210> SEQ ID NO 66
<211> LENGTH: 256
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Ala Ala Ser Gly Arg His His Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
            180                 185                 190

Ser Val Arg Gly Arg Phe Thr Ile Ser Arg Asp Asn Ala Lys Asn Thr
        195                 200                 205

Leu Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
225                 230                 235                 240

Asp Ser Tyr Asp Tyr Trp Gly Gln Gly Thr Leu Val Thr Val Ser Ser
                245                 250                 255

<210> SEQ ID NO 67
<211> LENGTH: 256
<212> TYPE: PRT
<213> ORGANISM: Artificial Sequence
<220> FEATURE:
<223> OTHER INFORMATION: Synthetic Construct

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
```

```
                35                  40                  45
Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
                100                 105                 110

Val Ser Ser Gly Gly Gly Gly Ser Gly Gly Gly Ser Gly Gly Gly
            115                 120                 125

Gly Ser Glu Val Gln Leu Val Glu Ser Gly Gly Leu Val Gln Pro
        130                 135                 140

Gly Gly Ser Leu Arg Leu Ser Cys Ala Ala Ser Gly Arg His Phe Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
                180                 185                 190

Ser Val Arg Gly Arg Phe Thr Ile Ser Arg Asp Asn Ser Lys Asn Thr
                195                 200                 205

Met Tyr Leu Gln Met Asn Ser Leu Arg Ala Glu Asp Thr Ala Val Tyr
            210                 215                 220

Tyr Cys Ala Ala Arg Gln Gly Gln Tyr Ile Tyr Ser Ser Met Arg Ser
225                 230                 235                 240

Asp Ser Tyr Asp Tyr Trp Gly Gln Gly Thr Leu Val Thr Val Ser Ser
                245                 250                 255

<210> SEQ ID NO 68
<211> LENGTH: 256
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
                100                 105                 110

Val Ser Ser Gly Gly Gly Gly Ser Gly Gly Gly Gly Ser Gly Gly Gly
            115                 120                 125

Gly Ser Glu Val Gln Leu Val Glu Ser Gly Gly Gly Leu Val Gln Pro
        130                 135                 140

Gly Gly Ser Leu Arg Leu Ser Cys Ala Ala Ser Gly Arg Ala His Ser
```

```
                145                 150                 155                 160
Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
            180                 185                 190

Ser Val Arg Gly Arg Phe Thr Ile Ser Arg Asp Asn Ser Lys Asn Thr
        195                 200                 205

Met Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
225                 230                 235                 240

Asp Ser Tyr Asp Tyr Trp Gly Gln Gly Thr Leu Val Thr Val Ser Ser
                245                 250                 255

<210> SEQ ID NO 69
<211> LENGTH: 256
<212> TYPE: PRT
<213> ORGANISM: Artificial Sequence
<220> FEATURE:
<223> OTHER INFORMATION: Synthetic Construct

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Arg His His Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
            180                 185                 190

Ser Val Arg Gly Arg Phe Thr Ile Ser Arg Asp Asn Ser Lys Asn Thr
        195                 200                 205

Met Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
225                 230                 235                 240

Asp Ser Tyr Asp Tyr Trp Gly Gln Gly Thr Leu Val Thr Val Ser Ser
                245                 250                 255
```

```
<210> SEQ ID NO 70
<211> LENGTH: 264
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160

Ala Ala Ser Gly Arg His Phe Ser Asp Tyr Ala Met Ala Trp Phe Arg
                165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Ile
        195                 200                 205

Ser Arg Asp Asn Ala Lys Asn Thr Leu Tyr Leu Gln Met Asn Ser Leu
    210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260

<210> SEQ ID NO 71
<211> LENGTH: 264
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45
```

```
Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Ala Val Phe Arg Val Val Ala Pro Lys Thr Gln Tyr Asp Tyr Asp Tyr
                100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160

Ala Ala Ser Gly Arg Ala His Ser Asp Tyr Ala Met Ala Trp Phe Arg
                165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Ile
            195                 200                 205

Ser Arg Asp Asn Ala Lys Asn Thr Leu Tyr Leu Gln Met Asn Ser Leu
210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260

<210> SEQ ID NO 72
<211> LENGTH: 264
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Glu Ser Gly Gly Gly Leu Val Lys Pro Gly Gly
 1               5                  10                  15

Ser Leu Arg Leu Ser Cys Ala Ala Ser Gly Arg Pro Val Ser Asn Tyr
                20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Ala Val Phe Arg Val Val Ala Pro Lys Thr Gln Tyr Asp Tyr Asp Tyr
                100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Glu Val Gln Leu Val Glu
    130                 135                 140
```

```
Ser Gly Gly Gly Leu Val Gln Pro Gly Gly Ser Leu Arg Leu Ser Cys
145                 150                 155                 160

Ala Ala Ser Gly Arg His His Ser Asp Tyr Ala Met Ala Trp Phe Arg
            165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Ile
            195                 200                 205

Ser Arg Asp Asn Ala Lys Asn Thr Leu Tyr Leu Gln Met Asn Ser Leu
            210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
            245                 250                 255

Gly Thr Leu Val Thr Val Ser Ser
            260

<210> SEQ ID NO 73
<211> LENGTH: 264
<212> TYPE: PRT
<213> ORGANISM: Artificial Sequence
<220> FEATURE:
<223> OTHER INFORMATION: Synthetic Construct

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Glu Val Gln Leu Val Glu
130                 135                 140

Ser Gly Gly Gly Leu Val Gln Pro Gly Gly Ser Leu Arg Leu Ser Cys
145                 150                 155                 160

Ala Ala Ser Gly Arg His Phe Ser Asp Tyr Ala Met Ala Trp Phe Arg
            165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Ile
            195                 200                 205

Ser Arg Asp Asn Ser Lys Asn Thr Met Tyr Leu Gln Met Asn Ser Leu
            210                 215                 220

Arg Ala Glu Asp Thr Ala Val Tyr Tyr Cys Ala Ala Arg Gln Gly Gln
225                 230                 235                 240
```

-continued

```
Tyr Ile Tyr Ser Ser Met Arg Ser Asp Ser Tyr Asp Tyr Trp Gly Gln
                245                 250                 255

Gly Thr Leu Val Thr Val Ser Ser
            260

<210> SEQ ID NO 74
<211> LENGTH: 264
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160

Ala Ala Ser Gly Arg Ala His Ser Asp Tyr Ala Met Ala Trp Phe Arg
                165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Ile
        195                 200                 205

Ser Arg Asp Asn Ser Lys Asn Thr Met Tyr Leu Gln Met Asn Ser Leu
    210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260

<210> SEQ ID NO 75
<211> LENGTH: 264
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Glu Val Gln Leu Val Glu
130                 135                 140

Ser Gly Gly Gly Leu Val Gln Pro Gly Gly Ser Leu Arg Leu Ser Cys
145                 150                 155                 160

Ala Ala Ser Gly Arg His His Ser Asp Tyr Ala Met Ala Trp Phe Arg
                165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Ile
        195                 200                 205

Ser Arg Asp Asn Ser Lys Asn Thr Met Tyr Leu Gln Met Asn Ser Leu
 210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260

<210> SEQ ID NO 76
<211> LENGTH: 262
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
 50                  55                  60

Asp Ser Val Lys Gly Arg Phe Thr Ile Ser Arg Asp Asn Ala Lys Asp
 65                  70                  75                  80

Ser Leu Tyr Leu Gln Met Asn Ser Leu Arg Ala Glu Asp Thr Ala Val
                 85                  90                  95

Tyr Tyr Cys Ala Val Arg Thr Arg Arg Tyr Gly Ser Asn Leu Gly Glu
            100                 105                 110
```

Val Pro Gln Glu Asn Glu Tyr Gly Tyr Trp Gly Gln Gly Thr Leu Val
            115                 120                 125
Thr Val Ser Ser Gly Gly Gly Gly Ser Gly Gly Gly Gly Ser Gly Gly
        130                 135                 140
Gly Gly Ser Glu Val Gln Leu Leu Glu Ser Gly Gly Gly Leu Val Gln
145                 150                 155                 160
Pro Gly Gly Ser Leu Arg Leu Ser Cys Ala Ala Ser Gly Phe Thr Phe
                165                 170                 175
Arg Ser Phe Gly Met Ser Trp Val Arg Gln Ala Pro Gly Lys Gly Pro
            180                 185                 190
Glu Trp Val Ser Ser Ile Ser Gly Ser Gly Ser Asp Thr Leu Tyr Ala
        195                 200                 205
Asp Ser Val Lys Gly Arg Phe Thr Ile Ser Arg Asp Asn Ser Lys Asn
    210                 215                 220
Thr Leu Tyr Leu Gln Met Asn Ser Leu Arg Pro Glu Asp Thr Ala Val
225                 230                 235                 240
Tyr Tyr Cys Thr Ile Gly Gly Ser Leu Ser Arg Ser Gln Gly Thr
                245                 250                 255
Leu Val Thr Val Ser Ser
            260

<210> SEQ ID NO 77
<211> LENGTH: 270
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Val Glu Ser Gly Gly Gly Leu Val Gln Pro Gly Gly
1               5                   10                  15
Ser Leu Arg Leu Ser Cys Ala Ala Ser Gly Arg Thr Phe Ser Gly Ile
            20                  25                  30
Leu Ser Pro Tyr Ala Val Gly Trp Phe Arg Gln Ala Pro Gly Lys Gly
        35                  40                  45
Leu Glu Phe Val Ser Thr Ile Thr Ser Gly Gly Ser Ala Ile Tyr Thr
    50                  55                  60
Asp Ser Val Lys Gly Arg Phe Thr Ile Ser Arg Asp Asn Ala Lys Asp
65                  70                  75                  80
Ser Leu Tyr Leu Gln Met Asn Ser Leu Arg Ala Glu Asp Thr Ala Val
                85                  90                  95
Tyr Tyr Cys Ala Val Arg Thr Arg Arg Tyr Gly Ser Asn Leu Gly Glu
            100                 105                 110
Val Pro Gln Glu Asn Glu Tyr Gly Tyr Trp Gly Gln Gly Thr Leu Val
        115                 120                 125
Thr Val Ser Ser Gly Gly Gly Gly Ser Gly Gly Gly Gly Ser Gly Gly
    130                 135                 140
Gly Gly Ser Glu Val Gln Leu Val Glu Ser Gly Gly Gly Leu Val Lys
145                 150                 155                 160
Pro Gly Gly Ser Leu Arg Leu Ser Cys Ala Ala Ser Gly Arg Pro Val
                165                 170                 175
Ser Asn Tyr Ala Ala Ala Trp Phe Arg Gln Ala Pro Gly Lys Glu Arg
            180                 185                 190
Glu Phe Val Ser Ala Ile Asn Trp Gln Lys Thr Ala Thr Tyr Ala Asp
        195                 200                 205

```
Ser Val Lys Gly Arg Phe Thr Ile Ser Arg Asp Asn Ala Lys Asn Ser
    210                 215                 220
Leu Tyr Leu Gln Met Asn Ser Leu Arg Ala Glu Asp Thr Ala Val Tyr
225                 230                 235                 240
Tyr Cys Ala Ala Val Phe Arg Val Val Ala Pro Lys Thr Gln Tyr Asp
                245                 250                 255
Tyr Asp Tyr Trp Gly Gln Gly Thr Leu Val Thr Val Ser Ser
            260                 265                 270
```

<210> SEQ ID NO 78
<211> LENGTH: 262
<212> TYPE: PRT
<213> ORGANISM: Artificial Sequence
<220> FEATURE:
<223> OTHER INFORMATION: Synthetic Construct

<400> SEQUENCE: 78

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Arg Thr Phe Ser Gly Ile
            20                  25                  30
Leu Ser Pro Tyr Ala Val Gly Trp Phe Arg Gln Ala Pro Gly Lys Gly
        35                  40                  45
Leu Glu Phe Val Ser Thr Ile Thr Ser Gly Gly Ser Ala Ile Tyr Thr
    50                  55                  60
Asp Ser Val Lys Gly Arg Phe Thr Ile Ser Arg Asp Asn Ala Lys Asn
65                  70                  75                  80
Thr Leu Tyr Leu Gln Met Asn Ser Leu Arg Ala Glu Asp Thr Ala Val
                85                  90                  95
Tyr Tyr Cys Ala Val Arg Thr Arg Arg Tyr Gly Ser Asn Leu Gly Glu
            100                 105                 110
Val Pro Gln Glu Asn Glu Tyr Gly Tyr Trp Gly Gln Gly Thr Leu Val
        115                 120                 125
Thr Val Ser Ser Gly Gly Gly Gly Ser Gly Gly Gly Gly Ser Gly Gly
    130                 135                 140
Gly Gly Ser Glu Val Gln Leu Leu Glu Ser Gly Gly Gly Leu Val Gln
145                 150                 155                 160
Pro Gly Gly Ser Leu Arg Leu Ser Cys Ala Ala Ser Gly Phe Thr Phe
                165                 170                 175
Arg Ser Phe Gly Met Ser Trp Val Arg Gln Ala Pro Gly Lys Gly Pro
            180                 185                 190
Glu Trp Val Ser Ser Ile Ser Gly Ser Gly Ser Asp Thr Leu Tyr Ala
        195                 200                 205
Asp Ser Val Lys Gly Arg Phe Thr Ile Ser Arg Asp Asn Ser Lys Asn
    210                 215                 220
Thr Leu Tyr Leu Gln Met Asn Ser Leu Arg Pro Glu Asp Thr Ala Val
225                 230                 235                 240
Tyr Tyr Cys Thr Ile Gly Gly Ser Leu Ser Arg Ser Ser Gln Gly Thr
                245                 250                 255
Leu Val Thr Val Ser Ser
            260
```

<210> SEQ ID NO 79
<211> LENGTH: 270
<212> TYPE: PRT
<213> ORGANISM: Artificial Sequence

```
<220> FEATURE:
<223> OTHER INFORMATION: Synthetic Construct

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser Gly Gly Gly Gly Ser Gly Gly Gly Gly Ser Gly Gly
    130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Arg Pro Val
                165                 170                 175

Ser Asn Tyr Ala Ala Ala Trp Phe Arg Gln Ala Pro Gly Lys Glu Arg
            180                 185                 190

Glu Phe Val Ser Ala Ile Asn Trp Gln Lys Thr Ala Thr Tyr Ala Asp
        195                 200                 205

Ser Val Lys Gly Arg Phe Thr Ile Ser Arg Asp Asn Ala Lys Asn Ser
    210                 215                 220

Leu Tyr Leu Gln Met Asn Ser Leu Arg Ala Glu Asp Thr Ala Val Tyr
225                 230                 235                 240

Tyr Cys Ala Ala Val Phe Arg Val Val Ala Pro Lys Thr Gln Tyr Asp
                245                 250                 255

Tyr Asp Tyr Trp Gly Gln Gly Thr Leu Val Thr Val Ser Ser
            260                 265                 270

<210> SEQ ID NO 80
<211> LENGTH: 262
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
    50                  55                  60

Asp Ser Val Lys Gly Arg Phe Thr Ile Ser Arg Asp Asn Ala Lys Asn
```

```
                65                  70                  75                  80
Ser Val Tyr Leu Gln Met Asn Ser Leu Arg Ala Glu Asp Thr Ala Val
                    85                  90                  95

Tyr Tyr Cys Ala Val Arg Thr Arg Arg Tyr Gly Ser Asn Leu Gly Glu
                100                 105                 110

Val Pro Gln Glu Asn Glu Tyr Gly Tyr Trp Gly Gln Gly Thr Leu Val
                115                 120                 125

Thr Val Ser Ser Gly Gly Gly Gly Ser Gly Gly Gly Ser Gly Gly
            130                 135                 140

Gly Gly Ser Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Arg Ser Phe Gly Met Ser Trp Val Arg Gln Ala Pro Gly Lys Gly Pro
                180                 185                 190

Glu Trp Val Ser Ser Ile Ser Gly Ser Gly Ser Asp Thr Leu Tyr Ala
                195                 200                 205

Asp Ser Val Lys Gly Arg Phe Thr Ile Ser Arg Asp Asn Ser Lys Asn
                210                 215                 220

Thr Leu Tyr Leu Gln Met Asn Ser Leu Arg Pro Glu Asp Thr Ala Val
225                 230                 235                 240

Tyr Tyr Cys Thr Ile Gly Gly Ser Leu Ser Arg Ser Gln Gly Thr
                245                 250                 255

Leu Val Thr Val Ser Ser
                260
```

<210> SEQ ID NO 81
<211> LENGTH: 270
<212> TYPE: PRT
<213> ORGANISM: Artificial Sequence
<220> FEATURE:
<223> OTHER INFORMATION: Synthetic Construct

<400> SEQUENCE: 81

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
                20                  25                  30

Leu Ser Pro Tyr Ala Val Gly Trp Phe Arg Gln Ala Pro Gly Lys Gly
                35                  40                  45

Leu Glu Phe Val Ser Thr Ile Thr Ser Gly Gly Ser Ala Ile Tyr Thr
            50                  55                  60

Asp Ser Val Lys Gly Arg Phe Thr Ile Ser Arg Asp Asn Ala Lys Asn
65                  70                  75                  80

Ser Val Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
                100                 105                 110

Val Pro Gln Glu Asn Glu Tyr Gly Tyr Trp Gly Gln Gly Thr Leu Val
                115                 120                 125

Thr Val Ser Ser Gly Gly Gly Gly Ser Gly Gly Gly Ser Gly Gly
            130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Arg Pro Val
```

```
                     165                 170                 175
Ser Asn Tyr Ala Ala Trp Phe Arg Gln Ala Pro Gly Lys Glu Arg
            180                 185                 190

Glu Phe Val Ser Ala Ile Asn Trp Gln Lys Thr Ala Thr Tyr Ala Asp
        195                 200                 205

Ser Val Lys Gly Arg Phe Thr Ile Ser Arg Asp Asn Ala Lys Asn Ser
210                 215                 220

Leu Tyr Leu Gln Met Asn Ser Leu Arg Ala Glu Asp Thr Ala Val Tyr
225                 230                 235                 240

Tyr Cys Ala Ala Val Phe Arg Val Val Ala Pro Lys Thr Gln Tyr Asp
                245                 250                 255

Tyr Asp Tyr Trp Gly Gln Gly Thr Leu Val Thr Val Ser Ser
            260                 265                 270

<210> SEQ ID NO 82
<211> LENGTH: 262
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Gln Gly
        35                  40                  45

Leu Glu Phe Val Ala Thr Ile Thr Ser Gly Gly Ser Ala Ile Tyr Thr
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser Gly Gly Gly Gly Ser Gly Gly Gly Gly Ser Gly Gly
    130                 135                 140

Gly Gly Ser Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Arg Ser Phe Gly Met Ser Trp Val Arg Gln Ala Pro Gly Lys Gly Pro
            180                 185                 190

Glu Trp Val Ser Ser Ile Ser Gly Ser Gly Ser Asp Thr Leu Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Pro Glu Asp Thr Ala Val
225                 230                 235                 240

Tyr Tyr Cys Thr Ile Gly Gly Ser Leu Ser Arg Ser Ser Gln Gly Thr
                245                 250                 255

Leu Val Thr Val Ser Ser
```

<210> SEQ ID NO 83
<211> LENGTH: 270
<212> TYPE: PRT
<213> ORGANISM: Artificial Sequence
<220> FEATURE:
<223> OTHER INFORMATION: Synthetic Construct

<400> SEQUENCE: 83

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Gln Gly
        35                  40                  45

Leu Glu Phe Val Ala Thr Ile Thr Ser Gly Gly Ser Ala Ile Tyr Thr
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser Gly Gly Gly Gly Ser Gly Gly Gly Gly Ser Gly Gly
    130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Arg Pro Val
                165                 170                 175

Ser Asn Tyr Ala Ala Ala Trp Phe Arg Gln Ala Pro Gly Lys Glu Arg
            180                 185                 190

Glu Phe Val Ser Ala Ile Asn Trp Gln Lys Thr Ala Thr Tyr Ala Asp
        195                 200                 205

Ser Val Lys Gly Arg Phe Thr Ile Ser Arg Asp Asn Ala Lys Asn Ser
    210                 215                 220

Leu Tyr Leu Gln Met Asn Ser Leu Arg Ala Glu Asp Thr Ala Val Tyr
225                 230                 235                 240

Tyr Cys Ala Ala Val Phe Arg Val Val Ala Pro Lys Thr Gln Tyr Asp
                245                 250                 255

Tyr Asp Tyr Trp Gly Gln Gly Thr Leu Val Thr Val Ser Ser
            260                 265                 270
```

<210> SEQ ID NO 84
<211> LENGTH: 256
<212> TYPE: PRT
<213> ORGANISM: Artificial Sequence
<220> FEATURE:
<223> OTHER INFORMATION: Synthetic Construct

<400> SEQUENCE: 84

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Arg Ser Phe
            20                  25                  30
```

```
Gly Met Ser Trp Val Arg Gln Ala Pro Gly Lys Pro Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Arg Ala Phe Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
            180                 185                 190

Ser Val Arg Gly Arg Phe Thr Asn Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
225                 230                 235                 240

Asp Ser Tyr Asp Tyr Trp Gly Gln Gly Thr Leu Val Thr Val Ser Ser
                245                 250                 255

<210> SEQ ID NO 85
<211> LENGTH: 264
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Lys Pro Gly Gly
 1               5                  10                  15

Ser Leu Arg Leu Ser Cys Ala Ala Ser Gly Arg Pro Val Ser Asn Tyr
                20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Glu Val Gln Leu Val Glu
    130                 135                 140
```

```
Ser Gly Gly Gly Leu Val Gln Pro Gly Gly Ser Leu Arg Leu Ser Cys
145                 150                 155                 160

Ala Ala Ser Gly Arg Ala Phe Ser Asp Tyr Ala Met Ala Trp Phe Arg
            165                 170                 175

Gln Ala Pro Gly Gln Glu Arg Glu Phe Val Ala Gly Ile Gly Trp Ser
        180                 185                 190

Gly Gly Asp Thr Leu Tyr Ala Asp Ser Val Arg Gly Arg Phe Thr Asn
    195                 200                 205

Ser Arg Asp Asn Ser Lys Asn Thr Leu Tyr Leu Gln Met Asn Ser Leu
210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260

<210> SEQ ID NO 86
<211> LENGTH: 256
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Arg Ala Phe Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
            180                 185                 190

Ser Val Arg Gly Arg Phe Thr Ile Ser Arg Asp Asn Ala Lys Asn Thr
        195                 200                 205

Leu Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
225                 230                 235                 240
```

```
Asp Ser Tyr Asp Tyr Trp Gly Gln Gly Thr Leu Val Thr Val Ser Ser
                245                 250                 255
```

<210> SEQ ID NO 87
<211> LENGTH: 264
<212> TYPE: PRT
<213> ORGANISM: Artificial Sequence
<220> FEATURE:
<223> OTHER INFORMATION: Synthetic Construct

<400> SEQUENCE: 87

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160

Ala Ala Ser Gly Arg Ala Phe Ser Asp Tyr Ala Met Ala Trp Phe Arg
                165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Ile
        195                 200                 205

Ser Arg Asp Asn Ala Lys Asn Thr Leu Tyr Leu Gln Met Asn Ser Leu
    210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260
```

<210> SEQ ID NO 88
<211> LENGTH: 256
<212> TYPE: PRT
<213> ORGANISM: Artificial Sequence
<220> FEATURE:
<223> OTHER INFORMATION: Synthetic Construct

<400> SEQUENCE: 88

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30
```

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly Gly
            115                 120                 125

Gly Ser Glu Val Gln Leu Val Glu Ser Gly Gly Leu Val Gln Pro
            130                 135                 140

Gly Gly Ser Leu Arg Leu Ser Cys Ala Ala Ser Gly Arg Ala Phe Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
            180                 185                 190

Ser Val Arg Gly Arg Phe Thr Ile Ser Arg Asp Asn Ser Lys Asn Thr
            195                 200                 205

Met Tyr Leu Gln Met Asn Ser Leu Arg Ala Glu Asp Thr Ala Val Tyr
        210                 215                 220

Tyr Cys Ala Ala Arg Gln Gly Gln Tyr Ile Tyr Ser Ser Met Arg Ser
225                 230                 235                 240

Asp Ser Tyr Asp Tyr Trp Gly Gln Gly Thr Leu Val Thr Val Ser Ser
                245                 250                 255

<210> SEQ ID NO 89
<211> LENGTH: 264
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Tyr Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Glu Val Gln Leu Val Glu
            130                 135                 140

Ser Gly Gly Gly Leu Val Gln Pro Gly Gly Ser Leu Arg Leu Ser Cys
145                 150                 155                 160

Ala Ala Ser Gly Arg Ala Phe Ser Asp Tyr Ala Met Ala Trp Phe Arg
            165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Ile
            195                 200                 205

Ser Arg Asp Asn Ser Lys Asn Thr Met Tyr Leu Gln Met Asn Ser Leu
210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
            245                 250                 255

Gly Thr Leu Val Thr Val Ser Ser
            260

<210> SEQ ID NO 90
<211> LENGTH: 256
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Gly Ser Gly Gly Gly
            115                 120                 125

Gly Ser Glu Val Gln Leu Val Glu Ser Gly Gly Leu Val Gln Pro
130                 135                 140

Gly Gly Ser Leu Arg Leu Ser Cys Ala Ala Ser Gly Arg Ala Phe Ser
145                 150                 155                 160

Asp Tyr Ala Met Ala Trp Phe Arg Gln Ala Pro Gly Gln Gly Leu Glu
            165                 170                 175

Phe Val Ala Gly Ile Gly Trp Ser Gly Gly Asp Thr Leu Tyr Ala Asp
            180                 185                 190

Ser Val Arg Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
        210                 215                 220

Tyr Cys Ala Ala Arg Gln Gly Gln Tyr Ile Tyr Ser Ser Met Arg Ser
225                 230                 235                 240

```
Asp Ser Tyr Asp Tyr Trp Gly Gln Gly Thr Leu Val Thr Val Ser Ser
            245                 250                 255
```

<210> SEQ ID NO 91
<211> LENGTH: 264
<212> TYPE: PRT
<213> ORGANISM: Artificial Sequence
<220> FEATURE:
<223> OTHER INFORMATION: Synthetic Construct

<400> SEQUENCE: 91

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160

Ala Ala Ser Gly Arg Ala Phe Ser Asp Tyr Ala Met Ala Trp Phe Arg
                165                 170                 175

Gln Ala Pro Gly Gln Gly Leu Glu Phe Val Ala Gly Ile Gly Trp Ser
            180                 185                 190

Gly Gly Asp Thr Leu Tyr Ala Asp Ser Val Arg Gly Arg Phe Thr Ile
        195                 200                 205

Ser Arg Asp Asn Ser Lys Asn Thr Leu Tyr Leu Gln Met Asn Ser Leu
    210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260
```

<210> SEQ ID NO 92
<211> LENGTH: 256
<212> TYPE: PRT
<213> ORGANISM: Artificial Sequence
<220> FEATURE:
<223> OTHER INFORMATION: Synthetic Construct

<400> SEQUENCE: 92

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
```

```
            20                  25                  30
Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Ser Gly Gly Gly Ser Gly Gly Gly
            115                 120                 125

Gly Ser Glu Val Gln Leu Val Glu Ser Gly Gly Leu Val Gln Pro
            130                 135                 140

Gly Gly Ser Leu Arg Leu Ser Cys Ala Ala Ser Gly Arg Ala His Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
                180                 185                 190

Ser Val Arg Gly Arg Phe Thr Asn Ser Arg Asp Asn Ser Lys Asn Thr
            195                 200                 205

Leu Tyr Leu Gln Met Asn Ser Leu Arg Ala Glu Asp Thr Ala Val Tyr
        210                 215                 220

Tyr Cys Ala Ala Arg Gln Gly Gln Tyr Ile Tyr Ser Ser Met Arg Ser
225                 230                 235                 240

Asp Ser Tyr Asp Tyr Trp Gly Gln Gly Thr Leu Val Thr Val Ser Ser
                245                 250                 255

<210> SEQ ID NO 93
<211> LENGTH: 264
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Glu Val Gln Leu Val Glu
```

```
                130                 135                 140
Ser Gly Gly Leu Val Gln Pro Gly Gly Ser Leu Arg Leu Ser Cys
145                 150                 155                 160

Ala Ala Ser Gly Arg Ala His Ser Asp Tyr Ala Met Ala Trp Phe Arg
                165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Asn
            195                 200                 205

Ser Arg Asp Asn Ser Lys Asn Thr Leu Tyr Leu Gln Met Asn Ser Leu
    210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
            245                 250                 255

Gly Thr Leu Val Thr Val Ser Ser
            260

<210> SEQ ID NO 94
<211> LENGTH: 256
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Ala Ala Ser Gly Arg Ala His Ser
145                 150                 155                 160

Asp Tyr Ala Met Ala Trp Phe Arg Gln Ala Pro Gly Gln Gly Leu Glu
                165                 170                 175

Phe Val Ala Gly Ile Gly Trp Ser Gly Gly Asp Thr Leu Tyr Ala Asp
            180                 185                 190

Ser Val Arg Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
```

```
                225                 230                 235                 240

Asp Ser Tyr Asp Tyr Trp Gly Gln Gly Thr Leu Val Thr Val Ser Ser
            245                 250                 255
```

<210> SEQ ID NO 95
<211> LENGTH: 264
<212> TYPE: PRT
<213> ORGANISM: Artificial Sequence
<220> FEATURE:
<223> OTHER INFORMATION: Synthetic Construct

<400> SEQUENCE: 95

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160

Ala Ala Ser Gly Arg Ala His Ser Asp Tyr Ala Met Ala Trp Phe Arg
                165                 170                 175

Gln Ala Pro Gly Gln Gly Leu Glu Phe Val Ala Gly Ile Gly Trp Ser
            180                 185                 190

Gly Gly Asp Thr Leu Tyr Ala Asp Ser Val Arg Gly Arg Phe Thr Ile
        195                 200                 205

Ser Arg Asp Asn Ser Lys Asn Thr Leu Tyr Leu Gln Met Asn Ser Leu
    210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260
```

<210> SEQ ID NO 96
<211> LENGTH: 264
<212> TYPE: PRT
<213> ORGANISM: Artificial Sequence
<220> FEATURE:
<223> OTHER INFORMATION: Synthetic Construct

<400> SEQUENCE: 96

```
Glu Val Gln Leu Val Glu Ser Gly Gly Gly Leu Val Lys Pro Gly Gly
1               5                   10                  15
```

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ala
        115                 120                 125

Gly Gly Gly Gly Ala Gly Gly Gly Ser Glu Val Gln Leu Val Glu
    130                 135                 140

Ser Gly Gly Gly Leu Val Gln Pro Gly Gly Ser Leu Arg Leu Ser Cys
145                 150                 155                 160

Ala Ala Ser Gly Arg Ala His Ser Asp Tyr Ala Met Ala Trp Phe Arg
                165                 170                 175

Gln Ala Pro Gly Gln Glu Arg Glu Phe Val Ala Gly Ile Gly Trp Ser
            180                 185                 190

Gly Gly Asp Thr Leu Tyr Ala Asp Ser Val Arg Gly Arg Phe Thr Asn
        195                 200                 205

Ser Arg Asp Asn Ser Lys Asn Thr Leu Tyr Leu Gln Met Asn Ser Leu
    210                 215                 220

Arg Ala Glu Asp Thr Ala Val Tyr Tyr Cys Ala Ala Arg Gln Gly Gln
225                 230                 235                 240

Tyr Ile Tyr Ser Ser Met Arg Ser Asp Ser Tyr Asp Tyr Trp Gly Gln
                245                 250                 255

Gly Thr Leu Val Thr Val Ser Ser
            260

<210> SEQ ID NO 97
<211> LENGTH: 270
<212> TYPE: PRT
<213> ORGANISM: Artificial Sequence
<220> FEATURE:
<223> OTHER INFORMATION: Synthetic Construct

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
    50                  55                  60

Asp Ser Val Lys Gly Arg Phe Thr Ile Ser Arg Asp Asn Ala Lys Asp
65                  70                  75                  80

Ser Leu Tyr Leu Gln Met Asn Ser Leu Arg Ala Glu Asp Thr Ala Val
                85                  90                  95

Tyr Tyr Cys Ala Val Arg Thr Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser Gly Gly Gly Gly Ala Gly Gly Gly Ala Gly Gly
130                 135                 140

Gly Gly Ser Glu Val Gln Leu Val Glu Ser Gly Gly Leu Val Lys
145                 150                 155                 160

Pro Gly Gly Ser Leu Arg Leu Ser Cys Ala Ala Ser Gly Arg Pro Val
                165                 170                 175

Ser Asn Tyr Ala Ala Ala Trp Phe Arg Gln Ala Pro Gly Lys Glu Arg
            180                 185                 190

Glu Phe Val Ser Ala Ile Asn Trp Gln Lys Thr Ala Thr Tyr Ala Asp
        195                 200                 205

Ser Val Lys Gly Arg Phe Thr Ile Ser Arg Asp Asn Ala Lys Asn Ser
    210                 215                 220

Leu Tyr Leu Gln Met Asn Ser Leu Arg Ala Glu Asp Thr Ala Val Tyr
225                 230                 235                 240

Tyr Cys Ala Ala Val Phe Arg Val Val Ala Pro Lys Thr Gln Tyr Asp
                245                 250                 255

Tyr Asp Tyr Trp Gly Gln Gly Thr Leu Val Thr Val Ser Ser
            260                 265                 270

<210> SEQ ID NO 98
<211> LENGTH: 266
<212> TYPE: PRT
<213> ORGANISM: Artificial Sequence
<220> FEATURE:
<223> OTHER INFORMATION: Synthetic Construct

<400> SEQUENCE: 98

Glu Val Gln Leu Val Glu Ser Gly Gly Gly Val Val Gln Ala Gly Asp
1               5                   10                  15

Ser Leu Thr Leu Thr Cys Thr Ala Pro Val Gly Thr Ile Ser Asp Tyr
            20                  25                  30

Gly Met Gly Trp Phe Arg Gln Ala Pro Gly Lys Glu Arg Glu Phe Val
        35                  40                  45

Ala Ser Ile Ser Trp Gly Gly Met Trp Thr Asp Tyr Ala Asp Ser Val
    50                  55                  60

Lys Gly Arg Phe Thr Ile Ser Arg Asp Asn Asp Lys Asn Ala Val Tyr
65                  70                  75                  80

Leu Arg Met Asn Ser Leu Asn Ala Glu Asp Thr Ala Val Tyr Tyr Cys
                85                  90                  95

Gly Arg Gly Arg Met Tyr Arg Gly Ile Gly Asn Ser Leu Ala Gln Pro
            100                 105                 110

Lys Ser Tyr Gly Tyr Trp Gly Gln Gly Thr Gln Val Thr Val Ser Ser
        115                 120                 125

Gly Gly Gly Gly Ala Gly Gly Gly Ala Gly Gly Gly Ser Glu
    130                 135                 140

Val Gln Leu Val Glu Ser Gly Gly Gly Leu Val Lys Pro Gly Gly Ser
145                 150                 155                 160

Leu Arg Leu Ser Cys Ala Ala Ser Gly Arg Pro Val Ser Asn Tyr Ala
                165                 170                 175

Ala Ala Trp Phe Arg Gln Ala Pro Gly Lys Glu Arg Glu Phe Val Ser
            180                 185                 190

Ala Ile Asn Trp Gln Lys Thr Ala Thr Tyr Ala Asp Ser Val Lys Gly
        195                 200                 205

Arg Phe Thr Ile Ser Arg Asp Asn Ala Lys Asn Ser Leu Tyr Leu Gln
210                 215                 220

Met Asn Ser Leu Arg Ala Glu Asp Thr Ala Val Tyr Tyr Cys Ala Ala
225                 230                 235                 240

Val Phe Arg Val Val Ala Pro Lys Thr Gln Tyr Asp Tyr Asp Tyr Trp
            245                 250                 255

Gly Gln Gly Thr Leu Val Thr Val Ser Ser
            260                 265

<210> SEQ ID NO 99
<211> LENGTH: 270
<212> TYPE: PRT
<213> ORGANISM: Artificial Sequence
<220> FEATURE:
<223> OTHER INFORMATION: Synthetic Construct

<400> SEQUENCE: 99

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Ile
            20                  25                  30

Leu Ser Ala Tyr Ala Val Gly Trp Phe Arg Gln Ala Pro Gly Lys Glu
        35                  40                  45

Arg Glu Phe Val Ser Thr Ile Thr Ser Gly Gly Ser Thr Leu Ser Ala
50                  55                  60

Asp Ser Val Lys Gly Arg Phe Thr Leu Ser Arg Asp Asn Ala Lys Asp
65                  70                  75                  80

Thr Val Tyr Leu Gln Met Asn Ser Leu Lys Pro Glu Asp Thr Ala Val
                85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Gln Val
        115                 120                 125

Thr Val Ser Ser Gly Gly Gly Gly Ala Gly Gly Gly Ala Gly Gly
130                 135                 140

Gly Gly Ser Glu Val Gln Leu Val Glu Ser Gly Gly Gly Leu Val Lys
145                 150                 155                 160

Pro Gly Gly Ser Leu Arg Leu Ser Cys Ala Ala Ser Gly Arg Pro Val
            165                 170                 175

Ser Asn Tyr Ala Ala Ala Trp Phe Arg Gln Ala Pro Gly Lys Glu Arg
        180                 185                 190

Glu Phe Val Ser Ala Ile Asn Trp Gln Lys Thr Ala Thr Tyr Ala Asp
    195                 200                 205

Ser Val Lys Gly Arg Phe Thr Ile Ser Arg Asp Asn Ala Lys Asn Ser
210                 215                 220

Leu Tyr Leu Gln Met Asn Ser Leu Arg Ala Glu Asp Thr Ala Val Tyr
225                 230                 235                 240

Tyr Cys Ala Ala Val Phe Arg Val Val Ala Pro Lys Thr Gln Tyr Asp
                245                 250                 255

Tyr Asp Tyr Trp Gly Gln Gly Thr Leu Val Thr Val Ser Ser
            260                 265                 270

<210> SEQ ID NO 100
<211> LENGTH: 266
<212> TYPE: PRT
<213> ORGANISM: Artificial Sequence
<220> FEATURE:

<223> OTHER INFORMATION: Synthetic Construct

<400> SEQUENCE: 100

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ala
        115                 120                 125

Gly Gly Gly Gly Ala Gly Gly Gly Ser Glu Val Gln Leu Val Glu
    130                 135                 140

Ser Gly Gly Gly Val Val Gln Ala Gly Asp Ser Leu Thr Leu Thr Cys
145                 150                 155                 160

Thr Ala Pro Val Gly Thr Ile Ser Asp Tyr Gly Met Gly Trp Phe Arg
                165                 170                 175

Gln Ala Pro Gly Lys Glu Arg Glu Phe Val Ala Ser Ile Ser Trp Gly
            180                 185                 190

Gly Met Trp Thr Asp Tyr Ala Asp Ser Val Lys Gly Arg Phe Thr Ile
        195                 200                 205

Ser Arg Asp Asn Asp Lys Asn Ala Val Tyr Leu Arg Met Asn Ser Leu
    210                 215                 220

Asn Ala Glu Asp Thr Ala Val Tyr Tyr Cys Gly Arg Gly Arg Met Tyr
225                 230                 235                 240

Arg Gly Ile Gly Asn Ser Leu Ala Gln Pro Lys Ser Tyr Gly Tyr Trp
                245                 250                 255

Gly Gln Gly Thr Gln Val Thr Val Ser Ser
            260                 265

<210> SEQ ID NO 101
<211> LENGTH: 270
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

```
Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ala
        115                 120                 125

Gly Gly Gly Gly Ala Gly Gly Gly Ser Glu Val Gln Leu Val Glu
    130                 135                 140

Ser Gly Gly Gly Leu Val Gln Ala Gly Gly Ser Leu Arg Leu Ser Cys
145                 150                 155                 160

Ala Ala Ser Gly Arg Thr Phe Ser Gly Ile Leu Ser Ala Tyr Ala Val
                165                 170                 175

Gly Trp Phe Arg Gln Ala Pro Gly Lys Glu Arg Glu Phe Val Ser Thr
            180                 185                 190

Ile Thr Ser Gly Gly Ser Thr Leu Ser Ala Asp Ser Val Lys Gly Arg
        195                 200                 205

Phe Thr Leu Ser Arg Asp Asn Ala Lys Asp Thr Val Tyr Leu Gln Met
    210                 215                 220

Asn Ser Leu Lys Pro Glu Asp Thr Ala Val Tyr Tyr Cys Ala Val Arg
225                 230                 235                 240

Thr Trp Pro Tyr Gly Ser Asn Arg Gly Glu Val Pro Thr Glu Asn Glu
                245                 250                 255

Tyr Gly His Trp Gly Gln Gly Thr Gln Val Thr Val Ser Ser
            260                 265                 270

<210> SEQ ID NO 102
<211> LENGTH: 15
<212> TYPE: PRT
<213> ORGANISM: Artificial Sequence
<220> FEATURE:
<223> OTHER INFORMATION: Synthetic Construct

<400> SEQUENCE: 102

Gly Gly Gly Gly Ala Gly Gly Gly Ala Gly Gly Gly Gly Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic Construct

<400> SEQUENCE: 103

Gly Gly Gly Gly Ser Gly Gly Gly Ser Gly Gly Gly Gly Ser
1               5                   10                  15

<210> SEQ ID NO 104
<211> LENGTH: 5
<212> TYPE: PRT
<213> ORGANISM: Artificial Sequence
<220> FEATURE:
<223> OTHER INFORMATION: Synthetic Construct

<400> SEQUENCE: 104

Gly Gly Gly Gly Ser
1               5

<210> SEQ ID NO 105
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 105

Gly Gly Gly Gly Ser Gly Gly Gly Gly Ser
1               5                   10

<210> SEQ ID NO 106
<211> LENGTH: 15
<212> TYPE: PRT
<213> ORGANISM: Artificial Sequence
<220> FEATURE:
<223> OTHER INFORMATION: Synthetic Construct

<400> SEQUENCE: 106

Gly Gly Gly Gly Ser Gly Gly Gly Gly Ser Gly Gly Gly Gly Ser
1               5                   10                  15

<210> SEQ ID NO 107
<211> LENGTH: 20
<212> TYPE: PRT
<213> ORGANISM: Artificial Sequence
<220> FEATURE:
<223> OTHER INFORMATION: Synthetic Construct

<400> SEQUENCE: 107

Gly Gly Gly Gly Ser Gly Gly Gly Gly Ser Gly Gly Gly Gly Ser Gly
1               5                   10                  15

Gly Gly Gly Ser
            20

<210> SEQ ID NO 108
<211> LENGTH: 25
<212> TYPE: PRT
<213> ORGANISM: Artificial Sequence
<220> FEATURE:
<223> OTHER INFORMATION: Synthetic Construct

<400> SEQUENCE: 108

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 109
<211> LENGTH: 30
<212> TYPE: PRT
<213> ORGANISM: Artificial Sequence
<220> FEATURE:
<223> OTHER INFORMATION: Synthetic Construct

<400> SEQUENCE: 109

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 110
<211> LENGTH: 15
<212> TYPE: PRT
<213> ORGANISM: Artificial Sequence
<220> FEATURE:
<223> OTHER INFORMATION: Synthetic Construct
```

```
<400> SEQUENCE: 110

Glu Ala Ala Lys Glu Ala Ala Lys Glu Ala Ala Lys
1               5                   10              15

<210> SEQ ID NO 111
<211> LENGTH: 5
<212> TYPE: PRT
<213> ORGANISM: Artificial Sequence
<220> FEATURE:
<223> OTHER INFORMATION: Synthetic Construct

<400> SEQUENCE: 111

Pro Ala Pro Ala Pro
1               5

<210> SEQ ID NO 112
<211> LENGTH: 10
<212> TYPE: PRT
<213> ORGANISM: Artificial Sequence
<220> FEATURE:
<223> OTHER INFORMATION: Synthetic Construct

<400> SEQUENCE: 112

Gly Gly Gly Gly Ser Pro Ala Pro Ala Pro
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic Construct

<400> SEQUENCE: 113

Pro Ala Pro Ala Pro Gly Gly Gly Gly Ser
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic Construct

<400> SEQUENCE: 114

Gly Ser Thr Ser Gly Lys Ser Ser Glu Gly Lys Gly
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic Construct

<400> SEQUENCE: 115

Gly Gly Gly Asp Ser Gly Gly Gly Asp Ser
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic Construct

<400> SEQUENCE: 116
```

```
Gly Gly Gly Glu Ser Gly Gly Gly Glu Ser
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthetic Construct

<400> SEQUENCE: 117

Gly Gly Gly Asp Ser Gly Gly Gly Gly Ser
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Synthetic Construct

<400> SEQUENCE: 118

Gly Gly Gly Ala Ser Gly Gly Gly Gly Ser
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic Construct

<400> SEQUENCE: 119

Gly Gly Gly Glu Ser Gly Gly Gly Gly Ser
1               5                   10

<210> SEQ ID NO 120
<211> LENGTH: 6
<212> TYPE: PRT
<213> ORGANISM: Artificial Sequence
<220> FEATURE:
<223> OTHER INFORMATION: Synthetic Construct

<400> SEQUENCE: 120

Ala Ser Thr Lys Gly Pro
1               5

<210> SEQ ID NO 121
<211> LENGTH: 13
<212> TYPE: PRT
<213> ORGANISM: Artificial Sequence
<220> FEATURE:
<223> OTHER INFORMATION: Synthetic Construct

<400> SEQUENCE: 121

Ala Ser Thr Lys Gly Pro Ser Val Phe Pro Leu Ala Pro
1               5                   10

<210> SEQ ID NO 122
<211> LENGTH: 4
<212> TYPE: PRT
<213> ORGANISM: Artificial Sequence
<220> FEATURE:
<223> OTHER INFORMATION: Synthetic Construct

<400> SEQUENCE: 122
```

```
Gly Gly Gly Pro
1

<210> SEQ ID NO 123
<211> LENGTH: 8
<212> TYPE: PRT
<213> ORGANISM: Artificial Sequence
<220> FEATURE:
<223> OTHER INFORMATION: Synthetic Construct

<400> SEQUENCE: 123

Gly Gly Gly Gly Gly Gly Gly Pro
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic Construct

<400> SEQUENCE: 124

Pro Ala Pro Asn Leu Leu Gly Gly Pro
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic Construct

<400> SEQUENCE: 125

Gly Gly Gly Gly Gly Gly
1               5

<210> SEQ ID NO 126
<211> LENGTH: 12
<212> TYPE: PRT
<213> ORGANISM: Artificial Sequence
<220> FEATURE:
<223> OTHER INFORMATION: Synthetic Construct

<400> SEQUENCE: 126

Gly Gly Gly Gly Gly Gly Gly Gly Gly Gly Gly Gly
1               5                   10

<210> SEQ ID NO 127
<211> LENGTH: 8
<212> TYPE: PRT
<213> ORGANISM: Artificial Sequence
<220> FEATURE:
<223> OTHER INFORMATION: Synthetic Construct

<400> SEQUENCE: 127

Ala Pro Glu Leu Pro Gly Gly Pro
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Construct

<400> SEQUENCE: 128

Ser Glu Pro Gln Pro Gln Pro Gly
```

```
1               5
```

<210> SEQ ID NO 129
<211> LENGTH: 15
<212> TYPE: PRT
<213> ORGANISM: Artificial Sequence
<220> FEATURE:
<223> OTHER INFORMATION: Synthetic Construct

<400> SEQUENCE: 129

```
Gly Gly Gly Ser Ser Gly Gly Gly Ser Ser Gly Gly Gly Ser Ser
1               5                   10                  15
```

<210> SEQ ID NO 130
<211> LENGTH: 14
<212> TYPE: PRT
<213> ORGANISM: Artificial Sequence
<220> FEATURE:
<223> OTHER INFORMATION: Synthetic Construct

<400> SEQUENCE: 130

```
Gly Gly Gly Gly Gly Gly Gly Gly Gly Ser Gly Gly Gly Ser
1               5                   10
```

<210> SEQ ID NO 131
<211> LENGTH: 15
<212> TYPE: PRT
<213> ORGANISM: Artificial Sequence
<220> FEATURE:
<223> OTHER INFORMATION: Synthetic Construct

<400> SEQUENCE: 131

```
Gly Gly Gly Gly Ser Gly Gly Gly Gly Gly Gly Gly Gly Gly Ser
1               5                   10                  15
```

<210> SEQ ID NO 132
<211> LENGTH: 15
<212> TYPE: PRT
<213> ORGANISM: Artificial Sequence
<220> FEATURE:
<223> OTHER INFORMATION: Synthetic Construct

<400> SEQUENCE: 132

```
Gly Gly Ser Ser Ser Gly Gly Ser Ser Ser Gly Gly Ser Ser Ser
1               5                   10                  15
```

<210> SEQ ID NO 133
<211> LENGTH: 15
<212> TYPE: PRT
<213> ORGANISM: Artificial Sequence
<220> FEATURE:
<223> OTHER INFORMATION: Synthetic Construct

<400> SEQUENCE: 133

```
Gly Ser Ser Ser Ser Gly Ser Ser Ser Ser Gly Ser Ser Ser Ser
1               5                   10                  15
```

<210> SEQ ID NO 134
<211> LENGTH: 15
<212> TYPE: PRT
<213> ORGANISM: Artificial Sequence
<220> FEATURE:
<223> OTHER INFORMATION: Synthetic Construct

<400> SEQUENCE: 134

```
Gly Gly Gly Gly Ala Gly Gly Gly Gly Ser Gly Gly Gly Gly Ser
1               5                   10                  15
```

<210> SEQ ID NO 135
<211> LENGTH: 15
<212> TYPE: PRT
<213> ORGANISM: Artificial Sequence
<220> FEATURE:
<223> OTHER INFORMATION: Synthetic Construct

<400> SEQUENCE: 135

Gly Gly Gly Gly Ser Gly Gly Gly Ala Gly Gly Gly Gly Ser
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic Construct

<400> SEQUENCE: 136

Gly Gly Gly Ala Ser Gly Gly Gly Gly Ser Gly Gly Gly Gly Ser
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Synthetic Construct

<400> SEQUENCE: 137

Gly Gly Gly Gly Ser Gly Gly Gly Ala Ser Gly Gly Gly Gly Ser
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic Construct

<400> SEQUENCE: 138

Gly Gly Gly Gly Ser Ala Gly Gly Gly Ser Gly Gly Gly Gly Ser
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic Construct

<400> SEQUENCE: 139

Gly Gly Gly Gly Ser Gly Gly Gly Gly Ser Ala Gly Gly Gly Ser
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Synthetic Construct

<400> SEQUENCE: 140

Gly Gly Gly Gly Ser Ala Gly Gly Gly Ser Ala Gly Gly Gly Ser
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Synthetic Construct

<400> SEQUENCE: 141

Gly Gly Gly Gly Asp Gly Gly Gly Ser Gly Gly Gly Gly Ser
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Synthetic Construct

<400> SEQUENCE: 142

Gly Gly Gly Gly Ser Gly Gly Gly Gly Asp Gly Gly Gly Gly Ser
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Synthetic Construct

<400> SEQUENCE: 143

Gly Gly Gly Gly Asp Gly Gly Gly Gly Asp Gly Gly Gly Gly Ser
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Synthetic Construct

<400> SEQUENCE: 144

Gly Gly Gly Gly Glu Gly Gly Gly Gly Ser Gly Gly Gly Gly Ser
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Synthetic Construct

<400> SEQUENCE: 145

Gly Gly Gly Gly Ser Gly Gly Gly Gly Glu Gly Gly Gly Gly Ser
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Synthetic Construct

<400> SEQUENCE: 146

Gly Gly Gly Gly Glu Gly Gly Gly Gly Glu Gly Gly Gly Gly Ser
1               5                   10                  15

```
<210> SEQ ID NO 147
<211> LENGTH: 5
<212> TYPE: PRT
<213> ORGANISM: Artificial Sequence
<220> FEATURE:
<223> OTHER INFORMATION: Synthetic Construct

<400> SEQUENCE: 147

Glu Val Gln Leu Val
1               5

<210> SEQ ID NO 148
<211> LENGTH: 11
<212> TYPE: PRT
<213> ORGANISM: Artificial Sequence
<220> FEATURE:
<223> OTHER INFORMATION: Synthetic Construct

<400> SEQUENCE: 148

Trp Gly Gln Gly Thr Leu Val Thr Val Ser Ser
1               5                   10

<210> SEQ ID NO 149
<211> LENGTH: 115
<212> TYPE: PRT
<213> ORGANISM: Artificial Sequence
<220> FEATURE:
<223> OTHER INFORMATION: Synthetic Construct

<400> SEQUENCE: 149

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 150
<211> LENGTH: 114
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Val Glu Ser Gly Gly Gly Leu Val Gln Thr Gly Gly
1               5                   10                  15

Ser Leu Arg Leu Ser Cys Ala Ala Ser Thr Ser Gly Ser Asp Phe Ser
            20                  25                  30

Gly Lys Lys Met Ala Trp Tyr Arg Gln Ala Pro Gly Asn Gly Arg Glu
        35                  40                  45

Phe Val Ala Ile Ile Phe Ser Asn Lys Val Thr Asp Tyr Ala Asp Ser
```

```
                    50                  55                  60
Val Lys Gly Arg Phe Thr Ile Ser Arg Asp Asn Ala Lys Lys Thr Val
 65                  70                  75                  80

Tyr Leu Gln Met Ser Ser Leu Thr Pro Thr Asp Thr Ala Val Tyr Tyr
                     85                  90                  95

Cys His Asp Gln Glu Ile Ser Trp Gly Gln Gly Thr Gln Val Thr Val
                    100                 105                 110

Ser Ser

<210> SEQ ID NO 151
<211> LENGTH: 122
<212> TYPE: PRT
<213> ORGANISM: Artificial Sequence
<220> FEATURE:
<223> OTHER INFORMATION: Synthetic Construct

<400> SEQUENCE: 151

Glu Val Gln Leu Val Glu Ser Gly Gly Gly Leu Val Gln Ala Gly Gly
 1               5                  10                  15

Ser Leu Arg Leu Ser Cys Ala Ala Ser Gly Thr Ser Val Val Ile Asn
                20                  25                  30

Ser Met Gly Trp Tyr Arg Gln Ala Pro Gly Lys Gln Arg Glu Leu Val
                35                  40                  45

Ala Thr Ile Asp Leu Ser Gly Thr Thr Asn Tyr Ala Asp Ser Ala Gln
         50                  55                  60

Gly Arg Phe Thr Ile Ser Arg Asp Asn Ala Glu Asn Leu Asn Leu Val
 65                  70                  75                  80

Tyr Leu Gln Met Asn Asn Leu Asn Pro Asp Asp Thr Ala Val Tyr Tyr
                 85                  90                  95

Cys Asn Ala Leu Leu Ser Arg Ala Val Ser Gly Ser Tyr Val Tyr Trp
                100                 105                 110

Gly Gln Gly Thr Gln Val Thr Val Ser Ser
            115                 120

<210> SEQ ID NO 152
<211> LENGTH: 118
<212> TYPE: PRT
<213> ORGANISM: Artificial Sequence
<220> FEATURE:
<223> OTHER INFORMATION: Synthetic Construct

<400> SEQUENCE: 152

Glu Val Gln Leu Val Glu Ser Gly Gly Gly Leu Val Gln Pro Gly Gly
 1               5                  10                  15

Ser Leu Arg Leu Ser Cys Thr Ser Arg Ile Gly Thr Ile Ser Asn Ile
                20                  25                  30

Asp Leu Met Asn Trp Tyr Arg Gln Ala Pro Gly Lys Gln Arg Glu Phe
                35                  40                  45

Val Ala Ser Leu Gln Ser Asn Gly Ala Thr Asn Tyr Ala Asp Ser Val
         50                  55                  60

Lys Gly Arg Phe Thr Ile Ser Arg Asp Asn Ala Lys Asn Thr Leu Phe
 65                  70                  75                  80

Leu Gln Met Asn Ser Leu Asn Pro Glu Asp Thr Ala Val Tyr Phe Cys
                 85                  90                  95

His Ala Leu Leu Pro Arg Ser Pro Tyr Asn Ser Trp Gly Gln Gly Thr
                100                 105                 110

Gln Val Thr Val Ser Ser
```

115

<210> SEQ ID NO 153
<211> LENGTH: 116
<212> TYPE: PRT
<213> ORGANISM: Artificial Sequence
<220> FEATURE:
<223> OTHER INFORMATION: Synthetic Construct

<400> SEQUENCE: 153

Glu Val Gln Leu Val Glu Ser Gly Gly Gly Leu Val Gln Ala Gly Gly
1               5                   10                  15

Ser Leu Arg Leu Ser Cys Ala Ala Ser Ser Ile Ile Pro Asn Ile Tyr
            20                  25                  30

Ala Met Gly Trp Tyr Arg Gln Ala Pro Gly Lys Gln Arg Glu Leu Val
        35                  40                  45

Ala Ser Ile Glu Asn Gly Leu Pro Ala Asn Tyr Ala Asp Ser Val Lys
    50                  55                  60

Gly Arg Phe Thr Ile Ser Arg Asp Asn Ala Lys Asn Thr Val Phe Leu
65                  70                  75                  80

Gln Met His Ser Leu Lys Ser Glu Asp Thr Ala Val Tyr Tyr Cys Tyr
                85                  90                  95

Ala Phe Arg Pro Gly Val Pro Thr Thr Trp Gly Gln Gly Thr Gln Val
            100                 105                 110

Thr Val Ser Ser
        115

<210> SEQ ID NO 154
<211> LENGTH: 116
<212> TYPE: PRT
<213> ORGANISM: Artificial Sequence
<220> FEATURE:
<223> OTHER INFORMATION: Synthetic Construct

<400> SEQUENCE: 154

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ser Ala Ile Asn
            20                  25                  30

Ala Met Gly Trp Tyr Arg Gln Ala Pro Gly Lys Gln Arg Glu Phe Val
        35                  40                  45

Ala Asp Ile Thr Arg Ala Gly Val Ser Asp Tyr Ala Asp Ala Val Lys
    50                  55                  60

Gly Arg Phe Thr Ile Ser Arg Asp Asn Ala Lys Asn Thr Phe Tyr Leu
65                  70                  75                  80

Gln Met Asn Asp Leu Lys Pro Glu Asp Thr Ala Val Tyr Tyr Cys Asp
                85                  90                  95

Ala Leu Leu Ile Ala Gly Gly Val Tyr Trp Gly Gln Gly Thr Gln Val
            100                 105                 110

Thr Val Ser Ser
        115

<210> SEQ ID NO 155
<211> LENGTH: 126
<212> TYPE: PRT
<213> ORGANISM: Artificial Sequence
<220> FEATURE:
<223> OTHER INFORMATION: Synthetic Construct

<400> SEQUENCE: 155

```
Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Ile Ser Thr Thr
            20                  25                  30

Val Met Gly Trp Phe Arg Gln Ala Pro Gly Lys Glu Arg Glu Phe Val
        35                  40                  45

Ala Ala Val His Trp Gly Asp Gly Asn Thr Val Tyr Ala Asp Ser Val
    50                  55                  60

Lys Gly Arg Phe Thr Ile Ser Arg Asp Asp Ala Lys Asn Thr Val Tyr
65                  70                  75                  80

Leu Gln Leu Asn Tyr Leu Lys Pro Glu Asp Ser Val Tyr Tyr Cys
                85                  90                  95

Ala Ala Arg Pro Pro Thr Tyr Val Gly Thr Ser Arg Asn Ser Arg Ser
            100                 105                 110

Tyr Asp Tyr Trp Gly Gln Gly Thr Gln Val Thr Val Ser Ser
            115                 120                 125
```

<210> SEQ ID NO 156
<211> LENGTH: 125
<212> TYPE: PRT
<213> ORGANISM: Artificial Sequence
<220> FEATURE:
<223> OTHER INFORMATION: Synthetic Construct

<400> SEQUENCE: 156

```
Glu Val Gln Leu Val Glu Ser Gly Gly Gly Leu Val Gln Ala Gly Gly
1               5                   10                  15

Ser Leu Arg Leu Ser Cys Val Val Ser Gly Arg Ala Ile Asp Arg Asn
            20                  25                  30

Ala Met Gly Trp Phe Arg Gln Ala Pro Gly Lys Glu Arg Glu Ser Val
        35                  40                  45

Ala Ala Ile Ser Ala Ser Ser Gly Asn Thr Tyr Ser Asp Ser Val
    50                  55                  60

Thr Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Ser Arg Gly Ser Trp Tyr Leu Phe Asp Arg Arg Glu Tyr
            100                 105                 110

Asp Tyr Trp Gly Gln Gly Thr Gln Val Thr Val Ser Ser
        115                 120                 125
```

<210> SEQ ID NO 157
<211> LENGTH: 120
<212> TYPE: PRT
<213> ORGANISM: Artificial Sequence
<220> FEATURE:
<223> OTHER INFORMATION: Synthetic Construct

<400> SEQUENCE: 157

```
Glu Val Gln Leu Val Glu Ser Gly Gly Gly Leu Val Gln Ala Gly Gly
1               5                   10                  15

Ser Leu Arg Leu Thr Cys Thr Ala Ser Glu Thr Ser Phe Asp Ile Asn
            20                  25                  30

Val Met Gly Trp Tyr Arg Gln Ala Pro Gly Lys Gln Arg Glu Leu Val
        35                  40                  45

Ala Ile Ile Thr Ala Ser Gly Asn Thr Glu Tyr Ala Asp Ser Ala Lys
```

```
                    50                  55                  60
Gly Arg Phe Thr Ile Ser Arg Asp Asn Thr Lys Asn Thr Val Ala Met
 65                  70                  75                  80

Gln Met Asn Asn Leu Lys Pro Asp Asp Thr Ala Val Tyr Tyr Cys Tyr
                     85                  90                  95

Val Leu Leu Ser Gly Ala Val Ser Gly Val Tyr Ala His Trp Gly Gln
                100                 105                 110

Gly Thr Gln Val Thr Val Ser Ser
            115                 120

<210> SEQ ID NO 158
<211> LENGTH: 130
<212> TYPE: PRT
<213> ORGANISM: Artificial Sequence
<220> FEATURE:
<223> OTHER INFORMATION: Synthetic Construct

<400> SEQUENCE: 158

Glu Val Gln Leu Val Glu Ser Gly Gly Gly Leu Val Gln Ala Gly Gly
  1               5                  10                  15

Ser Leu Thr Leu Ser Cys Ala Ala Ser Gly Arg Thr Asp Ser Arg Tyr
                 20                  25                  30

Ala Met Gly Trp Phe Arg Gln Ala Pro Gly Lys Glu Arg Glu Leu Met
             35                  40                  45

Ala Ala Ile Ser Trp Ser Gly Arg Pro Thr Tyr Tyr Ala Asp Ser Val
         50                  55                  60

Lys Gly Arg Phe Thr Ile Ser Arg Asp Asn Ala Lys Asn Thr Val Ser
 65                  70                  75                  80

Leu Gln Met Asn Ser Leu Lys Pro Glu Asp Thr Ala Val Tyr Tyr Cys
                 85                  90                  95

Ala Tyr Lys Arg Leu Pro Ala Trp Tyr Thr Gly Ser Ala Tyr Tyr Ser
                100                 105                 110

Gln Glu Ser Glu Tyr Asp Tyr Trp Gly Gln Gly Thr Gln Val Thr Val
            115                 120                 125

Ser Ser
    130

<210> SEQ ID NO 159
<211> LENGTH: 118
<212> TYPE: PRT
<213> ORGANISM: Artificial Sequence
<220> FEATURE:
<223> OTHER INFORMATION: Synthetic Construct

<400> SEQUENCE: 159

Glu Val Gln Leu Val Glu Ser Gly Gly Gly Leu Val Gln Pro Gly Gly
  1               5                  10                  15

Ser Leu Arg Leu Ser Cys Thr Ser Arg Ile Gly Thr Ile Ser Asn Ile
                 20                  25                  30

Asp Leu Met Asn Trp Tyr Arg Gln Ala Pro Gly Lys Gln Arg Glu Phe
             35                  40                  45

Val Ala Ser Leu Gln Ser Thr Gly Thr Thr Asp Tyr Ala Asp Ser Val
         50                  55                  60

Lys Gly Arg Phe Thr Ile Ser Arg Asp Asn Ala Lys Asn Thr Leu Phe
 65                  70                  75                  80

Leu Gln Met Asn Ser Leu Asn Pro Glu Asp Thr Ala Val Tyr Tyr Cys
                 85                  90                  95
```

His Ala Leu Ile Pro Arg Ser Pro Tyr Asn Val Trp Gly Gln Gly Thr
            100                 105                 110

Gln Val Thr Val Ser Ser
        115

<210> SEQ ID NO 160
<211> LENGTH: 126
<212> TYPE: PRT
<213> ORGANISM: Artificial Sequence
<220> FEATURE:
<223> OTHER INFORMATION: Synthetic Construct

<400> SEQUENCE: 160

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Ile Ser Thr Thr
            20                  25                  30

Val Met Ala Trp Phe Arg Gln Ala Pro Gly Lys Glu Arg Glu Phe Val
        35                  40                  45

Ala Ala Asp His Trp Gly Asp Ala Gly Thr Val Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Tyr Leu Lys Pro Glu Asp Thr Ser Val Tyr Tyr Cys
                85                  90                  95

Ala Ala Arg Pro Pro Thr Tyr Val Gly Thr Ser Arg Asp Ser Arg Ala
            100                 105                 110

Tyr Asp Tyr Trp Gly Gln Gly Thr Gln Val Thr Val Ser Ser
        115                 120                 125

<210> SEQ ID NO 161
<211> LENGTH: 117
<212> TYPE: PRT
<213> ORGANISM: Artificial Sequence
<220> FEATURE:
<223> OTHER INFORMATION: Synthetic Construct

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Glu Ser Ile Ser Ser Asp Ser
            20                  25                  30

Pro Met Ala Trp Tyr Arg Gln Ala Pro Gly Lys Gln Arg Glu Met Val
        35                  40                  45

Ala Arg Ile Leu Pro Ile Gly Pro Pro Asp Tyr Ala Asp Ala Val Lys
    50                  55                  60

Asp Arg Phe Ser Ile Ser Arg Glu Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Leu His Leu Pro Ser Gly Leu Asn Tyr Trp Gly Gln Gly Thr Gln
            100                 105                 110

Val Thr Val Ser Ser
        115

<210> SEQ ID NO 162
<211> LENGTH: 109
<212> TYPE: PRT
<213> ORGANISM: Artificial Sequence
<220> FEATURE:
<223> OTHER INFORMATION: Synthetic Construct

<400> SEQUENCE: 162

Glu Val Gln Leu Val Glu Ser Gly Gly Asp Leu Val Gln Ala Gly Gly
1               5                   10                  15

Ser Leu Arg Leu Ser Cys Val Ala Ser Arg Ser Ile Ser Ser Ala Met
            20                  25                  30

Asn Trp Tyr Arg Gln Pro Pro Gly Lys Gln Arg Glu Leu Val Ala Leu
        35                  40                  45

Ile Thr Arg Gly Phe Asn Thr Asn Tyr Ala Asp Ser Val Lys Gly Arg
50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Gly Val Tyr Tyr Cys Asn Ser Leu
                85                  90                  95

Asn Tyr Trp Gly Gln Gly Thr Gln Val Thr Val Ser Ser
            100                 105

<210> SEQ ID NO 163
<211> LENGTH: 124
<212> TYPE: PRT
<213> ORGANISM: Artificial Sequence
<220> FEATURE:
<223> OTHER INFORMATION: Synthetic Construct

<400> SEQUENCE: 163

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Asp Ser Met Trp
            20                  25                  30

Ser Met Gly Trp Phe Arg Gln Ala Pro Gly Gln Glu Arg Glu Phe Val
        35                  40                  45

Ala Ala Ile Ser Trp Ser Val Gly Thr Tyr Tyr Glu Asp Ser Val Lys
50                  55                  60

Gly Arg Phe Thr Leu Ser Arg Asp Asp Lys Asp Thr Ala Tyr Leu
65                  70                  75                  80

Glu Met Ser Asp Leu Lys Leu Glu Asp Thr Ala Asp Tyr Tyr Cys Ala
                85                  90                  95

Ala Ser Thr Arg His Gly Thr Asn Leu Val Leu Pro Arg Asp Tyr Asp
            100                 105                 110

Tyr Trp Gly Gln Gly Thr Gln Val Thr Val Ser Ser
        115                 120

<210> SEQ ID NO 164
<211> LENGTH: 118
<212> TYPE: PRT
<213> ORGANISM: Artificial Sequence
<220> FEATURE:
<223> OTHER INFORMATION: Synthetic Construct

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Thr Ser Arg Ile Gly Thr Ile Ser Asn Ile
            20                  25                  30

Asp Leu Met Asn Trp Tyr Arg Gln Ala Pro Gly Lys Gln Arg Glu Phe
        35                  40                  45

Val Ala Ser Leu Gln Ser Thr Gly Thr Thr Asp Tyr Ala Asp Ser Val
 50                  55                  60

Lys Gly Arg Phe Thr Ile Ser Arg Asp Asn Ala Lys Asn Thr Leu Phe
 65                  70                  75                  80

Leu Gln Met Asn Ser Leu Asn Pro Glu Asp Thr Ala Val Tyr Tyr Cys
                 85                  90                  95

His Ala Leu Leu Pro Arg Ser Pro Tyr Asn Ala Trp Gly Gln Gly Thr
                100                 105                 110

Gln Val Thr Val Ser Ser
            115

<210> SEQ ID NO 165
<211> LENGTH: 116
<212> TYPE: PRT
<213> ORGANISM: Artificial Sequence
<220> FEATURE:
<223> OTHER INFORMATION: Synthetic Construct

<400> SEQUENCE: 165

Glu Val Gln Leu Val Glu Ser Gly Gly Gly Leu Val Gln Ala Gly Gly
 1               5                  10                  15

Ser Leu Arg Leu Ser Cys Ala Ala Ser Gly Ile Ile Pro Asn Ile Tyr
                 20                  25                  30

Ala Met Gly Trp Tyr Arg Gln Ala Pro Gly Lys Gln Arg Glu Leu Val
             35                  40                  45

Ala Ser Ile Glu Asn Gly Gly Ser Thr Asn Tyr Ala Asp Ser Val Lys
 50                  55                  60

Gly Arg Phe Thr Ile Ser Arg Asp Asn Ala Arg Asn Thr Val Phe Leu
 65                  70                  75                  80

Gln Met His Ser Leu Lys Ser Glu Asp Thr Ala Val Tyr Tyr Cys Tyr
                 85                  90                  95

Ala Phe Arg Pro Gly Val Pro Thr Asp Trp Gly Gln Gly Thr Gln Val
                100                 105                 110

Thr Val Ser Ser
            115

<210> SEQ ID NO 166
<211> LENGTH: 118
<212> TYPE: PRT
<213> ORGANISM: Artificial Sequence
<220> FEATURE:
<223> OTHER INFORMATION: Synthetic Construct

<400> SEQUENCE: 166

Glu Val Gln Leu Val Glu Ser Gly Gly Gly Leu Val Gln Ala Gly Gly
 1               5                  10                  15

Ser Leu Thr Leu Ser Cys Val Ala Ser Gly Arg Thr Phe Ser Asn Tyr
                 20                  25                  30

Arg Met Gly Trp Phe Arg Gln Ala Pro Gly Ala Glu Arg Glu Phe Val
             35                  40                  45

Gly Thr Ile Tyr Trp Ser Thr Gly Arg Ser Tyr Tyr Gly Asp Ser Val
 50                  55                  60

Lys Gly Arg Phe Ile Ile Ser Asp Asn Ala Lys Asn Thr Ile His
 65                  70                  75                  80

Leu Gln Met Asn Ser Leu Lys Pro Glu Asp Thr Gly Val Tyr Tyr Cys
                 85                  90                  95

Ala Ser Gly Pro Glu Asn Ser Ala Phe Asp Ser Trp Gly Gln Gly Thr
                100                 105                 110

```
Gln Val Thr Val Ser Ser
        115

<210> SEQ ID NO 167
<211> LENGTH: 124
<212> TYPE: PRT
<213> ORGANISM: Artificial Sequence
<220> FEATURE:
<223> OTHER INFORMATION: Synthetic Construct

<400> SEQUENCE: 167

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Pro Phe Ser Ser Tyr
            20                  25                  30

Thr Met Gly Trp Phe Arg Gln Ala Pro Gly Lys Glu Arg Asp Phe Val
        35                  40                  45

Ala Thr Ile Ser Trp Ser Gly Gly Ile Lys Tyr Tyr Ala Asp Ser Val
    50                  55                  60

Glu Gly Arg Phe Ser Ile Ser Arg Asp Asn Ala Lys Asn Met Val Tyr
65                  70                  75                  80

Leu Gln Met Asn Ser Leu Lys Pro Glu Asp Thr Ala Val Tyr Tyr Cys
                85                  90                  95

Ala Ala Thr Glu Leu Arg Thr Trp Ser Arg Gln Thr Phe Glu Tyr Asp
            100                 105                 110

Tyr Trp Gly Gln Gly Thr Gln Val Thr Val Ser Ser
        115                 120

<210> SEQ ID NO 168
<211> LENGTH: 126
<212> TYPE: PRT
<213> ORGANISM: Artificial Sequence
<220> FEATURE:
<223> OTHER INFORMATION: Synthetic Construct

<400> SEQUENCE: 168

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Ile Ser Thr Thr
            20                  25                  30

Val Met Ala Trp Phe Arg Gln Ala Pro Gly Lys Glu Arg Glu Phe Val
        35                  40                  45

Ala Ala Val His Trp Gly Asp Glu Ser Thr Val Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Tyr Leu Lys Pro Glu Asp Thr Ser Val Tyr Tyr Cys
                85                  90                  95

Ala Ala Arg Pro Pro Thr Tyr Val Gly Ser Ser Arg Ser Ser Arg Ala
            100                 105                 110

Tyr Asp Tyr Trp Gly Gln Gly Thr Gln Val Thr Val Ser Ser
        115                 120                 125

<210> SEQ ID NO 169
<211> LENGTH: 120
<212> TYPE: PRT
<213> ORGANISM: Artificial Sequence
<220> FEATURE:
<223> OTHER INFORMATION: Synthetic Construct
```

<400> SEQUENCE: 169

Glu Val Gln Leu Val Glu Ser Gly Gly Gly Leu Val Gln Ala Gly Gly
1               5                   10                  15

Ser Leu Arg Leu Ser Cys Val Val Ser Gly Ser Ile Leu Asp Ile Asn
            20                  25                  30

Val Met Ala Trp Tyr Arg Gln Ala Pro Gly Lys Gln Arg Glu Phe Val
        35                  40                  45

Ala Arg Ile Thr Ser Gly Gly Asp Ile Asp Tyr Ala Asp Pro Val Lys
    50                  55                  60

Gly Arg Phe Thr Ile Ser Thr Asn Gly Ala Lys Asn Thr Val Tyr Leu
65                  70                  75                  80

Gln Met Asn Ser Leu Lys Pro Glu Asp Thr Ala Ala Tyr Tyr Cys Asn
                85                  90                  95

Val Leu Leu Ser Arg Ser Ser Ala Gly Arg Tyr Thr His Trp Gly Gln
            100                 105                 110

Gly Thr Gln Val Thr Val Ser Ser
            115                 120

<210> SEQ ID NO 170
<211> LENGTH: 112
<212> TYPE: PRT
<213> ORGANISM: Artificial Sequence
<220> FEATURE:
<223> OTHER INFORMATION: Synthetic Construct

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Leu Tyr
            20                  25                  30

Asp Met Gly Trp Tyr Arg Gln Ala Pro Glu Lys Gln Arg Glu Ser Val
        35                  40                  45

Ala Ile Ile Thr Gln Ser Gly Ser Thr Asp Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Arg
                85                  90                  95

Leu Val Gly Val Thr Trp Gly Gln Gly Thr Gln Val Thr Val Ser Ser
            100                 105                 110

<210> SEQ ID NO 171
<211> LENGTH: 120
<212> TYPE: PRT
<213> ORGANISM: Artificial Sequence
<220> FEATURE:
<223> OTHER INFORMATION: Synthetic Construct

<400> SEQUENCE: 171

Glu Val Gln Leu Val Glu Ser Gly Gly Gly Leu Val Gln Ala Gly Gly
1               5                   10                  15

Ser Leu Thr Leu Ser Cys Ala Ala Ser Gly Arg Thr Phe Ser Ser Tyr
            20                  25                  30

Gly Ile Gly Trp Phe Arg Gln Ala Pro Gly Lys Glu Arg Glu Phe Val
        35                  40                  45

Ala Ala Ile Ser Arg Thr Gly Gln Thr Thr His Tyr Ala Asp Ser Ile
    50                  55                  60

```
Arg Phe Thr Ile Ser Arg Asp Asn Ala Lys Asn Thr Val Tyr Leu Gln
 65                  70                  75                  80

Met Asn Ser Leu Lys Pro Glu Asp Thr Ala Val Tyr Tyr Cys Ala Ala
             85                  90                  95

Arg Thr Gly Gly Pro Ile Tyr Gly Ser Glu Tyr His Tyr Trp Gly Gln
            100                 105                 110

Gly Thr Gln Val Thr Val Ser Ser
        115                 120

<210> SEQ ID NO 172
<211> LENGTH: 124
<212> TYPE: PRT
<213> ORGANISM: Artificial Sequence
<220> FEATURE:
<223> OTHER INFORMATION: Synthetic Construct

<400> SEQUENCE: 172

Glu Val Gln Leu Val Glu Ser Gly Gly Gly Leu Val Gln Ala Gly Asp
 1               5                  10                  15

Ser Leu Thr Leu Ser Cys Ala Ala Ser Gly Arg Pro Phe Ser Ser Leu
             20                  25                  30

Thr Met Gly Trp Phe Arg Gln Ala Pro Gly Lys Gly Arg Glu Phe Val
         35                  40                  45

Ala Thr Thr Ser Trp Ser Gly Asp Ile Lys Tyr Ala Asp Phe Val
     50                  55                  60

Lys Gly Arg Phe Thr Ile Ser Arg Asp Asn Ala Lys Asn Met Val Tyr
 65                  70                  75                  80

Leu Gln Met Asn Ser Leu Lys Pro Glu Asp Thr Ala Val Tyr Tyr Cys
             85                  90                  95

Ala Ala Thr Leu Leu Arg Thr Trp Ser Arg Gln Thr Asn Glu Tyr Glu
            100                 105                 110

Tyr Trp Gly Gln Gly Thr Gln Val Thr Val Ser Ser
        115                 120

<210> SEQ ID NO 173
<211> LENGTH: 118
<212> TYPE: PRT
<213> ORGANISM: Artificial Sequence
<220> FEATURE:
<223> OTHER INFORMATION: Synthetic Construct

<400> SEQUENCE: 173

Glu Val Gln Leu Val Glu Ser Gly Gly Gly Leu Val Gln Pro Gly Gly
 1               5                  10                  15

Ser Leu Arg Leu Ser Cys Thr Ser Arg Ile Gly Thr Ile Ser Asn Ile
             20                  25                  30

Asp Leu Met Asn Trp Tyr Arg Gln Ala Pro Gly Lys Gln Arg Glu Phe
         35                  40                  45

Val Ala Ser Leu Gln Ser Thr Gly Thr Thr Asp Tyr Ala Asp Ser Val
     50                  55                  60

Arg Gly Arg Phe Thr Ile Ser Arg Asp Asn Ala Lys Asn Thr Leu Phe
 65                  70                  75                  80

Leu Gln Met Asn Ser Leu Asn Pro Glu Asp Thr Ala Val Tyr Tyr Cys
             85                  90                  95

His Ala Leu Leu Pro Arg Ser Pro Tyr Asn Val Trp Gly Gln Gly Thr
            100                 105                 110

Gln Val Thr Val Ser Ser
```

<210> SEQ ID NO 174
<211> LENGTH: 132
<212> TYPE: PRT
<213> ORGANISM: Artificial Sequence
<220> FEATURE:
<223> OTHER INFORMATION: Synthetic Construct

<400> SEQUENCE: 174

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Arg Glu Phe Val Ser Thr Ile Thr Ser Gly Gly Ser Ala Ile Tyr Thr
    50                  55                  60

Asp Ser Val Lys Gly Arg Phe Thr Leu Ser Arg Asp Asn Ala Lys Asp
65                  70                  75                  80

Thr Val Tyr Leu Gln Met Asn Ser Leu Lys Pro Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Gln Val
        115                 120                 125

Thr Val Ser Ser
    130

<210> SEQ ID NO 175
<211> LENGTH: 120
<212> TYPE: PRT
<213> ORGANISM: Artificial Sequence
<220> FEATURE:
<223> OTHER INFORMATION: Synthetic Construct

<400> SEQUENCE: 175

Glu Val Gln Leu Val Glu Ser Gly Gly Gly Leu Val Gln Ala Gly Gly
1               5                   10                  15

Ser Leu Arg Leu Ser Cys Ala Ala Pro Glu Thr Gly Ala Thr Ile Asn
            20                  25                  30

Val Met Ala Trp Tyr Arg Gln Ala Pro Gly Lys Gln Arg Glu Leu Val
        35                  40                  45

Ala Arg Val Ala Ile Asp Asn Asn Thr Asp Tyr Ala Asp His Ala Lys
    50                  55                  60

Gly Arg Phe Thr Ile Ser Arg Asp Asn Thr Lys Asn Thr Val Tyr Leu
65                  70                  75                  80

Gln Met Asn Asn Leu Lys Pro Asp Asp Thr Ala Val Tyr Tyr Cys Asn
                85                  90                  95

Val Leu Leu Ser Arg Gln Ile Ser Gly Ser Tyr Gly His Trp Gly Gln
            100                 105                 110

Gly Thr Gln Val Thr Val Ser Ser
        115                 120

<210> SEQ ID NO 176
<211> LENGTH: 133
<212> TYPE: PRT
<213> ORGANISM: Artificial Sequence
<220> FEATURE:

<223> OTHER INFORMATION: Synthetic Construct

<400> SEQUENCE: 176

Glu Val Gln Leu Val Glu Ser Gly Gly Gly Leu Val Gln Ala Gly Gly
1               5                   10                  15

Ser Leu Thr Leu Ser Cys Ala Met Ser Gly Gly Thr Arg Pro Phe Glu
            20                  25                  30

Asp Tyr Val Met Ala Trp Phe Arg Gln Ala Thr Gly Lys Glu Arg Glu
        35                  40                  45

Phe Val Ala Thr Ile Thr Trp Met Gly Glu Thr Thr Tyr Tyr Lys Asp
    50                  55                  60

Ser Val Asn Gly Arg Phe Ala Ile Ser Arg Asp Asn Ala Glu Asn Thr
65                  70                  75                  80

Val Ala Leu Gln Met Asn Ser Leu Glu Pro Glu Asp Thr Ala Val Tyr
                85                  90                  95

Phe Cys Ala Ala His Ser Arg Ser Ser Phe Ser Thr Ser Gly Gly Arg
            100                 105                 110

Tyr Asn Pro Arg Pro Thr Glu Tyr Asp Tyr Trp Gly Gln Gly Thr Gln
        115                 120                 125

Val Thr Val Ser Ser
    130

<210> SEQ ID NO 177
<211> LENGTH: 126
<212> TYPE: PRT
<213> ORGANISM: Artificial Sequence
<220> FEATURE:
<223> OTHER INFORMATION: Synthetic Construct

<400> SEQUENCE: 177

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Ile Ser Thr Thr
            20                  25                  30

Val Met Gly Trp Phe Arg Gln Ala Pro Gly Lys Glu Arg Glu Phe Val
        35                  40                  45

Ala Ala Val His Trp Gly Asp Glu Gly Thr Val Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ala Leu Lys Pro Glu Asp Thr Ser Val Tyr Tyr Cys
                85                  90                  95

Ala Ala Lys Pro Pro Thr Tyr Val Gly Thr Ser Arg Ser Ser Arg Ala
            100                 105                 110

Tyr Val Tyr Trp Gly Gln Gly Thr Gln Val Thr Val Ser Ser
        115                 120                 125

<210> SEQ ID NO 178
<211> LENGTH: 120
<212> TYPE: PRT
<213> ORGANISM: Artificial Sequence
<220> FEATURE:
<223> OTHER INFORMATION: Synthetic Construct

<400> SEQUENCE: 178

Glu Val Gln Leu Val Glu Ser Gly Gly Gly Leu Val Gln Ala Gly Asp
1               5                   10                  15

Ser Leu Thr Leu Ser Cys Ala Ala Ser Gly Ser Gly Phe Ser Ile Asn

```
                    20                  25                  30
Val Met Ala Trp Tyr Arg Gln Ala Pro Gly Lys Gln Arg Asp Leu Val
                35                  40                  45

Ala Ser Met Thr Ile Gly Gly Arg Thr Asn Tyr Lys Asp Ser Leu Lys
         50                  55                  60

Gly Arg Phe Thr Ile Ser Arg Asp Asn Thr Lys Asn Thr Ala Tyr Leu
 65                  70                  75                  80

Gln Met Asn Ser Leu Lys Pro Glu Asp Thr Ala Val Tyr Tyr Cys Tyr
                 85                  90                  95

Ala Leu Leu Asp Arg Gly Ile Gly Gly Asn Tyr Val Tyr Trp Gly Gln
            100                 105                 110

Gly Thr Gln Val Thr Val Ser Ser
            115                 120

<210> SEQ ID NO 179
<211> LENGTH: 125
<212> TYPE: PRT
<213> ORGANISM: Artificial Sequence
<220> FEATURE:
<223> OTHER INFORMATION: Synthetic Construct

<400> SEQUENCE: 179

Glu Val Gln Leu Val Glu Ser Gly Gly Gly Leu Val Gln Ala Gly Gly
 1               5                  10                  15

Ser Leu Arg Leu Ser Cys Ala Ala Ser Gly Leu Thr Phe Ser Asp Tyr
                20                  25                  30

Tyr Met Gly Trp Phe Arg Gln Ala Pro Gly Lys Glu Arg Asp Phe Leu
                35                  40                  45

Ala Arg Ile Gly Lys Ser Gly Ile Gly Lys Ser Tyr Ala Asp Ser Val
         50                  55                  60

Arg Gly Arg Phe Thr Ile Ser Arg Asp Asn Ala Lys Asn Thr Val Tyr
 65                  70                  75                  80

Leu Gln Met Asn Asn Leu Lys Leu Glu Asp Thr Ala Val Tyr Tyr Cys
                 85                  90                  95

Ala Ala Asp Arg Asp Ile Ala Tyr Asp Ala Arg Leu Thr Ala Glu Tyr
            100                 105                 110

Asp Tyr Trp Gly Gln Gly Thr Gln Val Thr Val Ser Ser
            115                 120                 125

<210> SEQ ID NO 180
<211> LENGTH: 126
<212> TYPE: PRT
<213> ORGANISM: Artificial Sequence
<220> FEATURE:
<223> OTHER INFORMATION: Synthetic Construct

<400> SEQUENCE: 180

Glu Val Gln Leu Val Glu Ser Gly Gly Gly Leu Val Gln Ala Gly Gly
 1               5                  10                  15

Ser Leu Arg Leu Ser Cys Thr Ala Ser Gly Arg Thr Ile Ser Thr Thr
                20                  25                  30

Val Met Gly Trp Phe Arg Gln Ala Pro Gly Lys Glu Arg Glu Phe Val
                35                  40                  45

Ala Ala Val His Trp Gly Asp Glu Ser Thr Val Tyr Ala Asp Ser Val
         50                  55                  60

Lys Gly Arg Phe Thr Ile Ser Arg Asp Asn Ala Lys Asn Thr Val Tyr
 65                  70                  75                  80
```

```
Leu Gln Met Asn Tyr Leu Lys Pro Glu Asp Thr Ala Val Tyr Tyr Cys
                85                  90                  95

Ala Ala Arg Pro Pro Thr Tyr Val Gly Thr Ser Arg Ser Ser Arg Ala
            100                 105                 110

Tyr Asp Tyr Trp Gly Gln Gly Thr Gln Val Thr Val Ser Ser
        115                 120                 125

<210> SEQ ID NO 181
<211> LENGTH: 123
<212> TYPE: PRT
<213> ORGANISM: Artificial Sequence
<220> FEATURE:
<223> OTHER INFORMATION: Synthetic Construct

<400> SEQUENCE: 181

Glu Val Gln Leu Val Glu Ser Gly Gly Gly Leu Val Gln Ala Gly Gly
1               5                   10                  15

Ser Leu Arg Leu Ser Cys Ala Ala Ser Val Ala Ser Glu Thr Ile Val
            20                  25                  30

Ser Ile Asn Asp Met Ala Trp Tyr Arg Gln Ala Pro Gly Lys Gln Arg
        35                  40                  45

Glu Leu Val Ala Ser Ile Thr Ile His Asn Asn Arg Asp Tyr Ala Asp
    50                  55                  60

Ser Ala Lys Gly Arg Phe Thr Ile Ser Arg Asp Asp Thr Lys Asn Thr
65                  70                  75                  80

Val Tyr Leu Gln Met Thr His Leu Lys Pro Asp Asp Thr Ala Val Tyr
                85                  90                  95

Tyr Cys Thr Val Leu Leu Ser Arg Ala Leu Ser Gly Ser Tyr Arg Phe
            100                 105                 110

Trp Gly Gln Gly Thr Gln Val Thr Val Ser Ser
        115                 120

<210> SEQ ID NO 182
<211> LENGTH: 123
<212> TYPE: PRT
<213> ORGANISM: Artificial Sequence
<220> FEATURE:
<223> OTHER INFORMATION: Synthetic Construct

<400> SEQUENCE: 182

Glu Val Gln Leu Val Glu Ser Gly Gly Gly Leu Val Gln Ala Gly Gly
1               5                   10                  15

Ser Leu Arg Leu Ser Cys Thr Gly Ser Glu Thr Ser Gly Thr Ile Phe
            20                  25                  30

Asn Ile Asn Val Met Gly Trp Tyr Arg Gln Ala Pro Gly Lys Gln Arg
        35                  40                  45

Glu Leu Val Ala Ile Met Asp Ile Gly Gly Thr Thr Asp Tyr Ala Asp
    50                  55                  60

Ser Val Lys Gly Arg Phe Thr Ile Ser Arg Asp Asn Ala Lys Asn Thr
65                  70                  75                  80

Val Tyr Val Gln Met Asn Asn Leu Lys Ser Glu Asp Thr Ala Val Tyr
                85                  90                  95

Tyr Cys Tyr Cys Ala Leu Asp Arg Ala Val Ala Gly Tyr Thr Tyr
            100                 105                 110

Trp Gly Gln Gly Thr Gln Val Thr Val Ser Ser
        115                 120

<210> SEQ ID NO 183
```

<211> LENGTH: 124
<212> TYPE: PRT
<213> ORGANISM: Artificial Sequence
<220> FEATURE:
<223> OTHER INFORMATION: Synthetic Construct

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Glu Ala Ser Gly Ile Ser Leu Asn Asp Tyr
            20                  25                  30

Asn Met Gly Trp Phe Arg Gln Ala Pro Gly Lys Asp Arg Glu Ile Val
        35                  40                  45

Ala Ala Leu Ser Arg Arg Ser His Gly Ile Tyr Gln Ser Asp Ser Val
    50                  55                  60

Lys Tyr Arg Phe Ser Ile Ser Arg Asp Asn Thr Lys Asn Met Val Ser
65                  70                  75                  80

Leu Gln Met Asp Ser Leu Arg Pro Glu Asp Thr Ala Val Tyr Tyr Cys
                85                  90                  95

Ala Ala Asp Gly Asp Pro Tyr Phe Thr Gly Arg Asp Met Asn Pro Glu
            100                 105                 110

Tyr Trp Gly Gln Gly Thr Gln Val Thr Val Ser Ser
        115                 120

<210> SEQ ID NO 184
<211> LENGTH: 124
<212> TYPE: PRT
<213> ORGANISM: Artificial Sequence
<220> FEATURE:
<223> OTHER INFORMATION: Synthetic Construct

<400> SEQUENCE: 184

Glu Val Gln Leu Val Glu Ser Gly Gly Gly Ser Val Gln Ala Gly Gly
1               5                   10                  15

Ser Leu Arg Leu Ser Cys Ala Phe Ser Gly Gly Arg Phe Ser Asp Tyr
            20                  25                  30

Gly Met Ala Trp Phe Arg Gln Gly Pro Gly Lys Glu Arg Glu Phe Val
        35                  40                  45

Ser Arg Ile Ser Gly Asn Gly Arg Thr Gln Tyr Thr Asp Ser Val
    50                  55                  60

Ser Gly Arg Phe Ile Ile Ser Arg Asp Asn Asp Lys Asn Thr Val Tyr
65                  70                  75                  80

Leu Gln Met Asn Asp Leu Lys Val Glu Asp Thr Ala Ile Tyr Tyr Cys
                85                  90                  95

Ala Arg Gly Ser Gly Pro Ser Ser Phe Asn Glu Gly Ser Val Tyr Asp
            100                 105                 110

Tyr Trp Gly Gln Gly Thr Gln Val Thr Val Ser Ser
        115                 120

<210> SEQ ID NO 185
<211> LENGTH: 113
<212> TYPE: PRT
<213> ORGANISM: Artificial Sequence
<220> FEATURE:
<223> OTHER INFORMATION: Synthetic Construct

<400> SEQUENCE: 185

Glu Val Gln Leu Val Glu Ser Gly Gly Gly Leu Val Gln Ser Gly Gly
1               5                   10                  15

Ser Leu Thr Leu Ser Cys Val Leu Ser Gly Ser Ile Phe Ser Ser Asn
            20                  25                  30

Thr Met Gly Trp His Arg Gln Ala Pro Gly Lys Gln Arg Glu Trp Val
        35                  40                  45

Ala Ile Thr Thr Ser Gly Gly Thr Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Arg Met Asn Asn Leu Lys Pro Glu Asp Thr Gly Val Tyr Phe Cys Tyr
                85                  90                  95

Ala Ser Leu Ala Gly Ile Trp Gly Gln Gly Thr Gln Val Thr Val Ser
            100                 105                 110

Ser

<210> SEQ ID NO 186
<211> LENGTH: 120
<212> TYPE: PRT
<213> ORGANISM: Artificial Sequence
<220> FEATURE:
<223> OTHER INFORMATION: Synthetic Construct

<400> SEQUENCE: 186

Glu Val Gln Leu Val Glu Ser Gly Gly Gly Leu Val Gln Ala Gly Gly
1               5                   10                  15

Ser Leu Arg Leu Ser Cys Ala Ala Pro Glu Thr Glu Ala Thr Tyr Asn
            20                  25                  30

Val Met Gly Trp Tyr Arg Arg Ala Pro Gly Lys Gln Arg Glu Leu Val
        35                  40                  45

Ala Thr Met Thr Ile Asp Tyr Asn Thr Asn Tyr Ala Asp Ser Ala Lys
    50                  55                  60

Gly Arg Phe Thr Ile Ser Arg Asp Asn Thr Lys Asn Thr Val Tyr Leu
65                  70                  75                  80

Gln Met Asn Asn Leu Arg Pro Asp Asp Thr Ala Val Tyr Tyr Cys Arg
                85                  90                  95

Val Asp Leu Ser Arg Gln Ile Ser Gly Ser Tyr Asn Tyr Trp Gly Gln
            100                 105                 110

Gly Thr Gln Val Thr Val Ser Ser
        115                 120

<210> SEQ ID NO 187
<211> LENGTH: 125
<212> TYPE: PRT
<213> ORGANISM: Artificial Sequence
<220> FEATURE:
<223> OTHER INFORMATION: Synthetic Construct

<400> SEQUENCE: 187

Glu Val Gln Leu Val Glu Ser Gly Gly Gly Leu Val Gln Pro Gly Glu
1               5                   10                  15

Ser Leu Arg Leu Ser Cys Ala Ile Ser Gly Phe Ala Phe Thr Asp Val
            20                  25                  30

Gly Met Ser Trp Val Arg Gln Ala Pro Gly Lys Gly Leu Glu Trp Val
        35                  40                  45

Ser Ser Ile Ser Ser Gly Ser Ser Ile Thr Thr Tyr Ser Asp Ser Val
    50                  55                  60

Lys Gly Arg Phe Thr Ile Ser Arg Asp Asn Ala Arg Asn Thr Leu Phe
65                  70                  75                  80

```
Leu Gln Met Asn Ser Leu Lys Pro Glu Asp Thr Ala Val Tyr Tyr Cys
                85                  90                  95

Gly Arg Tyr Tyr Cys Thr Gly Leu Gly Cys His Pro Arg Arg Asp Ser
            100                 105                 110

Ala Leu Trp Gly Gln Gly Thr Gln Val Thr Val Ser Ser
        115                 120                 125
```

<210> SEQ ID NO 188
<211> LENGTH: 127
<212> TYPE: PRT
<213> ORGANISM: Artificial Sequence
<220> FEATURE:
<223> OTHER INFORMATION: Synthetic Construct

<400> SEQUENCE: 188

```
Glu Val Gln Leu Val Glu Ser Gly Gly Gly Leu Val Gln Pro Gly Gly
1               5                   10                  15

Ser Leu Arg Leu Ser Cys Arg Ala Ser Gly Phe Thr Tyr Ser Thr Ala
            20                  25                  30

Ala Met Gly Trp Val Arg Gln Ala Pro Gly Lys Gly Leu Glu Trp Val
        35                  40                  45

Ser Ser Ile Ser Ser Leu Gly Ser Asp Arg Lys Ser Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Phe Ile Ser Asn Arg Trp Ser Arg Asp Val His Ala Pro Ser
            100                 105                 110

Asp Phe Gly Ser Arg Gly Gln Gly Thr Gln Val Thr Val Ser Ser
        115                 120                 125
```

<210> SEQ ID NO 189
<211> LENGTH: 122
<212> TYPE: PRT
<213> ORGANISM: Artificial Sequence
<220> FEATURE:
<223> OTHER INFORMATION: Synthetic Construct

<400> SEQUENCE: 189

```
Glu Val Gln Leu Val Glu Ser Gly Gly Gly Ser Val Pro Ala Gly Gly
1               5                   10                  15

Ser Leu Arg Leu Ser Cys Ala Ala Phe Gly Phe Thr Phe Asp Asn Tyr
            20                  25                  30

Ala Ile Ala Trp Phe Arg Gln Ala Pro Gly Lys Glu Arg Glu Gly Val
        35                  40                  45

Ser Cys Leu Ser Thr Asn Asp Gly Glu Thr Tyr Tyr Ala Asp Ser Val
    50                  55                  60

Lys Gly Arg Phe Thr Ile Ser Ser Asp His Ala Lys Asn Thr Val Tyr
65                  70                  75                  80

Leu Gln Met Asp Ser Leu Arg Pro Glu Asp Thr Ala Val Tyr Tyr Cys
                85                  90                  95

Ala Ala Ala Glu Gly Ser Trp Cys His Lys Tyr Glu Tyr Asp Tyr Trp
            100                 105                 110

Gly Gln Gly Thr Gln Val Thr Val Ser Ser
        115                 120
```

<210> SEQ ID NO 190

```
<211> LENGTH: 125
<212> TYPE: PRT
<213> ORGANISM: Artificial Sequence
<220> FEATURE:
<223> OTHER INFORMATION: Synthetic Construct

<400> SEQUENCE: 190

Glu Val Gln Leu Val Glu Ser Gly Gly Gly Leu Val Gln Ala Gly Glu
1               5                   10                  15

Ser Leu Arg Leu Ser Cys Ala Ala Ser Gly Arg Thr Ser Asp Leu Tyr
            20                  25                  30

Val Val Gly Trp Phe Arg Gln Thr Pro Gly Lys Glu Arg Glu Phe Val
        35                  40                  45

Ala Gly Ile Ala Trp Thr Gly Asp Ala Ser Tyr Tyr Ala Asp Ser Val
    50                  55                  60

Glu Gly Arg Phe Thr Ile Ala Arg Asp Asn Ala Glu Asn Arg Ile Asp
65                  70                  75                  80

Leu Gln Met Thr Ser Leu Lys Pro Glu Asp Thr Ala Val Tyr Tyr Cys
                85                  90                  95

Ala Ala Asp Ser Arg Ala Arg Phe Glu Arg Gln Arg Tyr Asn Asp Met
            100                 105                 110

Asn Tyr Trp Gly Gln Gly Thr Gln Val Thr Val Ser Ser
        115                 120                 125

<210> SEQ ID NO 191
<211> LENGTH: 120
<212> TYPE: PRT
<213> ORGANISM: Artificial Sequence
<220> FEATURE:
<223> OTHER INFORMATION: Synthetic Construct

<400> SEQUENCE: 191

Glu Val Gln Leu Val Glu Ser Gly Gly Gly Leu Val Gln Ala Gly Gly
1               5                   10                  15

Ser Leu Arg Leu Ser Cys Ile Ala Ser Val Thr Ile Ala Asp Ile Asn
            20                  25                  30

Val Met Gly Trp Tyr Arg Gln Ala Pro Gly Lys Gln Arg Glu Phe Val
        35                  40                  45

Ala Ser Ile Pro Thr Thr Gly Asp Lys Asn Tyr Ala Glu Ser Ala Lys
    50                  55                  60

Gly Arg Phe Thr Ile Ser Arg Asp Asn Ser Gln Asn Thr Val Ala Met
65                  70                  75                  80

Gln Met Asn Asn Leu Lys Pro Asp Asp Thr Ala Val Tyr Tyr Cys Tyr
                85                  90                  95

Val Leu Leu Ser Arg Ala Val Ser Gly Ser Tyr Gly His Trp Gly Gln
            100                 105                 110

Gly Thr Gln Val Thr Val Ser Ser
        115                 120

<210> SEQ ID NO 192
<211> LENGTH: 123
<212> TYPE: PRT
<213> ORGANISM: Artificial Sequence
<220> FEATURE:
<223> OTHER INFORMATION: Synthetic Construct

<400> SEQUENCE: 192

Glu Val Gln Leu Val Glu Ser Gly Gly Gly Leu Val Gln Val Gly Gly
1               5                   10                  15
```

```
Ser Leu Arg Leu Ser Cys Ala Ala Ser Gly Ser Ile Val Asp Ile Lys
            20                  25                  30

Val Met Gly Trp Tyr Arg Gln Ala Pro Gly Asn Glu Arg Glu Leu Val
        35                  40                  45

Ala Leu Ile Asn Asp Ala Asp Asp Ser Glu Tyr Ser Pro Ser Met Arg
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Ala Tyr Tyr Cys Ala
                85                  90                  95

Ala Asp Arg Asp Ser Ser Trp Phe Lys Ser Pro Tyr Ile Pro Gly Ser
            100                 105                 110

Trp Gly Gln Gly Thr Gln Val Thr Val Ser Ser
            115                 120
```

<210> SEQ ID NO 193
<211> LENGTH: 120
<212> TYPE: PRT
<213> ORGANISM: Artificial Sequence
<220> FEATURE:
<223> OTHER INFORMATION: Synthetic Construct

<400> SEQUENCE: 193

```
Glu Val Gln Leu Val Glu Ser Gly Gly Gly Leu Val Gln Ala Gly Gly
1               5                   10                  15

Ser Leu Arg Leu Ser Cys Ala Ala Pro Glu Met Gly Ala Thr Ile Asn
            20                  25                  30

Val Met Ala Trp Tyr Arg Gln Ala Pro Gly Lys Gln Arg Glu Leu Val
        35                  40                  45

Ala Arg Leu Pro Leu Asp Asn Asn Ile Asp Tyr Gly Asp Phe Ala Lys
    50                  55                  60

Gly Arg Phe Thr Ile Ser Arg Asp Ile Thr Arg Asn Thr Val Tyr Leu
65                  70                  75                  80

Gln Met Asn Asn Leu Lys Pro Asp Asp Thr Ala Val Tyr Tyr Cys Asn
                85                  90                  95

Val Leu Leu Ser Arg Gln Ile Asn Gly Ala Tyr Val His Trp Gly Gln
            100                 105                 110

Gly Thr Gln Val Thr Val Ser Ser
            115                 120
```

<210> SEQ ID NO 194
<211> LENGTH: 120
<212> TYPE: PRT
<213> ORGANISM: Artificial Sequence
<220> FEATURE:
<223> OTHER INFORMATION: Synthetic Construct

<400> SEQUENCE: 194

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Asp Gly Asp Ile Asn
            20                  25                  30

Val Met Ala Trp Tyr Arg Gln Ala Pro Gly Lys Gln Arg Glu Leu Val
        35                  40                  45

Ala Ser Ile Thr Ile Gly Gly Asn Thr Asn Tyr Ala Asp Ser Val Lys
    50                  55                  60

Gly Arg Phe Thr Ile Ala Arg Asp Asn Ala Lys Asn Arg Met Ser Leu
65                  70                  75                  80
```

```
Glu Met Asn Ser Leu Lys Ser Glu Asp Thr Ala Val Tyr Tyr Cys Asn
                 85                  90                  95

Thr Leu Leu Ser Arg Val His Asp Gly Gln Tyr Val Phe Trp Gly Gln
            100                 105                 110

Gly Thr Gln Val Thr Val Ser Ser
        115                 120

<210> SEQ ID NO 195
<211> LENGTH: 125
<212> TYPE: PRT
<213> ORGANISM: Artificial Sequence
<220> FEATURE:
<223> OTHER INFORMATION: Synthetic Construct

<400> SEQUENCE: 195

Glu Val Gln Leu Val Glu Ser Gly Gly Gly Leu Val Gln Ala Gly Gly
1               5                   10                  15

Ser Leu Arg Leu Ser Cys Val Ala Ser Glu Asp Ala Phe Lys Thr Asp
            20                  25                  30

Thr Leu Gly Trp Phe Arg Gln Ala Pro Gly Glu Glu Arg Glu Phe Val
        35                  40                  45

Ala Ala Phe Val Trp Ala Gly Gly Pro Phe Tyr Ala Asp Ser Val Lys
    50                  55                  60

Gly Arg Phe Thr Ile Ser Met Asp Glu Asp Arg Asn Thr Val Tyr Leu
65                  70                  75                  80

Gln Met Asn Ser Leu Lys Pro Glu Asp Thr Gly Val Tyr Tyr Cys Ala
                85                  90                  95

Ala Ser Leu Ser Arg Leu Arg Val Gly Glu Ile Thr Pro Arg His Met
            100                 105                 110

Asn Tyr Trp Gly Gln Gly Thr Gln Val Thr Val Ser Ser
        115                 120                 125

<210> SEQ ID NO 196
<211> LENGTH: 126
<212> TYPE: PRT
<213> ORGANISM: Artificial Sequence
<220> FEATURE:
<223> OTHER INFORMATION: Synthetic Construct

<400> SEQUENCE: 196

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Lys Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Asn Ser Lys Asp Asn Ala Lys Asn Arg Met Ser
65                  70                  75                  80

Leu Gln Met Asn Ser Leu Lys Pro Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Gln Val Thr Val Ser Ser
        115                 120                 125
```

```
<210> SEQ ID NO 197
<211> LENGTH: 124
<212> TYPE: PRT
<213> ORGANISM: Artificial Sequence
<220> FEATURE:
<223> OTHER INFORMATION: Synthetic Construct

<400> SEQUENCE: 197
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ser
            20                  25                  30

Asn Met Gly Trp Phe Arg Gln Ala Pro Gly Glu Glu Arg Glu Phe Val
        35                  40                  45

Thr Ala Ile Asp Trp Ser Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gln Gly Ser Gly Leu Asp Trp Gly Tyr Pro Trp Thr Tyr Asp
            100                 105                 110

Tyr Trp Gly Gln Gly Thr Gln Val Thr Val Ser Ser
        115                 120

```
<210> SEQ ID NO 198
<211> LENGTH: 115
<212> TYPE: PRT
<213> ORGANISM: Artificial Sequence
<220> FEATURE:
<223> OTHER INFORMATION: Synthetic Construct

<400> SEQUENCE: 198
```

Glu Val Gln Leu Val Glu Ser Gly Gly Gly Leu Val Gln Pro Gly Gly
1               5                   10                  15

Ser Leu Lys Leu Ser Cys Ala Thr Ser Gly Ser Val Leu Asn Ile Asp
            20                  25                  30

Ser Met Ala Trp Tyr Arg Gln Ala Pro Gly Lys Gln Arg Glu Leu Val
        35                  40                  45

Ala Glu Met Leu Trp Gly Gly Thr Lys Asn Tyr Gly Asp Ser Val Lys
    50                  55                  60

Gly Arg Phe Thr Ile Ser Gly Asp Ala Asp Trp Gly Thr Glu Leu Gln
65                  70                  75                  80

Met Ser Ser Leu Lys Pro Glu Asp Thr Ala Val Tyr Tyr Cys Asn Ala
                85                  90                  95

Val Gly Arg Gly Phe Arg Asp Ala Trp Gly Gln Gly Thr Gln Val Thr
            100                 105                 110

Val Ser Ser
        115

```
<210> SEQ ID NO 199
<211> LENGTH: 116
<212> TYPE: PRT
<213> ORGANISM: Artificial Sequence
<220> FEATURE:
<223> OTHER INFORMATION: Synthetic Construct

<400> SEQUENCE: 199
```

Glu Val Gln Leu Val Glu Ser Gly Gly Gly Leu Val Gln Ala Gly Gly
1               5                   10                  15

-continued

Ser Leu Arg Leu Ser Cys Val Ala Ser Gly Ser Gly Phe Gly Ile Leu
            20                  25                  30

Asp Met Gly Trp Tyr Arg Gln Ala Pro Gly Ser Arg Arg Glu Leu Val
        35                  40                  45

Gly Tyr Val Thr Arg Asp Gly Thr Thr Asn Tyr Gly Asn Ser Val Lys
    50                  55                  60

Gly Arg Ser Ile Ile Ser Glu Asp Ile Thr Lys Asn Thr Val Ile Leu
65                  70                  75                  80

Gln Met Asn Ser Leu Lys Pro Glu Asp Thr Ala Val Tyr Phe Cys Thr
                85                  90                  95

Ala Gly Leu Thr Asn Gln Pro Arg Ala Trp Gly Gln Gly Thr Gln Val
            100                 105                 110

Thr Val Ser Ser
        115

<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Ser Ser Ile Asn
            20                  25                  30

Val Met Gly Trp Tyr Arg Gln Thr Pro Gly Lys Gln Arg Glu Leu Val
        35                  40                  45

Ala Ala Ile Asn Arg Gly Gly Ser Thr Asn Val Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Pro Tyr Gly Leu Asp Trp Arg Tyr Asp Tyr Trp Gly Gln Gly
            100                 105                 110

Thr Gln Val Thr Val Ser Ser
        115

<210> SEQ ID NO 201
<211> LENGTH: 129
<212> TYPE: PRT
<213> ORGANISM: Artificial Sequence
<220> FEATURE:
<223> OTHER INFORMATION: Synthetic Construct

<400> SEQUENCE: 201

Glu Val Gln Leu Val Glu Ser Gly Gly Gly Leu Glu Gln Ala Gly Gly
1               5                   10                  15

Ser Leu Arg Leu Ser Cys Thr Ala Ser Gly Gly Thr Asp Ser Ile Tyr
            20                  25                  30

Gln Met Gly Trp Phe Arg Gln Thr Pro Gly Lys Glu Arg Glu Phe Val
        35                  40                  45

Ala Ala Ile Asn Trp Asn Tyr Gly Gly Ala Tyr Tyr Pro Asp Ser Val
    50                  55                  60

Lys Gly Arg Phe Thr Ile Ser Arg Asp Lys Ala Lys Asn Ile Gly Phe

```
                65                  70                  75                  80
Leu Gln Met Asn Ser Leu Lys Pro Glu Asp Thr Ala Val Tyr Tyr Cys
                85                  90                  95

Ala Thr Ser Gln Thr Ser Val Asp Ala Phe Ser Val Pro Ile Thr Thr
            100                 105                 110

Ala Arg Arg Tyr Gln Tyr Trp Gly Gln Gly Thr Gln Val Thr Val Ser
        115                 120                 125

Ser

<210> SEQ ID NO 202
<211> LENGTH: 118
<212> TYPE: PRT
<213> ORGANISM: Artificial Sequence
<220> FEATURE:
<223> OTHER INFORMATION: Synthetic Construct

<400> SEQUENCE: 202

Glu Val Gln Leu Val Glu Ser Gly Gly Gly Leu Val Gln Ala Gly Gly
1               5                   10                  15

Ser Leu Thr Leu Ser Cys Val Ala Ser Gly Arg Thr Phe Ser Asn Tyr
            20                  25                  30

Arg Met Gly Trp Phe Arg Gln Ala Pro Gly Lys Glu Arg Glu Phe Val
        35                  40                  45

Gly Thr Ile Tyr Trp Ser Thr Gly Arg Ser Tyr Tyr Gly Asp Ser Val
    50                  55                  60

Lys Gly Arg Phe Ile Ile Ser Gly Asp Asn Ala Lys Asn Thr Ile His
65                  70                  75                  80

Leu Gln Met Asn Ser Leu Lys Pro Asp Thr Gly Val Tyr Tyr Cys
                85                  90                  95

Ala Ser Gly Pro Glu Met Ser Ala Phe Asp Ser Trp Gly Gln Gly Thr
            100                 105                 110

Gln Val Thr Val Ser Ser
        115

<210> SEQ ID NO 203
<211> LENGTH: 127
<212> TYPE: PRT
<213> ORGANISM: Artificial Sequence
<220> FEATURE:
<223> OTHER INFORMATION: Synthetic Construct

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Gly Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Thr Gly Thr Pro Leu Ser Ser Tyr Tyr Gly Ser Cys Leu Asp Tyr
            100                 105                 110

Asp Met Ala Tyr Trp Gly Gln Gly Thr Gln Val Thr Val Ser Ser
```

-continued

```
<210> SEQ ID NO 204
<211> LENGTH: 124
<212> TYPE: PRT
<213> ORGANISM: Artificial Sequence
<220> FEATURE:
<223> OTHER INFORMATION: Synthetic Construct

<400> SEQUENCE: 204

Glu Val Gln Leu Val Glu Ser Gly Gly Gly Leu Val Gln Ala Gly Gly
1               5                   10                  15

Ser Leu Arg Leu Ser Cys Ala Ala Ser Gly Val Thr Phe Ser Asn Tyr
            20                  25                  30

Gly Met Ala Trp Phe Arg Gln Ala Pro Glu Lys Glu Arg Glu Phe Val
        35                  40                  45

Ala Arg Ile Ser Ser Asn Gly Arg Thr Glu Tyr Ala Asp Gly Val
    50                  55                  60

Ser Gly Arg Phe Thr Ile Ser Arg Asp Asn Ala Lys Asn Thr Val Tyr
65                  70                  75                  80

Leu Gln Met Asn Gly Leu Lys Pro Glu Asp Thr Ala Val Tyr Tyr Cys
                85                  90                  95

Ala Arg Ala Ala Gly Pro Ser Gly Phe His Glu Gln Ser Ile Tyr Asp
            100                 105                 110

Asp Trp Gly Gln Gly Thr Gln Val Thr Val Ser Ser
        115                 120

<210> SEQ ID NO 205
<211> LENGTH: 123
<212> TYPE: PRT
<213> ORGANISM: Artificial Sequence
<220> FEATURE:
<223> OTHER INFORMATION: Synthetic Construct

<400> SEQUENCE: 205

Glu Val Gln Leu Val Glu Ser Gly Gly Gly Leu Val Gln Ala Gly Gly
1               5                   10                  15

Ser Leu Arg Leu Ser Cys Ala Val Ser Gly Arg Ser Ile Ser Thr Tyr
            20                  25                  30

Val Ala Gly Trp Phe Arg Gln Gly Pro Gly Lys Glu Arg Glu Phe Val
        35                  40                  45

Ala Leu Ile Ser Arg Gly Gly Asp Ile Gln Tyr Ser Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Ala Asp Thr Ala Val Tyr Tyr Cys
                85                  90                  95

Ser Leu Asp Ala Ser Phe Gly Ser Arg Leu Val Ser Arg Trp Asp Tyr
            100                 105                 110

Trp Gly Gln Gly Thr Gln Val Thr Val Ser Ser
        115                 120

<210> SEQ ID NO 206
<211> LENGTH: 128
<212> TYPE: PRT
<213> ORGANISM: Artificial Sequence
<220> FEATURE:
<223> OTHER INFORMATION: Synthetic Construct

<400> SEQUENCE: 206
```

Glu Val Gln Leu Val Glu Ser Gly Gly Gly Val Gln Ala Gly Asp
1               5                   10                  15

Ser Leu Thr Leu Thr Cys Thr Ala Pro Val Gly Thr Ile Ser Asp Tyr
            20                  25                  30

Gly Met Gly Trp Phe Arg Gln Ala Pro Gly Lys Glu Arg Glu Phe Val
        35                  40                  45

Ala Ser Ile Ser Trp Gly Gly Met Trp Thr Asp Tyr Ala Asp Ser Val
    50                  55                  60

Lys Gly Arg Phe Thr Ile Ser Arg Asp Asn Asp Lys Asn Ala Val Tyr
65                  70                  75                  80

Leu Arg Met Asn Ser Leu Asn Ala Glu Asp Thr Ala Val Tyr Tyr Cys
            85                  90                  95

Gly Arg Gly Arg Met Tyr Arg Gly Ile Gly Asn Ser Leu Ala Gln Pro
        100                 105                 110

Lys Ser Tyr Gly Tyr Trp Gly Gln Gly Thr Gln Val Thr Val Ser Ser
    115                 120                 125

<210> SEQ ID NO 207
<211> LENGTH: 126
<212> TYPE: PRT
<213> ORGANISM: Artificial Sequence
<220> FEATURE:
<223> OTHER INFORMATION: Synthetic Construct

<400> SEQUENCE: 207

Glu Val Gln Leu Val Glu Ser Gly Gly Gly Leu Val Gln Ala Gly Gly
1               5                   10                  15

Ser Leu Arg Leu Ser Cys Ala Gly Ser Gly Phe Thr Ser Asp Asp Tyr
            20                  25                  30

Ala Ile Ala Trp Phe Arg Gln Ala Pro Gly Lys Glu Arg Glu Gly Val
        35                  40                  45

Ser Cys Ile Gly Ser Gly Asp Gly Thr Thr Tyr Tyr Ala Asp Ser Val
    50                  55                  60

Lys Gly Arg Phe Ile Ile Ser Ser Glu Asn Ala Lys Lys Thr Val Tyr
65                  70                  75                  80

Leu Gln Met Asn Ser Leu Lys Pro Glu Asp Thr Gly Ile Tyr Tyr Cys
            85                  90                  95

Ala Ala Asp Leu Tyr Pro Pro Asp Tyr Ala Leu Asp His Thr Trp
        100                 105                 110

Tyr Asp Tyr Trp Gly Gln Gly Thr Gln Val Thr Val Ser Ser
    115                 120                 125

<210> SEQ ID NO 208
<211> LENGTH: 113
<212> TYPE: PRT
<213> ORGANISM: Artificial Sequence
<220> FEATURE:
<223> OTHER INFORMATION: Synthetic Construct

<400> SEQUENCE: 208

Glu Val Gln Leu Val Glu Ser Gly Gly Gly Val Val Gln Pro Gly Gly
1               5                   10                  15

Ser Leu Arg Leu Ser Cys Val Val Ser Gly Ser Arg Phe Ser Leu Asp
            20                  25                  30

Thr Val Gly Trp His His Gln Ala Pro Gly Lys Leu Arg Glu Leu Val
        35                  40                  45

Ala Arg Ile Arg Asp Asp Gly Asp Thr Met Tyr Val Ala Ser Val Lys

```
                    50                  55                  60
Gly Arg Phe Ile Ile Ser Arg Asp Asp Ala Lys Asn Thr Val Tyr Leu
 65                  70                  75                  80

Gln Met Asn Ser Leu Lys Pro Glu Asp Thr Gly Val Tyr Tyr Cys Tyr
                     85                  90                  95

Phe Ser Arg Asn Gly Ala Trp Gly Gln Gly Thr Gln Val Thr Val Ser
                100                 105                 110

Ser

<210> SEQ ID NO 209
<211> LENGTH: 120
<212> TYPE: PRT
<213> ORGANISM: Artificial Sequence
<220> FEATURE:
<223> OTHER INFORMATION: Synthetic Construct

<400> SEQUENCE: 209

Glu Val Gln Leu Val Glu Ser Gly Gly Gly Leu Val Gln Ala Gly Gly
 1               5                  10                  15

Ser Leu Arg Leu Ser Cys Gly Ala Ser Gly Arg Ile Ser Asp Ile Asn
                20                  25                  30

Val Met Gly Trp Tyr Arg Gln Ala Pro Gly Lys Gln Arg Glu Met Val
             35                  40                  45

Ala Asp Ile Asp Ile Arg Gly Tyr Thr Asn Tyr Ala Asp Ser Val Lys
 50                  55                  60

Gly Arg Phe Thr Val Ser Arg Asp Asn Ala Glu Thr Met Tyr Leu Glu
 65                  70                  75                  80

Met Asn Ser Leu Lys Pro Glu Asp Thr Ala Val Tyr Arg Cys Asn Ala
                 85                  90                  95

Leu Thr Ser Arg Asp Trp Gly Thr Gly Lys Tyr Val Tyr Trp Gly Gln
                100                 105                 110

Gly Thr Gln Val Thr Val Ser Ser
        115                 120

<210> SEQ ID NO 210
<211> LENGTH: 111
<212> TYPE: PRT
<213> ORGANISM: Artificial Sequence
<220> FEATURE:
<223> OTHER INFORMATION: Synthetic Construct

<400> SEQUENCE: 210

Glu Val Gln Leu Val Glu Ser Gly Gly Asp Leu Val Gln Val Gly Gly
 1               5                  10                  15

Ser Leu Arg Leu Ser Cys Ala Phe Pro Gly Ser Met Ser Ser Arg Asn
                20                  25                  30

Ser Val Asn Trp Tyr Arg Gln Pro Pro Gly Lys Gln Arg Glu Trp Val
             35                  40                  45

Ala Thr Ile Ser Val Ser Gly Phe Thr Gln Tyr Ala Asp Ser Ala Lys
 50                  55                  60

Gly Arg Phe Thr Ile Ser Arg Asp Ser Ala Lys Asn Thr Val His Leu
 65                  70                  75                  80

Gln Met Asn Ser Leu Lys Pro Glu Asp Thr Gly Val Tyr Tyr Cys Asn
                 85                  90                  95

Tyr Met Asp Tyr Trp Gly Gln Gly Thr Gln Val Thr Val Ser Ser
                100                 105                 110
```

<210> SEQ ID NO 211
<211> LENGTH: 113
<212> TYPE: PRT
<213> ORGANISM: Artificial Sequence
<220> FEATURE:
<223> OTHER INFORMATION: Synthetic Construct

<400> SEQUENCE: 211

Glu Val Gln Leu Val Glu Ser Gly Gly Gly Val Val Arg Ala Gly Gly
1               5                   10                  15

Ser Leu Lys Leu Ser Cys Thr Ala Ala Gly Thr Asp Ile Asn Ile Val
            20                  25                  30

Thr Val Gly Trp His Arg Gln Ala Pro Gly Lys His Arg Glu Leu Val
        35                  40                  45

Ala Thr Ile Val Gly Ser Gly Ser Arg Thr Asn Tyr Ala Asp Ser Val
    50                  55                  60

Lys Gly Arg Phe Thr Ile Ser Arg Asp Asn Pro Lys Asn Thr Val Tyr
65                  70                  75                  80

Leu Gln Met Asn Ser Leu Lys Pro Glu Asp Thr Ala Val Tyr Tyr Cys
                85                  90                  95

Tyr Ala Thr Ser Ile Gly Trp Gly Gln Gly Thr Gln Val Thr Val Ser
            100                 105                 110

Ser

<210> SEQ ID NO 212
<211> LENGTH: 132
<212> TYPE: PRT
<213> ORGANISM: Artificial Sequence
<220> FEATURE:
<223> OTHER INFORMATION: Synthetic Construct

<400> SEQUENCE: 212

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Ile
            20                  25                  30

Leu Ser Ala Tyr Ala Val Gly Trp Phe Arg Gln Ala Pro Gly Lys Glu
        35                  40                  45

Arg Glu Phe Val Ser Thr Ile Thr Ser Gly Gly Ser Thr Leu Ser Ala
    50                  55                  60

Asp Ser Val Lys Gly Arg Phe Thr Leu Ser Arg Asp Asn Ala Lys Asp
65                  70                  75                  80

Thr Val Tyr Leu Gln Met Asn Ser Leu Lys Pro Glu Asp Thr Ala Val
                85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Gln Val
        115                 120                 125

Thr Val Ser Ser
    130

<210> SEQ ID NO 213
<211> LENGTH: 118
<212> TYPE: PRT
<213> ORGANISM: Artificial Sequence
<220> FEATURE:
<223> OTHER INFORMATION: Synthetic Construct

<400> SEQUENCE: 213

```
Glu Val Gln Leu Val Glu Ser Gly Gly Gly Ser Val Gln Ala Gly Gly
1               5                   10                  15

Ser Leu Arg Leu Thr Cys Thr Ala Ser Gly Asn Val Ser Ile Phe
            20                  25                  30

Thr Met Ala Trp Tyr Arg Gln Ala Pro Gly Lys Gln Arg Glu Leu Val
        35                  40                  45

Ala Ser Ala Ala Lys Gly Gly Asp Thr Tyr Tyr Ala Asp Ser Ala Lys
    50                  55                  60

Gly Arg Phe Thr Ile Ser Arg Asp Asp Ala Lys Ala Ile Val Ser Leu
65                  70                  75                  80

Gln Met Asn Ser Leu Lys Pro Glu Asp Thr Ala Val Tyr Tyr Cys Lys
                85                  90                  95

Thr Asp Gly Arg Pro Trp Phe Ser Glu Asp Tyr Trp Gly Gln Gly Thr
            100                 105                 110

Gln Val Thr Val Ser Ser
            115
```

<210> SEQ ID NO 214
<211> LENGTH: 111
<212> TYPE: PRT
<213> ORGANISM: Artificial Sequence
<220> FEATURE:
<223> OTHER INFORMATION: Synthetic Construct

<400> SEQUENCE: 214

```
Glu Val Gln Leu Val Glu Ser Gly Gly Gly Leu Val Gln Val Gly Asp
1               5                   10                  15

Ser Met Arg Leu Ser Cys Ala Val Phe Gly Asn Ile Phe Thr Arg Asp
            20                  25                  30

Pro Val Met Trp Phe Arg Gln Pro Pro Gly Lys Gln Arg Glu Trp Val
        35                  40                  45

Ala Thr Ile Thr Pro Ser Gly Phe Ala Asn Tyr Ala Asp Ser Val Lys
    50                  55                  60

Gly Arg Phe Thr Ile Ser Arg Tyr Ala Ala Asn Asn Thr Val His Leu
65                  70                  75                  80

Gln Met Asn Ser Leu Lys Pro Glu Asp Thr Gly Val Tyr Phe Cys Asn
                85                  90                  95

Phe Gly Tyr Trp Gly Gln Gly Thr Gln Val Thr Val Ser Ser
            100                 105                 110
```

<210> SEQ ID NO 215
<211> LENGTH: 120
<212> TYPE: PRT
<213> ORGANISM: Artificial Sequence
<220> FEATURE:
<223> OTHER INFORMATION: Synthetic Construct

<400> SEQUENCE: 215

```
Glu Val Gln Leu Val Glu Ser Gly Gly Gly Leu Val Gln Ala Gly Gly
1               5                   10                  15

Ser Leu Arg Leu Ser Cys Ala Ala Ser Lys Gly Ala Phe Asn Ile Asn
            20                  25                  30

Val Met Ala Trp Tyr Arg Gln Ala Pro Gly Lys Gln Arg Glu Leu Val
        35                  40                  45

Ala Arg Val Ala Leu Gly Gly Thr Thr Asp Tyr Ala Asp Ser Val Lys
    50                  55                  60

Gly Arg Phe Thr Ile Ser Arg Asn Asn Ala Gln Asp Thr Val Tyr Leu
65                  70                  75                  80
```

Gln Met Asn Ser Leu Lys Pro Glu Asp Thr Ala Val Tyr Tyr Cys Asn
                85                  90                  95

Val Leu Leu Asp Arg Gly Val Arg Gly Ser Tyr Ala Tyr Trp Gly Gln
            100                 105                 110

Gly Thr Gln Val Thr Val Ser Ser
        115                 120

<210> SEQ ID NO 216
<211> LENGTH: 122
<212> TYPE: PRT
<213> ORGANISM: Artificial Sequence
<220> FEATURE:
<223> OTHER INFORMATION: Synthetic Construct

<400> SEQUENCE: 216

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Tyr Ser Ser Tyr
            20                  25                  30

Val Ile Gly Trp Phe Arg Gln Ala Pro Gly Lys Glu Arg Glu Phe Val
        35                  40                  45

Ala Ser Ile Arg Trp Ala Gly Gly Asp Ser His Tyr Gln Glu Ser Val
    50                  55                  60

Lys Gly Arg Ser Thr Ile Ser Lys Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Gly Ala Ala Pro Val Pro Gly Gln Ser Tyr Glu Trp Ser Ser Trp
            100                 105                 110

Gly Gln Gly Thr Gln Val Thr Val Ser Ser
        115                 120

<210> SEQ ID NO 217
<211> LENGTH: 121
<212> TYPE: PRT
<213> ORGANISM: Artificial Sequence
<220> FEATURE:
<223> OTHER INFORMATION: Synthetic Construct

<400> SEQUENCE: 217

Glu Val Gln Leu Val Glu Ser Gly Gly Gly Leu Val Gln Ala Gly Gly
1               5                   10                  15

Ser Leu Arg Leu Ser Cys Val Ala Ser Gly Ser Ala Phe Tyr Val Gly
            20                  25                  30

Pro Met Ala Trp Tyr Arg Gln Ala Pro Gly Lys Glu Arg Glu Ser Val
        35                  40                  45

Ala Ser Ile Thr Lys Gly Gly Ile Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Asp Val Tyr Val Cys Asn
                85                  90                  95

Ala Arg Val Lys Leu Gln Glu Asp Arg Leu Phe Arg Asp Tyr Trp Gly
            100                 105                 110

Gln Gly Thr Gln Val Thr Val Ser Ser
        115                 120

-continued

<210> SEQ ID NO 218
<211> LENGTH: 116
<212> TYPE: PRT
<213> ORGANISM: Artificial Sequence
<220> FEATURE:
<223> OTHER INFORMATION: Synthetic Construct

<400> SEQUENCE: 218

Glu Val Gln Leu Val Glu Ser Gly Gly Gly Met Val Gln Pro Gly Gly
1               5                   10                  15

Ser Leu Arg Leu Ser Cys Val Val Gly Ala Ser Gly Asn Ile Asp
            20                  25                  30

Phe Val Thr Val Gly Trp His Arg Gln Ala Pro Gly Lys His Arg Glu
        35                  40                  45

Met Val Ala Val Ile Thr Gly Asp Gly Thr Arg Asn Tyr Arg Asp Ser
    50                  55                  60

Val Lys Gly Arg Phe Ser Ile Ser Arg Asp Asn Ala Lys Asn Thr Ile
65                  70                  75                  80

Tyr Leu Gln Met Asn Ser Leu Lys Pro Glu Asp Thr Ala Val Tyr Tyr
                85                  90                  95

Cys Tyr Met Ser Asn Pro Ile Ser Ser Trp Gly Gln Gly Thr Gln Val
            100                 105                 110

Thr Val Ser Ser
        115

<210> SEQ ID NO 219
<211> LENGTH: 126
<212> TYPE: PRT
<213> ORGANISM: Artificial Sequence
<220> FEATURE:
<223> OTHER INFORMATION: Synthetic Construct

<400> SEQUENCE: 219

Glu Val Gln Leu Val Glu Ser Gly Gly Gly Leu Val Gln Ala Gly Gly
1               5                   10                  15

Ser Arg Arg Leu Ser Cys Ala Val Ser Gly Arg Thr Leu Ser Ser Phe
            20                  25                  30

Gly Met Gly Trp Phe Arg Gln Ala Pro Glu Lys Pro Arg Glu Phe Val
        35                  40                  45

Ala Ala Ile Thr Trp Gly Gln Gly Gly Thr Phe Tyr Ala Asp Ser Val
    50                  55                  60

Lys Gly Arg Phe Thr Ile Ser Arg Asp Ile Val Lys Asn Thr Val Tyr
65                  70                  75                  80

Leu Gln Met Asn Asp Leu Lys Pro Asp Asp Thr Gly Leu Tyr Phe Cys
                85                  90                  95

Val Ser Ala Pro His Phe His Glu Ala Phe Pro Ser Arg Pro Pro Ala
            100                 105                 110

Tyr Ala Tyr Trp Gly Gln Gly Thr Gln Val Thr Val Ser Ser
        115                 120                 125

<210> SEQ ID NO 220
<211> LENGTH: 122
<212> TYPE: PRT
<213> ORGANISM: Artificial Sequence
<220> FEATURE:
<223> OTHER INFORMATION: Synthetic Construct

<400> SEQUENCE: 220

Glu Val Gln Leu Val Glu Ser Gly Gly Gly Leu Val Gln Ala Gly Gly
1               5                   10                  15

```
Ser Leu Arg Leu Ser Cys Ala Ala Ser Gly Arg Thr Tyr Gly Ser Tyr
        20                  25                  30

Val Ile Gly Trp Phe Arg Gln Ala Pro Gly Lys Glu Arg Glu Phe Val
            35                  40                  45

Ala Ser Ile Arg Trp Ala Gly Gly Asp Ser His Tyr Gly Asp Pro Leu
    50                  55                  60

Lys Gly Arg Ser Thr Ile Ser Lys Asp Asn Ala Lys Asn Thr Val Tyr
65                  70                  75                  80

Leu Gln Met Asn Ser Leu Lys Pro Glu Asp Ala Ala Val Tyr Tyr Cys
                85                  90                  95

Ala Gly Ala Ala Pro Val Pro Gly Ser Ser Tyr Glu Trp Thr Asn Trp
            100                 105                 110

Gly Gln Gly Thr Gln Val Thr Val Ser Ser
            115                 120
```

<210> SEQ ID NO 221
<211> LENGTH: 120
<212> TYPE: PRT
<213> ORGANISM: Artificial Sequence
<220> FEATURE:
<223> OTHER INFORMATION: Synthetic Construct

<400> SEQUENCE: 221

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser Val Asn
            20                  25                  30

Thr Met Gly Trp Tyr Arg Gln Ala Pro Gly Lys Gln Arg Glu Leu Val
        35                  40                  45

Ala Phe Ile Thr Ser Gly Asp Asp Thr Asn Tyr Ala Asp Ser Met Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Val
                85                  90                  95

Ala Thr Leu Gly Arg Ser Ser Ser Gly Thr Tyr Thr Tyr Trp Gly Gln
            100                 105                 110

Gly Thr Gln Val Thr Val Ser Ser
        115                 120
```

<210> SEQ ID NO 222
<211> LENGTH: 127
<212> TYPE: PRT
<213> ORGANISM: Artificial Sequence
<220> FEATURE:
<223> OTHER INFORMATION: Synthetic Construct

<400> SEQUENCE: 222

```
Glu Val Gln Leu Val Glu Ser Gly Gly Gly Leu Val Gln Ala Gly Gly
1               5                   10                  15

Ser Leu Arg Leu Ser Cys Ala Ala Ser Leu Arg Thr Leu Asp Asn Tyr
            20                  25                  30

Gly Val Gly Trp Phe Arg Gln Thr Pro Gly Arg Glu Arg Glu Phe Val
        35                  40                  45

Ser Ala Val Ser Trp Asn Gly Asp Arg Thr Tyr Tyr Gln Asp Ser Val
    50                  55                  60

Lys Gly Arg Phe Thr Ile Ser Arg Glu Tyr Ala Lys Asn Thr Val Tyr
```

```
                65                  70                  75                  80
Leu Gln Met Asp Ser Leu Lys Pro Glu Asp Thr Ala Val Tyr Tyr Cys
                    85                  90                  95

Ala Val Asn Met Tyr Gly Ser Thr Phe Pro Gly Leu Ser Val Glu Ser
                100                 105                 110

His Tyr Asp Tyr Trp Gly Gln Gly Thr Gln Val Thr Val Ser Ser
                115                 120                 125

<210> SEQ ID NO 223
<211> LENGTH: 117
<212> TYPE: PRT
<213> ORGANISM: Artificial Sequence
<220> FEATURE:
<223> OTHER INFORMATION: Synthetic Construct

<400> SEQUENCE: 223

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Ala Trp Tyr Arg Gln Ala Gln Gly Lys Gln Arg Glu Leu Val
        35                  40                  45

Ala Asp Ile Thr Lys Asn Asp Ile Thr Asp Tyr Ala Asp Ser Val Lys
    50                  55                  60

Gly Arg Phe Thr Ile Ala Arg Asp Asn Ala Lys Asn Thr Val Asp Leu
65                  70                  75                  80

Gln Met Asn Ser Leu Lys Pro Glu Asp Thr Ala Val Tyr Tyr Cys Thr
                85                  90                  95

Ala Ala Leu Ser Arg His Pro Tyr Arg Ser Trp Gly Gln Gly Thr Gln
                100                 105                 110

Val Thr Val Ser Ser
            115

<210> SEQ ID NO 224
<211> LENGTH: 122
<212> TYPE: PRT
<213> ORGANISM: Artificial Sequence
<220> FEATURE:
<223> OTHER INFORMATION: Synthetic Construct

<400> SEQUENCE: 224

Glu Val Gln Leu Val Glu Ser Gly Gly Gly Leu Val Gln Ala Gly Gly
1               5                   10                  15

Ser Leu Arg Leu Ser Cys Ala Ala Ala Gly Arg Ser Leu Ser Asp Tyr
            20                  25                  30

Tyr Ile Ile Trp Phe Arg Gln Pro Pro Gly Lys Glu Tyr Glu Phe Val
        35                  40                  45

Ser Ser Ile Arg Trp Asn Thr Gly Ser Thr Tyr Tyr Gly Asp Ser Val
    50                  55                  60

Lys Gly Arg Phe Thr Ile Ser Arg Asp Asn Ala Lys Ser Thr Val Tyr
65                  70                  75                  80

Leu Gln Met Asn Ser Leu Lys Pro Glu Asp Thr Ala Leu Tyr Trp Cys
                85                  90                  95

Ala Ala Gly Leu His Leu Thr Pro Thr Ser Arg Thr Tyr Asn Tyr Arg
                100                 105                 110

Gly Gln Gly Thr Gln Val Thr Val Ser Ser
            115                 120
```

<210> SEQ ID NO 225
<211> LENGTH: 120
<212> TYPE: PRT
<213> ORGANISM: Artificial Sequence
<220> FEATURE:
<223> OTHER INFORMATION: Synthetic Construct

<400> SEQUENCE: 225

```
Glu Val Gln Leu Val Glu Ser Gly Gly Gly Leu Val Gln Ala Gly Gly
1               5                  10                  15

Ser Leu Arg Leu Ser Cys Ala Ala Pro Glu Thr Ile Phe Thr Ile Asn
            20                  25                  30

Ser Met Gly Trp Tyr Arg Gln Ala Pro Gly Lys Gln Arg Glu Leu Val
        35                  40                  45

Ala Phe Ile Asn Leu Asp Gly Asn Thr Asn Tyr Ala Asp Ser Ala Lys
    50                  55                  60

Gly Arg Phe Thr Ile Ser Arg Asp Asn Ala Glu Asn Thr Val Tyr Leu
65                  70                  75                  80

Gln Met Asp Asn Leu Lys Pro Asp Asp Thr Ala Val Tyr Tyr Cys Asn
                85                  90                  95

Val Leu Leu Ser Arg Ala Ile Ser Gly Ser Tyr Val His Trp Gly Gln
            100                 105                 110

Gly Thr Gln Val Thr Val Ser Ser
        115                 120
```

<210> SEQ ID NO 226
<211> LENGTH: 132
<212> TYPE: PRT
<213> ORGANISM: Artificial Sequence
<220> FEATURE:
<223> OTHER INFORMATION: Synthetic Construct

<400> SEQUENCE: 226

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Gln Gly
        35                  40                  45

Leu Glu Ala Val Ala Thr Ile Thr Ser Gly Gly Ser Ala Ile Tyr Thr
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser
    130
```

<210> SEQ ID NO 227
<211> LENGTH: 120
<212> TYPE: PRT
<213> ORGANISM: Artificial Sequence
<220> FEATURE:
<223> OTHER INFORMATION: Synthetic Construct

<400> SEQUENCE: 227

Glu Val Gln Leu Val Glu Ser Gly Gly Gly Leu Val Gln Pro Gly Gly
1               5                   10                  15

Ser Leu Arg Leu Ser Cys Ala Ala Ser Glu Met Gly Ala Thr Ile Asn
            20                  25                  30

Val Met Ala Trp Phe Arg Gln Ala Pro Gly Gln Gly Leu Glu Ala Val
        35                  40                  45

Ala Arg Leu Pro Leu Asp Asn Asn Ile Asp Tyr Gly Asp Phe Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Val Leu Leu Ser Arg Gln Ile Asn Gly Ala Tyr Val His Trp Gly Gln
            100                 105                 110

Gly Thr Leu Val Thr Val Ser Ser
        115                 120

<210> SEQ ID NO 228
<211> LENGTH: 126
<212> TYPE: PRT
<213> ORGANISM: Artificial Sequence
<220> FEATURE:
<223> OTHER INFORMATION: Synthetic Construct

<400> SEQUENCE: 228

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Gly Leu Glu Ala Val
        35                  40                  45

Ala Gly Ile Gly Trp Ser Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 229
<211> LENGTH: 132
<212> TYPE: PRT
<213> ORGANISM: Artificial Sequence
<220> FEATURE:
<223> OTHER INFORMATION: Synthetic Construct

<400> SEQUENCE: 229

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Gln Gly
        35                  40                  45

```
Arg Glu Phe Val Ala Thr Ile Thr Ser Gly Gly Ser Ala Ile Tyr Thr
 50                  55                  60

Asp Ser Val Lys Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                 85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser
        130

<210> SEQ ID NO 230
<211> LENGTH: 120
<212> TYPE: PRT
<213> ORGANISM: Artificial Sequence
<220> FEATURE:
<223> OTHER INFORMATION: Synthetic Construct

<400> SEQUENCE: 230

Glu Val Gln Leu Val Glu Ser Gly Gly Gly Leu Val Gln Pro Gly Gly
 1               5                  10                  15

Ser Leu Arg Leu Ser Cys Ala Ala Pro Glu Met Gly Ala Thr Ile Asn
                 20                  25                  30

Val Met Ala Trp Tyr Arg Gln Ala Pro Gly Gln Gln Arg Glu Leu Val
             35                  40                  45

Ala Arg Leu Pro Leu Asp Asn Asn Ile Asp Tyr Gly Asp Phe Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Asn
                 85                  90                  95

Val Leu Leu Ser Arg Gln Ile Asn Gly Ala Tyr Val His Trp Gly Gln
            100                 105                 110

Gly Thr Leu Val Thr Val Ser Ser
        115                 120

<210> SEQ ID NO 231
<211> LENGTH: 126
<212> TYPE: PRT
<213> ORGANISM: Artificial Sequence
<220> FEATURE:
<223> OTHER INFORMATION: Synthetic Construct

<400> SEQUENCE: 231

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Ala Phe Ser Asp Tyr
                 20                  25                  30

Ala Met Ala Trp Phe Arg Gln Ala Pro Gly Gln Glu Arg Glu Phe Val
             35                  40                  45

Ala Gly Ile Gly Trp Ser Gly Asp Thr Leu Tyr Ala Asp Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 232
<211> LENGTH: 132
<212> TYPE: PRT
<213> ORGANISM: Artificial Sequence
<220> FEATURE:
<223> OTHER INFORMATION: Synthetic Construct

<400> SEQUENCE: 232

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Arg Glu Phe Val Ser Thr Ile Thr Ser Gly Gly Ser Ala Ile Tyr Thr
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser
    130

<210> SEQ ID NO 233
<211> LENGTH: 132
<212> TYPE: PRT
<213> ORGANISM: Artificial Sequence
<220> FEATURE:
<223> OTHER INFORMATION: Synthetic Construct

<400> SEQUENCE: 233

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser
```

<210> SEQ ID NO 234
<211> LENGTH: 120
<212> TYPE: PRT
<213> ORGANISM: Artificial Sequence
<220> FEATURE:
<223> OTHER INFORMATION: Synthetic Construct

<400> SEQUENCE: 234

Glu Val Gln Leu Val Glu Ser Gly Gly Gly Leu Val Lys Pro Gly Gly
1               5                   10                  15

Ser Leu Arg Leu Ser Cys Ala Ala Ser Glu Met Gly Ala Thr Ile Asn
            20                  25                  30

Val Met Ala Trp Tyr Arg Gln Ala Pro Gly Lys Gln Arg Glu Leu Val
        35                  40                  45

Ser Arg Leu Pro Leu Asp Asn Asn Ile Asp Tyr Gly Asp Phe Ala Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Asn
                85                  90                  95

Val Leu Leu Ser Arg Gln Ile Asn Gly Ala Tyr Val His Trp Gly Gln
            100                 105                 110

Gly Thr Leu Val Thr Val Ser Ser
            115                 120

<210> SEQ ID NO 235
<211> LENGTH: 120
<212> TYPE: PRT
<213> ORGANISM: Artificial Sequence
<220> FEATURE:
<223> OTHER INFORMATION: Synthetic Construct

<400> SEQUENCE: 235

Glu Val Gln Leu Val Glu Ser Gly Gly Gly Leu Val Lys Pro Gly Gly
1               5                   10                  15

Ser Leu Arg Leu Ser Cys Ala Ala Ser Glu Met Gly Ala Thr Ile Asn
            20                  25                  30

Val Met Ala Trp Tyr Arg Gln Ala Pro Gly Lys Gly Leu Glu Leu Val
        35                  40                  45

Ser Arg Leu Pro Leu Asp Asn Asn Ile Asp Tyr Gly Asp Phe Ala Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Asn
                85                  90                  95

Val Leu Leu Ser Arg Gln Ile Asn Gly Ala Tyr Val His Trp Gly Gln
            100                 105                 110

Gly Thr Leu Val Thr Val Ser Ser
            115                 120

<210> SEQ ID NO 236
<211> LENGTH: 126
<212> TYPE: PRT
<213> ORGANISM: Artificial Sequence
<220> FEATURE:
<223> OTHER INFORMATION: Synthetic Construct

<400> SEQUENCE: 236

Glu Val Gln Leu Val Glu Ser Gly Gly Gly Leu Val Gln Pro Gly Arg
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Lys Glu Arg Glu Phe Val
        35                  40                  45

Ser Gly Ile Gly Trp Ser Gly Gly Asp Thr Leu Tyr Ala Asp Ser Val
    50                  55                  60

Arg Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Leu Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 237
<211> LENGTH: 126
<212> TYPE: PRT
<213> ORGANISM: Artificial Sequence
<220> FEATURE:
<223> OTHER INFORMATION: Synthetic Construct

<400> SEQUENCE: 237

Glu Val Gln Leu Val Glu Ser Gly Gly Gly Leu Val Gln Pro Gly Arg
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Lys Gly Leu Glu Phe Val
        35                  40                  45

Ser Gly Ile Gly Trp Ser Gly Gly Asp Thr Leu Tyr Ala Asp Ser Val
    50                  55                  60

Arg Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Leu Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 238
<211> LENGTH: 128
<212> TYPE: PRT
<213> ORGANISM: Artificial Sequence
<220> FEATURE:
<223> OTHER INFORMATION: Synthetic Construct

<400> SEQUENCE: 238

Glu Val Gln Leu Val Glu Ser Gly Gly Gly Leu Val Gln Pro Gly Gly
1               5                   10                  15

Ser Leu Arg Leu Ser Cys Ala Ala Ser Val Gly Thr Ile Ser Asp Tyr
            20                  25                  30

Gly Met Gly Trp Phe Arg Gln Ala Pro Gly Gln Gly Leu Glu Ala Val
        35                  40                  45

Ala Ser Ile Ser Trp Gly Gly Met Trp Thr Asp Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Arg Gly Arg Met Tyr Arg Gly Ile Gly Asn Ser Leu Ala Gln Pro
            100                 105                 110

Lys Ser Tyr Gly Tyr Trp Gly Gln Gly Thr Leu Val Thr Val Ser Ser
            115                 120                 125
```

<210> SEQ ID NO 239
<211> LENGTH: 132
<212> TYPE: PRT
<213> ORGANISM: Artificial Sequence
<220> FEATURE:
<223> OTHER INFORMATION: Synthetic Construct

<400> SEQUENCE: 239

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Gly Ile
             20                  25                  30

Leu Ser Ala Tyr Ala Val Gly Trp Phe Arg Gln Ala Pro Gly Gln Gly
         35                  40                  45

Leu Glu Ala Val Ala Thr Ile Thr Ser Gly Gly Ser Thr Leu Ser Ala
     50                  55                  60

Asp Ser Val Lys Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                 85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Leu Val
            115                 120                 125

Thr Val Ser Ser
            130
```

<210> SEQ ID NO 240
<211> LENGTH: 128
<212> TYPE: PRT
<213> ORGANISM: Artificial Sequence
<220> FEATURE:
<223> OTHER INFORMATION: Synthetic Construct

<400> SEQUENCE: 240

```
Glu Val Gln Leu Val Glu Ser Gly Gly Gly Leu Val Gln Pro Gly Gly
 1               5                  10                  15

Ser Leu Arg Leu Ser Cys Ala Ala Ser Val Gly Thr Ile Ser Asp Tyr
             20                  25                  30

Gly Met Gly Trp Phe Arg Gln Ala Pro Gly Gln Glu Arg Glu Phe Val
         35                  40                  45

Ala Ser Ile Ser Trp Gly Gly Met Trp Thr Asp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Gly Arg Gly Arg Met Tyr Arg Gly Ile Gly Asn Ser Leu Ala Gln Pro
            100                 105                 110

Lys Ser Tyr Gly Tyr Trp Gly Gln Gly Thr Leu Val Thr Val Ser Ser
        115                 120                 125

<210> SEQ ID NO 241
<211> LENGTH: 132
<212> TYPE: PRT
<213> ORGANISM: Artificial Sequence
<220> FEATURE:
<223> OTHER INFORMATION: Synthetic Construct

<400> SEQUENCE: 241

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Ala Tyr Ala Val Gly Trp Phe Arg Gln Ala Pro Gly Gln Glu
        35                  40                  45

Arg Glu Phe Val Ala Thr Ile Thr Ser Gly Gly Ser Thr Leu Ser Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Leu Val
        115                 120                 125

Thr Val Ser Ser
    130

<210> SEQ ID NO 242
<211> LENGTH: 128
<212> TYPE: PRT
<213> ORGANISM: Artificial Sequence
<220> FEATURE:
<223> OTHER INFORMATION: Synthetic Construct

<400> SEQUENCE: 242

Glu Val Gln Leu Val Glu Ser Gly Gly Gly Leu Val Lys Pro Gly Gly
1               5                   10                  15

Ser Leu Arg Leu Ser Cys Ala Ala Ser Val Gly Thr Ile Ser Asp Tyr
            20                  25                  30

Gly Met Gly Trp Phe Arg Gln Ala Pro Gly Lys Glu Arg Glu Phe Val
        35                  40                  45

Ser Ser Ile Ser Trp Gly Gly Met Trp Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Gly Arg Met Tyr Arg Gly Ile Gly Asn Ser Leu Ala Gln Pro
            100                 105                 110

Lys Ser Tyr Gly Tyr Trp Gly Gln Gly Thr Leu Val Thr Val Ser Ser
        115                 120                 125

<210> SEQ ID NO 243

```
<211> LENGTH: 128
<212> TYPE: PRT
<213> ORGANISM: Artificial Sequence
<220> FEATURE:
<223> OTHER INFORMATION: Synthetic Construct

<400> SEQUENCE: 243

Glu Val Gln Leu Val Glu Ser Gly Gly Gly Leu Val Lys Pro Gly Gly
1               5                   10                  15

Ser Leu Arg Leu Ser Cys Ala Ala Ser Val Gly Thr Ile Ser Asp Tyr
            20                  25                  30

Gly Met Gly Trp Phe Arg Gln Ala Pro Gly Lys Gly Leu Glu Phe Val
        35                  40                  45

Ser Ser Ile Ser Trp Gly Gly Met Trp Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Gly Arg Met Tyr Arg Gly Ile Gly Asn Ser Leu Ala Gln Pro
            100                 105                 110

Lys Ser Tyr Gly Tyr Trp Gly Gln Gly Thr Leu Val Thr Val Ser Ser
        115                 120                 125

<210> SEQ ID NO 244
<211> LENGTH: 132
<212> TYPE: PRT
<213> ORGANISM: Artificial Sequence
<220> FEATURE:
<223> OTHER INFORMATION: Synthetic Construct

<400> SEQUENCE: 244

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Ala Tyr Ala Val Gly Trp Phe Arg Gln Ala Pro Gly Lys Glu
        35                  40                  45

Arg Glu Phe Val Ser Thr Ile Thr Ser Gly Gly Ser Thr Leu Ser Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Leu Val
        115                 120                 125

Thr Val Ser Ser
        130

<210> SEQ ID NO 245
<211> LENGTH: 132
<212> TYPE: PRT
<213> ORGANISM: Artificial Sequence
<220> FEATURE:
<223> OTHER INFORMATION: Synthetic Construct

<400> SEQUENCE: 245
```

```
Glu Val Gln Leu Leu Glu Ser Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Ala Tyr Ala Val Gly Trp Phe Arg Gln Ala Pro Gly Lys Gly
            35                  40                  45

Leu Glu Phe Val Ser Thr Ile Thr Ser Gly Gly Ser Thr Leu Ser Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Leu Val
            115                 120                 125

Thr Val Ser Ser
    130

<210> SEQ ID NO 246
<211> LENGTH: 132
<212> TYPE: PRT
<213> ORGANISM: Artificial Sequence
<220> FEATURE:
<223> OTHER INFORMATION: Synthetic Construct

<400> SEQUENCE: 246

Gln Val Gln Leu Val Gln Ser Gly Ala Glu Val Lys Lys Pro Gly Ala
1               5                   10                  15

Ser Val Lys Val Ser Cys Lys Ala Ser Gly Arg Ala Phe Ser Asp Tyr
            20                  25                  30

Ala Met Ala Trp Val Arg Gln Ala Pro Gly Gln Gly Leu Glu Trp Met
            35                  40                  45

Gly Gly Ile Gly Trp Ser Gly Gly Asp Thr Leu Tyr Ala Asp Ser Val
    50                  55                  60

Arg Gly Tyr Thr Glu Asn Phe Lys Asp Arg Val Thr Met Thr Arg Asp
65                  70                  75                  80

Thr Ser Thr Ser Thr Val Tyr Met Glu Leu Ser Ser Leu Arg Ser Glu
                85                  90                  95

Asp Thr Ala Val Tyr Tyr Cys Ala Arg Gln Gly Gln Tyr Ile Tyr Ser
            100                 105                 110

Ser Met Arg Ser Asp Ser Tyr Asp Tyr Trp Gly Gln Gly Thr Leu Val
            115                 120                 125

Thr Val Ser Ser
    130

<210> SEQ ID NO 247
<211> LENGTH: 132
<212> TYPE: PRT
<213> ORGANISM: Artificial Sequence
<220> FEATURE:
<223> OTHER INFORMATION: Synthetic Construct

<400> SEQUENCE: 247

Gln Val Gln Leu Val Gln Ser Gly Ala Glu Val Lys Lys Pro Gly Ala
1               5                   10                  15

Ser Val Lys Val Ser Cys Lys Ala Ser Gly Arg Ala Phe Ser Asp Tyr
            20                  25                  30
```

```
Ala Met Ala Trp Phe Arg Gln Ala Pro Gly Gln Glu Arg Glu Phe Met
        35                  40                  45

Gly Gly Ile Gly Trp Ser Gly Gly Asp Thr Leu Tyr Ala Asp Ser Val
    50                  55                  60

Arg Gly Tyr Thr Glu Asn Phe Lys Asp Arg Val Thr Met Thr Arg Asp
65                  70                  75                  80

Thr Ser Thr Ser Thr Val Tyr Met Glu Leu Ser Ser Leu Arg Ser Glu
                85                  90                  95

Asp Thr Ala Val Tyr Tyr Cys Ala Arg Gln Gly Gln Tyr Ile Tyr Ser
            100                 105                 110

Ser Met Arg Ser Asp Ser Tyr Asp Tyr Trp Gly Gln Gly Thr Leu Val
        115                 120                 125

Thr Val Ser Ser
    130

<210> SEQ ID NO 248
<211> LENGTH: 132
<212> TYPE: PRT
<213> ORGANISM: Artificial Sequence
<220> FEATURE:
<223> OTHER INFORMATION: Synthetic Construct

<400> SEQUENCE: 248

Gln Val Gln Leu Val Gln Ser Gly Ala Glu Val Lys Lys Pro Gly Ala
1               5                   10                  15

Ser Val Lys Val Ser Cys Lys Ala Ser Gly Arg Ala Phe Ser Asp Tyr
            20                  25                  30

Ala Met Ala Trp Phe Arg Gln Ala Pro Gly Gln Gly Leu Glu Phe Met
        35                  40                  45

Gly Gly Ile Gly Trp Ser Gly Gly Asp Thr Leu Tyr Ala Asp Ser Val
    50                  55                  60

Arg Gly Tyr Thr Glu Asn Phe Lys Asp Arg Val Thr Met Thr Arg Asp
65                  70                  75                  80

Thr Ser Thr Ser Thr Val Tyr Met Glu Leu Ser Ser Leu Arg Ser Glu
                85                  90                  95

Asp Thr Ala Val Tyr Tyr Cys Ala Arg Gln Gly Gln Tyr Ile Tyr Ser
            100                 105                 110

Ser Met Arg Ser Asp Ser Tyr Asp Tyr Trp Gly Gln Gly Thr Leu Val
        115                 120                 125

Thr Val Ser Ser
    130

<210> SEQ ID NO 249
<211> LENGTH: 137
<212> TYPE: PRT
<213> ORGANISM: Artificial Sequence
<220> FEATURE:
<223> OTHER INFORMATION: Synthetic Construct

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Val Gly Thr Ile Ser Asp Tyr
            20                  25                  30

Gly Met Gly Trp Val Arg Gln Ala Pro Gly Gln Gly Leu Glu Trp Met
        35                  40                  45

Gly Ser Ile Ser Trp Gly Gly Met Trp Thr Asp Tyr Ala Asp Ser Val
```

```
                50                  55                  60
Lys Gly Tyr Thr Glu Asn Phe Lys Asp Arg Val Thr Met Thr Arg Asp
 65                  70                  75                  80

Thr Ser Thr Ser Thr Val Tyr Met Glu Leu Ser Ser Leu Arg Ser Glu
                 85                  90                  95

Asp Thr Ala Val Tyr Tyr Cys Ala Arg Gly Arg Gly Arg Met Tyr Arg
            100                 105                 110

Gly Ile Gly Asn Ser Leu Ala Gln Pro Lys Ser Tyr Gly Tyr Trp Gly
        115                 120                 125

Gln Gly Thr Leu Val Thr Val Ser Ser
    130                 135

<210> SEQ ID NO 250
<211> LENGTH: 137
<212> TYPE: PRT
<213> ORGANISM: Artificial Sequence
<220> FEATURE:
<223> OTHER INFORMATION: Synthetic Construct

<400> SEQUENCE: 250

Gln Val Gln Leu Val Gln Ser Gly Ala Glu Val Lys Lys Pro Gly Ala
 1               5                  10                  15

Ser Val Lys Val Ser Cys Lys Ala Ser Val Gly Thr Ile Ser Asp Tyr
                20                  25                  30

Gly Met Gly Trp Phe Arg Gln Ala Pro Gly Gln Arg Glu Phe Met
             35                  40                  45

Gly Ser Ile Ser Trp Gly Gly Met Trp Thr Asp Tyr Ala Asp Ser Val
         50                  55                  60

Lys Gly Tyr Thr Glu Asn Phe Lys Asp Arg Val Thr Met Thr Arg Asp
 65                  70                  75                  80

Thr Ser Thr Ser Thr Val Tyr Met Glu Leu Ser Ser Leu Arg Ser Glu
                 85                  90                  95

Asp Thr Ala Val Tyr Tyr Cys Ala Arg Gly Arg Gly Arg Met Tyr Arg
            100                 105                 110

Gly Ile Gly Asn Ser Leu Ala Gln Pro Lys Ser Tyr Gly Tyr Trp Gly
        115                 120                 125

Gln Gly Thr Leu Val Thr Val Ser Ser
    130                 135

<210> SEQ ID NO 251
<211> LENGTH: 137
<212> TYPE: PRT
<213> ORGANISM: Artificial Sequence
<220> FEATURE:
<223> OTHER INFORMATION: Synthetic Construct

<400> SEQUENCE: 251

Gln Val Gln Leu Val Gln Ser Gly Ala Glu Val Lys Lys Pro Gly Ala
 1               5                  10                  15

Ser Val Lys Val Ser Cys Lys Ala Ser Val Gly Thr Ile Ser Asp Tyr
                20                  25                  30

Gly Met Gly Trp Phe Arg Gln Ala Pro Gly Gln Gly Leu Glu Phe Met
             35                  40                  45

Gly Ser Ile Ser Trp Gly Gly Met Trp Thr Asp Tyr Ala Asp Ser Val
         50                  55                  60

Lys Gly Tyr Thr Glu Asn Phe Lys Asp Arg Val Thr Met Thr Arg Asp
 65                  70                  75                  80
```

-continued

Thr Ser Thr Ser Thr Val Tyr Met Glu Leu Ser Ser Leu Arg Ser Glu
                85                  90                  95

Asp Thr Ala Val Tyr Tyr Cys Ala Arg Gly Arg Gly Arg Met Tyr Arg
            100                 105                 110

Gly Ile Gly Asn Ser Leu Ala Gln Pro Lys Ser Tyr Gly Tyr Trp Gly
        115                 120                 125

Gln Gly Thr Leu Val Thr Val Ser Ser
    130                 135

<210> SEQ ID NO 252
<211> LENGTH: 141
<212> TYPE: PRT
<213> ORGANISM: Artificial Sequence
<220> FEATURE:
<223> OTHER INFORMATION: Synthetic Construct

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Arg Thr Phe Ser Gly Ile
            20                  25                  30

Leu Ser Ala Tyr Ala Val Gly Trp Val Arg Gln Ala Pro Gly Gln Gly
        35                  40                  45

Leu Glu Trp Met Gly Thr Ile Thr Ser Gly Gly Ser Thr Leu Ser Ala
    50                  55                  60

Asp Ser Val Lys Gly Tyr Thr Glu Asn Phe Lys Asp Arg Val Thr Met
65                  70                  75                  80

Thr Arg Asp Thr Ser Thr Ser Thr Val Tyr Met Glu Leu Ser Ser Leu
                85                  90                  95

Arg Ser Glu Asp Thr Ala Val Tyr Tyr Cys Ala Arg Ala Val Arg Thr
            100                 105                 110

Trp Pro Tyr Gly Ser Asn Arg Gly Glu Val Pro Thr Glu Asn Glu Tyr
        115                 120                 125

Gly His Trp Gly Gln Gly Thr Leu Val Thr Val Ser Ser
    130                 135                 140

<210> SEQ ID NO 253
<211> LENGTH: 141
<212> TYPE: PRT
<213> ORGANISM: Artificial Sequence
<220> FEATURE:
<223> OTHER INFORMATION: Synthetic Construct

<400> SEQUENCE: 253

Gln Val Gln Leu Val Gln Ser Gly Ala Glu Val Lys Lys Pro Gly Ala
1               5                   10                  15

Ser Val Lys Val Ser Cys Lys Ala Ser Gly Arg Thr Phe Ser Gly Ile
            20                  25                  30

Leu Ser Ala Tyr Ala Val Gly Trp Phe Arg Gln Ala Pro Gly Gln Glu
        35                  40                  45

Arg Glu Phe Met Gly Thr Ile Thr Ser Gly Gly Ser Thr Leu Ser Ala
    50                  55                  60

Asp Ser Val Lys Gly Tyr Thr Glu Asn Phe Lys Asp Arg Val Thr Met
65                  70                  75                  80

Thr Arg Asp Thr Ser Thr Ser Thr Val Tyr Met Glu Leu Ser Ser Leu
                85                  90                  95

Arg Ser Glu Asp Thr Ala Val Tyr Tyr Cys Ala Arg Ala Val Arg Thr
            100                 105                 110

```
Trp Pro Tyr Gly Ser Asn Arg Gly Glu Val Pro Thr Glu Asn Glu Tyr
        115                 120                 125

Gly His Trp Gly Gln Gly Thr Leu Val Thr Val Ser Ser
        130                 135                 140

<210> SEQ ID NO 254
<211> LENGTH: 141
<212> TYPE: PRT
<213> ORGANISM: Artificial Sequence
<220> FEATURE:
<223> OTHER INFORMATION: Synthetic Construct

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Arg Thr Phe Ser Gly Ile
            20                  25                  30

Leu Ser Ala Tyr Ala Val Gly Trp Phe Arg Gln Ala Pro Gly Gln Gly
        35                  40                  45

Leu Glu Phe Met Gly Thr Ile Thr Ser Gly Gly Ser Thr Leu Ser Ala
    50                  55                  60

Asp Ser Val Lys Gly Tyr Thr Glu Asn Phe Lys Asp Arg Val Thr Met
65                  70                  75                  80

Thr Arg Asp Thr Ser Thr Ser Thr Val Tyr Met Glu Leu Ser Ser Leu
                85                  90                  95

Arg Ser Glu Asp Thr Ala Val Tyr Tyr Cys Ala Arg Ala Val Arg Thr
            100                 105                 110

Trp Pro Tyr Gly Ser Asn Arg Gly Glu Val Pro Thr Glu Asn Glu Tyr
        115                 120                 125

Gly His Trp Gly Gln Gly Thr Leu Val Thr Val Ser Ser
        130                 135                 140

<210> SEQ ID NO 255
<211> LENGTH: 126
<212> TYPE: PRT
<213> ORGANISM: Artificial Sequence
<220> FEATURE:
<223> OTHER INFORMATION: Synthetic Construct

<400> SEQUENCE: 255

Glu Val Gln Leu Val Glu Ser Gly Gly Gly Val Val Arg Pro Gly Gly
1               5                   10                  15

Ser Leu Arg Leu Ser Phe Ala Ala Ser Gly Arg Ala Phe Ser Asp Tyr
            20                  25                  30

Ala Met Ala Trp Phe Arg Gln Ala Pro Gly Lys Glu Arg Glu Phe Val
        35                  40                  45

Ser Gly Ile Gly Trp Ser Gly Gly Asp Thr Leu Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125
```

<210> SEQ ID NO 256
<211> LENGTH: 126
<212> TYPE: PRT
<213> ORGANISM: Artificial Sequence
<220> FEATURE:
<223> OTHER INFORMATION: Synthetic Construct

<400> SEQUENCE: 256

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Lys Glu Arg Glu Phe Val
        35                  40                  45

Ser Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125
```

<210> SEQ ID NO 257
<211> LENGTH: 126
<212> TYPE: PRT
<213> ORGANISM: Artificial Sequence
<220> FEATURE:
<223> OTHER INFORMATION: Synthetic Construct

<400> SEQUENCE: 257

```
Glu Val Gln Leu Val Glu Ser Gly Gly Val Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Lys Glu Arg Glu Phe Val
        35                  40                  45

Ser Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125
```

<210> SEQ ID NO 258
<211> LENGTH: 128
<212> TYPE: PRT
<213> ORGANISM: Artificial Sequence
<220> FEATURE:
<223> OTHER INFORMATION: Synthetic Construct

<400> SEQUENCE: 258

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Val Gly Thr Ile Ser Asp Tyr
            20                  25                  30

Gly Met Gly Trp Phe Arg Gln Ala Pro Gly Lys Glu Arg Glu Phe Val
        35                  40                  45

Ser Ser Ile Ser Trp Gly Gly Met Trp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Gly Arg Met Tyr Arg Gly Ile Gly Asn Ser Leu Ala Gln Pro
            100                 105                 110

Lys Ser Tyr Gly Tyr Trp Gly Gln Gly Thr Gln Val Thr Val Ser Ser
            115                 120                 125

<210> SEQ ID NO 259
<211> LENGTH: 128
<212> TYPE: PRT
<213> ORGANISM: Artificial Sequence
<220> FEATURE:
<223> OTHER INFORMATION: Synthetic Construct

<400> SEQUENCE: 259

Glu Val Gln Leu Val Glu Ser Gly Gly Gly Leu Val Gln Pro Gly Gly
1               5                   10                  15

Ser Leu Arg Leu Ser Cys Ala Ala Ser Val Gly Thr Ile Ser Asp Tyr
            20                  25                  30

Gly Met Gly Trp Phe His Gln Ala Pro Gly Lys Glu Arg Glu Phe Val
        35                  40                  45

Ser Ser Ile Ser Trp Gly Gly Met Trp Thr Asp Tyr Ala Asp Ser Val
    50                  55                  60

Lys Gly Arg Phe Ile Ile Ser Arg Asp Asn Ser Arg Asn Thr Leu Tyr
65                  70                  75                  80

Leu Gln Thr Asn Ser Leu Arg Ala Glu Asp Thr Ala Val Tyr Tyr Cys
                85                  90                  95

Gly Arg Gly Arg Met Tyr Arg Gly Ile Gly Asn Ser Leu Ala Gln Pro
            100                 105                 110

Lys Ser Tyr Gly Tyr Trp Gly Gln Gly Thr Leu Val Thr Val Ser Ser
            115                 120                 125

<210> SEQ ID NO 260
<211> LENGTH: 128
<212> TYPE: PRT
<213> ORGANISM: Artificial Sequence
<220> FEATURE:
<223> OTHER INFORMATION: Synthetic Construct

<400> SEQUENCE: 260

Glu Val Gln Leu Val Glu Ser Gly Gly Gly Val Val Gln Pro Gly Arg
1               5                   10                  15

Ser Leu Arg Leu Ser Cys Ala Ala Ser Val Gly Thr Ile Ser Asp Tyr
            20                  25                  30

Gly Met Gly Trp Phe Arg Gln Ala Pro Gly Lys Glu Arg Glu Phe Val
        35                  40                  45

Ala Ser Ile Ser Trp Gly Gly Met Trp Thr Asp Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                85                  90                  95

Gly Arg Gly Arg Met Tyr Arg Gly Ile Gly Asn Ser Leu Ala Gln Pro
            100                 105                 110

Lys Ser Tyr Gly Tyr Trp Gly Gln Gly Thr Gln Val Thr Val Ser Ser
            115                 120                 125

<210> SEQ ID NO 261
<211> LENGTH: 132
<212> TYPE: PRT
<213> ORGANISM: Artificial Sequence
<220> FEATURE:
<223> OTHER INFORMATION: Synthetic Construct

<400> SEQUENCE: 261

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Thr Phe Ser Gly Ile
            20                  25                  30

Leu Ser Ala Tyr Ala Val Gly Trp Phe Arg Gln Ala Pro Gly Lys Glu
        35                  40                  45

Arg Glu Phe Val Ser Thr Ile Thr Ser Gly Gly Ser Thr Leu Ser Ala
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Gln Val
            115                 120                 125

Thr Val Ser Ser
            130

<210> SEQ ID NO 262
<211> LENGTH: 132
<212> TYPE: PRT
<213> ORGANISM: Artificial Sequence
<220> FEATURE:
<223> OTHER INFORMATION: Synthetic Construct

<400> SEQUENCE: 262

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Ala Tyr Ala Val Gly Trp Phe Arg Gln Ala Pro Gly Lys Glu
        35                  40                  45

Arg Glu Phe Val Ser Thr Ile Thr Ser Gly Gly Ser Thr Leu Ser Ala
    50                  55                  60

Asp Ser Val Lys Gly Arg Phe Thr Ile Ser Arg Asp Asn Ser Lys Asn
65                  70                  75                  80

Thr Leu Tyr Val Gln Met Ser Ser Leu Arg Ala Glu Asp Thr Ala Val
                85                  90                  95

Tyr Tyr Cys Ala Val Arg Thr Trp Pro Tyr Gly Ser Asn Arg Gly Glu
            100                 105                 110
```

```
Val Pro Thr Glu Asn Glu Tyr Gly His Trp Gly Gln Gly Thr Gln Val
            115                 120                 125

Thr Val Ser Ser
    130

<210> SEQ ID NO 263
<211> LENGTH: 132
<212> TYPE: PRT
<213> ORGANISM: Artificial Sequence
<220> FEATURE:
<223> OTHER INFORMATION: Synthetic Construct

<400> SEQUENCE: 263

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Ala Tyr Ala Val Gly Trp Phe Arg Gln Ala Pro Gly Lys Glu
        35                  40                  45

Arg Glu Phe Val Ser Thr Ile Thr Ser Gly Gly Ser Thr Leu Ser Ala
    50                  55                  60

Asp Ser Val Lys Gly Arg Phe Thr Ile Ser Arg Asp Asn Ser Lys Asn
65                  70                  75                  80

Ser Leu Tyr Leu Gln Met Asn Ser Leu Arg Thr Glu Asp Thr Ala Leu
                85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Gln Val
            115                 120                 125

Thr Val Ser Ser
    130

<210> SEQ ID NO 264
<211> LENGTH: 10
<212> TYPE: PRT
<213> ORGANISM: Artificial Sequence
<220> FEATURE:
<223> OTHER INFORMATION: Synthetic Construct

<400> SEQUENCE: 264

Val Gly Thr Ile Ser Asp Tyr Gly Met Gly
1               5                   10

<210> SEQ ID NO 265
<211> LENGTH: 14
<212> TYPE: PRT
<213> ORGANISM: Artificial Sequence
<220> FEATURE:
<223> OTHER INFORMATION: Synthetic Construct

<400> SEQUENCE: 265

Gly Arg Thr Phe Ser Gly Ile Leu Ser Ala Tyr Ala Val Gly
1               5                   10

<210> SEQ ID NO 266
<211> LENGTH: 17
<212> TYPE: PRT
<213> ORGANISM: Artificial Sequence
<220> FEATURE:
<223> OTHER INFORMATION: Synthetic Construct

<400> SEQUENCE: 266
```

```
Ser Ile Ser Trp Gly Gly Met Trp Thr Asp Tyr Ala Asp Ser Val Lys
1               5                   10                  15

Gly
```

<210> SEQ ID NO 267
<211> LENGTH: 16
<212> TYPE: PRT
<213> ORGANISM: Artificial Sequence
<220> FEATURE:
<223> OTHER INFORMATION: Synthetic Construct

<400> SEQUENCE: 267

```
Thr Ile Thr Ser Gly Gly Ser Thr Leu Ser Ala Asp Ser Val Lys Gly
1               5                   10                  15
```

<210> SEQ ID NO 268
<211> LENGTH: 21
<212> TYPE: PRT
<213> ORGANISM: Artificial Sequence
<220> FEATURE:
<223> OTHER INFORMATION: Synthetic Construct

<400> SEQUENCE: 268

```
Gly Arg Gly Arg Met Tyr Arg Gly Ile Gly Asn Ser Leu Ala Gln Pro
1               5                   10                  15

Lys Ser Tyr Gly Tyr
            20
```

<210> SEQ ID NO 269
<211> LENGTH: 22
<212> TYPE: PRT
<213> ORGANISM: Artificial Sequence
<220> FEATURE:
<223> OTHER INFORMATION: Synthetic Construct

<400> SEQUENCE: 269

```
Ala Val Arg Thr Trp Pro Tyr Gly Ser Asn Arg Gly Glu Val Pro Thr
1               5                   10                  15

Glu Asn Glu Tyr Gly His
            20
```

<210> SEQ ID NO 270
<211> LENGTH: 132
<212> TYPE: PRT
<213> ORGANISM: Artificial Sequence
<220> FEATURE:
<223> OTHER INFORMATION: Synthetic Construct

<400> SEQUENCE: 270

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Ile
                20                  25                  30

Leu Ser Pro Tyr Ala Val Gly Trp Phe Arg Gln Ala Pro Gly Lys Gly
            35                  40                  45

Leu Glu Phe Val Ser Thr Ile Thr Ser Gly Gly Ser Ala Ile Tyr Thr
        50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
```

```
                100             105                 110
Val Pro Gln Glu Asn Glu Tyr Gly Tyr Trp Gly Gln Gly Thr Leu Val
            115                 120                 125

Thr Val Ser Ser
    130

<210> SEQ ID NO 271
<211> LENGTH: 132
<212> TYPE: PRT
<213> ORGANISM: Artificial Sequence
<220> FEATURE:
<223> OTHER INFORMATION: Synthetic Construct

<400> SEQUENCE: 271

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
    50                  55                  60

Asp Ser Val Lys Gly Arg Phe Thr Leu Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
            115                 120                 125

Thr Val Ser Ser
    130

<210> SEQ ID NO 272
<211> LENGTH: 132
<212> TYPE: PRT
<213> ORGANISM: Artificial Sequence
<220> FEATURE:
<223> OTHER INFORMATION: Synthetic Construct

<400> SEQUENCE: 272

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Lys Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
            115                 120                 125
```

Thr Val Ser Ser
    130

<210> SEQ ID NO 273
<211> LENGTH: 132
<212> TYPE: PRT
<213> ORGANISM: Artificial Sequence
<220> FEATURE:
<223> OTHER INFORMATION: Synthetic Construct

<400> SEQUENCE: 273

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Pro Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser
    130

<210> SEQ ID NO 274
<211> LENGTH: 126
<212> TYPE: PRT
<213> ORGANISM: Artificial Sequence
<220> FEATURE:
<223> OTHER INFORMATION: Synthetic Construct

<400> SEQUENCE: 274

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 275
<211> LENGTH: 126
<212> TYPE: PRT
<213> ORGANISM: Artificial Sequence
<220> FEATURE:
<223> OTHER INFORMATION: Synthetic Construct

<400> SEQUENCE: 275

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Lys Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 276
<211> LENGTH: 126
<212> TYPE: PRT
<213> ORGANISM: Artificial Sequence
<220> FEATURE:
<223> OTHER INFORMATION: Synthetic Construct

<400> SEQUENCE: 276

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 277
<211> LENGTH: 126
<212> TYPE: PRT
<213> ORGANISM: Artificial Sequence
<220> FEATURE:
<223> OTHER INFORMATION: Synthetic Construct

<400> SEQUENCE: 277

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

```
Ala Met Ala Trp Phe Arg Gln Ala Pro Gly Gln Glu Arg Glu Phe Val
            35                  40                  45

Ala Gly Ile Gly Trp Ser Gly Gly Asp Thr Leu Tyr Ala Asp Ser Val
 50                      55                  60

Arg Gly Arg Phe Thr Ile Ser Arg Asp Asn Ser Lys Asn Arg Leu Tyr
 65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
            115                 120                 125
```

<210> SEQ ID NO 278
<211> LENGTH: 126
<212> TYPE: PRT
<213> ORGANISM: Artificial Sequence
<220> FEATURE:
<223> OTHER INFORMATION: Synthetic Construct

<400> SEQUENCE: 278

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
            35                  40                  45

Ala Gly Ile Gly Trp Ser Gly Gly Asp Thr Leu Tyr Ala Asp Ser Val
 50                      55                  60

Arg Gly Arg Phe Thr Ile Ser Arg Asp Asn Ser Lys Asn Thr Leu Ser
 65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
            115                 120                 125
```

<210> SEQ ID NO 279
<211> LENGTH: 126
<212> TYPE: PRT
<213> ORGANISM: Artificial Sequence
<220> FEATURE:
<223> OTHER INFORMATION: Synthetic Construct

<400> SEQUENCE: 279

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
            35                  40                  45

Ala Gly Ile Gly Trp Ser Gly Gly Asp Thr Leu Tyr Ala Asp Ser Val
 50                      55                  60

Arg Gly Arg Phe Thr Ile Ser Arg Asp Asn Ser Lys Asn Thr Leu Tyr
 65                  70                  75                  80

Leu Gln Met Asn Ser Leu Lys Ala Glu Asp Thr Ala Val Tyr Tyr Cys
                85                  90                  95
```

```
Ala Ala Arg Gln Gly Gln Tyr Ile Tyr Ser Ser Met Arg Ser Asp Ser
                100                 105                 110

Tyr Asp Tyr Trp Gly Gln Gly Thr Leu Val Thr Val Ser Ser
            115                 120                 125

<210> SEQ ID NO 280
<211> LENGTH: 126
<212> TYPE: PRT
<213> ORGANISM: Artificial Sequence
<220> FEATURE:
<223> OTHER INFORMATION: Synthetic Construct

<400> SEQUENCE: 280

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Gln Gly Gln Tyr Ile Tyr Ser Ser Met Arg Ser Asp Ser
                100                 105                 110

Tyr Asp Tyr Trp Gly Gln Gly Thr Leu Val Thr Val Ser Ser
            115                 120                 125

<210> SEQ ID NO 281
<211> LENGTH: 132
<212> TYPE: PRT
<213> ORGANISM: Artificial Sequence
<220> FEATURE:
<223> OTHER INFORMATION: Synthetic Construct

<400> SEQUENCE: 281

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Arg Glu Phe Val Ser Thr Ile Thr Ser Gly Gly Ser Ala Ile Tyr Thr
    50                  55                  60

Asp Ser Val Lys Gly Arg Phe Thr Leu Ser Arg Asp Asn Ala Lys Asp
65                  70                  75                  80

Thr Val Tyr Leu Gln Met Asn Ser Leu Lys Pro Glu Asp Thr Ala Val
                85                  90                  95

Tyr Tyr Cys His Val Arg Thr Arg Arg Tyr Gly Ser Asn Leu Gly Glu
                100                 105                 110

Val Pro Gln Glu Asn Glu Tyr Gly Tyr Trp Gly Gln Gly Thr Gln Val
            115                 120                 125

Thr Val Ser Ser
    130
```

<210> SEQ ID NO 282
<211> LENGTH: 132
<212> TYPE: PRT
<213> ORGANISM: Artificial Sequence
<220> FEATURE:
<223> OTHER INFORMATION: Synthetic Construct

<400> SEQUENCE: 282

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Arg Glu Phe Val Ser Thr Ile Thr Ser Gly Gly Ser Ala Ile Tyr Thr
    50                  55                  60

Asp Ser Val Lys Gly Arg Phe Thr Leu Ser Arg Asp Asn Ala Lys Asp
65                  70                  75                  80

Thr Val Tyr Leu Gln Met Asn Ser Leu Lys Pro Glu Asp Thr Ala Val
                85                  90                  95

Tyr Tyr Cys Ala Val Arg Thr Arg Arg His Gly Ser Asn Leu Gly Glu
            100                 105                 110

Val Pro Gln Glu Asn Glu Tyr Gly Tyr Trp Gly Gln Gly Thr Gln Val
        115                 120                 125

Thr Val Ser Ser
    130

<210> SEQ ID NO 283
<211> LENGTH: 120
<212> TYPE: PRT
<213> ORGANISM: Artificial Sequence
<220> FEATURE:
<223> OTHER INFORMATION: Synthetic Construct

<400> SEQUENCE: 283

Glu Val Gln Leu Val Glu Ser Gly Gly Gly Leu Val Gln Ala Gly Gly
1               5                   10                  15

Ser Leu Arg Leu Ser Cys Ala Ala Pro Glu Met Gly Ala Thr Ile Asn
            20                  25                  30

Val Met Ala Trp Tyr Arg Gln Ala Pro Gly Lys Gln Arg Glu Leu Val
        35                  40                  45

Ala Arg Leu Pro His Asp Asn Asn Ile Asp Tyr Gly Asp Phe Ala Lys
    50                  55                  60

Gly Arg Phe Thr Ile Ser Arg Asp Ile Thr Arg Asn Thr Val Tyr Leu
65                  70                  75                  80

Gln Met Asn Asn Leu Lys Pro Asp Asp Thr Ala Val Tyr Tyr Cys Asn
                85                  90                  95

Val Leu Leu Ser Arg Gln Ile Asn Gly Ala Tyr Val His Trp Gly Gln
            100                 105                 110

Gly Thr Gln Val Thr Val Ser Ser
        115                 120

<210> SEQ ID NO 284
<211> LENGTH: 120
<212> TYPE: PRT
<213> ORGANISM: Artificial Sequence
<220> FEATURE:
<223> OTHER INFORMATION: Synthetic Construct

<400> SEQUENCE: 284

Glu Val Gln Leu Val Glu Ser Gly Gly Gly Leu Val Gln Ala Gly Gly
1               5                   10                  15

Ser Leu Arg Leu Ser Cys Ala Ala Pro Glu Met Gly Ala Thr Ile Asn
            20                  25                  30

Val Met Ala Trp Tyr Arg Gln Ala Pro Gly Lys Gln Arg Glu Leu Val
        35                  40                  45

Ala Arg Leu Pro Leu His Asn Asn Ile Asp Tyr Gly Asp Phe Ala Lys
    50                  55                  60

Gly Arg Phe Thr Ile Ser Arg Asp Ile Thr Arg Asn Thr Val Tyr Leu
65                  70                  75                  80

Gln Met Asn Asn Leu Lys Pro Asp Asp Thr Ala Val Tyr Tyr Cys Asn
                85                  90                  95

Val Leu Leu Ser Arg Gln Ile Asn Gly Ala Tyr Val His Trp Gly Gln
            100                 105                 110

Gly Thr Gln Val Thr Val Ser Ser
            115                 120

<210> SEQ ID NO 285
<211> LENGTH: 120
<212> TYPE: PRT
<213> ORGANISM: Artificial Sequence
<220> FEATURE:
<223> OTHER INFORMATION: Synthetic Construct

<400> SEQUENCE: 285

Glu Val Gln Leu Val Glu Ser Gly Gly Gly Leu Val Gln Ala Gly Gly
1               5                   10                  15

Ser Leu Arg Leu Ser Cys Ala Ala Pro Glu Met Gly Ala Thr Ile Asn
            20                  25                  30

Val Met Ala Trp Tyr Arg Gln Ala Pro Gly Lys Gln Arg Glu Leu Val
        35                  40                  45

Ala Arg Leu Pro Leu Asp Asn Asn Ile Asp Tyr Gly Asp Phe Ala Lys
    50                  55                  60

Gly Arg Phe Thr Ile Ser Arg Asp Ile Thr Arg Asn Thr Val Tyr Leu
65                  70                  75                  80

Gln Met Asn Asn Leu Lys Pro Asp Asp Thr Ala Val Tyr Tyr Cys His
                85                  90                  95

Val Leu Leu Ser Arg Gln Ile Asn Gly Ala Tyr Val His Trp Gly Gln
            100                 105                 110

Gly Thr Gln Val Thr Val Ser Ser
            115                 120

<210> SEQ ID NO 286
<211> LENGTH: 120
<212> TYPE: PRT
<213> ORGANISM: Artificial Sequence
<220> FEATURE:
<223> OTHER INFORMATION: Synthetic Construct

<400> SEQUENCE: 286

Glu Val Gln Leu Val Glu Ser Gly Gly Gly Leu Val Gln Ala Gly Gly
1               5                   10                  15

Ser Leu Arg Leu Ser Cys Ala Ala Pro Glu Met Gly Ala Thr Ile Asn
            20                  25                  30

Val Met Ala Trp Tyr Arg Gln Ala Pro Gly Lys Gln Arg Glu Leu Val
        35                  40                  45

Ala Arg Leu Pro Leu Asp Asn Asn Ile Asp Tyr Gly Asp Phe Ala Lys

```
                    50                   55                    60

Gly Arg Phe Thr Ile Ser Arg Asp Ile Thr Arg Asn Thr Val Tyr Leu
 65                  70                   75                    80

Gln Met Asn Asn Leu Lys Pro Asp Asp Thr Ala Val Tyr Tyr Cys Asn
                     85                   90                    95

Val His Leu Ser Arg Gln Ile Asn Gly Ala Tyr Val His Trp Gly Gln
                    100                  105                   110

Gly Thr Gln Val Thr Val Ser Ser
            115                  120

<210> SEQ ID NO 287
<211> LENGTH: 120
<212> TYPE: PRT
<213> ORGANISM: Artificial Sequence
<220> FEATURE:
<223> OTHER INFORMATION: Synthetic Construct

<400> SEQUENCE: 287

Glu Val Gln Leu Val Glu Ser Gly Gly Gly Leu Val Gln Ala Gly Gly
  1               5                   10                  15

Ser Leu Arg Leu Ser Cys Ala Ala Pro Glu Met Gly Ala Thr Ile Asn
                 20                  25                  30

Val Met Ala Trp Tyr Arg Gln Ala Pro Gly Lys Gln Arg Glu Leu Val
             35                  40                  45

Ala Arg Leu Pro Leu Asp Asn Asn Ile Asp Tyr Gly Asp Phe Ala Lys
         50                  55                  60

Gly Arg Phe Thr Ile Ser Arg Asp Ile Thr Arg Asn Thr Val Tyr Leu
 65                  70                   75                    80

Gln Met Asn Asn Leu Lys Pro Asp Asp Thr Ala Val Tyr Tyr Cys Asn
                     85                   90                    95

Val Leu Leu Ser Arg Gln Ile Asn Gly Ala His Val His Trp Gly Gln
                    100                  105                   110

Gly Thr Gln Val Thr Val Ser Ser
            115                  120

<210> SEQ ID NO 288
<211> LENGTH: 126
<212> TYPE: PRT
<213> ORGANISM: Artificial Sequence
<220> FEATURE:
<223> OTHER INFORMATION: Synthetic Construct

<400> SEQUENCE: 288

Glu Val Gln Leu Val Glu Ser Gly Gly Gly Leu Val Gln Ala Gly Gly
  1               5                   10                  15

Ser Leu Arg Leu Ser Cys Ala Ala Ser Gly Arg His Phe Ser Asp Tyr
                 20                  25                  30

Ala Met Ala Trp Phe Arg Gln Ala Pro Gly Lys Glu Arg Glu Phe Val
             35                  40                  45

Ala Gly Ile Gly Trp Ser Gly Gly Asp Thr Leu Tyr Ala Asp Ser Val
         50                  55                  60

Arg Gly Arg Phe Thr Asn Ser Lys Asp Asn Ala Lys Asn Arg Met Ser
 65                  70                   75                    80

Leu Gln Met Asn Ser Leu Lys Pro Glu Asp Thr Ala Val Tyr Tyr Cys
                     85                   90                    95

Ala Ala Arg Gln Gly Gln Tyr Ile Tyr Ser Ser Met Arg Ser Asp Ser
                    100                  105                   110
```

Tyr Asp Tyr Trp Gly Gln Gly Thr Gln Val Thr Val Ser Ser
            115                 120                 125

<210> SEQ ID NO 289
<211> LENGTH: 126
<212> TYPE: PRT
<213> ORGANISM: Artificial Sequence
<220> FEATURE:
<223> OTHER INFORMATION: Synthetic Construct

<400> SEQUENCE: 289

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala His Ser Asp Tyr
            20                  25                  30

Ala Met Ala Trp Phe Arg Gln Ala Pro Gly Lys Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Asn Ser Lys Asp Asn Ala Lys Asn Arg Met Ser
65                  70                  75                  80

Leu Gln Met Asn Ser Leu Lys Pro Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Gln Val Thr Val Ser Ser
            115                 120                 125

<210> SEQ ID NO 290
<211> LENGTH: 126
<212> TYPE: PRT
<213> ORGANISM: Artificial Sequence
<220> FEATURE:
<223> OTHER INFORMATION: Synthetic Construct

<400> SEQUENCE: 290

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Lys Glu Arg Glu Phe Val
        35                  40                  45

Ala Gly Ile Gly Trp Ser Gly Gly Asp Thr His Tyr Ala Asp Ser Val
    50                  55                  60

Arg Gly Arg Phe Thr Asn Ser Lys Asp Asn Ala Lys Asn Arg Met Ser
65                  70                  75                  80

Leu Gln Met Asn Ser Leu Lys Pro Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Gln Val Thr Val Ser Ser
            115                 120                 125

<210> SEQ ID NO 291
<211> LENGTH: 126
<212> TYPE: PRT
<213> ORGANISM: Artificial Sequence
<220> FEATURE:
<223> OTHER INFORMATION: Synthetic Construct

<400> SEQUENCE: 291

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Lys Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Asn Ser Lys Asp Asn Ala Lys Asn Arg Met Ser
65                  70                  75                  80

Leu Gln Met Asn Ser Leu Lys Pro Glu Asp Thr Ala Val Tyr Tyr Cys
                85                  90                  95

Ala Ala Arg Gln Gly Gln His Ile Tyr Ser Ser Met Arg Ser Asp Ser
            100                 105                 110

Tyr Asp Tyr Trp Gly Gln Gly Thr Gln Val Thr Val Ser Ser
        115                 120                 125

<210> SEQ ID NO 292
<211> LENGTH: 132
<212> TYPE: PRT
<213> ORGANISM: Artificial Sequence
<220> FEATURE:
<223> OTHER INFORMATION: Synthetic Construct

<400> SEQUENCE: 292

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Ile
            20                  25                  30

Leu Ser His Tyr Ala Val Gly Trp Phe Arg Gln Ala Pro Gly Lys Glu
        35                  40                  45

Arg Glu Phe Val Ser Thr Ile Thr Ser Gly Gly Ser Thr Leu Ser Ala
    50                  55                  60

Asp Ser Val Lys Gly Arg Phe Thr Leu Ser Arg Asp Asn Ala Lys Asp
65                  70                  75                  80

Thr Val Tyr Leu Gln Met Asn Ser Leu Lys Pro Glu Asp Thr Ala Val
                85                  90                  95

Tyr Tyr Cys Ala Val Arg Thr Trp Pro Tyr Gly Ser Asn Arg Gly Glu
            100                 105                 110

Val Pro Thr Glu Asn Glu Tyr Gly His Trp Gly Gln Gly Thr Gln Val
        115                 120                 125

Thr Val Ser Ser
    130

<210> SEQ ID NO 293
<211> LENGTH: 132
<212> TYPE: PRT
<213> ORGANISM: Artificial Sequence
<220> FEATURE:
<223> OTHER INFORMATION: Synthetic Construct

<400> SEQUENCE: 293

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
            35                  40                  45

Leu Glu Phe Val Ser Thr Ile Thr Ser Gly Gly Ser Ala Ile Tyr Thr
 50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Val Arg Thr Arg His Gly Ser Asn Leu Gly Glu
                100                 105                 110

Val Pro Gln Glu Asn Glu Tyr Gly Tyr Trp Gly Gln Gly Thr Leu Val
            115                 120                 125

Thr Val Ser Ser
    130

<210> SEQ ID NO 294
<211> LENGTH: 126
<212> TYPE: PRT
<213> ORGANISM: Artificial Sequence
<220> FEATURE:
<223> OTHER INFORMATION: Synthetic Construct

<400> SEQUENCE: 294

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
            35                  40                  45

Ala Gly Ile Gly Trp Ser Gly Gly Asp Thr His Tyr Ala Asp Ser Val
         50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
                100                 105                 110

Tyr Asp Tyr Trp Gly Gln Gly Thr Leu Val Thr Val Ser Ser
            115                 120                 125

<210> SEQ ID NO 295
<211> LENGTH: 126
<212> TYPE: PRT
<213> ORGANISM: Artificial Sequence
<220> FEATURE:
<223> OTHER INFORMATION: Synthetic Construct

<400> SEQUENCE: 295

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
            35                  40                  45

Ala Gly Ile Gly Trp Ser Gly Gly Asp Thr Leu Tyr Ala Asp Ser Val
         50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln His Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 296
<211> LENGTH: 126
<212> TYPE: PRT
<213> ORGANISM: Artificial Sequence
<220> FEATURE:
<223> OTHER INFORMATION: Synthetic Construct

<400> SEQUENCE: 296

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala His Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr His Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 297
<211> LENGTH: 126
<212> TYPE: PRT
<213> ORGANISM: Artificial Sequence
<220> FEATURE:
<223> OTHER INFORMATION: Synthetic Construct

<400> SEQUENCE: 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr His Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln His Ile Tyr Ser Ser Met Arg Ser Asp Ser
            100                 105                 110

Tyr Asp Tyr Trp Gly Gln Gly Thr Leu Val Thr Val Ser Ser
        115                 120                 125

```
<210> SEQ ID NO 298
<211> LENGTH: 126
<212> TYPE: PRT
<213> ORGANISM: Artificial Sequence
<220> FEATURE:
<223> OTHER INFORMATION: Synthetic Construct

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg His Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr His Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 299
<211> LENGTH: 126
<212> TYPE: PRT
<213> ORGANISM: Artificial Sequence
<220> FEATURE:
<223> OTHER INFORMATION: Synthetic Construct

<400> SEQUENCE: 299

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg His Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln His Ile Tyr Ser Ser Met Arg Ser Asp Ser
            100                 105                 110

Tyr Asp Tyr Trp Gly Gln Gly Thr Leu Val Thr Val Ser Ser
        115                 120                 125

<210> SEQ ID NO 300
<211> LENGTH: 126
<212> TYPE: PRT
<213> ORGANISM: Artificial Sequence
<220> FEATURE:
<223> OTHER INFORMATION: Synthetic Construct

<400> SEQUENCE: 300

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Arg Ala His Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln His Ile Tyr Ser Ser Met Arg Ser Asp Ser
            100                 105                 110

Tyr Asp Tyr Trp Gly Gln Gly Thr Leu Val Thr Val Ser Ser
                115                 120                 125

<210> SEQ ID NO 301
<211> LENGTH: 126
<212> TYPE: PRT
<213> ORGANISM: Artificial Sequence
<220> FEATURE:
<223> OTHER INFORMATION: Synthetic Construct

<400> SEQUENCE: 301

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg His His Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr His Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser
                115                 120                 125

<210> SEQ ID NO 302
<211> LENGTH: 126
<212> TYPE: PRT
<213> ORGANISM: Artificial Sequence
<220> FEATURE:
<223> OTHER INFORMATION: Synthetic Construct

<400> SEQUENCE: 302

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg His His Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Ala Arg Gln Gly Gln His Ile Tyr Ser Ser Met Arg Ser Asp Ser
                100                 105                 110

Tyr Asp Tyr Trp Gly Gln Gly Thr Leu Val Thr Val Ser Ser
            115                 120                 125

<210> SEQ ID NO 303
<211> LENGTH: 126
<212> TYPE: PRT
<213> ORGANISM: Artificial Sequence
<220> FEATURE:
<223> OTHER INFORMATION: Synthetic Construct

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala His Ser Asp Tyr
                20                  25                  30

Ala Met Ala Trp Phe Arg Gln Ala Pro Gly Gln Glu Arg Glu Phe Val
            35                  40                  45

Ala Gly Ile Gly Trp Ser Gly Gly Asp Thr His Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ala Arg Gln Gly Gln His Ile Tyr Ser Ser Met Arg Ser Asp Ser
                100                 105                 110

Tyr Asp Tyr Trp Gly Gln Gly Thr Leu Val Thr Val Ser Ser
            115                 120                 125

<210> SEQ ID NO 304
<211> LENGTH: 126
<212> TYPE: PRT
<213> ORGANISM: Artificial Sequence
<220> FEATURE:
<223> OTHER INFORMATION: Synthetic Construct

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg His Phe Ser Asp Tyr
                20                  25                  30

Ala Met Ala Trp Phe Arg Gln Ala Pro Gly Gln Glu Arg Glu Phe Val
            35                  40                  45

Ala Gly Ile Gly Trp Ser Gly Gly Asp Thr His Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ala Arg Gln Gly Gln His Ile Tyr Ser Ser Met Arg Ser Asp Ser
                100                 105                 110

Tyr Asp Tyr Trp Gly Gln Gly Thr Leu Val Thr Val Ser Ser
            115                 120                 125
```

<210> SEQ ID NO 305
<211> LENGTH: 262
<212> TYPE: PRT
<213> ORGANISM: Artificial Sequence
<220> FEATURE:
<223> OTHER INFORMATION: Synthetic Construct

<400> SEQUENCE: 305

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Ser Ala Ile Tyr Thr
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
        115                 120                 125

Thr Val Ser Ser Gly Gly Gly Ser Gly Gly Gly Ser Gly Gly
130                 135                 140

Gly Gly Ser Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Arg Ser Phe Gly Met Ser Trp Val Arg Gln Ala Pro Gly Lys Gly Pro
            180                 185                 190

Glu Trp Val Ser Ser Ile Ser Gly Ser Gly Ser Asp Thr Leu Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Pro Glu Asp Thr Ala Val
225                 230                 235                 240

Tyr Tyr Cys Thr Ile Gly Gly Ser Leu Ser Arg Ser Ser Gln Gly Thr
                245                 250                 255

Leu Val Thr Val Ser Ser
            260
```

<210> SEQ ID NO 306
<211> LENGTH: 267
<212> TYPE: PRT
<213> ORGANISM: Artificial Sequence
<220> FEATURE:
<223> OTHER INFORMATION: Synthetic Construct

<400> SEQUENCE: 306

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45
```

Leu Glu Phe Val Ser Thr Ile Thr Ser Gly Gly Ser Ala Ile Tyr Thr
            50                  55                  60

Asp Ser Val Lys Gly Arg Phe Thr Ile Ser Arg Asp Asn Ala Lys Asn
 65                  70                  75                  80

Ser Leu Tyr Leu Gln Met Asn Ser Leu Arg Ala Glu Asp Thr Ala Val
                 85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
            115                 120                 125

Thr Val Ser Ser Gly Gly Gly Gly Ser Gly Gly Gly Gly Ser Gly Gly
            130                 135                 140

Gly Gly Ser Gly Gly Gly Gly Ser Glu Val Gln Leu Leu Glu Ser Gly
145                 150                 155                 160

Gly Gly Leu Val Gln Pro Gly Gly Ser Leu Arg Leu Ser Cys Ala Ala
            165                 170                 175

Ser Gly Phe Thr Phe Arg Ser Phe Gly Met Ser Trp Val Arg Gln Ala
            180                 185                 190

Pro Gly Lys Gly Pro Glu Trp Val Ser Ile Ser Gly Ser Gly Ser
            195                 200                 205

Asp Thr Leu Tyr Ala Asp Ser Val Lys Gly Arg Phe Thr Ile Ser Arg
            210                 215                 220

Asp Asn Ser Lys Asn Thr Leu Tyr Leu Gln Met Asn Ser Leu Arg Pro
225                 230                 235                 240

Glu Asp Thr Ala Val Tyr Tyr Cys Thr Ile Gly Gly Ser Leu Ser Arg
            245                 250                 255

Ser Ser Gln Gly Thr Leu Val Thr Val Ser Ser
            260                 265

<210> SEQ ID NO 307
<211> LENGTH: 272
<212> TYPE: PRT
<213> ORGANISM: Artificial Sequence
<220> FEATURE:
<223> OTHER INFORMATION: Synthetic Construct

<400> SEQUENCE: 307

Glu Val Gln Leu Val Glu Ser Gly Gly Gly Leu Val Gln Pro Gly Gly
 1               5                   10                  15

Ser Leu Arg Leu Ser Cys Ala Ala Ser Gly Arg Thr Phe Ser Gly Ile
                20                  25                  30

Leu Ser Pro Tyr Ala Val Gly Trp Phe Arg Gln Ala Pro Gly Lys Gly
            35                  40                  45

Leu Glu Phe Val Ser Thr Ile Thr Ser Gly Gly Ser Ala Ile Tyr Thr
            50                  55                  60

Asp Ser Val Lys Gly Arg Phe Thr Ile Ser Arg Asp Asn Ala Lys Asn
 65                  70                  75                  80

Ser Leu Tyr Leu Gln Met Asn Ser Leu Arg Ala Glu Asp Thr Ala Val
                 85                  90                  95

Tyr Tyr Cys Ala Val Arg Thr Arg Arg Tyr Gly Ser Asn Leu Gly Glu
            100                 105                 110

Val Pro Gln Glu Asn Glu Tyr Gly Tyr Trp Gly Gln Gly Thr Leu Val
            115                 120                 125

Thr Val Ser Ser Gly Gly Gly Gly Ser Gly Gly Gly Gly Ser Gly Gly
            130                 135                 140

Gly Gly Ser Gly Gly Gly Ser Gly Gly Gly Ser Glu Val Gln
145                 150                 155                 160

Leu Leu Glu Ser Gly Gly Leu Val Gln Pro Gly Gly Ser Leu Arg
            165                 170                 175

Leu Ser Cys Ala Ala Ser Gly Phe Thr Phe Arg Ser Phe Gly Met Ser
        180                 185                 190

Trp Val Arg Gln Ala Pro Gly Lys Gly Pro Glu Trp Val Ser Ser Ile
            195                 200                 205

Ser Gly Ser Gly Ser Asp Thr Leu Tyr Ala Asp Ser Val Lys Gly Arg
    210                 215                 220

Phe Thr Ile Ser Arg Asp Asn Ser Lys Asn Thr Leu Tyr Leu Gln Met
225                 230                 235                 240

Asn Ser Leu Arg Pro Glu Asp Thr Ala Val Tyr Tyr Cys Thr Ile Gly
            245                 250                 255

Gly Ser Leu Ser Arg Ser Ser Gln Gly Thr Leu Val Thr Val Ser Ser
        260                 265                 270

<210> SEQ ID NO 308
<211> LENGTH: 277
<212> TYPE: PRT
<213> ORGANISM: Artificial Sequence
<220> FEATURE:
<223> OTHER INFORMATION: Synthetic Construct

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Gly Ile
            20                  25                  30

Leu Ser Pro Tyr Ala Val Gly Trp Phe Arg Gln Ala Pro Gly Lys Gly
        35                  40                  45

Leu Glu Phe Val Ser Thr Ile Thr Ser Gly Gly Ser Ala Ile Tyr Thr
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
            85                  90                  95

Tyr Tyr Cys Ala Val Arg Thr Arg Arg Tyr Gly Ser Asn Leu Gly Glu
        100                 105                 110

Val Pro Gln Glu Asn Glu Tyr Gly Tyr Trp Gly Gln Gly Thr Leu Val
    115                 120                 125

Thr Val Ser Ser Gly Gly Gly Ser Gly Gly Gly Ser Gly Gly Gly
130                 135                 140

Gly Gly Ser Gly Gly Gly Ser Gly Gly Gly Ser Gly Gly Gly
145                 150                 155                 160

Gly Ser Glu Val Gln Leu Leu Glu Ser Gly Gly Leu Val Gln Pro
            165                 170                 175

Gly Gly Ser Leu Arg Leu Ser Cys Ala Ala Ser Gly Phe Thr Phe Arg
        180                 185                 190

Ser Phe Gly Met Ser Trp Val Arg Gln Ala Pro Gly Lys Gly Pro Glu
    195                 200                 205

Trp Val Ser Ser Ile Ser Gly Ser Gly Ser Asp Thr Leu Tyr Ala Asp
    210                 215                 220

Ser Val Lys Gly Arg Phe Thr Ile Ser Arg Asp Asn Ser Lys Asn Thr
225                 230                 235                 240

```
Leu Tyr Leu Gln Met Asn Ser Leu Arg Pro Glu Asp Thr Ala Val Tyr
            245                 250                 255

Tyr Cys Thr Ile Gly Gly Ser Leu Ser Arg Ser Ser Gln Gly Thr Leu
        260                 265                 270

Val Thr Val Ser Ser
        275

<210> SEQ ID NO 309
<211> LENGTH: 262
<212> TYPE: PRT
<213> ORGANISM: Artificial Sequence
<220> FEATURE:
<223> OTHER INFORMATION: Synthetic Construct

<400> SEQUENCE: 309

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Arg Thr Phe Ser
145                 150                 155                 160

Gly Ile Leu Ser Pro Tyr Ala Val Gly Trp Phe Arg Gln Ala Pro Gly
                165                 170                 175

Lys Gly Leu Glu Phe Val Ser Thr Ile Thr Ser Gly Gly Ser Ala Ile
            180                 185                 190

Tyr Thr Asp Ser Val Lys Gly Arg Phe Thr Ile Ser Arg Asp Asn Ala
        195                 200                 205

Lys Asn Ser Leu Tyr Leu Gln Met Asn Ser Leu Arg Ala Glu Asp Thr
    210                 215                 220

Ala Val Tyr Tyr Cys Ala Val Arg Thr Arg Arg Tyr Gly Ser Asn Leu
225                 230                 235                 240

Gly Glu Val Pro Gln Glu Asn Glu Tyr Gly Tyr Trp Gly Gln Gly Thr
                245                 250                 255

Leu Val Thr Val Ser Ser
            260

<210> SEQ ID NO 310
<211> LENGTH: 267
<212> TYPE: PRT
<213> ORGANISM: Artificial Sequence
<220> FEATURE:
<223> OTHER INFORMATION: Synthetic Construct
```

<400> SEQUENCE: 310

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly
        115                 120                 125

Gly Ser Gly Gly Gly Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Arg Thr Phe Ser Gly Ile Leu Ser Pro Tyr Ala Val Gly Trp Phe
                165                 170                 175

Arg Gln Ala Pro Gly Lys Gly Leu Glu Phe Val Ser Thr Ile Thr Ser
            180                 185                 190

Gly Gly Ser Ala Ile Tyr Thr Asp Ser Val Lys Gly Arg Phe Thr Ile
        195                 200                 205

Ser Arg Asp Asn Ala Lys Asn Ser Leu Tyr Leu Gln Met Asn Ser Leu
    210                 215                 220

Arg Ala Glu Asp Thr Ala Val Tyr Tyr Cys Ala Val Arg Thr Arg Arg
225                 230                 235                 240

Tyr Gly Ser Asn Leu Gly Glu Val Pro Gln Glu Asn Glu Tyr Gly Tyr
                245                 250                 255

Trp Gly Gln Gly Thr Leu Val Thr Val Ser Ser
            260                 265

<210> SEQ ID NO 311
<211> LENGTH: 272
<212> TYPE: PRT
<213> ORGANISM: Artificial Sequence
<220> FEATURE:
<223> OTHER INFORMATION: Synthetic Construct

<400> SEQUENCE: 311

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys

```
                85                  90                  95
Thr Ile Gly Gly Ser Leu Ser Arg Ser Ser Gln Gly Thr Leu Val Thr
            100                 105                 110
Val Ser Ser Gly Gly Gly Gly Ser Gly Gly Gly Ser Gly Gly Gly
        115                 120                 125
Gly Ser Gly Gly Gly Ser Gly Gly Gly Ser Glu Val Gln Leu
    130                 135                 140
Val Glu Ser Gly Gly Leu Val Gln Pro Gly Gly Ser Leu Arg Leu
145                 150                 155                 160
Ser Cys Ala Ala Ser Gly Arg Thr Phe Ser Gly Ile Leu Ser Pro Tyr
                165                 170                 175
Ala Val Gly Trp Phe Arg Gln Ala Pro Gly Lys Gly Leu Glu Phe Val
            180                 185                 190
Ser Thr Ile Thr Ser Gly Gly Ser Ala Ile Tyr Thr Asp Ser Val Lys
        195                 200                 205
Gly Arg Phe Thr Ile Ser Arg Asp Asn Ala Lys Asn Ser Leu Tyr Leu
    210                 215                 220
Gln Met Asn Ser Leu Arg Ala Glu Asp Thr Ala Val Tyr Tyr Cys Ala
225                 230                 235                 240
Val Arg Thr Arg Tyr Gly Ser Asn Leu Gly Val Pro Gln Glu
                245                 250                 255
Asn Glu Tyr Gly Tyr Trp Gly Gln Gly Thr Leu Val Thr Val Ser Ser
            260                 265                 270

<210> SEQ ID NO 312
<211> LENGTH: 277
<212> TYPE: PRT
<213> ORGANISM: Artificial Sequence
<220> FEATURE:
<223> OTHER INFORMATION: Synthetic Construct

<400> SEQUENCE: 312

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Arg Ser Phe
            20                  25                  30
Gly Met Ser Trp Val Arg Gln Ala Pro Gly Lys Gly Pro Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser Gly Gly Gly Gly Ser Gly Gly Gly Ser Gly Gly Gly
        115                 120                 125
Gly Ser Gly Gly Gly Ser Gly Gly Gly Ser Gly Gly Gly Gly
    130                 135                 140
Ser Glu Val Gln Leu Val Glu Ser Gly Gly Gly Leu Val Gln Pro Gly
145                 150                 155                 160
Gly Ser Leu Arg Leu Ser Cys Ala Ala Ser Gly Arg Thr Phe Ser Gly
                165                 170                 175
Ile Leu Ser Pro Tyr Ala Val Gly Trp Phe Arg Gln Ala Pro Gly Lys
```

```
                180                 185                 190
Gly Leu Glu Phe Val Ser Thr Ile Thr Ser Gly Gly Ser Ala Ile Tyr
            195                 200                 205

Thr Asp Ser Val Lys Gly Arg Phe Thr Ile Ser Arg Asp Asn Ala Lys
        210                 215                 220

Asn Ser Leu Tyr Leu Gln Met Asn Ser Leu Arg Ala Glu Asp Thr Ala
225                 230                 235                 240

Val Tyr Tyr Cys Ala Val Arg Thr Arg Arg Tyr Gly Ser Asn Leu Gly
                245                 250                 255

Glu Val Pro Gln Glu Asn Glu Tyr Gly Tyr Trp Gly Gln Gly Thr Leu
            260                 265                 270

Val Thr Val Ser Ser
            275

<210> SEQ ID NO 313
<211> LENGTH: 256
<212> TYPE: PRT
<213> ORGANISM: Artificial Sequence
<220> FEATURE:
<223> OTHER INFORMATION: Synthetic Construct

<400> SEQUENCE: 313

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ala Phe Ser Asp Tyr
            20                  25                  30

Ala Met Ala Trp Phe Arg Gln Ala Pro Gly Gln Glu Arg Glu Phe Val
        35                  40                  45

Ala Gly Ile Gly Trp Ser Gly Gly Asp Thr Leu Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Gly Gln Tyr Ile Tyr Ser Ser Met Arg Ser Asp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Phe Thr Phe Arg Ser Phe Gly Met Ser
                165                 170                 175

Trp Val Arg Gln Ala Pro Gly Lys Gly Pro Glu Trp Val Ser Ser Ile
            180                 185                 190

Ser Gly Ser Gly Ser Asp Thr Leu Tyr Ala Asp Ser Val Lys Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Thr Ile Gly
225                 230                 235                 240

Gly Ser Leu Ser Arg Ser Ser Gln Gly Thr Leu Val Thr Val Ser Ser
                245                 250                 255
```

```
<210> SEQ ID NO 314
<211> LENGTH: 261
<212> TYPE: PRT
<213> ORGANISM: Artificial Sequence
<220> FEATURE:
<223> OTHER INFORMATION: Synthetic Construct

<400> SEQUENCE: 314
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Arg | Ala | Phe | Ser | Asp | Tyr |
|---|---|---|---|---|---|---|---|---|---|---|---|---|---|---|---|
| | | | 20 | | | | | 25 | | | | | 30 | | |

| Ala | Met | Ala | Trp | Phe | Arg | Gln | Ala | Pro | Gly | Gln | Glu | Arg | Glu | Phe | Val |
|---|---|---|---|---|---|---|---|---|---|---|---|---|---|---|---|
| | | 35 | | | | | 40 | | | | | 45 | | | |

| Ala | Gly | Ile | Gly | Trp | Ser | Gly | Gly | Asp | Thr | Leu | Tyr | Ala | Asp | Ser | Val |
|---|---|---|---|---|---|---|---|---|---|---|---|---|---|---|---|
| | 50 | | | | | 55 | | | | | 60 | | | | |

| Arg | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ala | Arg | Gln | Gly | Gln | Tyr | Ile | Tyr | Ser | Ser | Met | Arg | Ser | Asp | Ser |
|---|---|---|---|---|---|---|---|---|---|---|---|---|---|---|---|
| | | | 100 | | | | | 105 | | | | | 110 | | |

| Tyr | Asp | Tyr | Trp | Gly | Gln | Gly | Thr | Leu | Val | Thr | Val | Ser | Ser | Gly | Gly |
|---|---|---|---|---|---|---|---|---|---|---|---|---|---|---|---|
| | | 115 | | | | | 120 | | | | | 125 | | | |

| Gly | Gly | Ser | Gly | Gly | Gly | Gly | Ser | Gly | Gly | Gly | Gly | Ser | Gly | Gly | Gly |
|---|---|---|---|---|---|---|---|---|---|---|---|---|---|---|---|
| | 130 | | | | | 135 | | | | | 140 | | | | |

| Gly | Ser | Glu | Val | Gln | Leu | Leu | Glu | Ser | Gly | Gly | Gly | Leu | Val | Gln | Pro |
|---|---|---|---|---|---|---|---|---|---|---|---|---|---|---|---|
| 145 | | | | | 150 | | | | | 155 | | | | | 160 |

| Gly | Gly | Ser | Leu | Arg | Leu | Ser | Cys | Ala | Ala | Ser | Gly | Phe | Thr | Phe | Arg |
|---|---|---|---|---|---|---|---|---|---|---|---|---|---|---|---|
| | | | | 165 | | | | | 170 | | | | | 175 | |

| Ser | Phe | Gly | Met | Ser | Trp | Val | Arg | Gln | Ala | Pro | Gly | Lys | Gly | Pro | Glu |
|---|---|---|---|---|---|---|---|---|---|---|---|---|---|---|---|
| | | | 180 | | | | | 185 | | | | | 190 | | |

| Trp | Val | Ser | Ser | Ile | Ser | Gly | Ser | Gly | Ser | Asp | Thr | Leu | Tyr | Ala | Asp |
|---|---|---|---|---|---|---|---|---|---|---|---|---|---|---|---|
| | | 195 | | | | | 200 | | | | | 205 | | | |

| Ser | Val | Lys | Gly | Arg | Phe | Thr | Ile | Ser | Arg | Asp | Asn | Ser | Lys | Asn | Thr |
|---|---|---|---|---|---|---|---|---|---|---|---|---|---|---|---|
| | 210 | | | | | 215 | | | | | 220 | | | | |

| Leu | Tyr | Leu | Gln | Met | Asn | Ser | Leu | Arg | Pro | Glu | Asp | Thr | Ala | Val | Tyr |
|---|---|---|---|---|---|---|---|---|---|---|---|---|---|---|---|
| 225 | | | | | 230 | | | | | 235 | | | | | 240 |

| Tyr | Cys | Thr | Ile | Gly | Gly | Ser | Leu | Ser | Arg | Ser | Ser | Gln | Gly | Thr | Leu |
|---|---|---|---|---|---|---|---|---|---|---|---|---|---|---|---|
| | | | | 245 | | | | | 250 | | | | | 255 | |

| Val | Thr | Val | Ser | Ser |
|---|---|---|---|---|
| | | | | 260 |

```
<210> SEQ ID NO 315
<211> LENGTH: 266
<212> TYPE: PRT
<213> ORGANISM: Artificial Sequence
<220> FEATURE:
<223> OTHER INFORMATION: Synthetic Construct

<400> SEQUENCE: 315
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Arg | Ala | Phe | Ser | Asp | Tyr |
|---|---|---|---|---|---|---|---|---|---|---|---|---|---|---|---|
| | | | 20 | | | | | 25 | | | | | 30 | | |

| Ala | Met | Ala | Trp | Phe | Arg | Gln | Ala | Pro | Gly | Gln | Glu | Arg | Glu | Phe | Val |
|---|---|---|---|---|---|---|---|---|---|---|---|---|---|---|---|
| | | 35 | | | | | 40 | | | | | 45 | | | |

Ala Gly Ile Gly Trp Ser Gly Gly Asp Thr Leu Tyr Ala Asp Ser Val
         50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Arg Gln Gly Gln Tyr Ile Tyr Ser Ser Met Arg Ser Asp Ser
                100                 105                 110

Tyr Asp Tyr Trp Gly Gln Gly Thr Leu Val Thr Val Ser Ser Gly Gly
            115                 120                 125

Gly Gly Ser Gly Gly Gly Ser Gly Gly Gly Ser Gly Gly Gly
130                 135                 140

Gly Ser Gly Gly Gly Ser Glu Val Gln Leu Leu Glu Ser Gly Gly
145                 150                 155                 160

Gly Leu Val Gln Pro Gly Gly Ser Leu Arg Leu Ser Cys Ala Ala Ser
                165                 170                 175

Gly Phe Thr Phe Arg Ser Phe Gly Met Ser Trp Val Arg Gln Ala Pro
                180                 185                 190

Gly Lys Gly Pro Glu Trp Val Ser Ser Ile Ser Gly Ser Gly Ser Asp
            195                 200                 205

Thr Leu Tyr Ala Asp Ser Val Lys Gly Arg Phe Thr Ile Ser Arg Asp
            210                 215                 220

Asn Ser Lys Asn Thr Leu Tyr Leu Gln Met Asn Ser Leu Arg Pro Glu
225                 230                 235                 240

Asp Thr Ala Val Tyr Tyr Cys Thr Ile Gly Gly Ser Leu Ser Arg Ser
                245                 250                 255

Ser Gln Gly Thr Leu Val Thr Val Ser Ser
            260                 265

<210> SEQ ID NO 316
<211> LENGTH: 270
<212> TYPE: PRT
<213> ORGANISM: Artificial Sequence
<220> FEATURE:
<223> OTHER INFORMATION: Synthetic Construct

<400> SEQUENCE: 316

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Ala Phe Ser Asp Tyr
                 20                  25                  30

Ala Met Ala Trp Phe Arg Gln Ala Pro Gly Gln Glu Arg Glu Phe Val
             35                  40                  45

Ala Gly Ile Gly Trp Ser Gly Gly Asp Thr Leu Tyr Ala Asp Ser Val
         50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Arg Gln Gly Gln Tyr Ile Tyr Ser Ser Met Arg Ser Asp Ser
                100                 105                 110

Tyr Asp Tyr Trp Gly Gln Gly Thr Leu Val Thr Val Ser Ser Gly Gly
            115                 120                 125

Gly Gly Ser Gly Gly Gly Gly Ser Gly Gly Gly Gly Gly Gly
130                 135                 140

```
Gly Ser Gly Gly Gly Ser Gly Gly Gly Ser Glu Val Gln Leu
145                 150                 155                 160

Leu Glu Ser Gly Gly Gly Leu Val Gln Pro Gly Gly Ser Leu Arg Leu
                165                 170                 175

Ser Cys Ala Ala Ser Gly Phe Thr Phe Arg Ser Phe Gly Met Ser Trp
            180                 185                 190

Val Arg Gln Ala Pro Gly Lys Gly Pro Glu Trp Val Ser Ser Ile Ser
        195                 200                 205

Gly Ser Gly Ser Asp Thr Leu Tyr Ala Asp Ser Val Lys Gly Arg Phe
    210                 215                 220

Thr Ile Ser Arg Asp Asn Ser Asn Thr Leu Tyr Leu Gln Met Asn Ser
225                 230                 235                 240

Leu Arg Pro Glu Asp Thr Ala Val Tyr Tyr Cys Thr Ile Gly Gly Ser
                245                 250                 255

Leu Ser Arg Ser Ser Gln Gly Thr Leu Val Thr Val Ser Ser
            260                 265                 270

<210> SEQ ID NO 317
<211> LENGTH: 256
<212> TYPE: PRT
<213> ORGANISM: Artificial Sequence
<220> FEATURE:
<223> OTHER INFORMATION: Synthetic Construct

<400> SEQUENCE: 317

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Arg Ala Phe Ser
145                 150                 155                 160

Asp Tyr Ala Met Ala Trp Phe Arg Gln Ala Pro Gly Gln Glu Arg Glu
                165                 170                 175

Phe Val Ala Gly Ile Gly Trp Ser Gly Gly Asp Thr Leu Tyr Ala Asp
            180                 185                 190

Ser Val Arg Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Ala Arg Gln Gly Gln Tyr Ile Tyr Ser Ser Met Arg Ser
225                 230                 235                 240
```

```
Asp Ser Tyr Asp Tyr Trp Gly Gln Gly Thr Leu Val Thr Val Ser Ser
            245                 250                 255
```

<210> SEQ ID NO 318
<211> LENGTH: 261
<212> TYPE: PRT
<213> ORGANISM: Artificial Sequence
<220> FEATURE:
<223> OTHER INFORMATION: Synthetic Construct

<400> SEQUENCE: 318

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gly Gly Gly
        115                 120                 125

Gly Ser Gly Gly Gly Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Arg Ala Phe Ser Asp Tyr Ala Met Ala Trp Phe Arg Gln Ala Pro
                165                 170                 175

Gly Gln Glu Arg Glu Phe Val Ala Gly Ile Gly Trp Ser Gly Gly Asp
            180                 185                 190

Thr Leu Tyr Ala Asp Ser Val Arg Gly Arg Phe Thr Ile Ser Arg Asp
        195                 200                 205

Asn Ser Lys Asn Thr Leu Tyr Leu Gln Met Asn Ser Leu Arg Ala Glu
    210                 215                 220

Asp Thr Ala Val Tyr Tyr Cys Ala Ala Arg Gln Gly Gln Tyr Ile Tyr
225                 230                 235                 240

Ser Ser Met Arg Ser Asp Ser Tyr Asp Tyr Trp Gly Gln Gly Thr Leu
                245                 250                 255

Val Thr Val Ser Ser
            260
```

<210> SEQ ID NO 319
<211> LENGTH: 266
<212> TYPE: PRT
<213> ORGANISM: Artificial Sequence
<220> FEATURE:
<223> OTHER INFORMATION: Synthetic Construct

<400> SEQUENCE: 319

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30
```

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Glu Val Gln Leu
        130                 135                 140

Val Glu Ser Gly Gly Gly Leu Val Gln Pro Gly Gly Ser Leu Arg Leu
145                 150                 155                 160

Ser Cys Ala Ala Ser Gly Arg Ala Phe Ser Asp Tyr Ala Met Ala Trp
                165                 170                 175

Phe Arg Gln Ala Pro Gly Gln Glu Arg Glu Phe Val Ala Gly Ile Gly
            180                 185                 190

Trp Ser Gly Gly Asp Thr Leu Tyr Ala Asp Ser Val Arg Gly Arg Phe
        195                 200                 205

Thr Ile Ser Arg Asp Asn Ser Lys Asn Thr Leu Tyr Leu Gln Met Asn
    210                 215                 220

Ser Leu Arg Ala Glu Asp Thr Ala Val Tyr Tyr Cys Ala Ala Arg Gln
225                 230                 235                 240

Gly Gln Tyr Ile Tyr Ser Ser Met Arg Ser Asp Ser Tyr Asp Tyr Trp
                245                 250                 255

Gly Gln Gly Thr Leu Val Thr Val Ser Ser
            260                 265

<210> SEQ ID NO 320
<211> LENGTH: 271
<212> TYPE: PRT
<213> ORGANISM: Artificial Sequence
<220> FEATURE:
<223> OTHER INFORMATION: Synthetic Construct

<400> SEQUENCE: 320

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Ser Gly Gly Gly Ser Gly Gly Gly
         130                 135                 140

Ser Glu Val Gln Leu Val Glu Ser Gly Gly Leu Val Gln Pro Gly
145                 150                 155                 160

Gly Ser Leu Arg Leu Ser Cys Ala Ala Ser Gly Arg Ala Phe Ser Asp
                165                 170                 175

Tyr Ala Met Ala Trp Phe Arg Gln Ala Pro Gly Gln Glu Arg Glu Phe
            180                 185                 190

Val Ala Gly Ile Gly Trp Ser Gly Gly Asp Thr Leu Tyr Ala Asp Ser
        195                 200                 205

Val Arg Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Ala Arg Gln Gly Gln Tyr Ile Tyr Ser Ser Met Arg Ser Asp
                245                 250                 255

Ser Tyr Asp Tyr Trp Gly Gln Gly Thr Leu Val Thr Val Ser Ser
            260                 265                 270

<210> SEQ ID NO 321
<211> LENGTH: 9
<212> TYPE: PRT
<213> ORGANISM: Artificial Sequence
<220> FEATURE:
<223> OTHER INFORMATION: Synthetic Construct

<400> SEQUENCE: 321

Gly Gly Gly Gly Gly Gly Gly Gly Pro
1               5

<210> SEQ ID NO 322
<211> LENGTH: 117
<212> TYPE: PRT
<213> ORGANISM: Artificial Sequence
<220> FEATURE:
<223> OTHER INFORMATION: Synthetic Construct

<400> SEQUENCE: 322

Leu Glu Gln Val Gln Leu Gln Glu Ser Gly Gly Gly Leu Val Gln Pro
1               5                   10                  15

Gly Gly Ser Leu Arg Leu Ser Cys Glu Ala Ser Gly Phe Thr Phe Ser
            20                  25                  30

Arg Phe Gly Met Thr Trp Val Arg Gln Ala Pro Gly Lys Gly Val Glu
        35                  40                  45

Trp Val Ser Gly Ile Ser Ser Leu Gly Asp Ser Thr Leu Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Thr Ile Gly Gly Ser Leu Asn Pro Gly Gly Gln Gly Thr Gln
            100                 105                 110

Val Thr Val Ser Ser
        115

<210> SEQ ID NO 323
<211> LENGTH: 7
<212> TYPE: PRT

```
<213> ORGANISM: Artificial Sequence
<220> FEATURE:
<223> OTHER INFORMATION: Synthetic Construct

<400> SEQUENCE: 323

Pro Asn Leu Leu Gly Gly Pro
1               5

<210> SEQ ID NO 324
<211> LENGTH: 6
<212> TYPE: PRT
<213> ORGANISM: Artificial Sequence
<220> FEATURE:
<223> OTHER INFORMATION: Synthetic Construct

<400> SEQUENCE: 324

His His His His His His
1               5

<210> SEQ ID NO 325
<211> LENGTH: 16
<212> TYPE: PRT
<213> ORGANISM: Artificial Sequence
<220> FEATURE:
<223> OTHER INFORMATION: Synthetic Construct

<400> SEQUENCE: 325

Arg Leu Pro Leu Asp Asn Asn Ile Asp Tyr Gly Asp Phe Ala Lys Gly
1               5                   10                  15

<210> SEQ ID NO 326
<211> LENGTH: 14
<212> TYPE: PRT
<213> ORGANISM: Artificial Sequence
<220> FEATURE:
<223> OTHER INFORMATION: Synthetic Construct

<400> SEQUENCE: 326

Asn Val Leu Leu Ser Arg Gln Ile Asn Gly Ala Tyr Val His
1               5                   10

<210> SEQ ID NO 327
<211> LENGTH: 10
<212> TYPE: PRT
<213> ORGANISM: Artificial Sequence
<220> FEATURE:
<223> OTHER INFORMATION: Synthetic Construct

<400> SEQUENCE: 327

Glu Met Gly Ala Thr Ile Asn Val Met Ala
1               5                   10
```

POLYPEPTIDES THAT BIND COMPLEMENT COMPONENT C5 OR SERUM ALBUMIN AND FUSION PROTEINS THEREOF

RELATED INFORMATION PARAGRAPH

This application claims the benefit of the priority date of U.S. Provisional Application No. 62/531,215, filed on Jul. 11, 2017, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created Jan. 6, 2020, is named 51196-005002_Sequence_Listing_01.06.20_ST25 and is 357,627 bytes in size.

BACKGROUND

Complement component 5 (C5) is the fifth component of complement, which plays an important role in inflammatory and cell killing processes. An activation peptide, C5a, which is an anaphylatoxin that possesses potent spasmogenic and chemotactic activity, is derived from the alpha polypeptide via cleavage with a C5-convertase. The C5b macromolecular cleavage product can form a complex with the C6 complement component, and this complex is the basis for formation of the membrane attack complex (MAC), which includes additional complement components.

Improperly regulated C5 can lead to immuno-compromised patients or disorders characterized by excessive cellular degradation (e.g., hemolytic disorders cause by C5-mediated hemolysis).

As misregulated C5 can lead to severe and devastating phenotypes, modulators of C5 activity with favorable pharmaceutical properties (e.g., half-life) are needed.

SUMMARY

The disclosure provides engineered polypeptides that specifically bind to complement component C5 or serum albumin, wherein such engineered polypeptides may be sdAbs or Ig variable domains. In some embodiments, the engineered polypeptides do not significantly reduce or inhibit the binding of serum albumin to FcRn or do not significantly reduce the half-life of serum albumin. The disclosure also provides fusion proteins comprising such engineered polypeptides, wherein such fusion proteins may be multivalent and multi-specific fusion proteins. The disclosure further provides nucleic acid molecules that encode such engineered polypeptides or fusion proteins, and methods of making such engineered polypeptides or fusion proteins. The disclosure further provides pharmaceutical compositions that comprise such engineered polypeptides or fusion proteins, and methods of treatment using such engineered polypeptides or fusion proteins.

In one embodiment, the disclosure is directed to a fusion protein comprising an engineered polypeptide that specifically binds to human complement component C5 and an engineered polypeptide that specifically binds to human serum albumin, wherein the engineered polypeptide that specifically binds to human complement component C5 is fused to the polypeptide that specifically binds to human serum albumin either directly or via a peptide linker. In a particular embodiment, the C-terminal residue of the polypeptide that specifically binds to human serum albumin is fused either directly or via a linker to the N-terminal residue of the polypeptide that specifically binds to human complement component C5. In a particular embodiment, the C-terminal residue of the polypeptide that specifically binds to human complement component C5 is fused either directly or via a linker to the N-terminal residue of the polypeptide that specifically binds to human serum albumin. In a particular embodiment, the polypeptide that specifically binds to human complement component C5 comprises an amino acid sequence selected from the group consisting of SEQ ID NOS:1-12 and fragments thereof; and the polypeptide that specifically binds to human serum albumin comprises an amino acid selected from the group consisting of SEQ ID NOs:22-34 and fragments thereof. In a particular embodiment, the polypeptide that specifically binds to human complement component C5 comprises the amino acid sequence of SEQ ID NO:11 and the polypeptide that specifically binds to human serum albumin comprises the amino acid sequence of SEQ ID NO:26. In a particular embodiment, the fusion proteins described herein further comprise a peptide linker having an amino acid sequence of SEQ ID NO:102 or 103. In a particular embodiment, the fusion protein comprises a sequence that is at least 95% identical to a sequence selected from the group consisting of SEQ ID NOS:96-101. In a particular embodiment, the fusion protein consists of a sequence selected from the group consisting of SEQ ID NOS:96-101. In a particular embodiment, the fusion protein consists of a polypeptide sequence of SEQ ID NO:96. In a particular embodiment, the polypeptide that specifically binds to human complement component C5 comprises three complementarity determining regions, CDR1, CDR2 and CDR3, wherein CDR1 comprises any one of the amino acid sequences of SEQ ID NOS:13-17, CDR2 comprises an amino acid sequences of SEQ ID NO:18 or 19, and CDR3 comprises an amino acid sequences of SEQ ID NO:20 or 21. In a particular embodiment, the polypeptide that specifically binds to human serum albumin comprises three complementarity determining regions, CDR1, CDR2 and CDR3, wherein CDR1 comprises any one of the amino acid sequences of SEQ ID NOS:35-43, CDR2 comprises any one of the amino acid sequences of SEQ ID NOS:44-51, and CDR3 comprises any one of the amino acid sequences of SEQ ID NOS:52-63. In some embodiments, the antigen-binding domains described herein, can be engineered or further engineered to bind antigen in a pH-dependent manner, e.g., high affinity for antigen at high pH and a lower affinity for antigen binding at lower pH, or vice versa.

In one embodiment, the disclosure is directed to a pharmaceutical composition comprising a therapeutically effective amount of a fusion protein described herein and a pharmaceutically acceptable carrier. In a particular embodiment, the pharmaceutical compositions can contain an agent that degrades or inactivates hyaluronan, e.g., hyaluronidase or a recombinant hyaluronidase.

In one embodiment, the disclosure is directed to an isolated nucleic acid molecule comprising a nucleotide sequence encoding a fusion protein described herein. The nucleic acid molecule can be, for example, an expression vector. The disclosure is directed to host cells, (e.g., Chinese hamster ovary (CHO) cells, HEK293 cells, *Pichia pastoris* cells, mammalian cells, yeast cells, plant cells) and expression systems that comprise or utilize the nucleic acids that encode a fusion proteins described herein.

In one embodiment, the disclosure is directed to an engineered polypeptide that binds to human complement component C5, wherein the engineered polypeptide comprises an amino acid sequence selected from the group consisting of SEQ ID NOS:1-12 and fragments thereof. In a particular embodiment, the engineered polypeptide comprises an amino acid sequence that is at least 90% identical (e.g., 90%, 91%, 92%, 93%, 94%, 95%, 96%, 97%, 98%, or 99% identical) to a sequence selected from the group consisting of SEQ ID NOS:1-12. For example, in one embodiment, the engineered polypeptide comprises the amino acid sequence set forth in SEQ ID NO:1 or a sequence at least 90% identical thereto. In another embodiment, the engineered polypeptide comprises the amino acid sequence set forth in SEQ ID NO:2 or a sequence at least 90% identical thereto. In another embodiment, the engineered polypeptide comprises the amino acid sequence set forth in SEQ ID NO:3 or a sequence at least 90% identical thereto. In another embodiment, the engineered polypeptide comprises the amino acid sequence set forth in SEQ ID NO:4 or a sequence at least 90% identical thereto. In another embodiment, the engineered polypeptide comprises the amino acid sequence set forth in SEQ ID NO:5 or a sequence at least 90% identical thereto. In another embodiment, the engineered polypeptide comprises the amino acid sequence set forth in SEQ ID NO:6 or a sequence at least 90% identical thereto. In another embodiment, the engineered polypeptide comprises the amino acid sequence set forth in SEQ ID NO:7 or a sequence at least 90% identical thereto. In another embodiment, the engineered polypeptide comprises the amino acid sequence set forth in SEQ ID NO:8 or a sequence at least 90% identical thereto. In another embodiment, the engineered polypeptide comprises the amino acid sequence set forth in SEQ ID NO:9 or a sequence at least 90% identical thereto. In another embodiment, the engineered polypeptide comprises the amino acid sequence set forth in SEQ ID NO:10 or a sequence at least 90% identical thereto. In another embodiment, the engineered polypeptide comprises the amino acid sequence set forth in SEQ ID NO:11 or a sequence at least 90% identical thereto. In another embodiment, the engineered polypeptide comprises the amino acid sequence set forth in SEQ ID NO:12 or a sequence at least 90% identical thereto.

In another embodiment, an engineered polypeptide is provided that binds to human complement component C5, wherein the engineered polypeptide consists of an amino acid sequence selected from the group consisting of SEQ ID NOS:1-12 and fragments thereof. For example, in one embodiment, the engineered polypeptide consists of the amino acid sequence set forth in SEQ ID NO:1. In another embodiment, the engineered polypeptide consists of the amino acid sequence set forth in SEQ ID NO:2. In another embodiment, the engineered polypeptide consists of the amino acid sequence set forth in SEQ ID NO:3. In another embodiment, the engineered polypeptide consists of the amino acid sequence set forth in SEQ ID NO:4. In another embodiment, the engineered polypeptide consists of the amino acid sequence set forth in SEQ ID NO:5. In another embodiment, the engineered polypeptide consists of the amino acid sequence set forth in SEQ ID NO:6. In another embodiment, the engineered polypeptide consists of the amino acid sequence set forth in SEQ ID NO:7. In another embodiment, the engineered polypeptide consists of the amino acid sequence set forth in SEQ ID NO:8. In another embodiment, the engineered polypeptide consists of the amino acid sequence set forth in SEQ ID NO:9. In another embodiment, the engineered polypeptide consists of the amino acid sequence set forth in SEQ ID NO:10. In another embodiment, the engineered polypeptide consists of the amino acid sequence set forth in SEQ ID NO:11. In another embodiment, the engineered polypeptide consists of the amino acid sequence set forth in SEQ ID NO:12.

In one embodiment, the disclosure is directed to an engineered polypeptide that specifically binds to human serum albumin, wherein the polypeptide comprises and amino acid sequence selected from the group consisting of SEQ ID NOS:22-34 and fragments thereof. In a particular embodiment, the engineered polypeptide comprises an amino acid sequence that is at least 90% identical (e.g., 90%, 91%, 92%, 93%, 94%, 95%, 96%, 97%, 98%, or 99% identical) to any one of the amino acid sequences of SEQ ID NOS:22-34. For example, in one embodiment, the engineered polypeptide comprises the amino acid sequence set forth in SEQ ID NO:22 or a sequence at least 90% identical thereto. In another embodiment, the engineered polypeptide comprises the amino acid sequence set forth in SEQ ID NO:23 or a sequence at least 90% identical thereto. In another embodiment, the engineered polypeptide comprises the amino acid sequence set forth in SEQ ID NO:24 or a sequence at least 90% identical thereto. In another embodiment, the engineered polypeptide comprises the amino acid sequence set forth in SEQ ID NO:25 or a sequence at least 90% identical thereto. In another embodiment, the engineered polypeptide comprises the amino acid sequence set forth in SEQ ID NO:26 or a sequence at least 90% identical thereto. In another embodiment, the engineered polypeptide comprises the amino acid sequence set forth in SEQ ID NO:27 or a sequence at least 90% identical thereto. In another embodiment, the engineered polypeptide comprises the amino acid sequence set forth in SEQ ID NO:28 or a sequence at least 90% identical thereto. In another embodiment, the engineered polypeptide comprises the amino acid sequence set forth in SEQ ID NO:29 or a sequence at least 90% identical thereto. In another embodiment, the engineered polypeptide comprises the amino acid sequence set forth in SEQ ID NO:30 or a sequence at least 90% identical thereto. In another embodiment, the engineered polypeptide comprises the amino acid sequence set forth in SEQ ID NO:31 or a sequence at least 90% identical thereto. In another embodiment, the engineered polypeptide comprises the amino acid sequence set forth in SEQ ID NO:32 or a sequence at least 90% identical thereto. In another embodiment, the engineered polypeptide comprises the amino acid sequence set forth in SEQ ID NO:33 or a sequence at least 90% identical thereto. In another embodiment, the engineered polypeptide comprises the amino acid sequence set forth in SEQ ID NO:34 or a sequence at least 90% identical thereto.

In another embodiment, the engineered polypeptide that specifically binds to human serum albumin consists of an amino acid sequence selected from the group consisting of SEQ ID NOS:22-34 and fragments thereof. For example, in one embodiment, the engineered polypeptide consists of the amino acid sequence set forth in SEQ ID NO:22. In another embodiment, the engineered polypeptide consists of the amino acid sequence set forth in SEQ ID NO:23. In another embodiment, the engineered polypeptide consists of the amino acid sequence set forth in SEQ ID NO:24. In another embodiment, the engineered polypeptide consists of the amino acid sequence set forth in SEQ ID NO:25. In another embodiment, the engineered polypeptide consists of the amino acid sequence set forth in SEQ ID NO:26. In another embodiment, the engineered polypeptide consists of the amino acid sequence set forth in SEQ ID NO:27. In another embodiment, the engineered polypeptide consists of the amino acid sequence set forth in SEQ ID NO:28. In another embodiment, the engineered polypeptide consists of the amino acid sequence set forth in SEQ ID NO:29. In another embodiment, the engineered polypeptide consists of the amino acid sequence set forth in SEQ ID NO:30. In another embodiment, the engineered polypeptide consists of the amino acid sequence set forth in SEQ ID NO:31. In another embodiment, the engineered polypeptide consists of the amino acid sequence set forth in SEQ ID NO:32. In another embodiment, the engineered polypeptide consists of the amino acid sequence set forth in SEQ ID NO:33. In another embodiment, the engineered polypeptide consists of the amino acid sequence set forth in SEQ ID NO:34.

In a particular embodiment, the engineered polypeptide that specifically binds to human serum albumin comprises three complementarity determining regions, CDR1, CDR2 and CDR3, wherein CDR1 comprises an amino acid sequence selected from the group consisting of SEQ ID NOs:35-43, CDR2 comprises an amino acid sequence selected from the group consisting of SEQ ID NOs:44-51, and CDR3 comprises an amino acid sequence selected from the group consisting of SEQ ID NOs:52-63. In a particular embodiment, the polypeptide specifically binds to the same epitope on human serum albumin as Alb1.

In one embodiment, the disclosure is directed to a method for making a fusion protein described herein, comprising expressing in a host cell at least one nucleic acid molecule comprising a nucleotide sequence encoding the fusion protein.

In one embodiment, the disclosure is directed to a therapeutic kit comprising: (a) a container comprising a label; and (b) a composition comprising the fusion protein described herein; wherein the label indicates that the composition is to be administered to a patient having, or that is suspected of having, a complement-mediated disorder. The kit can optionally comprise an agent that degrades or inactivates hyaluronan, e.g., hyaluronidase or a recombinant hyaluronidase.

In one embodiment, the disclosure is directed to a method for treating a patient having a complement-mediated disorder, the method comprising administering to the patient a therapeutically effective amount of a fusion protein described herein. In a particular embodiment, the complement-mediated disorder is selected from the group consisting of: rheumatoid arthritis; lupus nephritis; asthma; ischemia-reperfusion injury; atypical hemolytic uremic syndrome; dense deposit disease; paroxysmal nocturnal hemoglobinuria; macular degeneration; hemolysis, elevated liver enzymes, and low platelets (HELLP) syndrome; Guillain-Barré Syndrome; CHAPLE syndrome; myasthenia gravis; neuromyelitis optica; post-hematopoietic stem cell transplant thrombotic microangiopathy (post-HSCT-TMA); post-bone marrow transplant TMA (post-BMT TMA); Degos disease; Gaucher's disease; glomerulonephritis; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis.

DETAILED DESCRIPTION

Figure 1A:
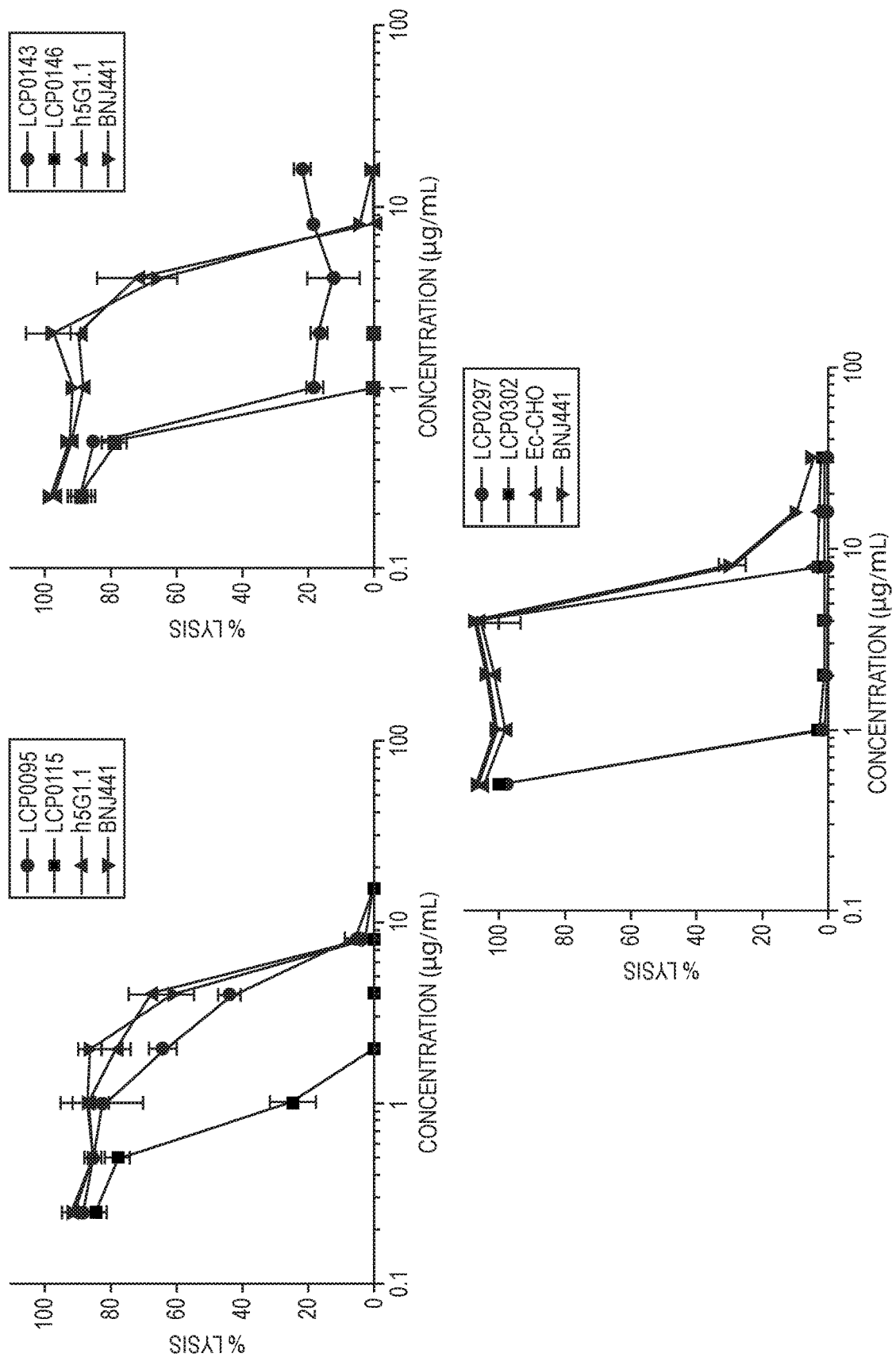
FIGS. 1A and 1B show the results of a Complement Classical Pathway (CCP) hemolysis assay for anti-C5 VHH domains.

The disclosure provides engineered polypeptides that specifically bind to serum albumin or complement component C5, wherein the engineered polypeptides can be, for example, single-domain antibodies (sdAb's) or immunoglobulin (IgG) variable domains. In some embodiments, the engineered polypeptides do not significantly reduce or inhibit the binding of serum albumin to FcRn or do not significantly reduce the half-life of serum albumin. The disclosure also provides fusion proteins comprising engineered polypeptides, wherein the fusion proteins can be, for example, multivalent and multi-specific fusion proteins. The disclosure further provides nucleic acid molecules that encode engineered polypeptides or fusion proteins, and methods of making such engineered polypeptides or fusion proteins. The disclosure further provides pharmaceutical compositions that comprise engineered polypeptides or fusion proteins, and methods of treatment using such engineered polypeptides or fusion proteins.

Standard recombinant DNA methodologies are used to construct polynucleotides encoding the engineered polypeptides or fusion proteins of the disclosure, incorporate such polynucleotides into recombinant expression vectors, and introduce such vectors into host cells to produce the engineered polypeptides or fusion proteins of the disclosure. See e.g., Sambrook et al., 2001, MOLECULAR CLONING: A LABORATORY MANUAL (Cold Spring Harbor Laboratory Press, 3rd ed.). Unless specific definitions are provided, the nomenclature utilized in connection with, and the laboratory procedures and techniques of, analytical chemistry, synthetic organic chemistry, and medicinal and pharmaceutical chemistry described herein are those known and commonly used in the art. Similarly, conventional techniques can be used for chemical syntheses, chemical analyses, pharmaceutical preparation, formulation, delivery and treatment of patients.

Definitions

As utilized in accordance with the present disclosure, the following terms, unless otherwise indicated, shall be understood to have the following meanings. Unless otherwise required by context, singular terms shall include pluralities and plural terms shall include the singular.

As used herein, the term "binding domain" refers to the portion of a protein or antibody which comprises the amino acid residues that interact with an antigen. Binding domains include, but are not limited to, antibodies (e.g., full length antibodies), as well as antigen-binding portions thereof. The binding domain confers on the binding agent its specificity and affinity for the antigen. The term also covers any protein having a binding domain which is homologous or largely homologous to an immunoglobulin-binding domain.

The term "antibody" as referred to herein includes whole antibodies and any antigen binding fragment (i.e., "antigen-binding portion") or single chain version thereof. An "antibody" refers, in one preferred embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding fragment" of an antibody (or simply "antibody fragment"), as used herein, refers to one or more fragments or portions of an antibody that retain the ability to specifically bind to an antigen. Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (sFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

The term "human antibody," as used herein, refers to an immunoglobulin (Ig) that is used, for example, by the immune system to bind and neutralize pathogens. The term includes antibodies having variable and constant regions substantially corresponding to human germline Ig sequences. In some embodiments, human antibodies are produced in non-human mammals, including, but not limited to, rodents, such as mice and rats, and lagomorphs, such as rabbits. In other embodiments, human antibodies are produced in hybridoma cells. In still other embodiments, human antibodies are produced recombinantly. As used herein, human antibodies include all or a portion of an antibody, including, for example, heavy and light chains, variable regions, constant regions, proteolytic fragments, complementarity determining regions (CDRs), and other functional fragments.

As used herein, "biologically active fragment" refers to a portion of a molecule, e.g., a gene, coding sequence, mRNA, polypeptide or protein, which has a desired length or biological function. A biologically active fragment of a protein, for example, can be a fragment of the full-length protein that retains one or more biological activities of the protein. A biologically active fragment of an mRNA, for example, can be a fragment that, when translated, expresses a biologically active protein fragment. A biologically active mRNA fragment, furthermore, can comprise shortened versions of non-coding sequences, e.g., regulatory sequences, UTRs, etc. In general, a fragment of an enzyme or signaling molecule can be, for example, that portion(s) of the molecule that retains its signaling or enzymatic activity. A fragment of a gene or coding sequence, for example, can be that portion of the gene or coding sequence that produces an expression product fragment. A fragment does not necessarily have to be defined functionally, as it can also refer to a portion of a molecule that is not the whole molecule, but has some desired characteristic or length (e.g., restriction fragments, proteolytic fragment of a protein, amplification fragments, etc.).

Ordinary or conventional mammalian antibodies comprise a tetramer, which is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain," as used herein, refer to any Ig polypeptide having sufficient variable domain sequence to confer specificity for a target antigen. The N-terminal portion of each light and heavy chain typically includes a variable domain of about 100 to 110 or more amino acids that typically is responsible for antigen recognition. The C-terminal portion of each chain typically defines a constant domain responsible for effector function. Thus, in a naturally occurring antibody, a full-length heavy chain Ig polypeptide includes a variable domain ($V_H$ or VH) and three constant domains ($C_{H1}$ or CH1, $C_{H2}$ or CH2, and $C_{H3}$ or CH3), wherein the $V_H$ domain is at the N-terminus of the polypeptide and the $C_{H3}$ domain is at the C-terminus, and a full-length light chain Ig polypeptide includes a variable domain ($V_L$ or VL) and a constant domain ($C_L$ or CL), wherein the $V_L$ domain is at the N-terminus of the polypeptide and the $C_L$ domain is at the C-terminus.

Within full-length light and heavy chains, the variable and constant domains typically are joined by a "J" region of about 12 or more amino acids, with the heavy chain also including a "D" region of about 10 more amino acids. The variable regions of each light/heavy chain pair typically form an antigen-binding site. The variable domains of naturally occurring antibodies typically exhibit the same general structure of relatively conserved framework regions (FR) joined by three hypervariable regions called CDRs. The CDRs from the two chains of each pair typically are aligned by the framework regions, which enables binding to a specific epitope. From the N-terminus to the C-terminus, both light and heavy chain variable domains typically comprise the domains FR1, CDR1, FR2, CDR2, FR3, CDR3 and FR4.

The terms "substantially pure" or "substantially purified," as used herein, refer to a compound or species that is the predominant species present in a composition (i.e., on a molar basis it is more abundant than any other individual species in the composition). A substantially purified fraction, for example, can be a composition wherein the predominant species comprises at least about 50% (on a molar basis) of all macromolecular species present. A substantially pure composition, for example, can comprise a predominant species that represents more than about 80%, 85%, 90%, 95% or 99% of all macromolar species present in the composition. In other embodiments, the predominant species can be purified to substantial homogeneity (contaminant species cannot be detected in the composition by conventional detection methods) wherein the composition consists essentially of a single macromolecular species.

The terms "antigen" or "antigen target," as used herein, refer to a molecule or a portion of a molecule that is capable of being bound to by an antibody, one or more Ig binding domain, or other immunological binding moiety, including, for example, the engineered polypeptides or fusion proteins disclosed herein. An antigen is capable of being used in an animal to produce antibodies capable of binding to an epitope of that antigen. An antigen may have one or more epitopes.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from the antigen are tested for reactivity with the given antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

The terms "activity," "biological activity," or "biological property," as used in reference to the engineered polypeptides or fusion proteins of the disclosure, include, but are not limited to, epitope affinity and specificity, ability to antagonize the activity of an antigen target, the in vivo stability of the engineered polypeptides or fusion proteins of the disclosure, and the immunogenic properties of the engineered polypeptides or fusion proteins of the disclosure. Other identifiable biological properties include, for example, cross-reactivity (e.g., with non-human homologs of the antigen target, or with other antigen targets or tissues, generally), and ability to preserve high expression levels of protein in mammalian cells.

An antibody, immunoglobulin, or immunologically functional immunoglobulin fragment, or the engineered polypeptides or fusion proteins disclosed herein, are said to "specifically" bind an antigen when the molecule preferentially recognizes its antigen target in a complex mixture of proteins and/or macromolecules. The term "specifically binds," as used herein, refers to the ability of an antibody, immunoglobulin, or immunologically functional immunoglobulin fragment, or an engineered polypeptide or fusion protein of the disclosure, to bind to an antigen containing an epitope with an $K_D$ of at least about $10^{-6}$ M, $10^{-7}$ M, $10^{-8}$ M, $10^{-9}$ M, $10^{-10}$ M, $10^{-11}$ M, $10^{-12}$ M, or more, and/or to bind to an epitope with an affinity that is at least two-fold greater than its affinity for a nonspecific antigen.

The term "$K_D$," as used herein, refers to the dissociation constant of the interaction between an antibody, immunoglobulin, or immunologically functional immunoglobulin fragment, or an engineered polypeptide or fusion protein disclosed herein, and an antigen target. When an engineered polypeptide or fusion protein of the disclosure comprises a monovalent Ig sequence, the monovalent Ig sequence preferably binds to a desired antigen, for example, with a $K_D$ of $10^{-5}$ to $10^{-12}$ M or less, or $10^{-7}$ to $10^{-12}$ M or less, or $10^{-3}$ to $10^{-12}$ M, and/or with a binding affinity of at least $10^{-7}$ M$^{-1}$, at least $10^{-8}$ M$^{-1}$, at least $10^{-9}$ M$^{-1}$, or at least $10^{-12}$ M$^{-1}$. A $K_D$ value greater than $10^{-4}$ M is generally considered to indicate non-specific binding. In some embodiments, a monovalent Ig sequence of an engineered polypeptide or fusion protein of the disclosure binds to a desired antigen with an affinity less than 500 mM, less than 200 nM, less than 10 nM, or less than 500 pM.

A $K_D$ can be determined by methods known in the art, including, for example, surface plasmon resonance (SPR). Generally, SPR analysis measures real-time binding interactions between a ligand (a target antigen on a biosensor matrix) and an analyte using, for example, the BIAcore system (Pharmacia Biosensor; Piscataway, N.J.). SPR analysis can also be performed by immobilizing an analyte and presenting the ligand. Specific binding of an engineered polypeptide or fusion protein of the disclosure to an antigen or antigenic determinant can also be determined in any suitable manner known in the art, including, for example, Scatchard analysis and/or competitive binding assays, such as radioimmunoassays (RIA), enzyme immunoassays (EIA) and sandwich competition assays.

The term "bispecific" refers to a fusion protein of the disclosure that is capable of binding two antigens. The term "multivalent fusion protein" means a fusion protein comprising two or more antigen binding sites.

The term "multi-specific fusion protein" refers to a fusion protein of the disclosure that is capable of binding two or more related or unrelated targets.

The term "fused to" as used herein refers to a polypeptide made by combining more than one sequence, typically by cloning one sequence, e.g., a coding sequence, into an expression vector in frame with one or more second coding sequence(s) such that the two (or more) coding sequences are transcribed and translated into a single continuous polypeptide. In addition to being made by recombinant technology, parts of a polypeptide can be "fused to" each other by means of chemical reaction, or other means known in the art for making custom polypeptides.

The term "vector," as used herein, refers to any molecule (e.g., nucleic acid, plasmid or virus) that is used to transfer coding information to an expression system (e.g., a host cell or in vitro expression system). One type of vector is a "plasmid," which refers to a circular double-stranded DNA (dsDNA) molecule into which additional DNA segments can be inserted. Another type of vector is a viral vector, wherein additional DNA segments can be inserted into a viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of coding sequences to which they are operatively linked. Such vectors are referred to herein as "expression vectors."

The term "operably linked," as used herein, refers to an arrangement of flanking sequences wherein the flanking sequences are configured or assembled to perform a desired function. Thus, a flanking sequence operably linked to a coding sequence may be capable of effecting the replication, transcription, and/or translation of the coding sequence. A coding sequence is operably linked to a promoter, for example, where the promoter is capable of directing transcription of that coding sequence. A flanking sequence need not be contiguous with the coding sequence to be considered operably linked, so long as it functions correctly.

The term "host cell," as used herein, refers to a cell into which an expression vector has been introduced. A host cell is intended to refer not only to the particular subject cell, but also to the progeny of such a cell. Because certain modifications may occur in succeeding generations due to either mutation or environmental influences, such progeny may not be, in fact, identical to the parent cell, but such cells are still included within the scope of the term "host cell" as used herein. A wide variety of host cell expression systems can be used to express the engineered polypeptides or fusion proteins of the disclosure, including bacterial, yeast, baculoviral, and mammalian expression systems (as well as phage display expression systems).

The term "naturally occurring," as used herein and applied to a particular molecule, refers to a molecule that is found in nature and has not been manipulated by man. Similarly, the term "non-naturally occurring," as used herein, refers to a molecule that is not found in nature or that has been modified or artificially synthesized.

The term "engineered," as used herein and applied to a particular molecule, such as, for example, a polypeptide, that has been modified or manipulated, such as by mutation, truncation, deletion, substitution, addition, conjugation or by otherwise changing the primary sequence, chemical or three-dimensional structure, chemical signature, folding behavior, glycosylation state, or any other attribute of the molecule, such that the molecule differs from its naturally occurring counterpart.

The term "patient" as used herein includes human and animal subjects.

A "disorder" is any condition that would benefit from treatment using the engineered polypeptides or fusion proteins of the disclosure. "Disorder" and "condition" are used interchangeably herein.

A "complement-mediated disorder" as used herein refers to a disorder caused, directly or indirectly, by mis-regulation of the complement pathway, e.g., activation or suppression of the complement pathway, or a disorder that is mediated, directly or indirectly, by one or more components of the complement pathway, or a product generated by the complement pathway. The term also refers to a disorder that is exacerbated by one or more components of the complement pathway, or a product generated by the complement pathway.

The terms "treatment" or "treat," as used herein, refer to both therapeutic treatment and prophylactic or preventative measures. Those in need of treatment include those having the disorder as well as those at risk of having the disorder or those in which the disorder is to be prevented.

As used herein, a "therapeutically effective" amount of, for example, a fusion protein or engineered polypeptide described herein, is an amount that, when administered, results in a decrease in severity of disease symptoms (e.g., a decrease in symptoms of disorders associated with a complement-mediated disorder, an increase in frequency and duration of disease symptom free periods, or a prevention of impairment or disability due to the disease affliction. In certain embodiments, a therapeutically effective amount of a therapeutic agent described herein can include an amount (or various amounts in the case of multiple administrations) that reduces hemolysis, or improves symptoms of a complement-mediated disorder.

The terms "pharmaceutical composition" or "therapeutic composition," as used herein, refer to a compound or composition capable of inducing a desired therapeutic effect when administered to a patient.

The term "pharmaceutically acceptable carrier" or "physiologically acceptable carrier," as used herein, refers to one or more formulation materials suitable for accomplishing or enhancing the delivery of the engineered polypeptides or fusion proteins of the disclosure.

The term "therapeutically effective amount," as used in reference to a pharmaceutical composition comprising one or more engineered polypeptides or fusion proteins of the disclosure, refers to an amount or dosage sufficient to produce a desired therapeutic result. More specifically, a therapeutically effective amount is an amount of one or more engineered polypeptides or fusion proteins of the disclosure sufficient to inhibit, for some period of time, one or more of the clinically defined pathological processes associated with the condition being treated, e.g., a complement-mediated disorder. The therapeutically effective amount may vary depending on the specific engineered polypeptide or fusion protein that is being used, and depends on a variety of factors and conditions related to the patient being treated and the severity of the disorder.

Complement System

The complement system acts in conjunction with other immunological systems of the body to defend against intrusion of cellular and viral pathogens. There are at least 25 complement proteins, which are a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory and lytic functions.

The complement cascade can progress via the classical pathway (CP), the lectin pathway or the alternative pathway (AP). The lectin pathway is typically initiated with binding of mannose-binding lectin (MBL) to high mannose substrates. The AP can be antibody independent and initiated by certain molecules on pathogen surfaces. The CP is typically initiated by antibody recognition of, and binding to, an antigenic site on a target cell. These pathways converge at the C3 convertase— where complement component C3 is cleaved by an active protease to yield C3a and C3b.

Spontaneous hydrolysis of complement component C3, which is abundant in the plasma fraction of blood, can also lead to AP C3 convertase initiation. This process, known as "tickover," occurs through the spontaneous cleavage of a thioester bond in C3 to form C3i or C3($H_2$0). Tickover is facilitated by the presence of surfaces that support the binding of activated C3 and/or have neutral or positive charge characteristics (e.g., bacterial cell surfaces). Formation of C3($H_2$0) allows for the binding of plasma protein Factor B, which in turn allows Factor D to cleave Factor B into Ba and Bb. The Bb fragment remains bound to C3 to form a complex containing C3($H_2$0)Bb—the "fluid-phase" or "initiation" C3 convertase. Although only produced in small amounts, the fluid-phase C3 convertase can cleave multiple C3 proteins into C3a and C3b and results in the generation of C3b and its subsequent covalent binding to a surface (e.g., a bacterial surface). Factor B bound to the surface-bound C3b is cleaved by Factor D to form the surface-bound AP C3 convertase complex containing C3b, Bb.

The AP C5 convertase ((C3b)$_2$,Bb) is formed upon addition of a second C3b monomer to the AP C3 convertase. The role of the second C3b molecule is to bind C5 and present it for cleavage by Bb. The AP C3 and C5 convertases are stabilized by the addition of the trimeric protein properdin. Properdin binding, however, is not required to form a functioning alternative pathway C3 or C5 convertase.

The CP C3 convertase is formed upon interaction of complement component C1, which is a complex of C1q, C1r and C1s, with an antibody that is bound to a target antigen (e.g., a microbial antigen). The binding of the C1q portion of C1 to the antibody-antigen complex causes a conformational change in C1 that activates C1r. Active C1r then cleaves the C1-associated C1s to generate an active serine protease. Active C1s cleaves complement component C4 into C4b and C4a. Like C3b, the newly generated C4b fragment contains a highly reactive thiol that readily forms amide or ester bonds with suitable molecules on a target surface (e.g., a microbial cell surface). C1s also cleaves complement component C2 into C2b and C2a. The complex formed by C4b and C2a is the CP C3 convertase, which is capable of processing C3 into C3a and C3b. The CP C5 convertase (C4b,C2a,C3b) is formed upon addition of a C3b monomer to the CP C3 convertase.

In addition to its role in C3 and C5 convertases, C3b also functions as an opsonin through its interaction with complement receptors present on the surfaces of antigen-presenting cells such as macrophages and dendritic cells. The opsonic function of C3b is generally considered one of the most important anti-infective functions of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone.

The AP and CP C5 convertases cleave C5 into C5a and C5b. Cleavage of C5 releases C5a, a potent anaphylatoxin and chemotactic factor, and C5b, which allows for the formation of the lytic terminal complement complex, C5b-9. C5b combines with C6, C7 and C8 to form the C5b-8 complex at the surface of the target cell. Upon binding of several C9 molecules, the membrane attack complex (MAC, C5b-9, terminal complement complex ("TCC")) is formed. When sufficient numbers of MACs insert into target cell membranes, the openings they create (MAC pores) mediate rapid osmotic lysis of the target cells.

While a properly functioning complement system provides a robust defense against infecting microbes, inappropriate regulation or activation of the complement pathways has been implicated in the pathogenesis of a variety of disorders including, e.g., rheumatoid arthritis (RA); lupus nephritis; asthma; ischemia-reperfusion injury; atypical hemolytic uremic syndrome (aHUS); dense deposit disease (DDD); paroxysmal nocturnal hemoglobinuria (PNH); macular degeneration (e.g., age-related macular degeneration (AMD)); hemolysis, elevated liver enzymes and low platelets (HELLP) syndrome; Guillain-Barré Syndrome (GBS); protein-losing enteropathy (e.g., CHAPLE syndrome); myasthenia gravis (MG); neuromyelitis optica (NMO); post-hematopoietic stem cell transplant thrombotic microangiopathy (post-HSCT-TMA); post-bone marrow transplant TMA (post-BMT TMA); Degos disease; Gaucher's disease; glomerulonephritis; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis (Holers, V., *Immunol. Rev.*, 223:

300-16, 2008). The down-regulation of complement activation has been demonstrated to be effective in treating several disease indications in a variety of animal models (Rother, R. et al., *Nat. Biotechnol.*, 25:1256-64, 2007; Wang, Y. et al., *Proc. Natl. Acad. Sci. USA*, 93:8563-8, 1996; Wang, Y. et al., *Proc. Natl. Acad. Sci. USA*, 92:8955-9, 1995; Rinder, C. et al., *J. Clin. Invest.*, 96:1564-72, 1995; Kroshus, T. et al., *Transplantation*, 60:1194-202, 1995; Homeister, J. et al., *J. Immunol.*, 150:1055-64, 1993; Weisman, H. et al., *Science*, 249:146-51, 1990; Amsterdam, E. et al., *Am. J. Physiol.*, 268:H448-57, 1995; and Rabinovici, R. et al., *J. Immunol.*, 149:1744-50, 1992).

Human Serum Albumin and Neonatal Fc Receptor

Polypeptides that can bind to human serum albumin (HSA) to increase the half-life of therapeutically relevant proteins have been described (WO 91/01743, WO 01/45746 and WO 02/076489). The described peptide moieties, however, are of bacterial or synthetic origin, which is not preferred for use in therapeutics in humans. WO 04/041865 describes single-domain antibodies (sdAb's or Nanobodies®) directed against serum albumin (and in particular against HSA) that can be linked to other proteins (such as one or more other sdAb's directed against a desired target) to increase the half-life of the protein.

The neonatal Fc receptor (FcRn), also termed "Brambell receptor," is involved in prolonging the lifespan of albumin in circulation (Chaudhury, C. et al., *J. Exp. Med.*, 3:315-22, 2003). FcRn is an integral membrane glycoprotein consisting of a soluble light chain consisting of β2-microglobulin (β2m), non-covalently bound to a 43 kDa α chain with three extracellular domains, a transmembrane region and a cytoplasmic tail of about 50 amino acids. The cytoplasmic tail contains a dinucleotide motif endocytosis signal implicated in the internalization of the receptor. The α chain is a member of the non-classical MHC I family of proteins. The β2m association with the α chain is critical for correct folding of FcRn and exiting the endoplasmic reticulum for routing to endosomes and the cell surface.

The overall structure of FcRn is similar to that of class I molecules. The α-1 and α-2 regions resemble a platform composed of eight antiparallel strands forming a single β-sheet topped by two antiparallel α-helices very closely resembling the peptide cleft in MHC I molecules. Owing to an overall repositioning of the α-1 helix and bending of the C-terminal portion of the α-2 helix due to a break in the helix introduced by the presence of Pro162, the FcRn helices are close in proximity, occluding peptide binding. The side chain of Arg164 of FcRn also occludes the potential interaction of the peptide N-terminus with the MHC pocket. Further, salt bridge and hydrophobic interaction between the α-1 and α-2 helices may also contribute to the groove closure. FcRn therefore, does not participate in antigen presentation and the peptide cleft is empty.

FcRn binds and transports IgG across the placental syncytiotrophoblast from maternal circulation to fetal circulation and protects IgG from degradation in adults. In addition to homeostasis, FcRn controls transcytosis of IgG in tissues. FcRn is localized in epithelial cells, endothelial cells, and hepatocytes.

HSA binds FcRn to form a tri-molecular complex with IgG. Both albumin and IgG bind non-cooperatively to distinct sites on FcRn. Binding of human FcRn to Sepharose-HSA and Sepharose-hIgG is pH dependent, being maximal at pH 5 and undetectable at pH 7 through pH 8. The observation that FcRn binds albumin in the same pH-dependent fashion as it binds IgG suggests that the mechanism by which albumin interacts with FcRn and thus is protected from degradation is identical to that of IgG, and mediated via a similarly pH-sensitive interaction with FcRn. Using surface plasmon resonance to measure the capacity of individual HSA domains to bind immobilized soluble hFcRn, FcRn and albumin have been shown to interact via the D-III domain of albumin in a pH-dependent manner, on a site distinct from the IgG binding site (Chaudhury, C. et al., *Biochemistry*, 45:4983-90, 2006).

Engineered Polypeptides Specifically Bind Complement C5 or Serum Albumin

Described herein are engineered polypeptides comprising Ig sequences, e.g., Ig variable domain sequences, that can bind or otherwise associate with complement component C5 or serum albumin. Engineered polypeptides described herein can specifically bind serum albumin in such a way that, when the engineered polypeptide is bound to or otherwise associated with a serum albumin molecule, the binding of the serum albumin molecule to FcRn is not significantly reduced or inhibited as compared to the binding of the serum albumin molecule to FcRn when the polypeptide is not bound thereto. In this embodiment, "not significantly reduced or inhibited" means that the binding affinity for serum albumin to FcRn (as measured using a suitable assay, such as, for example, SPR) is not reduced by more than 50%, or by more than 30%, or by more than 10%, or by more than 5%, or not reduced at all. In this embodiment, "not significantly reduced or inhibited" also means that the half-life of the serum albumin molecule is not significantly reduced. In particular, the engineered polypeptides can to amino acid residues on serum albumin that are not involved in binding of serum albumin to FcRn. More particularly, engineered polypeptides can bind to amino acid residues or sequences of serum albumin that do not form part of domain III of serum albumin, e.g., engineered polypeptides that are capable of binding to amino acid residues or sequences of serum albumin that form part of domain I and/or domain II.

In some embodiments, the engineered polypeptides are sdAbs or suitable for use as sdAbs, and as such may be a heavy chain variable domain sequence or a light chain variable domain sequence, and in certain embodiments, are heavy chain variable domain sequences of a heavy chain antibody. In cases where the engineered polypeptides are single domain, heavy chain variable domain sequences from a heavy chain antibody, such sequences may be referred to as VHH or $V_HH$ antibodies, VHH or $V_HH$ antibody fragments, or VHH or $V_HH$ domains.

A "heavy chain antibody" refers to an antibody that consists of two heavy chains and lacks the two light chains found in conventional antibodies. Camelids (members of the biological family Camelidae, the only currently living family in the suborder Tylopoda; extant camelids include dromedary camels, Bactrian camels, wild or feral camels, llamas, alpacas, vicunas and guanacos) are the only mammals with single chain VHH antibodies. About 50% of the antibodies in camelids are heavy chain antibodies with the other 50% being of the ordinary or conventional mammalian heavy/light chain antibody type.

"VHH domain" refers to variable domains present in naturally occurring heavy chain antibodies to distinguish them from the heavy chain variable domains that are present in conventional four chain antibodies (referred to herein as "VH domains") and from the light chain variable domains that present in conventional four chain antibodies (referred to herein as "VL domains").

VHH domains have a number of unique structural characteristics and functional properties that make isolated VHH domains (as well as sdAbs, which are based on VHH domains and share these structural characteristics and functional properties with the naturally occurring VHH domains) and proteins containing the VHH domains highly advantageous for use as functional antigen binding domains or proteins. For example, VHH domains, which bind to an antigen without the presence of a VL, and sdAbs can function as a single, relatively small, functional antigen binding structural unit, domain or protein. The small size of these molecules distinguishes VHH domains from the VH and VL domains of conventional four-chain antibodies. The use of VHH domains and sdAbs as single antigen-binding proteins or as antigen-binding domains (e.g., as part of a larger protein or polypeptide) offers a number of significant advantages over the use of conventional VH and VL domains, as well as scFv or conventional antibody fragments (such as Fab or F(ab')2 fragments). Only a single domain is required to bind an antigen with high affinity and with high selectivity, for example, so that there is no need to have two separate domains present, nor to assure that these two domains are present in a particular spatial conformation and configuration (e.g., through the use of specific linkers, as with an scFv). VHH domains and sdAbs can also be expressed from a single gene and require no post-translational folding or modifications. VHH domains and sdAbs can easily be engineered into multivalent and multi-specific formats. VHH domains and sdAbs are also highly soluble and do not have a tendency to aggregate (Ward, E. et al., *Nature,* 341:544-6, 1989), and they are highly stable to heat, pH, proteases and other denaturing agents or conditions (Ewert, S. et al., *Biochemistry,* 41:3628-36, 2002). VHH domains and sdAbs are relatively easy and cheap to prepare, even on a scale required for production. For example, VHH domains, sdAbs, and polypeptides containing VHH domains or sdAbs can be produced using microbial fermentation using methods known in the art and do not require the use of mammalian expression systems, as with, for example, conventional antibody fragments. VHH domains and sdAbs are relatively small (approximately 15 kDa, or 10 times smaller than a conventional IgG) compared to conventional four-chain antibodies and antigen-binding fragments thereof, and therefore show higher penetration into tissues (including but not limited to solid tumors and other dense tissues) than conventional four-chain antibodies and antigen-binding fragments thereof. VHH domains and sdAbs can show so-called "cavity-binding" properties (due to, for example, their extended CDR3 loop) and can access targets and epitopes not accessible to conventional four-chain antibodies and antigen-binding fragments thereof. It has been shown, for example, that VHH domains and sdAbs can inhibit enzymes (WO 97/49805; Transue, T. et al., *Proteins,* 32:515-22, 1998; Lauwereys, M. et al., *EMBO J.,* 17:3512-20, 1998).

The term "single-domain antibody," or "sdAb," as used herein, is an antibody or fragment thereof consisting of a single monomeric variable antibody domain. It is not limited to a specific biological source or to a specific method of preparation. A sdAb can be obtained, for example, by (1) isolating the VHH domain of a naturally occurring heavy chain antibody; (2) expressing a nucleotide sequence encoding a naturally occurring VHH domain; (3) "humanization" of a naturally occurring VHH domain or by expression of a nucleic acid encoding such humanized VHH domain; (4) "camelization" of a naturally occurring VH domain from any animal species, in particular a species of mammal, such as from a human being, or by expression of a nucleic acid encoding such a camelized VH domain; (5) "camelization" of a "domain antibody" ("Dab") or by expression of a nucleic acid encoding such a camelized VH domain; (6) using synthetic or semi-synthetic techniques for preparing engineered polypeptides or fusion proteins; (7) preparing a nucleic acid encoding a sdAb using techniques for nucleic acid synthesis, followed by expression of the nucleic acid thus obtained; and/or (8) any combination of the above.

The engineered polypeptides or fusion proteins described herein can comprise, for example, amino acid sequences of naturally occurring VHH domains that have been "humanized," e.g., by replacing one or more amino acid residues in the amino acid sequence of the naturally occurring VHH sequence by one or more of the amino acid residues that occur at the corresponding positions in a VH domain from a human being.

The engineered polypeptides or fusion proteins described herein can comprise, for example, amino acid sequences of naturally occurring VH domains that have been "camelized," i.e., by replacing one or more amino acid residues in the amino acid sequence of a naturally occurring VH domain with one or more of the amino acid residues that occur at the corresponding positions in a VHH domain of, for example, a camelid antibody. This can be performed in a manner known in the art. Such camelization may preferentially occur at amino acid positions that are present at the VH-VL interface and at the so-called "Camelidae hallmark residues" (WO 94/04678). The VH domain or sequence that is used as a parental sequence or starting material for generating or designing the camelized sequence can be, for example, a VH sequence from a mammal, and in certain embodiments, the VH sequence of a human. It should be noted, however, that such camelized sequences can be obtained in any suitable manner known in the art and thus are not strictly limited to polypeptides that have been obtained using a polypeptide that comprises a naturally occurring parental VH domain.

Both "humanization" and "camelization" can be performed by providing a nucleotide sequence that encodes a naturally occurring VHH domain or $V_H$ domain, respectively, and then changing, in a manner known to those skilled in the art, one or more codons in the nucleotide sequence such that the new nucleotide sequence encodes a humanized or camelized sequence, respectively. Also, based on the amino acid sequence or nucleotide sequence of a naturally occurring VHH domain or VH domain, a nucleotide sequence encoding a desired humanized or camelized sequence can be designed and synthesized de novo using techniques for nucleic acid synthesis known in the art, after which the nucleotide sequence thus obtained can be expressed in a manner known in the art.

In some embodiments, the disclosure provides an engineered polypeptide that specifically binds to the same epitope on human C5 as eculizumab, or that binds to an epitope on C5 that prevents cleavage of C5 into C5a and C5b. In some embodiments, the disclosure provides an engineered polypeptide that specifically binds to human complement component C5, wherein the polypeptide comprises any one of the amino acid sequences of SEQ ID NOs:1-12 or a fragment thereof. In other embodiments, the disclosure provides an engineered polypeptide that specifically binds to human complement component C5, wherein the polypeptide comprises an amino acid sequence that is at least 90% identical to any one of the amino acid sequences of SEQ ID NOs:1-12. In other embodiments, the disclosure provides an engineered polypeptide that specifically binds to human complement component C5, wherein the polypeptide comprises an amino acid sequence that is at least 95% identical, at least 96% identical, at least 97% identical, at least 98% identical, or at least 99% identical to any one of the amino acid sequences of SEQ ID NOs:1-12. For example, in one embodiment, the engineered polypeptide comprises the amino acid sequence set forth in SEQ ID NO:1 or a sequence at least 90% identical thereto. In another embodiment, the engineered polypeptide comprises the amino acid sequence set forth in SEQ ID NO:2 or a sequence at least 90% identical thereto. In another embodiment, the engineered polypeptide comprises the amino acid sequence set forth in SEQ ID NO:3 or a sequence at least 90% identical thereto. In another embodiment, the engineered polypeptide comprises the amino acid sequence set forth in SEQ ID NO:4 or a sequence at least 90% identical thereto. In another embodiment, the engineered polypeptide comprises the amino acid sequence set forth in SEQ ID NO:5 or a sequence at least 90% identical thereto. In another embodiment, the engineered polypeptide comprises the amino acid sequence set forth in SEQ ID NO:6 or a sequence at least 90% identical thereto. In another embodiment, the engineered polypeptide comprises the amino acid sequence set forth in SEQ ID NO:7 or a sequence at least 90% identical thereto. In another embodiment, the engineered polypeptide comprises the amino acid sequence set forth in SEQ ID NO:8 or a sequence at least 90% identical thereto. In another embodiment, the engineered polypeptide comprises the amino acid sequence set forth in SEQ ID NO:9 or a sequence at least 90% identical thereto. In another embodiment, the engineered polypeptide comprises the amino acid sequence set forth in SEQ ID NO:10 or a sequence at least 90% identical thereto. In another embodiment, the engineered polypeptide comprises the amino acid sequence set forth in SEQ ID NO:11 or a sequence at least 90% identical thereto. In another embodiment, the engineered polypeptide comprises the amino acid sequence set forth in SEQ ID NO:12 or a sequence at least 90% identical thereto.

In another embodiment, an engineered polypeptide is provided that binds to human complement component C5, wherein the engineered polypeptide consists of an amino acid sequence selected from the group consisting of SEQ ID NOS:1-12 and fragments thereof. For example, in one embodiment, the engineered polypeptide consists of the amino acid sequence set forth in SEQ ID NO:1. In another embodiment, the engineered polypeptide consists of the amino acid sequence set forth in SEQ ID NO:2. In another embodiment, the engineered polypeptide consists of the amino acid sequence set forth in SEQ ID NO:3. In another embodiment, the engineered polypeptide consists of the amino acid sequence set forth in SEQ ID NO:4. In another embodiment, the engineered polypeptide consists of the amino acid sequence set forth in SEQ ID NO:5. In another embodiment, the engineered polypeptide consists of the amino acid sequence set forth in SEQ ID NO:6. In another embodiment, the engineered polypeptide consists of the amino acid sequence set forth in SEQ ID NO:7. In another embodiment, the engineered polypeptide consists of the amino acid sequence set forth in SEQ ID NO:8. In another embodiment, the engineered polypeptide consists of the amino acid sequence set forth in SEQ ID NO:9. In another embodiment, the engineered polypeptide consists of the amino acid sequence set forth in SEQ ID NO:10. In another embodiment, the engineered polypeptide consists of the amino acid sequence set forth in SEQ ID NO:11. In another embodiment, the engineered polypeptide consists of the amino acid sequence set forth in SEQ ID NO:12.

In another embodiment, the disclosure provides an engineered polypeptide that specifically binds to human complement component C5, wherein the polypeptide comprises three complementarity determining regions, CDR1, CDR2 and CDR3, wherein CDR1 comprises any one of the amino acid sequences of SEQ ID NOs:13-17 or a sequence that is at least 90% identical to SEQ ID NOs:13-17; CDR2 comprises an amino acid sequence of SEQ ID NOs:18 or 19 or a sequence that is at least 90% identical to SEQ ID NOs:18 or 19; and CDR3 comprises an amino acid sequence of SEQ ID NOs:20 or 21 or a sequence that is at least 90% identical to SEQ ID NOs:20 or 21.

In other embodiments, the disclosure provides an engineered polypeptide that specifically binds to human serum albumin, wherein the polypeptide comprises any one of the amino acid sequences of SEQ ID NOs:22-34, or a fragment thereof. In other embodiments, the disclosure provides an engineered polypeptide that specifically binds to human serum albumin, wherein the polypeptide comprises an amino acid sequence that is at least 90% identical to any one of the amino acid sequences of SEQ ID NOs:22-34. In other embodiments, the disclosure provides an engineered polypeptide that specifically binds to human serum albumin, wherein the polypeptide comprises an amino acid sequence that is at least 95% identical, at least 96% identical, at least 97% identical, at least 98% identical, or at least 99% identical to any one of the amino acid sequences of SEQ ID NOs:22-34. For example, in one embodiment, the engineered polypeptide comprises the amino acid sequence set forth in SEQ ID NO:22 or a sequence at least 90% identical thereto. In another embodiment, the engineered polypeptide comprises the amino acid sequence set forth in SEQ ID NO:23 or a sequence at least 90% identical thereto. In another embodiment, the engineered polypeptide comprises the amino acid sequence set forth in SEQ ID NO:24 or a sequence at least 90% identical thereto. In another embodiment, the engineered polypeptide comprises the amino acid sequence set forth in SEQ ID NO:25 or a sequence at least 90% identical thereto. In another embodiment, the engineered polypeptide comprises the amino acid sequence set forth in SEQ ID NO:26 or a sequence at least 90% identical thereto. In another embodiment, the engineered polypeptide comprises the amino acid sequence set forth in SEQ ID NO:27 or a sequence at least 90% identical thereto. In another embodiment, the engineered polypeptide comprises the amino acid sequence set forth in SEQ ID NO:28 or a sequence at least 90% identical thereto. In another embodiment, the engineered polypeptide comprises the amino acid sequence set forth in SEQ ID NO:29 or a sequence at least 90% identical thereto. In another embodiment, the engineered polypeptide comprises the amino acid sequence set forth in SEQ ID NO:30 or a sequence at least 90% identical thereto. In another embodiment, the engineered polypeptide comprises the amino acid sequence set forth in SEQ ID NO:31 or a sequence at least 90% identical thereto. In another embodiment, the engineered polypeptide comprises the amino acid sequence set forth in SEQ ID NO:32 or a sequence at least 90% identical thereto. In another embodiment, the engineered polypeptide comprises the amino acid sequence set forth in SEQ ID NO:33 or a sequence at least 90% identical thereto. In another embodiment, the engineered polypeptide comprises the amino acid sequence set forth in SEQ ID NO:34 or a sequence at least 90% identical thereto.

In another embodiment, the engineered polypeptide that specifically binds to human serum albumin consists of an amino acid sequence selected from the group consisting of SEQ ID NOS:22-34 and fragments thereof. For example, in one embodiment, the engineered polypeptide consists of the amino acid sequence set forth in SEQ ID NO:22. In another embodiment, the engineered polypeptide consists of the amino acid sequence set forth in SEQ ID NO:23. In another embodiment, the engineered polypeptide consists of the amino acid sequence set forth in SEQ ID NO:24. In another embodiment, the engineered polypeptide consists of the amino acid sequence set forth in SEQ ID NO:25. In another embodiment, the engineered polypeptide consists of the amino acid sequence set forth in SEQ ID NO:26. In another embodiment, the engineered polypeptide consists of the amino acid sequence set forth in SEQ ID NO:27. In another embodiment, the engineered polypeptide consists of the amino acid sequence set forth in SEQ ID NO:28. In another embodiment, the engineered polypeptide consists of the amino acid sequence set forth in SEQ ID NO:29. In another embodiment, the engineered polypeptide consists of the amino acid sequence set forth in SEQ ID NO:30. In another embodiment, the engineered polypeptide consists of the amino acid sequence set forth in SEQ ID NO:31. In another embodiment, the engineered polypeptide consists of the amino acid sequence set forth in SEQ ID NO:32. In another embodiment, the engineered polypeptide consists of the amino acid sequence set forth in SEQ ID NO:33. In another embodiment, the engineered polypeptide consists of the amino acid sequence set forth in SEQ ID NO:34.

In another embodiment, the disclosure provides an engineered polypeptide that specifically binds to human serum albumin, wherein the polypeptide comprises three complementarity determining regions, CDR1, CDR2 and CDR3, wherein CDR1 comprises any one of the amino acid sequences of SEQ ID NOs:35-43 or a sequence that is at least 90% identical to SEQ ID Nos:35-43; CDR2 comprises any one of the amino acid sequences of SEQ ID NOs:44-51 or a sequence that is at least 90% identical to SEQ ID Nos:44-51; and CDR3 comprises any one of the amino acid sequences of SEQ ID NOs:52-63 or a sequence that is at least 90% identical to SEQ ID Nos:52-63.

The engineered polypeptide disclosed herein can specifically bind, for example, to the same epitope on human serum albumin as Alb1 (AVQLVESGGG LVQPGNSLRL SCAASGFTFR SFGMSWVRQA PGKEPEWVSS ISGSGSDTLY ADSVKGRFTI SRDNAKTTLY LQMNSLKPED TAVYYCTIGG SLSRSSQGTQ VTVSS; SEQ ID NO: 149). In other embodiments, the engineered polypeptide competitively inhibits the binding of Alb1 to human serum albumin.

When the engineered polypeptide comprises an Ig, a suitable fragment of the Ig, such as an Ig variable domain, may also be used in place of a full Ig.

Methods for identifying CDRs from within a given immunoglobulin variable domain are known in the art (Wu, T. & Kabat, E., *J. Exp. Med.*, 132:211-50, 1970; Clothia, C. et al., *Nature*, 342:877-83, 1989; Al-Lazikani, B. et al., *J. Mol. Biol.*, 273:927-48, 1997; and Ofran, Y. et al., *J. Immunol.*, 181:6230-35, 2008).

Fusion Proteins that Specifically Bind Complement Component C5 and Serum Albumin Described herein are fusion proteins that comprise engineered polypeptides that specifically bind albumin and complement component C5, wherein the engineered polypeptides are fused directly or are linked via one or more suitable linkers or spacers. The term "peptide linker" as used herein refers to one or more amino acid residues inserted or included between the engineered polypeptides of the fusion protein(s). The peptide linker can be, for example, inserted or included at the transition between the engineered polypeptides of the fusion protein at the sequence level. The identity and sequence of amino acid residues in the linker may vary depending on the desired secondary structure. For example, glycine, serine and alanine are useful for linkers having maximum flexibility. Any amino acid residue can be considered as a linker in combination with one or more other amino acid residues, which may be the same as or different from the first amino acid residue, to construct larger peptide linkers as necessary depending on the desired properties. In other embodiments, the linker is GGGGAGGGGAGGGGS (SEQ ID NO:102). In other embodiments, the linker is GGGGSGGGGSGGGGS (SEQ ID NO:103). Additional peptide linkers suitable for use in creating fusion proteins described herein include, for example, G45 (SEQ ID NO:104), $(G_4S)_2$ (SEQ ID NO:105), $(G_4S)_3$ (SEQ ID NO:106), $(G_4S)_4$ (SEQ ID NO:107), $(G_4S)_5$ (SEQ ID NO:108), $(G_4S)_6$ (SEQ ID NO:109), $(EAAAK)_3$ (SEQ ID NO:110), PAPAP (SEQ ID NO:111), $G_4$SPAPAP (SEQ ID NO:112), PAPAPG$_4$S (SEQ ID NO:113), GST-SGKSSEGKG (SEQ ID NO:114), $(GGGDS)_2$ (SEQ ID NO:115), $(GGGES)_2$ (SEQ ID NO:116), GGGDSGGGGS (SEQ ID NO:117), GGGASGGGGS (SEQ ID NO:118), GGGESGGGGS (SEQ ID NO:119), ASTKGP (SEQ ID NO:120), ASTKGPSVFPLAP (SEQ ID NO:121), $G_3P$ (SEQ ID NO:122), $G_7P$ (SEQ ID NO:123), PAPNLLGGP (SEQ ID NO:124), $G_6$ (SEQ ID NO:125), $G_{12}$ (SEQ ID NO:126), APELPGGP (SEQ ID NO:127), SEPQPQPG (SEQ ID NO:128), $(G_3S_2)_3$ (SEQ ID NO:129), GGGGGGGGGSGGGS (SEQ ID NO:130), GGGGSGGGGGGGGGS (SEQ ID NO:131), $(GGSSS)_3$ (SEQ ID NO:132), $(GS_4)_3$ (SEQ ID NO:133), $G_4A(G_4S)_2$ (SEQ ID NO:134), $G_4SG_4AG_4S$ (SEQ ID NO:135), $G_3AS(G_4S)_2$ (SEQ ID NO:136), $G_4SG_3ASG_4S$ (SEQ ID NO:137), $G_4SAG_3SG_4S$ (SEQ ID NO:138), $(G_4S)_2AG_3S$ (SEQ ID NO:139), $G_4SAG_3SAG_3S$ (SEQ ID NO:140), $G_4D(G_4S)_2$ (SEQ ID NO:141), $G_4SG_4DG_4S$ (SEQ ID NO:142), $(G_4D)_2G_4S$ (SEQ ID NO:143), $G_4E(G_4S)_2$ (SEQ ID NO:144), $G_4SG_4EG_4S$ (SEQ ID NO:145) and $(G_4E)_2G_4S$ (SEQ ID NO:146). One of skill in the art can select a linker, for example, to reduce or eliminate post-translational modification, e.g., glycosylation, e.g., xylosylation. In certain embodiments, the fusion protein comprises at least two sdAbs, Dabs, VHH antibodies, VHH antibody fragments, or combination thereof wherein at least one of the sdAbs, Dabs, VHH antibodies, or VHH antibody fragments is directed against albumin and one of the sdAbs, Dabs, VHH antibodies, or VHH antibody fragments is directed against complement component C5, so that the resulting fusion protein is multivalent or multi-specific. The binding domains or moieties can be directed against, for example, HSA, cynomolgus monkey serum albumin, human C5 and/or cynomolgus monkey C5.

In some embodiments, the C-terminal residue of the albumin-binding domain of the fusion protein can be fused either directly or via a peptide to the N-terminal residue of the complement component C5 binding domain. In other embodiments, the C-terminal residue of the complement component C5 binding domain of the fusion protein can be fused either directly or via a peptide to the N-terminal residue of the albumin-binding domain.

In some embodiments, a fusion protein comprises a complement component C5 binding comprising an amino acid sequences of SEQ ID NOs:1-12 or a fragment thereof; and the polypeptide that specifically binds to human serum albumin can comprise an amino acid sequence of SEQ ID NOs:22-34 or a fragment thereof. In some embodiments, the first polypeptide is derived from an amino acid sequence set forth in any of SEQ ID NOs:1-12 and the second polypeptide is derived from an amino acid sequence set forth in any of SEQ ID NOs:22-34. The human complement component C5-binding domain can comprise, for example, the amino acid sequence of SEQ ID NO:5 or 11, and the albumin-binding domain can comprise, for example the amino acid sequence of SEQ ID NO:26. In another embodiment, the disclosure provides a fusion protein having any one of the amino acid sequences of SEQ ID NOs:64-95. In another embodiment, the disclosure provides a fusion protein having the amino acid sequence of SEQ ID NO:93. In another embodiment, the disclosure provides a fusion protein having the amino acid sequence of SEQ ID NO:77. In another embodiment, the disclosure provides for a fusion protein having any one of the amino acid sequences of SEQ ID NOs:96-101.

The fusion proteins disclosed herein can be made by expressing in a host cell at least one nucleic acid molecule comprising a nucleotide sequence encoding the fusion protein. Host cells can be mammalian, plant or microbial in origin. In addition to known mammalian host cells, yeast host cells, e.g., *Pichia pastoris, Saccharomyces cerevisiae,* and/or plant host cells can be used.

Therapeutic Compositions Comprising Polypeptides that Specifically Bind Complement C5 or Serum Albumin, or Fusion Proteins Thereof, and Administration Thereof In another embodiment, the disclosure provides engineered polypeptides comprising or consisting of an amino acid sequence as disclosed herein. In another embodiment, the disclosure provides fusion proteins and multivalent and multi-specific fusion proteins comprising or consisting of at least one engineered polypeptide of the disclosure that is linked to at least one therapeutic or targeting moiety, optionally via one or more suitable linkers or spacers.

The disclosure further relates to therapeutic uses of the engineered polypeptides of the disclosure, or fusion proteins and multivalent and multi-specific fusion proteins comprising or consisting of such engineered polypeptides, or to pharmaceutical compositions comprising such engineered polypeptides, fusion proteins, or multivalent and multi-specific fusion proteins.

In some embodiments, the therapeutic or targeting moiety can comprise, for example, at least one sdAb, Dab, VHH or fragment(s) thereof. In certain embodiments, the engineered polypeptide of the disclosure is a multivalent and/or multi-specific fusion protein comprising at least two sdAbs, Dabs, VHH antibodies, VHH antibody fragments, or combination(s) thereof.

In some embodiments, the engineered polypeptides, fusion proteins, or multivalent and multi-specific fusion proteins show an affinity for HSA that is higher than the affinity for mouse serum albumin. In certain embodiments, the engineered polypeptides, fusion proteins, or multivalent and multi-specific fusion proteins show an affinity for cynomolgus monkey serum albumin that is higher than the affinity for mouse serum albumin. In other embodiments, the engineered polypeptides, fusion proteins, or multivalent and multi-specific fusion proteins show an affinity for HSA that is higher than the affinity for cynomolgus monkey serum albumin.

In some embodiments, the engineered polypeptides, fusion proteins, or multivalent and multi-specific fusion proteins show an affinity for human C5 that is higher than the affinity for mouse C5. In certain embodiments, the engineered polypeptides, fusion proteins, or multivalent and multi-specific fusion proteins show an affinity for cynomolgus monkey C5 that is higher than the affinity for mouse C5. In other embodiments, the engineered polypeptides, fusion proteins, or multivalent and multi-specific fusion proteins show an affinity for human C5 that is higher than the affinity for cynomolgus monkey C5.

The engineered polypeptides, fusion proteins, or multivalent and multi-specific fusion proteins described herein can exhibit, for example, improved therapeutic properties, including, for example, increased efficacy, bioavailability, half-life or other therapeutically desirable properties when compared to antibody therapeutics or other therapeutics. In one embodiment, a fusion protein of the disclosure comprises at least one engineered polypeptide disclosed herein and at least one therapeutic or targeting moiety. In such fusion proteins, the fusion protein can exhibit, for example, an increased half-life compared to the therapeutic binding domain alone. Generally, such fusion proteins have a half-life that is at least 1.5 times, or at least 2 times, or at least 5 times, or at least 10 times, or more than 20 times greater than the half-life of the corresponding therapeutic or targeting moiety alone. In some embodiments, a fusion protein of the disclosure has a half-life that is increased by more than 1 hour, more than 2 hours, more than 6 hours, or more than 12 hours as compared to the half-life of the corresponding therapeutic or targeting moiety. In other embodiments, a fusion protein has a half-life that is more than 1 hour, more than 2 hours, more than 6 hours, more than 12 hours, about one day, about two days, about one week, about two weeks, about three weeks, or no more than 2 months.

The term "half-life," as used herein, refers to the time taken for the serum concentration of the engineered polypeptide, fusion protein, or multivalent and multi-specific fusion protein to be reduced by 50%, in vivo, as a result, for example, of the degradation of the molecule and/or clearance or sequestration of the molecule by physiological mechanisms. Methods for pharmacokinetic analysis and determination of half-life are known to those skilled in the art.

A general description of multivalent and multi-specific fusion proteins containing one or more VHH antibodies and their preparation are known (Els Conrath, K. et al., *J. Biol. Chem.*, 276:7346-50, 2001; Muyldermans, S., *J. Biotechnol.,* 74:277-302 2001; International Publication Nos. WO 96/34103, WO 99/23221 and WO 04/041865).

The engineered polypeptides, fusion proteins, and multivalent and multi-specific fusion proteins disclosed herein can be expressed from or associated with constructs that include, for example, one or more elements such as expression vectors (WO 04/041862).

The engineered polypeptides, fusion proteins, and multivalent and multi-specific fusion proteins disclosed herein can be expressed in, for example, isolated host cells comprising nucleic acid molecules that encode the engineered polypeptides, fusion proteins, and multivalent and multi-specific fusion proteins disclosed herein. Suitable host cells include but are not limited to mammalian and yeast cells.

The therapeutic or pharmaceutical compositions disclosed herein can comprise a therapeutically effective amount of one or more engineered polypeptides, fusion proteins, or multivalent and multi-specific fusion proteins as disclosed herein in admixture with a pharmaceutically or physiologically acceptable formulation agent selected for suitability with the mode of administration. Acceptable formulation materials are preferably nontoxic to recipients at the dosages and concentrations to be employed.

Acceptable formulation materials can be used to modify, maintain, or preserve, for example, the pH, osmolarity, viscosity, clarity, color, isotonicity, odor, sterility, stability, rate of dissolution or release, adsorption, or penetration of the composition. Acceptable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, which are incorporated herein by reference).

A skilled artisan can develop a pharmaceutical composition comprising the engineered polypeptides, fusion proteins, or multivalent and multi-specific fusion proteins disclosed herein depending upon, for example, the intended route of administration, delivery format, and desired dosage.

Since the engineered polypeptides, fusion proteins, and multivalent and multi-specific fusion proteins disclosed herein can exhibit, for example, an increased half-life, they may, in some embodiments, be administered to be in circulation. As such, they can be administered in any suitable manner, such as intravenously, subcutaneously, via injection or infusion, or in any other suitable manner that allows the engineered polypeptides, fusion proteins, or multivalent and multi-specific fusion proteins to enter circulation. The preparation of such pharmaceutical compositions is within the knowledge of one of skill in the art.

Any of the engineered polypeptides, fusion proteins, and multivalent and multi-specific fusion proteins disclosed herein, can be administered in combination with an additional therapy, i.e., combined with other agents. The term "coadministered" as used herein includes any or all of simultaneous, separate, or sequential administration of the engineered polypeptides, fusion proteins, and multivalent and multi-specific fusion proteins described herein with adjuvants and other agents, including administration as part of a dosing regimen.

Pharmaceutical compositions described herein can include one or more agents to improve, for example, delivery of the therapeutic agent. Additional agents can be co-administered, for example, as a co-injectable. Agents that degrade hyaluronan, for example, can be included in the pharmaceutical compositions described herein, or such agents can be co-administered with the pharmaceutical compositions described herein to facilitate, for example, dispersion and absorption of the therapeutic agents described herein upon administration. An example of such an agent is recombinant hyaluronidase.

The pharmaceutical compositions can also be selected for parenteral delivery. Alternatively, the compositions can be selected for inhalation or for delivery through the digestive tract, such as orally. The preparation of such pharmaceutical compositions is within the knowledge of one of skill in the art.

Additional pharmaceutical compositions will be evident to those of skill in the art, including formulations involving sustained-delivery or controlled-delivery formulations. Techniques for formulating sustained-delivery or controlled-delivery formulations, using, for example, liposome carriers, bio-erodible microparticles or porous beads, and depot injections, are known to those of skill in the art.

The disclosure also encompasses therapeutic kits comprising the engineered polypeptides, fusion proteins, and multivalent and multi-specific fusion proteins disclosed herein. In some embodiments, the kits comprise both a first container having a dried protein and a second container having an aqueous formulation. In other embodiments, the kits comprise single and multi-chambered pre-filled syringes (e.g., liquid syringes and lyosyringes).

The disclosure also encompasses an article of manufacture comprising a container comprising a label and a composition comprising the engineered polypeptides, fusion proteins, and multivalent and multi-specific fusion proteins disclosed herein wherein the label indicates that the composition is to be administered to a patient having, or that is suspected of having, a complement-mediated disorder.

In one embodiment, the disclosure provides a method for preventing and/or treating at least one disease, condition, or disorder that can be prevented or treated using an engineered polypeptide, fusion protein, or multivalent and multi-specific fusion protein disclosed herein, the method comprising administering to a patient in need thereof a therapeutically or pharmaceutically effective amount of an engineered polypeptide, fusion protein, or multivalent and multi-specific fusion protein disclosed herein. In particular embodiments, the disorder is a complement-mediated disorder such as, for example, rheumatoid arthritis (RA); lupus nephritis; asthma; ischemia-reperfusion injury; atypical hemolytic uremic syndrome (aHUS); dense deposit disease (DDD); paroxysmal nocturnal hemoglobinuria (PNH); macular degeneration (e.g., age-related macular degeneration (AMD); hemolysis, elevated liver enzymes, and low platelets (HELLP) syndrome; Guillain-Barré Syndrome (GBS); CHAPLE syndrome; myasthenia gravis (MG); neuromyelitis optica (NMO); post-hematopoietic stem cell transplant thrombotic microangiopathy (post-HSCT-TMA); post-bone marrow transplant TMA (post-BMT TMA); Degos disease; Gaucher's disease; glomerulonephritis; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis.

The effective amount of a pharmaceutical composition as disclosed herein to be employed therapeutically will depend, for example, upon the therapeutic context and objectives. One of skill in the art will appreciate that an appropriate dosage level for treatment will vary depending, in part, upon the molecule being delivered, the indication for which the composition is being used, the route of administration, and the size (body weight, body surface, or organ size) and condition (age and general health) of the patient.

EXAMPLES

The Examples that follow are illustrative of specific embodiments of the disclosure, and various uses thereof. They are set forth for explanatory purposes only, and should not be construed as limiting the scope of the invention in any way.

Example 1. Llama Immunization and Anti-C5 VHH Phage Library Construction

Llama immunizations were performed starting with a primary injection followed by secondary boosts. Briefly, primary immunization was initiated with 500 µg of human complement protein C5 and subsequent 500 µg human complement protein C5 antigen boosts administered at week 2 (boost 1), week 4 (boost 2), week 8 (boost 3), and week 12 (boost 4). Serum titers were measured by ELISA and titers after boost 3 were found to be the highest—10-fold above the pre-bleed signal at the 1:1,000,000 dilution. Peripheral blood mononuclear cells (PBMCs) were isolated from blood samples after boost 3. Cell viability was found to be 98% by trypan blue staining. Cells were lysed in RNA lysis buffer immediately after PBMC isolation. Total RNA was isolated from PBMCs and cDNA was synthesized using llama heavy chain specific primers. VHH (heavy chain only) fragments were separated from VH (conventional heavy chain) fragments via gel electrophoresis. The VHH fragments were cloned into pADL-10b (Antibody Design Labs, San Diego, Calif.), and the DNA library was transformed into TG1 cells. 114 colonies were randomly sequenced and 101 (89%) correct sequences were obtained. The library was scraped and suspended in 25% glycerol, then stored at −80 C.

Example 2. Phage Display Panning and Screening for Anti-C5 VHH Domains

TG1 cells containing the anti-human complement protein C5 VHH domain library were grown to logarithmic phase ($OD_{600}$=0.4-0.8) at 37 C in 2×YT media containing 100 µg/mL carbenicillin and 2% glucose. The cells were infected with M13K07 helper phage with and without shaking at 37 C for 30 minutes. Infected cells were pelleted at 4000×g for 10 minutes and resuspended in 2×YT media containing 100 µg/mL carbenicillin, 50 µg/mL kanamycin, and 1 mM IPTG, and the bacteriophage was propagated by overnight growth at 30 C and 250 rpm. The overnight culture was centrifuged at 9000×g for 10 minutes at 4 C, and phage was precipitated with one-fifth volume of a PEG-NaCl solution [20% polyethyleneglycol 6000, 1.5 M NaCl] by incubation for 1 hour on ice. Phage particles were pelleted by centrifugation at 9000×g for 15 minutes at 4 C and the supernatant was discarded. Phage particles were resuspended in superblock blocking buffer and cell debris was pelleted by centrifugation for 10 minutes at 7500×g in a microcentrifuge tube. The supernatant containing phage particles was transferred to a new tube and phage was precipitated again as described above. Concentrated phage particles were subjected to a thermal challenge for 1 hour at 70 C, and the phage titer before and after heating was determined by infection of logarithmic phase TG1 cells followed by plating on 2×YT agar plates with 100 µg/mL carbenicillin, 50 µg/mL kanamycin, and 2% glucose.

The library selection strategy included selection with biotinylated cynomolgus monkey (cyno) complement protein C5 and competition with molar equivalent non-biotinylated human complement protein C5 to obtain affinity matched anti-C5 VHH domains with reactivity to both human and cyno species. The phage display VHH library was subjected to a deselection step against Dynabeads® M-280 streptavidin for 1 hour at room temperature. The deselected phage particles were selected for matched affinity to human and cyno C5 by incubating in an equimolar solution of biotinylated cyno C5 and non-biotinylated human C5 with Dynabeads® M-280 Streptavidin for 30 minutes at room temperature. After 5 rounds of washing with PBST and PBS, phage was eluted off the beads using 0.1 M glycine (pH 2.2) with 1 mg/mL BSA. The eluted supernatant was neutralized with 1 M Tris pH 8.0. Log phase TG1 cells were infected with the neutralized phage and plated on 2YTCG medium to measure the output titer. Output and input titers were compared to calculate the enrichment ratio; a higher ratio suggested the successful isolation of C5 specific clones.

Individual clones were picked, inoculated in a 96-well deep well plate in 2×YT media with 100 µg/mL carbenicillin and 2% glucose, and grown to log phase. The cells were infected with M13K07 and cultured overnight at 30 C for the production of phage particles displaying individual VHH domains in culture supernatant. Phage ELISA screening of four 96-well plates with human C5 captured on streptavidin-coated plates suggested ~60% positive clones. 72 unique clones out of a total of 76 were selected as representatives based on sequence analysis of CDR H3. The sequences of these representative VHH clones are provided in Table 1. For cloning purposes, the N- and C-terminal amino acids were modified to match the N- and C-terminal amino acids of human VH-3 germline.

Amino acid sequences suitable for use in the engineered polypeptides of the disclosure include the amino acid sequences disclosed in Tables 1 or fragments thereof.

TABLE 1

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0081 | EVQLVESGGGLVQTGGSLRLSCAASTSGSDFSGKKMAWYRQAPGNGRE FVAIIFSNKVTDYADSVKGRFTISRDNAKKTVYLQMSSLTPTDTAVYY CHDQEISWGQGTQVTVSS (SEQ ID NO: 150) | + | − |
| LCP0082 | EVQLVESGGGLVQAGGSLRLSCAASGTSVVINSMGWYRQAPGKQRELV ATIDLSGTTNYADSAQGRFTISRDNAENLNLVYLQMNNLNPDDTAVYY CNALLSRAVSGSYVYWGQGTQVTVSS (SEQ ID NO: 151) | + | + |

TABLE 1-continued

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0083 | EVQLVESGGGLVQPGGSLRLSCTSRIGTISNIDLMNWYRQAPGKQREF VASLQSNGATNYADSVKGRFTISRDNAKNTLFLQMNSLNPEDTAVYFC HALLPRSPYNSWGQGTQVTVSS (SEQ ID NO: 152) | + | + |
| LCP0085 | EVQLVESGGGLVQAGGSLRLSCAASSIIPNIYAMGWYRQAPGKQRELV ASIENGLPANYADSVKGRFTISRDNAKNTVFLQMHSLKSEDTAVYCY AFRPGVPTTWGQGTQVTVSS (SEQ ID NO: 153) | + | + |
| LCP0086 | EVQLVESGGGLVQAGESLRLSCAASGSISAINAMGWYRQAPGKQREFV ADITRAGVSDYADAVKGRFTISRDNAKNTFYLQMNDLKPEDTAVYYCD ALLIAGGVYWGQGTQVTVSS (SEQ ID NO: 154) | + | − |
| LCP0088 | EVQLVESGGGLVQAGGSLRLSCTASGRTISTTVMGWFRQAPGKEREFV AAVHWDGNTVYADSVKGRFTISRDDAKNTVYLQLNYLKPEDTSVYYC AARPPTYVGTSRNSRSYDYWGQGTQVTVSS (SEQ ID NO: 155) | + | + |
| LCP0089 | EVQLVESGGGLVQAGGSLRLSCVVSGRAIDRNAMGWFRQAPGKERESV AAISASSGNTYYSDSVTGRFTISRDNTKNTVYLQMNSLKPEDTAVYYC AAGSRGSWYLFDRREYDYWGQGTQVTVSS (SEQ ID NO: 156) | + | − |
| LCP0090 | EVQLVESGGGLVQAGGSLRLTCTASETSFDINVMGWYRQAPGKQRELV AIITASGNTEYADSAKGRFTISRDNTKNTVAMQMNNLKPDDTAVYYCY VLLSGAVSGVYAHWGQGTQVTVSS (SEQ ID NO: 157) | + | + |
| LCP0091 | EVQLVESGGGLVQAGGSLTLSCAASGRTDSRYAMGWFRQAPGKERELM AAISWSGRPTYYADSVKGRFTISRDNAKNTVSLQMNSLKPEDTAVYYC AYKRLPAWYTGSAYYSQESEYDYWGQGTQVTVSS (SEQ ID NO: 158) | + | + |
| LCP0092 | EVQLVESGGGLVQPGGSLRLSCTSRIGTISNIDLMNWYRQAPGKQREF VASLQSTGTTDYADSVKGRFTISRDNAKNTLFLQMNSLNPEDTAVYYC HALIPRSPYNVWGQGTQVTVSS (SEQ ID NO: 159) | + | + |
| LCP0095 | EVQLVESGGGLVQAGGSLRLSCTASGRTISTTVMAWFRQAPGKEREFV AADHWGDAGTVYADSVKGRFTISRDNAKNTVYLQMNYLKPEDTSVYYC AARPPTYVGTSRDSRAYDYWGQGTQVTVSS (SEQ ID NO: 160) | + | + |
| LCP0097 | EVQLVESGGGLVQPGGSLRLSCAASESISSDSPMAWYRQAPGKQREMV ARILPIGPPDYADAVKDRFSISRENAKNTVYLQMNSLKPEDTAVYYCN LLHLPSGLNYWGQGTQVTVSS (SEQ ID NO: 161) | + | + |
| LCP0098 | EVQLVESGGDLVQAGGSLRLSCVASRSISSAMNWYRQPPGKQRELVAL ITRGFNTNYADSVKGRFTISRDNAKNTVYLQMNSLKPEDTGVYYCNSL NYWGQGTQVTVSS (SEQ ID NO: 162) | + | − |
| LCP0100 | EVQLVESGGGLVQAGGSLRLSCAASGRTDSMWSMGWFRQAPGQEREFV AAISWSVGTYYEDSVKGRFTLSRDDDKDTAYLEMSDLKLEDTADYYCA ASTRHGTNLVLPRDYDYWGQGTQVTVSS (SEQ ID NO: 163) | + | − |
| LCP0101 | EVQLVESGGGLVQPGGSLRLSCTSRIGTISNIDLMNWYRQAPGKQREF VASLQSTGTTDYADSVKGRFTISRDNAKNTLFLQMNSLNPEDTAVYYC HALLPRSPYNAWGQGTQVTVSS (SEQ ID NO: 164) | + | + |
| LCP0102 | EVQLVESGGGLVQAGGSLRLSCAASGIIPNIYAMGWYRQAPGKQRELV ASIENGGSTNYADSVKGRFTISRDNARNTVFLQMHSLKSEDTAVYCY AFRPGVPTDWGQGTQVTVSS (SEQ ID NO: 165) | + | + |
| LCP0103 | EVQLVESGGGLVQAGGSLTLSCVASGRTFSNYRMGWFRQAPGAEREFV GTIYWSTGRSYYGDSVKGRFIISGDNAKNTIHLQMNSLKPEDTGVYYC ASGPENSAFDSWGQGTQVTVSS (SEQ ID NO: 166) | + | + |
| LCP0104 | EVQLVESGGGLVQAGDSLRLSCAASGRPFSSYTMGWFRQAPGKERDFV ATISWSGGIKYYADSVEGRFSISRDNAKNMVYLQMNSLKPEDTAVYYC AATELRTWSRQTFEYDYWGQGTQVTVSS (SEQ ID NO: 167) | + | − |
| LCP0105 | EVQLVESGGGLVQAGGSLRLSCTASGRTISTTVMAWFRQAPGKEREFV AAVHWGDESTVYADSVKGRFTISRDNAKNTVYLQMNYLKPEDTSVYYC AARPPTYVGSSRSSRAYDYWGQGTQVTVSS (SEQ ID NO: 168) | + | + |
| LCP0106 | EVQLVESGGGLVQAGGSLRLSCVVSGSILDINVMAWYRQAPGKQREFV ARITSGGDIDYADPVKGRFTISTNGAKNTVYLQMNSLKPEDTAAYYCN VLLSRSSAGRYTHWGQGTQVTVSS (SEQ ID NO: 169) | + | + |

TABLE 1-continued

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0111 | EVQLVESGGGLVQPGGSLRLSCAASGFPFSLYDMGWYRQAPEKQRESV AIITQSGSTDYADSVKGRFTISRDNAKNTLYLQMNSLKPEDTAVYYCR LVGVTWGQGTQVTSS (SEQ ID NO: 170) | + | − |
| LCP0112 | EVQLVESGGGLVQAGGSLTLSCAASGRTFSSYGIGWFRQAPGKEREFV AAISRTGQTTHYADSIRFTISRDNAKNTVYLQMNSLKPEDTAVYYCAA RTGGPIYGSEYHYWGQGTQVTVSS (SEQ ID NO: 171) | + | − |
| LCP0113 | EVQLVESGGGLVQAGDSLTLSCAASGRPFSSLTMGWFRQAPGKGREFV ATTSWSGDIKYYADFVKGRFTISRDNAKNMVYLQMNSLKPEDTAVYYC AATLLRTWSRQTNEYEYWGQGTQVTVSS (SEQ ID NO: 172) | + | − |
| LCP0114 | EVQLVESGGGLVQPGGSLRLSCTSRIGTISNIDLMNWYRQAPGKQREF VASLQSTGTTDYADSVRGRFTISRDNAKNTLFLQMNSLNPEDTAVYYC HALLPRSPYNVWGQGTQVTVSS (SEQ ID NO: 173) | + | + |
| LCP0115 | EVQLVESGGGLVQAGGSLRLSCAASGRTFSGILSPYAVGWFRQAPGKG REFVSTITSGGSAIYTDSVKGRFTLSRDNAKDTVYLQMNSLKPEDTAV YYCAVRTRRYGSNLGEVPQENEYGYWGQGTQVTVSS (SEQ ID NO: 174) | + | + |
| LCP0122 | EVQLVESGGGLVQAGGSLRLSCAAPETGATINVMAWYRQAPGKQRELV ARVAIDNNTDYADHAKGRFTISRDNTKNTVYLQMNNLKPDDTAVYYCN VLLSRQISGSYGHWGQGTQVTVSS (SEQ ID NO: 175) | + | + |
| LCP0123 | EVQLVESGGGLVQAGGSLTLSCAMSGGTRPFEDYVMAWFRQATGKERE FVATITWMGETTYYKDSVNGRFAISRDNAENTVALQMNSLEPEDTAVY FCAAHSRSSFSTSGGRYNPRPTEYDYWGQGTQVTVSS (SEQ ID NO: 176) | + | + |
| LCP0125 | EVQLVESGGGLVQAGGSLTLSCTASGRTISTTVMGWFRQAPGKEREFV AAVHWGDEGTVYADSVKGRFTISRDNAKNTVYLQMNALKPEDTSVYYC AAKPPTYVGTSRSSRAYVYWGQGTQVTVSS (SEQ ID NO: 177) | + | + |
| LCP0126 | EVQLVESGGGLVQAGDSLTLSCAASGSGFSINVMAWYRQAPGKQRDLV ASMTIGGRTNYKDSLKGRFTISRDNTKNTAYLQMNSLKPEDTAVYYCY ALLDRGIGGNYVYWGQGTQVTVSS (SEQ ID NO: 178) | + | + |
| LCP0127 | EVQLVESGGGLVQAGGSLRLSCAASGLTFSDYYMGWFRQAPGKERDFL ARIGKSGIGKSYADSVRGRFTISRDNAKNTVYLQMNNLKLEDTAVYYC AADRDIAYDARLTAEYDYWGQGTQVTVSS (SEQ ID NO: 179) | + | + |
| LCP0128 | EVQLVESGGGLVQAGGSLRLSCTASGRTISTTVMGWFRQAPGKEREFV AAVHWGDESTVYADSVKGRFTISRDNAKNTVYLQMNYLKPEDTAVYYC AARPPTYVGTSRSSRAYDYWGQGTQVTVSS (SEQ ID NO: 180) | + | − |
| LCP0129 | EVQLVESGGGLVQAGGSLRLSCAASVASETIVSINDMAWYRQAPGKQR ELVASITIHNNRDYADSAKGRFTISRDDTKNTVYLQMTHLKPDDTAVY YCTVLLSRALSGSYRFWGQGTQVTVSS (SEQ ID NO: 181) | + | + |
| LCP0130 | EVQLVESGGGLVQAGGSLRLSCTGSETSGTIFNINVMGWYRQAPGKQR ELVAIMDIGGTTDYADSVKGRFTISRDNAKNTVYVQMNNLKSEDTAVY YCYCALDRAVAGRYTYWGQGTQVTVSS (SEQ ID NO: 182) | ND | ND |
| LCP0132 | EVQLVESGGGLVQPGGSLRLSCEASGISLNDYNMGWFRQAPGKDREIV AALSRRSHGIYQSDSVKYRFSISRDNTKNMVSLQMDSLRPEDTAVYYC AADGDPYFTGRDMNPEYWGQGTQVTVSS (SEQ ID NO: 183) | + | − |
| LCP0133 | EVQLVESGGGSVQAGGSLRLSCAFSGGRFSDYGMAWFRQGPGKEREFV SRISGNGRGTQYTDSVSGRFIISRDNDKNTVYLQMNDLKVEDTAIYYC ARGSGPSSFNEGSVYDYWGQGTQVTVSS (SEQ ID NO: 184) | + | + |
| LCP0134 | EVQLVESGGGLVQSGGSLTLSCVLSGSIFSSNTMGWHRQAPGKQREWV AITTSGGTTKYADSVKGRFTISRDNAKNTVYLRMNNLKPEDTGVYFCY ASLAGIWGQGTQVTVSS (SEQ ID NO: 185) | + | + |
| LCP0135 | EVQLVESGGGLVQAGGSLRLSCAAPETEATYNVMGWYRRAPGKQRELV ATMTIDYNTNYADSAKGRFTISRDNTKNTVYLQMNNLRPDDTAVYYCR VDLSRQISGSYNYWGQGTQVTVSS (SEQ ID NO: 186) | + | + |
| LCP0136 | EVQLVESGGGLVQPGESLRLSCAISGFAFTDVGMSWVRQAPGKGLEWV SSISSGSSITTYSDSVKGRFTISRDNARNTFLQMNSLKPEDTAVYYC GRYYCTGLGCHPRRDSALWGQGTQVTVSS (SEQ ID NO: 187) | + | + |

TABLE 1-continued

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0137 | EVQLVESGGGLVQPGGSLRLSCRASGFTYSTAAMGWVRQAPGKGLEWVSSISSLGSDRKSADSVKGRFTISRDNAKNTLYLQMNSLKPEDTAVYYCARFISNRWSRDVHAPSDFGSRGQGTQVTVSS (SEQ ID NO: 188) | + | + |
| LCP0138 | EVQLVESGGGSVPAGGSLRLSCAAFGFTFDNYAIAWFRQAPGKEREGVSCLSTNDGETYYADSVKGRFTISSDHAKNTVYLQMDSLRPEDTAVYYCAAAEGSWCHKYEYDYWGQGTQVTVSS (SEQ ID NO: 189) | + | - |
| LCP0139 | EVQLVESGGGLVQAGESLRLSCAASGRTSDLYVVGWFRQTPGKEREFVAGIAWTGDASYYADSVEGRFTIARDNAENRIDLQMTSLKPEDTAVYYCAADSRARFERQRYNDMNYWGQGTQVTVSS (SEQ ID NO: 190) | + | - |
| LCP0141 | EVQLVESGGGLVQAGGSLRLSCIASVTIADINVMGWYRQAPGKQREFVASIPTTGDKNYAESAKGRFTISRDNSQNTVAMQMNNLKPDDTAVYYCYVLLSRAVSGSYGHWGQGTQVTVSS (SEQ ID NO: 191) | + | + |
| LCP0142 | EVQLVESGGGLVQVGGSLRLSCAASGSIVDIKVMGWYRQAPGNERELVALINDADDSEYSPSMRGRFTISRDNSKNTVYLQMNSLKPEDTAAYYCAADRDSSWFKSPYIPGSWGQGTQVTVSS (SEQ ID NO: 192) | + | + |
| LCP0143 | EVQLVESGGGLVQAGGSLRLSCAAPEMGATINVMAWYRQAPGKQRELVARLPLDNNIDYGDFAKGRFTISRDITRNTVYLQMNNLKPDDTAVYYCNVLLSRQINGAYVHWGQGTQVTVSS (SEQ ID NO: 193) | + | + |
| LCP0144 | EVQLVESGGGLVQAGGSLRLSCAASGIDGDINVMAWYRQAPGKQRELVASITIGGNTNYADSVKGRFTIARDNAKNRMSLEMNSLKSEDTAVYYCNTLLSRVHDGQYVFWGQGTQVTVSS (SEQ ID NO: 194) | + | + |
| LCP0145 | EVQLVESGGGLVQAGGSLRLSCVASEDAFKTDTLGWFRQAPGEEREFVAAFVWAGGPFYADSVKGRFTISMDEDRNTVYLQMNSLKPEDTGVYYCAASLSRLRVGEITPRHMNYWGQGTQVTVSS (SEQ ID NO: 195) | + | - |
| LCP0146 | EVQLVESGGGLVQAGGSLRLSCAASGRAFSDYAMAWFRQAPGKEREFVAGIGWSGGDTLYADSVRGRFTNSKDNAKNRMSLQMNSLKPEDTAVYYCAARQGQYIYSSMRSDSYDYWGQGTQVTVSS (SEQ ID NO: 196) | + | + |
| LCP0147 | EVQLVESGGGLVQAGGSLRLSCAASGRTFSSSNMGWFRQAPGEEREFVTAIDWSGGRTYYADSVKGRFTISRDNAKNTVYLQMDSLKPEDTAVYYCAAQGSGLDWGYPWTYDYWGQGTQVTVSS (SEQ ID NO: 197) | + | + |
| LCP0149 | EVQLVESGGGLVQPGGSLKLSCATSGSVLNIDSMAWYRQAPGKQRELVAEMLWGGTKNYGDSVKGRFTISGDADWGTELQMSSLKPEDTAVYYCNAVGRGFRDAWGQGTQVTVSS (SEQ ID NO: 198) | + | - |
| LCP0150 | EVQLVESGGGLVQAGGSLRLSCVASGSGFGILDMGWYRQAPGSRRELVGYVTRDGTTNYGNSVKGRSIISEDITKNTVILQMNSLKPEDTAVYFCTAGLTNQPRAWGQGTQVTVSS (SEQ ID NO: 199) | + | + |
| LCP0151 | EVQLVESGGGLVQPGGSLRLSCAASGSVSSINVMGWYRQTPGKQRELVAAINRGGSTNVADSVKGRFTISRDNAKNTVYLQMNSLKPEDTAVYYCNAEPYGLDWRYDYWGQGTQVTVSS (SEQ ID NO: 200) | + | + |
| LCP0152 | EVQLVESGGGLEQAGGSLRLSCTASGGTDSIYQMGWFRQTPGKEREFVAAINWNYGGAYYPDSVKGRFTISRDKAKNIGFLQMNSLKPEDTAVYYCATSQTSVDAFSVPITTARRYQYWGQGTQVTVSS (SEQ ID NO 201) | + | - |
| LCP0153 | EVQLVESGGGLVQAGGSLTLSCVASGRTFSNYRMGWFRQAPGKEREFVGTIYWSTGRSYYGDSVKGRFIISGDNAKNTIHLQMNSLKPGDTGVYYCASGPEMSAFDSWGQGTQVTVSS (SEQ ID NO: 202) | + | + |
| LCP0154 | EVQLVESGGGLVQPGGSLRLSCAASGFTLDDYAIGWFRQAPGKEREGVSCISSSDGSTYYGDSVKGRFTISRDNAKNTMYLQMNSLKPEDTAVYYCATGTPLSSYYGSCLDYDMAYWGQGTQVTVSS (SEQ ID NO: 203) | + | + |
| LCP0155 | EVQLVESGGGLVQAGGSLRLSCAASGVTFSNYGMAWFRQAPEKEREFVARISSNGRRTEYADGVSGRFTISRDNAKNTVYLQMNGLKPEDTAVYYCARAAGPSGFHEQSIYDDWGQGTQVTVSS (SEQ ID NO: 204) | + | + |
| LCP0295 | EVQLVESGGGLVQAGGSLRLSCAVSGRSISTYVAGWFRQGPGKEREFVALISRGGGDIQYSDSVKGRFTISRDNAKNAVYLQMNSLKPADTAVYYCSLDASFGSRLVSRWDYWGQGTQVTVSS (SEQ ID NO: 205) | + | + |

TABLE 1-continued

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0296 | EVQLVESGGGVVQAGDSLTLTCTAPVGTISDYGMGWFRQAPGKEREFV ASISWGGMWTDYADSVKGRFTISRDNDKNAVYLRMNSLNAEDTAVYYC GRGRMYRGIGNSLAQPKSYGYWGQGTQVTVSS (SEQ ID NO: 206) | + | + |
| LCP0297 | EVQLVESGGGLVQAGGSLRLSCAGSGFTSDDYAIAWFRQAPGKEREGV SCIGSGDGTTYYADSVKGRFIISSENAKKTVYLQMNSLKPEDTGIYYC AADLYPPADYALDHTWYDYWGQGTQVTVSS (SEQ ID NO: 207) | + | + |
| LCP0298 | EVQLVESGGGVVQPGGSLRLSCVVSGSRFSLDTVGWHHQAPGKLRELV ARIRDDGDTMYVASVKGRFIISRDDAKNTVYLQMNSLKPEDTGVYYCY FSRNGAWGQGTQVTVSS (SEQ ID NO: 208) | + | + |
| LCP0299 | EVQLVESGGGLVQAGGSLRLSCGASGRISDINVMGWYRQAPGKQREMV ADIDIRGYTNYADSVKGRFTVSRDNAETMYLEMNSLKPEDTAVYRCNA LTSRDWGTGKYVYWGQGTQVTVSS (SEQ ID NO: 209) | + | + |
| LCP0300 | EVQLVESGGDLVQVGGSLRLSCAFPGSMSSRNSVNWYRQPPGKQREWV ATISVSGFTQYADSAKGRFTISRDSAKNTVHLQMNSLKPEDTGVYYCN YMDYWGQGTQVTVSS (SEQ ID NO: 210) | + | + |
| LCP0301 | EVQLVESGGGVVRAGGSLKLSCTAAGTDINIVTVGWHRQAPGKHRELV ATIVGSGSRTNYADSVKGRFTISRDNPKNTVYLQMNSLKPEDTAVYYC YATSIGWGQGTQVTVSS (SEQ ID NO: 211) | + | + |
| LCP0302 | EVQLVESGGGLVQAGGSLRLSCAASGRTFSGILSAYAVGWFRQAPGKE REFVSTITSGGSTLSADSVKGRFTLSRDNAKDTVYLQMNSLKPEDTAV YYCAVRTWPYGSNRGEVPTENEYGHWGQGTQVTVSS (SEQ ID NO: 212) | + | + |
| LCP0303 | EVQLVESGGGSVQAGGSLRLTCTASGNVRSIFTMAWYRQAPGKQRELV ASAAKGGDTYYADSAKGRFTISRDDAKAIVSLQMNSLKPEDTAVYYCK TDGRPWFSEDYWGQGTQVTVSS (SEQ ID NO: 213) | + | + |
| LCP0304 | EVQLVESGGGLVQVGDSMRLSCAVFGNIFTRDPVMWFRQPPGKQREWV ATITPSGFANYADSVKGRFTISRYAANNTVHLQMNSLKPEDTGVYFCN FGTYWGQGTQVTVSS (SEQ ID NO: 214) | + | + |
| LCP0306 | EVQLVESGGGLVQAGGSLRLSCAASKGAFNINVMAWYRQAPGKQRELV ARVALGGTTDYADSVKGRFTISRNNAQDTVYLQMNSLKPEDTAVYYCN VLLDRGVRGSYAYWGQGTQVTVSS (SEQ ID NO: 215) | + | + |
| LCP0309 | EVQLVESGGGLVQAGGSLRLSCAASGRTYSSYVIGWFRQAPGKEREFV ASIRWAGGDSHYQESVKGRSTISKDNARNTVYLQMNSLKPEDTAVYYC AGAAPVPGQSYEWSSWGQGTQVTVSS (SEQ ID NO: 216) | + | + |
| LCP0310 | EVQLVESGGGLVQAGGSLRLSCVASGSAFYVGPMAWYRQAPGKERESV ASITKGGITNYADSVKGRFTISRDNAKNTVYLQMNSLKPEDTDVYVCN ARVKLQEDRLFRDYWGQGTQVTVSS (SEQ ID NO: 217) | + | + |
| LCP0311 | EVQLVESGGGMVQPGGSLRLSCVVSGASGNIDFVTVGWHRQAPGKHRE MVAVITGDGTRNYRDSVKGRFSISRDNAKNTIYLQMNSLKPEDTAVYY CYMSNPISSWGQGTQVTVSS (SEQ ID NO: 218) | + | + |
| LCP0312 | EVQLVESGGGLVQAGGSRRLSCAVSGRTLSSFGMGWFRQAPEKPREFV AAITWGQGGTFYADSVKGRFTISRDIVKNTVYLQMNDLKPDDTGLYFC VSAPHFHEAFPSRPPAYAYWGQGTQVTVSS (SEQ ID NO: 219) | + | + |
| LCP0313 | EVQLVESGGGLVQAGGSLRLSCAASGRTYGSYVIGWFRQAPGKEREFV ASIRWAGGDSHYGDPLKGRSTISKDNAKNTVYLQMNSLKPEDAAVYYC AGAAPVPGSSYEWTNWGQGTQVTVSS (SEQ ID NO: 220) | + | + |
| LCP0314 | EVQLVESGGGLVQAGGSLRLSCAASGSISSVNTMGWYRQAPGKQRELV AFITSGDDTNYADSMKGRFTISRDNAKNTLYLQMNSLKPEDTAVYYCV ATLGRSSSGTYTYWGQGTQVTVSS (SEQ ID NO: 221) | + | + |
| LCP0316 | EVQLVESGGGLVQAGGSLRLSCAASLRTLDNYGVGWFRQTPGREREFV SAVSWNGDRTYYQDSVKGRFTISREYAKNTVYLQMDSLKPEDTAVYYC AVNMYGSTFPGLSVESHYDYWGQGTQVTVSS (SEQ ID NO: 222) | + | + |
| LCP0317 | EVQLVESGGGLVQAGGSLRLSCAASGSIFSINAMAWYRQAQGKQRELV ADITKNDITDYADSVKGRFTIARDNAKNTVDLQMNSLKPEDTAVYYCT AALSRHPYRSWGQGTQVTVSS (SEQ ID NO: 223) | + | + |

TABLE 1-continued

Representative llama-derived anti-C5 VHH domains and
whether each clone binds to human complement protein
C5 (hC5) and/or cyno complement protein C5 (cC5).

| VHH domain | Sequence | Binds hC5 | Binds cC5 |
|---|---|---|---|
| LCP0319 | EVQLVESGGGLVQAGGSLRLSCAAAGRSLSDYYIIWFRQPPGKEYEFV SSIRWNTGSTTYGDSVKGRFTISRDNAKSTVYLQMNSLKPEDTALYWC AAGLHLTPTSRTYNYRGQGTQVTVSS (SEQ ID NO: 224) | + | + |
| LCP0320 | EVQLVESGGGLVQAGGSLRLSCAAPETIFTINSMGWYRQAPGKQRELV AFINLDGNTNYADSAKGRFTISRDNAENTVYLQMDNLKPDDTAVYYCN VLLSRAISGSYVHWGQGTQVTVSS (SEQ ID NO: 225) | + | + |

Example 3. Cloning and Expression of Anti-C5 VHH Domains

Representative anti-C5 VHH domains were subcloned into a mammalian expression vector and expressed as VHH-His-tag fusions in Expi293F cells. Culture supernatants were harvested when cell viability dropped to 50-60%. The supernatants were analyzed via SDS-PAGE under reducing conditions, followed by Coomassie brilliant blue staining. Expression levels were calculated using biolayer interferometry on an Octet (ForteBio Inc.) instrument. His-tagged VHH domains were purified by Immobilized Metal Affinity Chromatography (IMAC) on an AKTA (GE Healthcare) from the culture supernatants.

Example 4. Binding and Functional Analysis of Anti-C5 VHH Domains

Binding analysis to complement component C5. Representative anti-C5 VHH domains were sequenced, characterized, and evaluated for binding to human, cynomolgus monkey (cyno), and mouse C5 protein using Biolayer Interferometry on an Octet (ForteBio Inc.) instrument. Cell culture supernatants from expressed VHH-His domains were normalized to a concentration of 20 µg/mL in 2× kinetics buffer and loaded on anti-penta-HIS (HIS1K) biosensor tips (ForteBio Inc.) for 300 seconds to fully saturate the sensor tips. The saturated tips were then exposed to a solution containing 50 nM of soluble C5 (human, cyno or mouse) in 2× kinetics buffer each for 600 seconds in separate experiments and dissociation was followed for 600 seconds into 2× kinetics buffer. VHH domains that showed binding to human (hC5) or cyno C5 (cC5) are marked with a '+' in Table 1.

Hemolysis assays for C5 antagonism. A hemolysis assay measures the release of hemoglobin from sensitized chicken erythrocytes lysed on exposure to Complement Classical Pathway (CCP)-activated serum. His-tagged VHH domains were expressed in Expi293 cells. Preliminary assays were used to select functional anti-C5 VHH domains, which were purified by IMAC. Ten purified VHH domains were analyzed for their ability to inhibit CCP-mediated hemolysis of sensitized chicken erythrocytes at different concentrations.

Figure 1B:
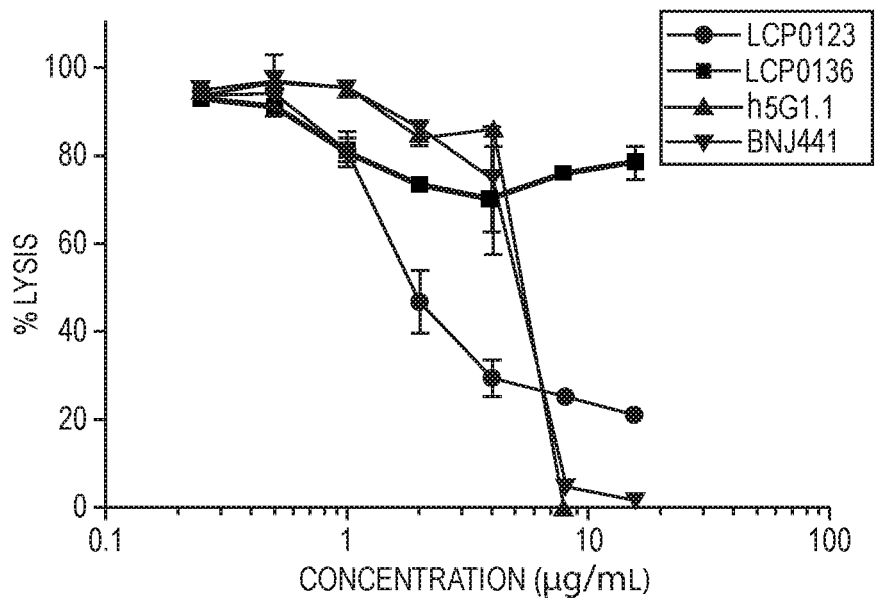
Figure 1B:
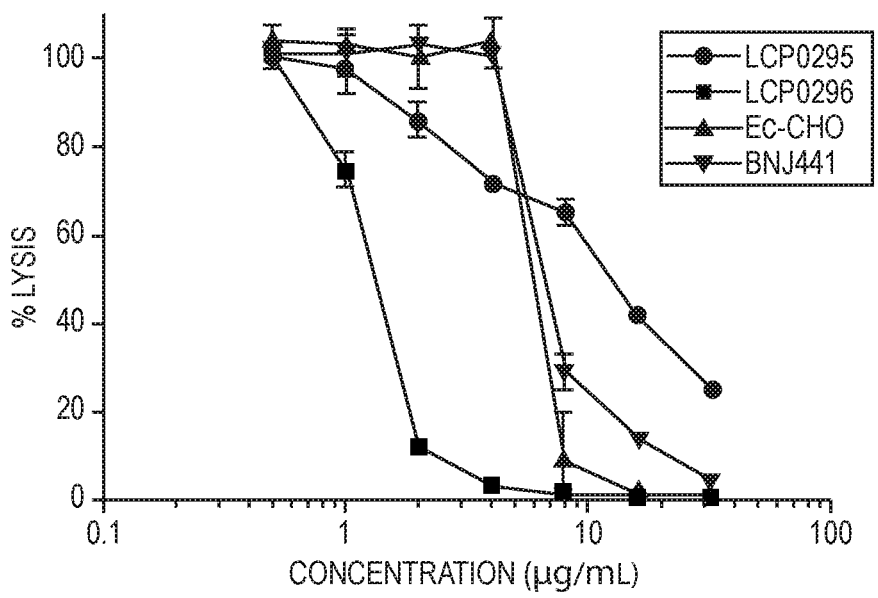

No antibody and 20 mM EDTA were used as complete lysis and no lysis controls for the assay, respectively. The ten VHH domains and the control anti-C5 IgGs (denoted h5G1.1, BNJ441 and Ec-CHO) at different concentrations (32 µg/mL to 0.5 µg/mL) were pre-incubated with 20% normal human serum (NHS) in 0.1 mL gelatin veronal buffered saline (GVB++, cat #B100, Comptech) for 30 minutes at room temperature. 400 µL chicken erythrocytes (Lampire Biologicals, cat #7201403) were washed four times with 1 mL of GVB++ and sensitized cRBCs were prepared by incubating $5\times10^7$ cells/mL with 1:500 (v/v) dilution of rabbit-anti-chicken IgG (cat #203-4139, Rockland) and incubated at 4 C for 15 minutes. The cells were washed twice with GVB++ and resuspended in a final volume of 3.6 mL GVB++. 30 µL of sensitized cRBCs ($2.5\times10^6$ cells) were added to the pre-incubated human serum and antibodies, and incubated at 37 C for 30 minutes. The cells were pelleted by centrifugation at 1700×g for 3 minutes at 4 C and the supernatant (85 µL) was transferred to a new flat bottom 96 well plate. Absorbance was measured at 415 nm. Percent lysis was calculated for each VHH domain and the control antibodies as:

$$((A_{415 sample}-A_{415\ no\ lysis})/(A_{415 complete\ lysis}-A_{415\ no\ lysis}))\times100$$

where $A_{415ssample}$ is the absorbance at 415 nm for the sample antibody, $A_{415no\ lysis}$ is the absorbance at 415 nm for no lysis control (20 mM EDTA), and $A_{415\ complete\ lysis}$ is the absorbance at 415 nm for complete lysis control. The results are shown in FIG. 1.

Figure 2:
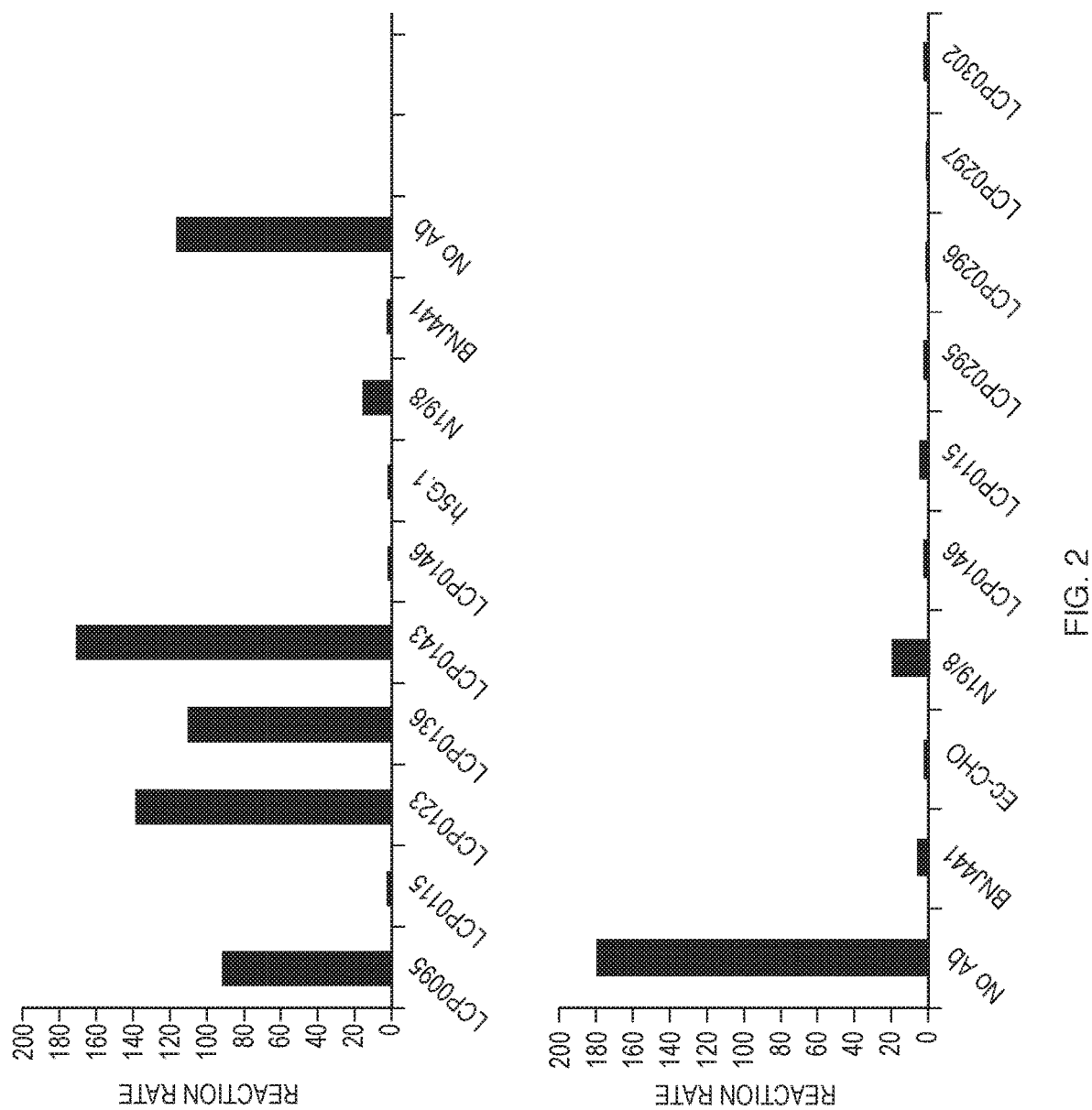
FIG. 2 shows the results of a C5a liberation assay for anti-C5 VHH domains.

Identification of VHH domains that inhibit C5a liberation. Human C5 protein cleavage (e.g., C5a liberation with Complement Alternative Pathway C5 convertase deposited on CAP-activator Zymosan) was measured using a Meso Scale Discovery (MSD)-based immunoassay. Anti-C5 VHH domains were expressed and purified as in the previous section and were analyzed for their ability to block the cleavage of human C5 protein by measuring the amount of hC5a released. Optimal concentration for the sample VHH domain was determined in pilot experiments. The sample VHH domains and control antibodies (h5G1.1, N19/8, BNJ441 and Ec-CHO) were added to human C5 protein (final concentration 25 nM) (CompTech Inc.) in GVB++ buffer containing 1% gelatin, and 2.5 mM NiCl for 30 minutes at 37 C and stored at 4 C until further use. A MSD high-binding 96 well plate was coated with an anti-C5a antibody at 2 µg/mL in BupH Phosphate Buffered Saline (ThermoFisher) and incubated for 1 hour. Zymosan was then added to NHS in equal proportion to activate the complement alternative pathway. This mixture of zymosan-NHS was then added to pre-incubated VHH-hC5 solution and incubated at 37 C. The reaction was stopped at different time points (0, 30, 60 and 90 minutes) by addition of futhan-EDTA. The plate was centrifuged at 3600 rpm for 2 minutes and supernatant was transferred to a new polypropylene plate. Blocker A was added for 1 hour at room temperature to block non-specific binding to the coated MSD plate. The MSD plate was washed and supernatant from samples from above were added. This plate was incubated at room temperature for 15 minutes. A mixture of detection antibody biotin-Ab2942 (Abcam) at 1 μg/mL and streptavidin conjugated sulfo tag at 0.5 μg/mL was prepared and then added to each well and incubated at room temperature for 30 minutes. MSD 2× read buffer was added to each well and the electro-chemiluminescent signal was measured. Raw data was analyzed using the MSD workbench software. The results from this experiment are shown in FIG. 2.

LCP0115, LCP0146, LCP0295, LCP0296, LCP0297 and LCP0302 inhibited the release of C5a and were used for further characterization.

Example 5. Affinity Analysis of Anti-C5 VHH Domains by Biacore

Anti-C5 VHH domains were prioritized based on cross reactivity to cyno C5 and eight purified anti-C5 VHH domains were subjected to affinity analysis by Biacore. The kinetic parameters for binding to human and cyno C5 for the initial eight candidates are shown in Table 2. Out of the eight affinity-analyzed candidates, five anti-C5 domains (LCP0115, LCP0143, LCP0146, LCP0296, and LCP0302) were chosen and prioritized for humanization and further analysis based on matched affinity to human and cyno C5.

TABLE 2

Results of Biacore characterization of VHH domains.

| Sample  | C5  | $k_a$ (1/Ms) | $k_d$ (1/s) | $K_D$ (M) | Chi$^2$ |
|---------|-----|--------------|-------------|-----------|---------|
| LCP0095 | hC5 | 2.86e5       | 7.14e-4     | 2.50e-9   | 6.94    |
|         | cC5 | 4.56e5       | 1.68e-3     | 3.69e-9   | 12.9    |
| LCP0115 | hC5 | 1.13e5       | 3.48e-5     | 3.09e-10  | 0.08    |
|         | cC5 | 9.53e4       | 1.02e-5     | 1.07e-10  | 0.10    |
| LCP0123 | hC5 | 1.08e5       | 2.16e-4     | 1.99e-9   | 0.13    |
|         | cC5 | 1e5          | 3.81e-4     | 3.8e-9    | 0.14    |

TABLE 2-continued

Results of Biacore characterization of VHH domains.

| Sample  | C5  | $k_a$ (1/Ms) | $k_d$ (1/s) | $K_D$ (M) | Chi$^2$ |
|---------|-----|--------------|-------------|-----------|---------|
| LCP0136 | hC5 | 4.86e5       | 8.82e-4     | 1.81e-9   | 2.47    |
|         | cC5 | 7.89e5       | 2.51e-4     | 3.18e-10  | 1.01    |
| LCP0143 | hC5 | 6.91e5       | 5.66e-5     | 8.2e-11   | 0.90    |
|         | cC5 | 7.41e5       | 1.24e-4     | 1.67e-10  | 0.81    |
| LCP0146 | hC5 | 2.24e6       | 9.75e-5     | 4.35e-11  | 0.42    |
|         | cC5 | 2.64e6       | 2.44e-4     | 9.22e-11  | 0.47    |
| LCP0296 | hC5 | 9.34e4       | 3.9e-5      | 4.17e-10  | 0.06    |
|         | cC5 | 6.84e4       | 1.06e-4     | 1.55e-9   | 0.03    |
| LCP0302 | hC5 | 1.14e5       | 2.22e-5     | 1.95e-10  | 0.03    |
|         | cC5 | 1.03e5       | 2.38e-5     | 2.32e-10  | 0.03    |

Example 6. Humanization of Anti-C5 VHH Domains

Five prioritized anti-C5 VHH domains (LCP0115, LCP0143, LCP0146, LCP0296 and LCP0302) were humanized by CDR grafting onto human germlines with sequence similarity to the llama sequence. CDRs were based on higher amino acid coverage among the IMGT and Kabat definitions. Back mutations to llama FR2 hallmark residues were made to maintain VHH domain stability. The humanized variants were expressed in Expi293 cells and tested for binding to human C5 using biolayer interferometry.

Further back mutations to parental llama residues were introduced in selected frameworks for several of the variants to improve their affinity for human C5. Constructs were expressed in HEK293F cells and evaluated for binding by biolayer interferometry. Additional mutations were made in some of the variants to further optimize their affinity, and the N-termini were humanized to EVQLV (SEQ ID NO:147; where necessary) and the C-termini were humanized to WGQGTLVTVSS (SEQ ID NO:148; where necessary). Resulting prioritized anti-C5 VHH candidates are shown in Table 3 below. The CDRs from these candidates are shown in Table 4.

TABLE 3

Humanized anti-C5 VHH domain candidates

| VHH anti-C5 candidate name | Candidate sequence | SEQ ID NO: |
|---|---|---|
| LCP0177 | EVQLVESGGGLVQPGGSLRLSCAASGRTFSGILSPYAVGWFRQAPGQGLEAVATITSGGSAIYTDSVKGRFTISRDNSKNTLYLQMNSLRAEDTAVYYCAVRTRRYGSNLGEVPQENEYGYWGQGTLVTVSS | 226 |
| LCP0178 | EVQLVESGGGLVQPGGSLRLSCAASEMGATINVMAWFRQAPGQGLEAVARLPDNNIDYGDFAKGRFTISRDNSKNTLYLQMNSLRAEDTAVYYCNVLLSRQINGAYVHWGQGTLVTVSS | 227 |
| LCP0179 | EVQLVESGGGLVQPGGSLRLSCAASGRAFSDYAMAWFRQAPGQGLEAVAGIGWSGGDTLYADSVRGRFTISRDNSKNTLYLQMNSLRAEDTAVYYCAARQGQYIYSSMRSDSYDYWGQGTLVTVSS | 228 |
| LCP0180 | EVQLVESGGGLVQPGGSLRLSCAASGRTFSGILSPYAVGWFRQAPGQGREFVATITSGGSAIYTDSVKGRFTISRDNSKNTLYLQMNSLRAEDTAVYYCAVRTRRYGSNLGEVPQENEYGYWGQGTLVTVSS | 229 |
| LCP0181 | EVQLVESGGGLVQPGGSLRLSCAAPEMGATINVMAWYRQAPGQQRELVARLPDNNIDYGDFAKGRFTISRDNSKNTLYLQMNSLRAEDTAVYYCNVLLSRQINGAYVHWGQGTLVTVSS | 230 |
| LCP0182 | EVQLVESGGGLVQPGGSLRLSCAASGRAFSDYAMAWFRQAPGQEREFVAGIGWSGGDTLYADSVRGRFTISRDNSKNTLYLQMNSLRAEDTAVYYCAARQGQYIYSSMRSDSYDYWGQGTLVTVSS | 231 |

TABLE 3-continued

Humanized anti-C5 VHH domain candidates

| VHH anti-C5 candidate name | Candidate sequence | SEQ ID NO: |
|---|---|---|
| LCP0183 | EVQLVESGGGLVQPGGSLRLSCAASGRTFSGILSPYAVGWFRQ APGKGREFVSTITSGGSAIYTDSVKGRFTISRDNAKNSLYLQM NSLRAEDTAVYYCAVRTRRYGSNLGEVPQENEYGYWGQGTLVT VSS | 232 |
| LCP0184 | EVQLVESGGGLVQPGGSLRLSCAASGRTFSGILSPYAVGWFRQ APGKGLEFVSTITSGGSAIYTDSVKGRFTISRDNAKNSLYLQM NSLRAEDTAVYYCAVRTRRYGSNLGEVPQENEYGYWGQGTLVT VSS | 233 |
| LCP0185 | EVQLVESGGGLVKPGGSLRLSCAASEMGATINVMAWYRQAPGK QRELVSRLPLDNNIDYGDFAKGRFTISRDNAKNSLYLQMNSLR AEDTAVYYCNVLLSRQINGAYVHWGQGTLVTVSS | 234 |
| LCP0186 | EVQLVESGGGLVKPGGSLRLSCAASEMGATINVMAWYRQAPGK GLELVSRLPLDNNIDYGDFAKGRFTISRDNAKNSLYLQMNSLR AEDTAVYYCNVLLSRQINGAYVHWGQGTLVTVSS | 235 |
| LCP0187 | EVQLVESGGGLVQPGRSLRLSCAASGRAFSDYAMAWFRQAPGK EREFVSGIGWSGGDTLYADSVRGRFTISRDNAKNSLYLQMNSL RAEDTALYYCAARQGQYIYSSMRSDSYDYWGQGTLVTVSS | 236 |
| LCP0188 | EVQLVESGGGLVQPGRSLRLSCAASGRAFSDYAMAWFRQAPGK GLEFVSGIGWSGGDTLYADSVRGRFTISRDNAKNSLYLQMNSL RAEDTALYYCAARQGQYIYSSMRSDSYDYWGQGTLVTVSS | 237 |
| LCP0195 | EVQLVESGGGLVQPGGSLRLSCAASGRAFSDYAMAWFRQAPGQ EREFVAGIGWSGGDTLYADSVRGRFTNSRDNSKNTLYLQMNSL RAEDTAVYYCAARQGQYIYSSMRSDSYDYWGQGTLVTVSS | 1 |
| LCP0197 | EVQLVESGGGLVQPGGSLRLSCAASGRAFSDYAMAWFRQAPGQ EREFVAGIGWSGGDTLYADSVRGRFTISRDNAKNTLYLQMNSL RAEDTAVYYCAARQGQYIYSSMRSDSYDYWGQGTLVTVSS | 2 |
| LCP0199 | EVQLVESGGGLVQPGGSLRLSCAASGRAFSDYAMAWFRQAPGQ EREFVAGIGWSGGDTLYADSVRGRFTISRDNSKNTMYLQMNSL RAEDTAVYYCAARQGQYIYSSMRSDSYDYWGQGTLVTVSS | 3 |
| LCP0203 | EVQLVESGGGLVQPGGSLRLSCAASGRAFSDYAMAWFRQAPGQ GLEFVAGIGWSGGDTLYADSVRGRFTISRDNSKNTLYLQMNSL RAEDTAVYYCAARQGQYIYSSMRSDSYDYWGQGTLVTVSS | 4 |
| LCP0207 | EVQLVESGGGLVQPGGSLRLSCAASGRTFSGILSPYAVGWFRQ APGKGLEFVSTITSGGSAIYTDSVKGRFTISRDNAKDSLYLQM NSLRAEDTAVYYCAVRTRRYGSNLGEVPQENEYGYWGQGTLVT VSS | 5 |
| LCP0208 | EVQLVESGGGLVQPGGSLRLSCAASGRTFSGILSPYAVGWFRQ APGKGLEFVSTITSGGSAIYTDSVKGRFTISRDNAKNTLYLQM NSLRAEDTAVYYCAVRTRRYGSNLGEVPQENEYGYWGQGTLVT VSS | 6 |
| LCP0209 | EVQLVESGGGLVQPGGSLRLSCAASGRTFSGILSPYAVGWFRQ APGKGLEFVSTITSGGSAIYTDSVKGRFTISRDNAKNSVYLQM NSLRAEDTAVYYCAVRTRRYGSNLGEVPQENEYGYWGQGTLVT VSS | 7 |
| LCP0212 | EVQLVESGGGLVQPGGSLRLSCAASGRTFSGILSPYAVGWFRQ APGQGLEFVATITSGGSAIYTDSVKGRFTISRDNSKNTLYLQM NSLRAEDTAVYYCAVRTRRYGSNLGEVPQENEYGYWGQGTLVT VSS | 8 |
| CRL0303 | EVQLVESGGGLVQPGGSLRLSCAASGRHFSDYAMAWFRQAPGQ EREFVAGIGWSGGDTLYADSVRGRFTISRDNSKNTLYLQMNSL RAEDTAVYYCAARQGQYIYSSMRSDSYDYWGQGTLVTVSS | 9 |
| CRL0304 | EVQLVESGGGLVQPGGSLRLSCAASGRAHSDYAMAWFRQAPGQ EREFVAGIGWSGGDTLYADSVRGRFTISRDNSKNTLYLQMNSL RAEDTAVYYCAARQGQYIYSSMRSDSYDYWGQGTLVTVSS | 10 |
| CRL0305 | EVQLVESGGGLVQPGGSLRLSCAASGRAHSDYAMAWFRQAPGQ EREFVAGIGWSGGDTLYADSVRGRFTNSRDNSKNTLYLQMNSL RAEDTAVYYCAARQGQYIYSSMRSDSYDYWGQGTLVTVSS | 11 |

TABLE 3-continued

Humanized anti-C5 VHH domain candidates

| VHH anti-C5 candidate name | Candidate sequence | SEQ ID NO: |
|---|---|---|
| CRL0307 | EVQLVESGGGLVQPGGSLRLSCAASGRHHSDYAMAWFRQAPGQ EREFVAGIGWSGGDTLYADSVRGRFTISRDNSKNTLYLQMNSL RAEDTAVYYCAARQGQYIYSSMRSDSYDYWGQGTLVTVSS | 12 |
| CRL0726 | EVQLVESGGGLVQPGGSLRLSCAASVGTISDYGMGWFRQAPGQ GLEAVASISWGGMWTDYADSVKGRFTISRDNSKNTLYLQMNSL RAEDTAVYYCGRGRMYRGIGNSLAQPKSYGYWGQGTLVTVSS | 238 |
| CRL0727 | EVQLVESGGGLVQPGGSLRLSCAASGRTFSGILSAYAVGWFRQ APGQGLEAVATITSGGSTLSADSVKGRFTISRDNSKNTLYLQM NSLRAEDTAVYYCAVRTWPYGSNRGEVPTENEYGHWGQGTLVT VSS | 239 |
| CRL0728 | EVQLVESGGGLVQPGGSLRLSCAASVGTISDYGMGWFRQAPGQ EREFVASISWGGMWTDYADSVKGRFTISRDNSKNTLYLQMNSL RAEDTAVYYCGRGRMYRGIGNSLAQPKSYGYWGQGTLVTVSS | 240 |
| CRL0729 | EVQLVESGGGLVQPGGSLRLSCAASGRTFSGILSAYAVGWFRQ APGQEREFVATITSGGSTLSADSVKGRFTISRDNSKNTLYLQM NSLRAEDTAVYYCAVRTWPYGSNRGEVPTENEYGHWGQGTLVT VSS | 241 |
| CRL0730 | EVQLVESGGGLVKPGGSLRLSCAASVGTISDYGMGWFRQAPGK EREFVSSISWGGMWTDYADSVKGRFTISRDNAKNSLYLQMNSL RAEDTAVYYCGRGRMYRGIGNSLAQPKSYGYWGQGTLVTVSS | 242 |
| CRL0731 | EVQLVESGGGLVKPGGSLRLSCAASVGTISDYGMGWFRQAPGK GLEFVSSISWGGMWTDYADSVKGRFTISRDNAKNSLYLQMNSL RAEDTAVYYCGRGRMYRGIGNSLAQPKSYGYWGQGTLVTVSS | 243 |
| CRL0732 | EVQLLESGGGLVQPGGSLRLSCAASGRTFSGILSAYAVGWFRQ APGKEREFVSTITSGGSTLSADSVKGRFTISRDNSKNTLYLQM NSLRAEDTAVYYCAVRTWPYGSNRGEVPTENEYGHWGQGTLVT VSS | 244 |
| CRL0733 | EVQLLESGGGLVQPGGSLRLSCAASGRTFSGILSAYAVGWFRQ APGKGLEFVSTITSGGSTLSADSVKGRFTISRDNSKNTLYLQM NSLRAEDTAVYYCAVRTWPYGSNRGEVPTENEYGHWGQGTLVT VSS | 245 |
| CRL0960 | QVQLVQSGAEVKKPGASVKVSCKASGRAFSDYAMAWVRQAPGQ GLEWMGGIGWSGGDTLYADSVRGYTENFKDRVTMTRDTSTSTV YMELSSLRSEDTAVYYCARQGQYIYSSMRSDSYDYWGQGTLVT VSS | 246 |
| CRL0961 | QVQLVQSGAEVKKPGASVKVSCKASGRAFSDYAMAWFRQAPGQ EREFMGGIGWSGGDTLYADSVRGYTENFKDRVTMTRDTSTSTV YMELSSLRSEDTAVYYCARQGQYIYSSMRSDSYDYWGQGTLVT VSS | 247 |
| CRL0962 | QVQLVQSGAEVKKPGASVKVSCKASGRAFSDYAMAWFRQAPGQ GLEFMGGIGWSGGDTLYADSVRGYTENFKDRVTMTRDTSTSTV YMELSSLRSEDTAVYYCARQGQYIYSSMRSDSYDYWGQGTLVT VSS | 248 |
| CRL0963 | QVQLVQSGAEVKKPGASVKVSCKASVGTISDYGMGWVRQAPGQ GLEWMGSISWGGMWTDYADSVKGYTENFKDRVTMTRDTSTSTV YMELSSLRSEDTAVYYCARGRGRMYRGIGNSLAQPKSYGYWGQ GTLVTVSS | 249 |
| CRL0964 | QVQLVQSGAEVKKPGASVKVSCKASVGTISDYGMGWFRQAPGQ EREFMGSISWGGMWTDYADSVKGYTENFKDRVTMTRDTSTSTV YMELSSLRSEDTAVYYCARGRGRMYRGIGNSLAQPKSYGYWGQ GTLVTVSS | 250 |
| CRL0965 | QVQLVQSGAEVKKPGASVKVSCKASVGTISDYGMGWFRQAPGQ GLEFMGSISWGGMWTDYADSVKGYTENFKDRVTMTRDTSTSTV YMELSSLRSEDTAVYYCARGRGRMYRGIGNSLAQPKSYGYWGQ GTLVTVSS | 251 |
| CRL0966 | QVQLVQSGAEVKKPGASVKVSCKASGRTFSGILSAYAVGWVRQ APGQGLEWMGTITSGGSTLSADSVKGYTENFKDRVTMTRDTST STVYMELSSLRSEDTAVYYCARAVRTWPYGSNRGEVPTENEYG HWGQGTLVTVSS | 252 |

TABLE 3-continued

Humanized anti-C5 VHH domain candidates

| VHH anti-C5 candidate name | Candidate sequence | SEQ ID NO: |
|---|---|---|
| CRL0967 | QVQLVQSGAEVKKPGASVKVSCKASGRTFSGILSAYAVGWFRQAPGQEREFMGTITSGGSTLSADSVKGYTENFKDRVTMTRDTSTSTVYMELSSLRSEDTAVYYCARAVRTWPYGSNRGEVPTENEYGHWGQGTLVTVSS | 253 |
| CRL0968 | QVQLVQSGAEVKKPGASVKVSCKASGRTFSGILSAYAVGWFRQAPGQGLEFMGTITSGGSTLSADSVKGYTENFKDRVTMTRDTSTSTVYMELSSLRSEDTAVYYCARAVRTWPYGSNRGEVPTENEYGHWGQGTLVTVSS | 254 |
| CRL0972 | EVQLVESGGGVVRPGGSLRLSFAASGRAFSDYAMAWFRQAPGKEREFVSGIGWSGGDTLYADSVRGRFTISRDNAKNSLYLQMNSLRAEDTALYHCAARQGQYIYSSMRSDSYDYWGQGTLVTVSS | 255 |
| CRL0973 | EVQLLESGGGLVQPGGSLRLSCAASGRAFSDYAMAWFRQAPGKEREFVSGIGWSGGDTLYADSVRGRFTISRDNSKNTLYLQMNSLRAEDTAVYYCAARQGQYIYSSMRSDSYDYWGQGTLVTVSS | 256 |
| CRL0974 | EVQLVESGGVVVQPGGSLRLSCAASGRAFSDYAMAWFRQAPGKEREFVSGIGWSGGDTLYADSVRGRFTISRDNSKNSLYLQMNSLRAEDTALYYCAARQGQYIYSSMRSDSYDYWGQGTLVTVSS | 257 |
| CRL0975 | EVQLVESGGGLVQPGGSLRLSCAASVGTISDYGMGWFRQAPGKEREFVSSISWGGMWTDYADSVKGRFTISRDNSKNTLYLQMNSLRAEDTAVYYCGRGRMYRGIGNSLAQPKSYGYWGQGTQVTVSS | 258 |
| CRL0976 | EVQLVESGGGLVQPGGSLRLSCAASVGTISDYGMGWFHQAPGKEREFVSSISWGGMWTDYADSVKGRFIISRDNSRNTLYLQTNSLRAEDTAVYYCGRGRMYRGIGNSLAQPKSYGYWGQGTLVTVSS | 259 |
| CRL0977 | EVQLVESGGGVVQPGRSLRLSCAASVGTISDYGMGWFRQAPGKEREFVASISWGGMWTDYADSVKGRFTISRDNSKNTLYLQMNSLRAEDTAVYYCGRGRMYRGIGNSLAQPKSYGYWGQGTQVTVSS | 260 |
| CRL0978 | EVQLVESGGGLVKPGGSLRLSCAASGRTFSGILSAYAVGWFRQAPGKEREFVSTITSGGSTLSADSVKGRFTISRDNAKNSLYLQMNSLRAEDTAVYYCAVRTWPYGSNRGEVPTENEYGHWGQGTQVTVSS | 261 |
| CRL0979 | EVQLVESGGGLVQPGGSLRLSCAASGRTFSGILSAYAVGWFRQAPGKEREFVSTITSGGSTLSADSVKGRFTISRDNSKNTLYVQMSSLRAEDTAVYYCAVRTWPYGSNRGEVPTENEYGHWGQGTQVTVSS | 262 |
| CRL0980 | EVQLVESGGGVVQPGGSLRLSCAASGRTFSGILSAYAVGWFRQAPGKEREFVSTITSGGSTLSADSVKGRFTISRDNSKNSLYLQMNSLRTEDTALYYCAVRTWPYGSNRGEVPTENEYGHWGQGTQVTVSS | 263 |

TABLE 4

CDRs of humanized anti-C5 VHH domain candidates

| VHH domain | CDR1 sequence [SEQ ID NO:] | CDR2 sequence [SEQ ID NO:] | CDR3 sequence [SEQ ID NO:] |
|---|---|---|---|
| LCP0146 | GRAFSDYAMA | GIGWSGGDTLYADSVRG | AARQGQYIYSSMRSDSYDY |
| LCP0179 | [13] | [18] | [20] |
| LCP0182 | | | |
| LCP0187 | | | |
| LCP0188 | | | |
| LCP0195 | | | |
| LCP0197 | | | |
| LCP0199 | | | |
| LCP0203 | | | |
| CRL0960 | | | |
| CRL0961 | | | |
| CRL0962 | | | |
| CRL0972 | | | |
| CRL0973 | | | |
| CRL0974 | | | |

TABLE 4-continued

CDRs of humanized anti-C5 VHH domain candidates

| VHH domain | CDR1 sequence [SEQ ID NO:] | CDR2 sequence [SEQ ID NO:] | CDR3 sequence [SEQ ID NO:] |
|---|---|---|---|
| LCP0115<br>LCP0177<br>LCP0180<br>LCP0183<br>LCP0184<br>LCP0207<br>LCP0208<br>LCP0209<br>LCP0212 | GRTFSGILSPYAVG<br>[14] | TITSGGSAIYTDSVKG<br>[19] | AVRTRRYGSNLGEVPQENEYGY<br>[21] |
| LCP0143<br>LCP0178<br>LCP0181<br>LCP0185<br>LCP0186 | EMGATINVMA<br>[327] | RLPLDNNIDYGDFAKG<br>[325] | NVLLSRQINGAYVH<br>[326] |
| CRL0303 | GRHFSDYAMA<br>[15] | GIGWSGGDTLYADSVRG<br>[18] | AARQGQYIYSSMRSDSYDY<br>[20] |
| CRL0304<br>CRL0305 | GRAHSDYAMA<br>[16] | GIGWSGGDTLYADSVRG<br>[18] | AARQGQYIYSSMRSDSYDY<br>[20] |
| CRL0307 | GRHHSDYAMA<br>[17] | GIGWSGGDTLYADSVRG<br>[18] | AARQGQYIYSSMRSDSYDY<br>[20] |
| LCP0296<br>CRL0726<br>CRL0728<br>CRL0730<br>CRL0731<br>CRL0963<br>CRL0964<br>CRL0965<br>CRL0975<br>CRL0976<br>CRL0977 | VGTISDYGMG<br>[264] | SISWGGMWTDYADSVKG<br>[266] | GRGRMYRGIGNSLAQPKSYGY<br>[268] |
| LCP0302<br>CRL0727<br>CRL0729<br>CRL0732<br>CRL0733<br>CRL0966<br>CRL0967<br>CRL0968<br>CRL0978<br>CRL0979<br>CRL0980 | GRTFSGILSAYAVG<br>[265] | TITSGGSTLSADSVKG<br>[267] | AVRTWPYGSNRGEVPTENEYGH<br>[269] |

Back mutations to parental llama residues were introduced in selected frameworks from humanization assessments to improve the affinity of the selected variants. The sequences of the back mutated variants are shown in Table 5. Constructs were expressed in HEK293F cells and evaluated for binding by biolayer interferometry.

TABLE 5

Anti-C5 VHH humanized variants with back mutations

| Variant name | Back mutated variant sequence | SEQ ID NO |
|---|---|---|
| LCP0115 variants | | |
| LCP0204 | EVQLVESGGGLVQAGGSLRLSCAASGRTFSGILSPYAVGWFRQAPGKGLEF VSTITSGGSAIYTDSVKGRFTISRDNAKNSLYLQMNSLRAEDTAVYYCAVR TRRYGSNLGEVPQENEYGYWGQGTLVTVSS | 270 |
| LCP0205 | EVQLVESGGGLVQPGGSLRLSCAASGRTFSGILSPYAVGWFRQAPGKGREF VSTITSGGSAIYTDSVKGRFTISRDNAKNSLYLQMNSLRAEDTAVYYCAVR TRRYGSNLGEVPQENEYGYWGQGTLVTVSS | 232 |
| LCP0206 | EVQLVESGGGLVQPGGSLRLSCAASGRTFSGILSPYAVGWFRQAPGKGLEF VSTITSGGSAIYTDSVKGRFTLSRDNAKNSLYLQMNSLRAEDTAVYYCAVR TRRYGSNLGEVPQENEYGYWGQGTLVTVSS | 271 |

TABLE 5-continued

Anti-C5 VHH humanized variants with back mutations

| Variant name | Back mutated variant sequence | SEQ ID NO |
|---|---|---|
| LCP0207 | EVQLVESGGGLVQPGGSLRLSCAASGRTFSGILSPYAVGWFRQAPGKGLEFVSTITSGGSAIYTDSVKGRFTISRDNAKDSLYLQMNSLRAEDTAVYYCAVRTRRYGSNLGEVPQENEYGYWGQGTLVTVSS | 5 |
| LCP0208 | EVQLVESGGGLVQPGGSLRLSCAASGRTFSGILSPYAVGWFRQAPGKGLEFVSTITSGGSAIYTDSVKGRFTISRDNAKNTLYLQMNSLRAEDTAVYYCAVRTRRYGSNLGEVPQENEYGYWGQGTLVTVSS | 6 |
| LCP0209 | EVQLVESGGGLVQPGGSLRLSCAASGRTFSGILSPYAVGWFRQAPGKGLEFVSTITSGGSAIYTDSVKGRFTISRDNAKNSVYLQMNSLRAEDTAVYYCAVRTRRYGSNLGEVPQENEYGYWGQGTLVTVSS | 7 |
| LCP0210 | EVQLVESGGGLVQPGGSLRLSCAASGRTFSGILSPYAVGWFRQAPGKGLEFVSTITSGGSAIYTDSVKGRFTISRDNAKNSLYLQMNSLKAEDTAVYYCAVRTRRYGSNLGEVPQENEYGYWGQGTLVTVSS | 272 |
| LCP0211 | EVQLVESGGGLVQPGGSLRLSCAASGRTFSGILSPYAVGWFRQAPGKGLEFVSTITSGGSAIYTDSVKGRFTISRDNAKNSLYLQMNSLRPEDTAVYYCAVRTRRYGSNLGEVPQENEYGYWGQGTLVTVSS | 273 |
| LCP0212 | EVQLVESGGGLVQPGGSLRLSCAASGRTFSGILSPYAVGWFRQAPGQGLEFVATITSGGSAIYTDSVKGRFTISRDNSKNTLYLQMNSLRAEDTAVYYCAVRTRRYGSNLGEVPQENEYGYWGQGTLVTVSS | 8 |

LCP0146 variants

| | | |
|---|---|---|
| LCP0193 | EVQLVESGGGLVQAGGSLRLSCAASGRAFSDYAMAWFRQAPGQEREFVAGIGWSGGDTLYADSVRGRFTISRDNSKNTLYLQMNSLRAEDTAVYYCAARQGQYIYSSMRSDSYDYWGQGTLVTVSS | 274 |
| LCP0194 | EVQLVESGGGLVQPGGSLRLSCAASGRAFSDYAMAWFRQAPGKEREFVAGIGWSGGDTLYADSVRGRFTISRDNSKNTLYLQMNSLRAEDTAVYYCAARQGQYIYSSMRSDSYDYWGQGTLVTVSS | 275 |
| LCP0195 | EVQLVESGGGLVQPGGSLRLSCAASGRAFSDYAMAWFRQAPGQEREFVAGIGWSGGDTLYADSVRGRFTNSRDNSKNTLYLQMNSLRAEDTAVYYCAARQGQYIYSSMRSDSYDYWGQGTLVTVSS | 1 |
| LCP0196 | EVQLVESGGGLVQPGGSLRLSCAASGRAFSDYAMAWFRQAPGQEREFVAGIGWSGGDTLYADSVRGRFTISKDNSKNTLYLQMNSLRAEDTAVYYCAARQGQYIYSSMRSDSYDYWGQGTLVTVSS | 276 |
| LCP0197 | EVQLVESGGGLVQPGGSLRLSCAASGRAFSDYAMAWFRQAPGQEREFVAGIGWSGGDTLYADSVRGRFTISRDNAKNTLYLQMNSLRAEDTAVYYCAARQGQYIYSSMRSDSYDYWGQGTLVTVSS | 2 |
| LCP0198 | EVQLVESGGGLVQPGGSLRLSCAASGRAFSDYAMAWFRQAPGQEREFVAGIGWSGGDTLYADSVRGRFTISRDNSKNRLYLQMNSLRAEDTAVYYCAARQGQYIYSSMRSDSYDYWGQGTLVTVSS | 277 |
| LCP0199 | EVQLVESGGGLVQPGGSLRLSCAASGRAFSDYAMAWFRQAPGQEREFVAGIGWSGGDTLYADSVRGRFTISRDNSKNTMYLQMNSLRAEDTAVYYCAARQGQYIYSSMRSDSYDYWGQGTLVTVSS | 3 |
| LCP0200 | EVQLVESGGGLVQPGGSLRLSCAASGRAFSDYAMAWFRQAPGQEREFVAGIGWSGGDTLYADSVRGRFTISRDNSKNTLSLQMNSLRAEDTAVYYCAARQGQYIYSSMRSDSYDYWGQGTLVTVSS | 278 |
| LCP0201 | EVQLVESGGGLVQPGGSLRLSCAASGRAFSDYAMAWFRQAPGQEREFVAGIGWSGGDTLYADSVRGRFTISRDNSKNTLYLQMNSLKAEDTAVYYCAARQGQYIYSSMRSDSYDYWGQGTLVTVSS | 279 |
| LCP0202 | EVQLVESGGGLVQPGGSLRLSCAASGRAFSDYAMAWFRQAPGQEREFVAGIGWSGGDTLYADSVRGRFTISRDNSKNTLYLQMNSLRPEDTAVYYCAARQGQYIYSSMRSDSYDYWGQGTLVTVSS | 280 |
| LCP0203 | EVQLVESGGGLVQPGGSLRLSCAASGRAFSDYAMAWFRQAPGQGLEFVAGIGWSGGDTLYADSVRGRFTISRDNSKNTLYLQMNSLRAEDTAVYYCAARQGQYIYSSMRSDSYDYWGQGTLVTVSS | 4 |

Example 7. Isolation of VHH Domains Binding to Human Serum Albumin

Albumin is an abundant protein in serum and has sufficient molecular weight to avoid removal by filtration through the glomerular filtration barrier. Removal of albumin from serum by intracellular degradation is inhibited by the interaction of FcRn with albumin that occurs at low pH. This interaction results in trafficking of the albumin-FcRn complex back to the plasma membrane where albumin is released back into blood upon exposure to the more neutral pH of the blood.

Overview of the Process for Generating Anti-HSA VHH

An immune biased VHH anti-HSA phage display library was produced from B cells of an immunized llama for anti-C5 VHH domains and for anti-HSA VHH domains. Upon obtaining endpoint titers greater than 1,000,000 towards HSA, PBMCs were harvested, RNA isolated and VHH regions genetically isolated. As described in detail for anti-C5 VHH domains in Examples 2-4, these anti-HSA VHH sequences were cloned into a pIII fusion phagemid, resulting in a library of 6×10$^8$ independent clones. Standard phage display panning techniques were used to select VHH domains reactive towards HSA and CSA (Cynomolgus monkey serum albumin). Outputs from three rounds of panning were analyzed by ELISA and Sanger sequencing. In parallel, next generation sequencing (NGS) was used to examine populations of sequences within the original library, or sequences that were enriched by panning. A total of ~1000 clones were isolated and analyzed using these methods.

Llama immunization and VHH phage library construction. A llama was immunized with HSA. The primary boost consisted of 500 µg antigen mixed with complete Freunds adjuvant. Boost immunizations of 500 µg antigen in incomplete Freunds adjuvant were given at 2 weeks, 4 weeks, 8 weeks and 12 weeks. Sera titers were monitored with test bleeds approximately 2 weeks after each boost. Test bleeds were analyzed by ELISA to determine titer of immune response. An anti-HSA sera titer was detected at 20× signal above the pre-bleed for the 1:100,000 dilution, therefore a production bleed of 500 mL was processed to obtain ~7×10$^8$ PBMCs for RNA isolation and library production. Total RNA from PBMCs was purified with phenol/chloroform extraction, followed by a silica-spin column, and total RNA was eluted with RNase free water. Quality of RNA was evaluated by determining the OD2601280 ratio and by agarose gel electrophoresis. cDNA was synthesized using llama heavy chain specific reverse primers. VHH (heavy chain only) fragments were separated from VH (conventional heavy chain) fragments via gel electrophoresis.

The VHH fragments were modified with SfiI sites and cloned into pADL-10b, and the DNA library was transformed into TG1 cells. A total of 6×10$^8$ independent clones were obtained for the library. All clones were harvested and stored in 25% glycerol at −80 C until use. Library quality was validated by analysis of 105 clones for the presence of an insert with a correct reading frame, uniqueness, and presence of primer sequences.

Phage display panning and screening. An aliquot of the anti-HSA VHH library glycerol stock comprising 3.75×10$^{10}$ cells was cultured in 2×YT media supplemented with 2% glucose and 100 µg/mL carbenicillin. Cells were grown at 37 C with shaking at −250 rpm until and an OD600 of ~0.6 was obtained. Helper phage was added at a multiplicity of infection (MOI) of 20 and the culture was incubated for 30 minutes without shaking, followed by incubation for 30 minutes with shaking at 37 C. Cells were harvested and resuspended in 2×YT media supplemented with 25 µg/mL Carbenicillin, 50 µg/mL kanamycin, and 200 µM IPTG. Cultures were shaken overnight at 30 C and 250 rpm. Media was clarified by centrifugation, phage were precipitated by addition of ¼th volume of 10% PEG-8000/2.5 M NaCl and incubation on ice for 30 minutes. Phage were pelleted by centrifugation at 7500 rpm for 15 minutes at 4 C in an SLA3000 rotor. The pellet was resuspended in Superblock (Thermo Scientific, 37515).

An aliquot of phage was deselected with M280 Streptavidin beads (Life Technologies, 11205D) for 30 minutes at room temperature, the beads were removed using a magnet, and phage-containing supernatant was transferred to a new Eppendorf tube. Phage were supplemented with 10 µg of biotinylated HSA, incubated with rotation at room temperature for 30 minutes, and then supplemented with M280 streptavidin beads to immobilize biotinylated HSA. Beads were washed 11 times with PBS/0.05% Tween wash buffer, eluted with 0.1 M glycine, pH 2.7, and then the elution buffer was neutralized with 1 M Tris, pH 9.0. Eluted phage were rescued into log phage TG1 cells and outgrowths recovered on 250 cm×250 cm LB Carbenicillin, 2% glucose trays. Titers were determined by serial dilution of an aliquot of the phage rescue. A second round of panning was performed essentially as described above, using an aliquot of the round one outgrowth and 5 µg of biotinylated HSA for selections.

To screen clones for reactivity to HSA, individual clones were picked into 96 well plates, cultured in a volume of 250 µL 2×YT supplemented with 100 µg/mL Carbenicillin and 2% glucose overnight at 37 C. Each well was subcultured by transfer of 5 µL dense overnight culture into 250 µL fresh media. An aliquot was submitted for rolling circle amplification sequence analysis to determine the encoded insert. Cells were grown to an OD600 of ~0.6, then supplemented with M13 helper phage at an MOI of 20 for one hour. Cells were harvested by centrifugation and media replaced with 250 µL per well of 2×YT supplemented with 100 µg/mL Carbenicillin and 50 µg/mL kanamycin. Plates were then incubated overnight at 30 C with shaking at 250 rpm. Media was clarified by centrifugation to prepare phage supernatants for use in ELISA assays.

For ELISA analysis, streptavidin-coated, pre-blocked 96-well plates (Pierce, 15500) were incubated with has-Biotin at 2 µg/mL for 30 minutes at room temperature with shaking. Plates were washed and then blocking was repeated for 1 hour at room temperature. Plates were again washed and supplemented with 50 µL of clarified supernatant for 30 minutes at room temperature. Plates were washed three times, then incubated with anti-M13 HRP antibody (GE Healthcare, Cat #27-9421-01) in blocking buffer for 30 minutes at room temperature. Plates were washed four times, then supplemented with 1-step Ultra TMB-ELISA reagent (Thermo Scientific, Cat #34029), color developed, and the reaction stopped using 2 M sulfuric acid stop solutions. OD450 readings were determined using a BioRad iMark plate reader.

NGS was used to examine populations of sequences within the original library, or sequences that were enriched by panning. For NGS, phagemid DNA was isolated from outgrowths of the initial library, round 1 panning, and round 2 panning. The VHH cassette was released from the phagemid by restriction digestion, VHH encoding bands isolated by agarose gel electrophoresis, and DNA purified using DNA affinity columns. This DNA was submitted for library production and analysis on the MiSeq 2×300 platform.

Example 8. Expression and Purification of VHH Domains Binding to HSA

VHH sequences selected using the above methodologies were synthesized with N-terminal signal peptides and C-terminal 6×His-tags (SEQ ID NO: 324) and cloned into a mammalian expression construct. The published MSA21 VHH domain (International Publication No. WO 2004/062551 A2) and genetically modified versions of individual clones (deglycosylated or humanized) were prepared by synthesis of GeneBlocks (Integrated DNA Technologies) and infusion cloning into a standard mammalian expression vector. These constructs were transfected into 293expi cells and supernatant harvested at 96 hours post-transfection. Supernatants were dialyzed against PBS and VHH-His proteins purified using standard chromatography methods. Purified proteins were buffer exchanged into PBS and quantified using OD and extinction coefficient.

Example 9. Characterization of Immobilized VHH Domains Binding to Soluble HSA, CSA and Mouse Serum Albumin Mammalian expression vectors were created for 112 VHH sequences and protein produced in the 293 expi expression system. VHH sequences were first analyzed by SDS-PAGE and Coomassie staining to determine approximate concentration relative to a known standard. Supernatant concentrations were then normalized and subjected to biolayer interferometry on an Octet HTX (Pall/ForteBio). Penta-His sensors were exposed to kinetics buffer for 60 seconds to establish baseline measurements. The sensors were then loaded with VHH-His containing supernatants for 300 seconds before a second baseline was established in kinetics buffer over 120 seconds. Tips were then incubated with 100 nM HSA or CSA in kinetics buffer for 600 seconds and dissociation measured over an additional 600 seconds.

Of the 112 VHH domains analyzed, 12 domains demonstrated binding to biotinylated HSA and three clones (HAS040, HAS041 and HAS042) interacted with both biotinylated CSA and biotinylated HSA. The sequences of these 12 anti-HSA VHH domains, including one or more humanized versions thereof, are shown in Table 6, with the CDRs of these anti-HSA VHH domains shown in Table 7.

TABLE 6

Sequences for anti-albumin VHH HASdomains

| VHH domain | Sequence | SEQ ID NO: |
|---|---|---|
| HAS020 | QVQLVESGGGLVQAGGSLRLSCAASGRTFGSDAAGWFRQASGK EREFVASISWSGGYTYYADSVKGRFTISSDNVKNTVYLQMNSL TPEDTAVYFCATGNRYSDYRISLVTPSQYEYWGQGTLVTVS | 22 |
| HAS038 | QVQLVESGGGLVQPGGSLRLSCTGSGHSFSTYTVGWFRQAPGE ERKFVASISWSGEVTLYGDSVKGRFTISRDNRKKTVYLQMHSL KPEDSAIYYCAAKRGGRPTDSSDDYFYWGQGTQVTVSS | 23 |
| HAS040 | QVQLNESGGGMVQAGGSLRLSCAASGRTVSNYAAGWFRQAPGK EREFVAAINWNKTTTYADSVKGRFIISREYAKNTVALQMNSLK PEDTAVYYCAAVFRIVAPKTQYEYDYWGQGTQVTVSS | 24 |
| HAS041 | QVQLIESGGGLVQAGGSLGLSCAASGRPVSNYAAAWFRQAPGK EREFVAAINWNKTATYADSVKGRFTISRDNAKSTVALQMNSLK PEDTAVYYCAAVFRVVAPKTQYDYDYWGQGTQVTVSS | 25 |
| HAS042 | EVQLVESGGGLVKPGGSLRLSCAASGRPVSNYAAAWFRQAPGK EREFVSAINWQKTATYADSVKGRFTISRDNAKNSLYLQMNSLR AEDTAVYYCAAVFRVVAPKTQYDYDYWGQGTLVTVSS | 26 |
| HAS044 | QVQLVESGGGLVQAGGSLRLSCAASGRTFSSYAIGWFRQAPGK AREFVARVSTIAGDTDYADSVKGRFTISRDNAKNTVYLQMNSL KPEDTAVYYCAADSYNVRLVTGEADYWGEGTQVTVSS | 27 |
| HAS077 | QVQLVESGGGLVQAGGSLRLSCAASGRTFSSYAIGWFRQAPGK AREFVARVSTIAGDTDYADSVKGRFTISRDNAKNTVYLQMNSL KPEDTAVYYCAADSYNVRLGTGEADYWGEGTQVTVSS | 28 |
| HAS079 | EVQLVESGGGLVQAGDSLRLSCAASGFTFSNYAIGWFRQAPGK AREFVARVSTIAGDTDYANAVKGRFTISRDNAKNTVYLQMNSL KPDDTAVYYCAAESYNVRLVTGEADYWGEGTQVTVSS | 29 |
| HAS080 | QVRLAESGGGRVQAGESLRLSCVASGRTFSNDAAGWFREASGK EREFVASISWSGNYTYYADSVKGRFTISEDNVKNTVYLQMTSL KPEDTAVYYCAAGNRYSDYRISLVTPRLYEYWGQGTQVTVS | 30 |
| HAS081 | QVQLVESGGGLVQAGGSLRLSCAASGRTFSSDAAGWFRQASGK EREFVAAISWSGNYTYSADSVKGRFTISSDNVKNTVYLQMNSL KPEDTAVYLCAAGNRYSDYRISLVTPSQYEYWGQGTQVTVS | 31 |
| HAS091 | QVQLVESGGGLVQAGGSLRLSCAASGRTFGSDAAGWFRQASGK EREFVASISWSGGYTYYADSGTGRFTISSDNVKNTVYLQMNSL TPEDTAVYFCATGNRDSDYRISLVTPSQYEYWGQGTQVTVSS | 32 |
| HAS093 | QVQLVESGGGLVQAGGSLRLSCAASGRTFGSDAAGWFRQASGK EREFVASISWSGGYTYYADSGKGRFTISSDNVKNTVYLQMNSL TPEDTAVYFCATGNRYSDYRISLVTPSQYDYWGQGTQVTVSS | 33 |
| HAS096 | QVQLVESGGGLVQAGGSLRLSCAASGRTFGSDAAGWFRQASGK EREFVASISWSGGYTYYADSVKGRFTSSSDNVKNTVYLQMNSL TPEDTAVYFCATVNRYSDYRISLVTPSQYEYWGQGTQVTVS | 34 |

TABLE 7

CDR sequences for anti-albumin VHH domains.

| VHH domain | CDR1 sequence [SEQ ID NO:] | CDR2 sequence [SEQ ID NO] | CDR3 sequence [SEQ ID NO:] |
|---|---|---|---|
| HAS020 | GRTFGSDA [35] | ISWSGGYT [44] | ATGNRYSDYRISLVTPSQYEY [52] |
| HAS038 | GHSFSTYT [36] | ISWSGEVT [45] | AAKRGGRPTDSSDDYFY [53] |
| HAS040 | GRTVSNYA [37] | INWNKTTT [46] | AAVFRIVAPKTQYEYDY [54] |
| HAS041 | GRPVSNYA [38] | INWNKTAT [47] | AAVFRVVAPKTQYDYDY [55] |
| HAS042 | GRPVSNYA [38] | INWQKTAT [48] | AAVFRVVAPKTQYDYDY [55] |
| HAS044 | GRTFSSYA [39] | VSTIAGDT [49] | AADSYNVRLVTGEADY [56] |
| HAS077 | GRTFSSYA [39] | VSTIAGDT [49] | AADSYNVRLGTGEADY [57] |
| HAS079 | GFTFSNYA [40] | VSTIAGDT [49] | AAESYNVRLVTGEADY [58] |
| HAS080 | GRTFSNDA [41] | ISWSGNYT [50] | AAGNRYSDYRISLVTPRLYEY [59] |
| HAS081 | GRTFSSDA [42] | ISWSGNYT [50] | AAGNRYSDYRISLVTPSQYEY [60] |
| HAS091 | GRTFGSDA [43] | ISWSGGYT [51] | ATGNRDSDYRISLVTPSQYEY [61] |
| HAS093 | GRTFGSDA [43] | ISWSGGYT [51] | ATGNRYSDYRISLVTPSQYDY [62] |
| HAS096 | GRTFGSDA [43] | ISWSGGYT [51] | ATVNRYSDYRISLVTPSQYEY [63] |

Example 10. Characterization of Albumin-Binding Kinetics by Biacore

The binding kinetics of the VHH domains HAS040 and HAS041 to HSA or CSA were determined using SPR on a Biacore 3000 instrument. Biotinylated albumin was captured onto a CAP chip saturated with Biotin CAPture reagent containing deoxyribooligonucleotides (obtained from GE Healthcare). Concentrations of purified VHH domains were injected for 5 minutes at a flowrate of 50 µL/min. Three concentrations were assessed per VHH domain. Bound analyte was allowed to dissociate for 600 seconds. The chip surface was regenerated after each concentration by injecting 6 M guanidine HCl/0.25 M NaOH for 2 minutes at 10 µL/min. Kinetics were determined at pH 7.4 and pH 6.0 in HBS-EP buffer using a 1:1 Langmuir model (local $R_{max}$ and constant RI) and double reference subtraction (subtraction of a buffer concentration cycle from the sample concentration cycle and subtraction of a parallel reference flow cell). The MSA21 VHH domain (International Publication No. WO 2004/062551 A2) (sequence:

LEQVQLQESGGGLVQPGGSLRLS-
CEASGFTFSRFGMTWVRQAPGKGVEW
VSGISSLGDSTLYADSVKGRFTISRDNAKNT-
LYLQMNSLKPEDTAVYYC
TIGGSLNPGGQGTQVTVSS (SEQ ID NO:322)

was prepared and used as a comparator in these assays.

The results of this assay are shown in Table 8. Binding affinities were observed in the 0.3-5 nM range, indicating that the HAS040 and HAS041 domains have sufficient affinity at both pH 6 and pH 7.4 to facilitate half-life extension. Furthermore, these VHH domains demonstrated binding to CSA and HSA with very similar affinities, strengthening the predictive nature of half-life extension studies to be performed in primates.

TABLE 8

Results of Biacore characterization of anti-albumin VHH domains.

| Sample | Albumin/pH | $k_a$ (1/Ms) | $k_d$ (1/s) | $K_D$ (M) | Chi$^2$ |
|---|---|---|---|---|---|
| HAS40 | CSA/pH 6.0 | 3.68E+05 | 2.81E-04 | 7.64E-10 | 0.05 |
| | CSA/pH 7.4 | 1.04E+06 | 5.62E-04 | 5.39E-10 | 0.1 |
| | HSA/pH 6.0 | 4.45E+05 | 2.08E-04 | 4.66E-10 | 0.09 |
| | HSA/pH 7.4 | 1.29E+06 | 4.40E-04 | 3.41E-10 | 0.03 |
| HAS41 | CSA/pH 6.0 | 3.12E+05 | 7.39E-04 | 2.37E-09 | 0.41 |
| | CSA/pH 7.4 | 1.07E+06 | 1.23E-03 | 1.15E-09 | 0.18 |
| | HSA/pH 6.0 | 3.73E+05 | 3.87E-04 | 1.04E-09 | 0.12 |
| | HSA/pH 7.4 | 1.23E+06 | 5.66E-04 | 4.61E-10 | 0.03 |
| MSA21 | CSA/pH 6.0 | 2.80E+05 | 1.53E-03 | 5.47E-09 | 0.05 |
| | CSA/pH 7.4 | 5.61E+05 | 2.16E-03 | 3.85E-09 | 0.05 |
| | HSA/pH 6.0 | 3.30E+05 | 1.81E-03 | 5.46E-09 | 0.06 |
| | HSA/pH 7.4 | 1.13E+06 | 3.93E-03 | 3.49E-09 | 0.07 |

Example 11. Demonstration of Non-Competitive Albumin Binding by VHH and FcRn

Recycling of albumin from endocytic vesicles is mediated by interaction with FcRn. It was, therefore, important to determine whether the VHH would interfere with the interaction of HSA and FcRn. To determine whether the HAS040 and HAS041 VHH domains bind to the same epitope as FcRn, the binding of FcRn to HSA that had been saturated with anti-HSA VHH domains was analyzed on a Biacore 3000 instrument at pH 6.0 in HBS-EP buffer. HSA was directly immobilized onto a CM5 chip to reach a target density of 250 RUs (resonance units) using amine coupling. VHH domains were diluted to approximately 1-10 µg/mL and injected to achieve saturation (3 minutes at 50 µL/min). One concentration of FcRn was injected over the HSA:VHH surface to obtain kinetics for 5 minutes at 50 µL/min. Dissociation was allowed for 180 seconds before regeneration. The chip surface was regenerated by injecting 20 µL of 25 mM NaOH at 100 µL/min. Kinetics were determined using a 1:1 Langmuir model (local $R_{max}$ and constant RI)

and double reference subtraction (subtraction of a buffer concentration cycle from the sample concentration cycle and subtraction of a parallel reference flow cell).

Results are shown in FIG. 7. In FIG. 7A, the direct interaction of FcRn with an HSA saturated surface resulted in a response difference of 30 RUs. Similar RUs were obtained when 400 nM FcRn was injected over surfaced saturated with complexes of HSA with MSA21 (ADL021) (FIG. 7B), HAS040 (FIG. 7C) or HAS041 (FIG. 7D). Based on these data, HAS040 and HAS041 do not to interfere with FcRn binding and are expected to be recycled from the endosome via the interaction of albumin with FcRn.

Example 12. Generation of Anti-C5 and Anti-Albumin Bispecific Fusion Proteins

Anti-C5 VHH domains were fused to an anti-albumin domain to generate bispecific molecules. Four different linker lengths $(G_4S)_3$ (SEQ ID NO: 106), $(G_4S)_4$ (SEQ ID NO: 107), $(G_4S)_5$ (SEQ ID NO: 108) and $(G_4S)_6$ (SEQ ID NO: 109), and two different orientations (N-terminal or C-terminal) of anti-albumin domain were evaluated. Constructs were expressed in HEK293F cells and purified using Protein A affinity chromatography. Purified fusion molecules were evaluated in Biacore experiments. Human C5 was biotinylated and immobilized on a biacore chip, purified bispecific molecules were injected to saturate the chip followed by three different concentrations of human serum albumin to obtain kinetics. Measured affinity to human serum albumin was used as a proxy to compare the different linker lengths. $(G_4S)_3$ (SEQ ID NO: 106) was chosen as the optimal linker length to generate bispecific fusions. N-terminal or C-terminal anti-albumin fusions were also evaluated in the same experiment. Different orientations were found to be optimal for different anti-C5 VHH domains. The N-versus C-terminal orientation of the constructs is specified below the construct name in Table 9 with (C5/HSA) indicating the anti-C5 domain is located N-terminal to the anti-HSA domain. Likewise, with (HSA/C5) indicates the anti-HSA domain is located N-terminal to the anti-C5 domain.

Figure 3A:
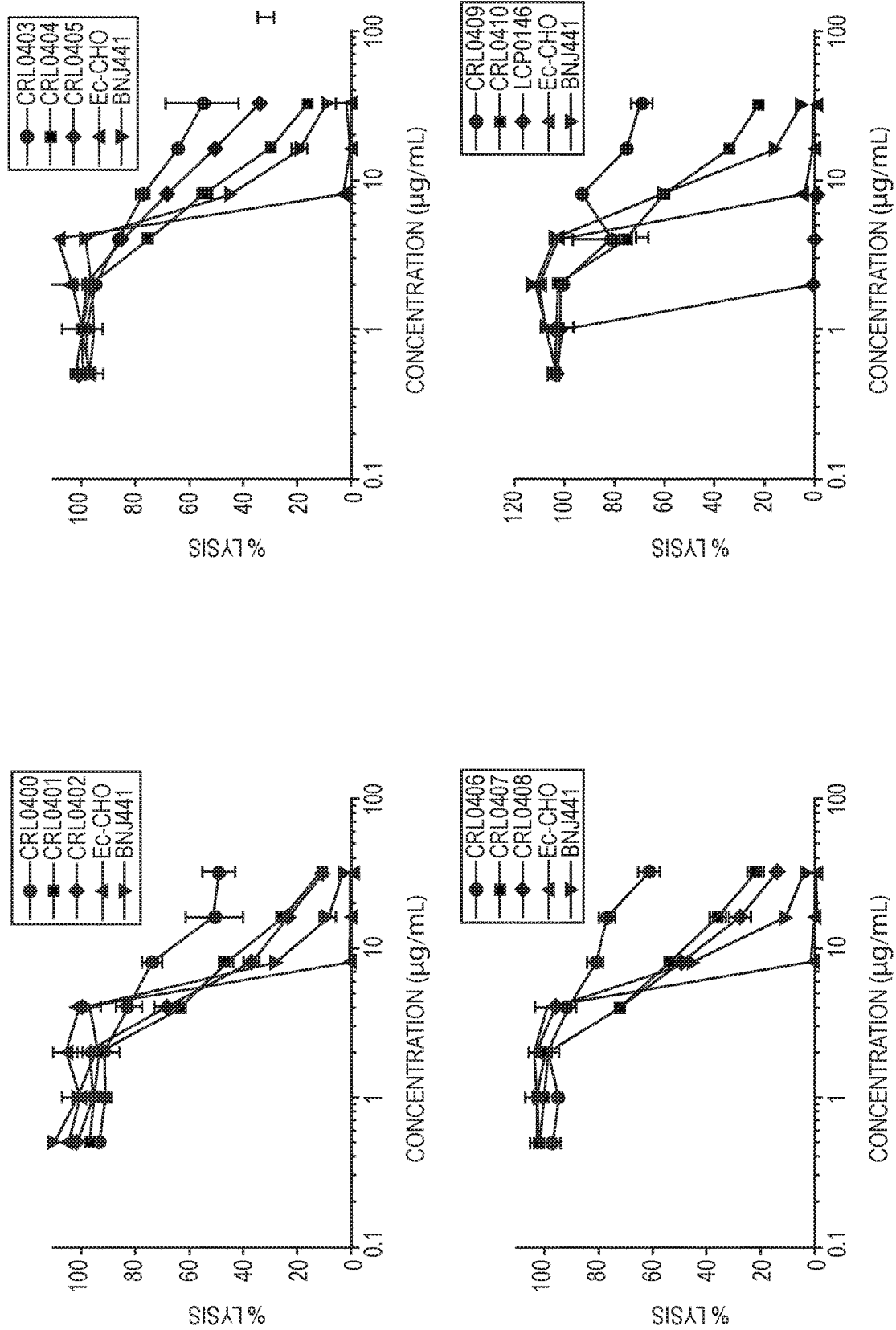
FIGS. 3A-3D show the results of a CCP hemolysis assay for bispecific fusion proteins.
Figure 3B:
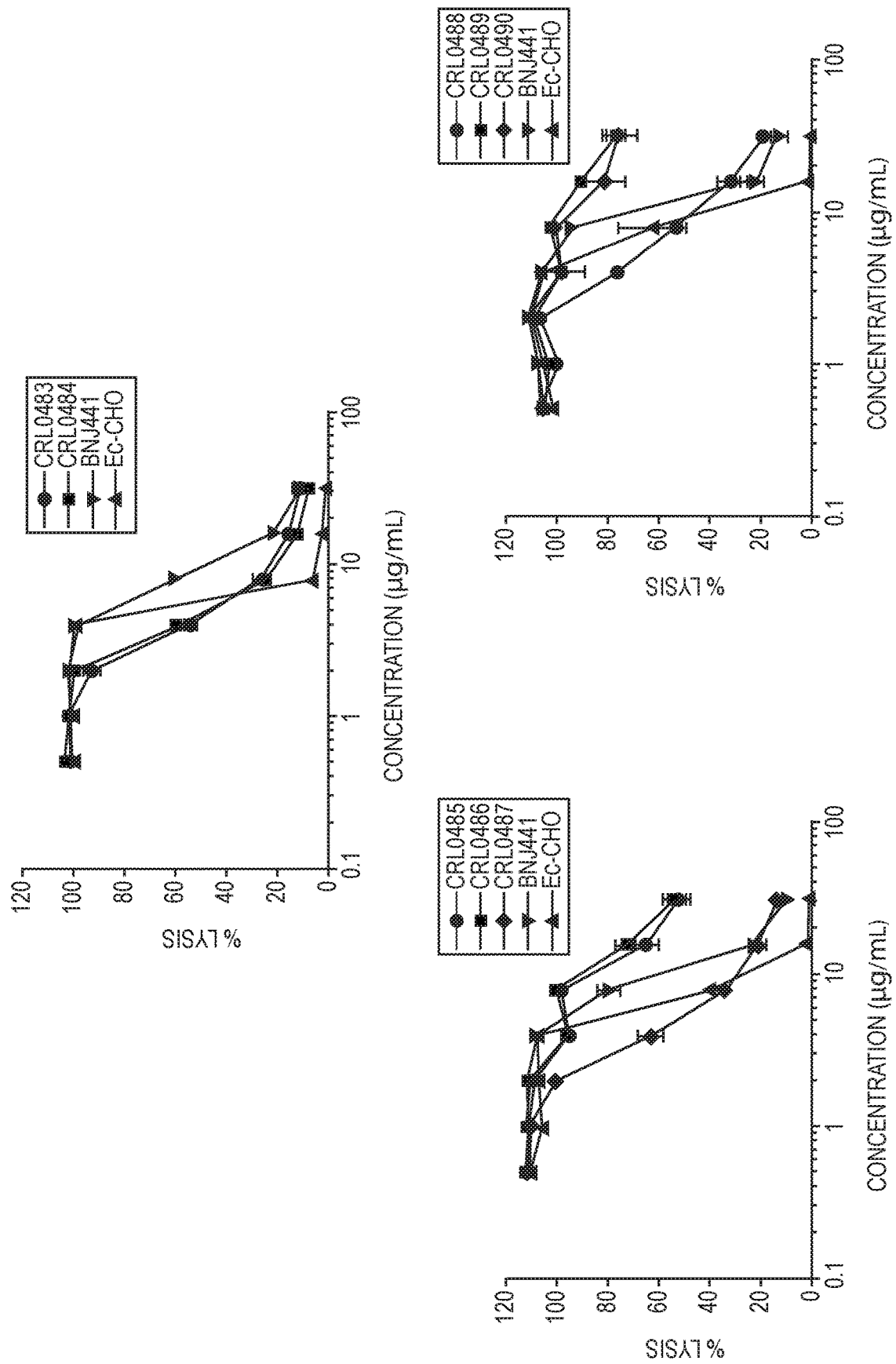
Figure 3C:
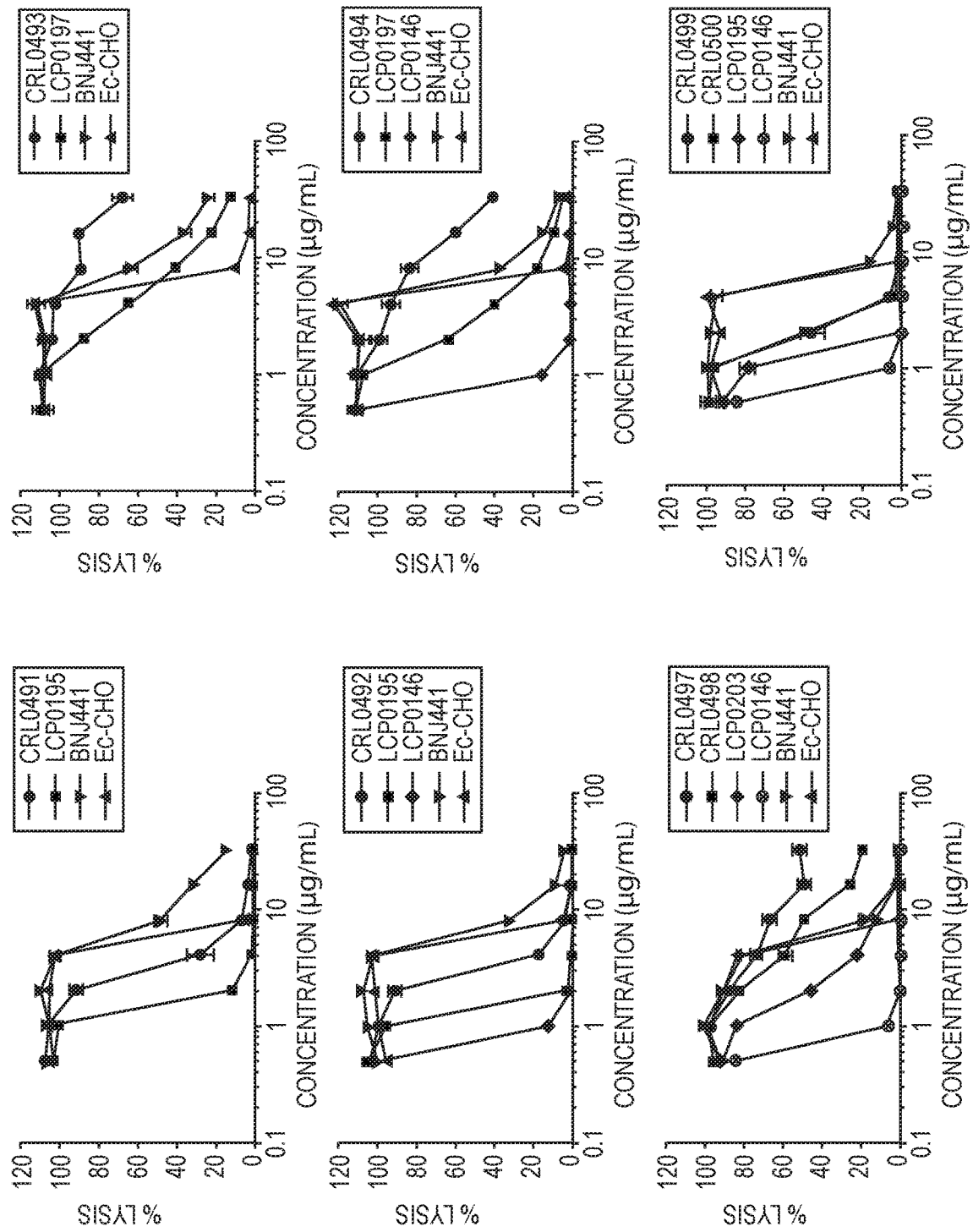
Figure 3D:
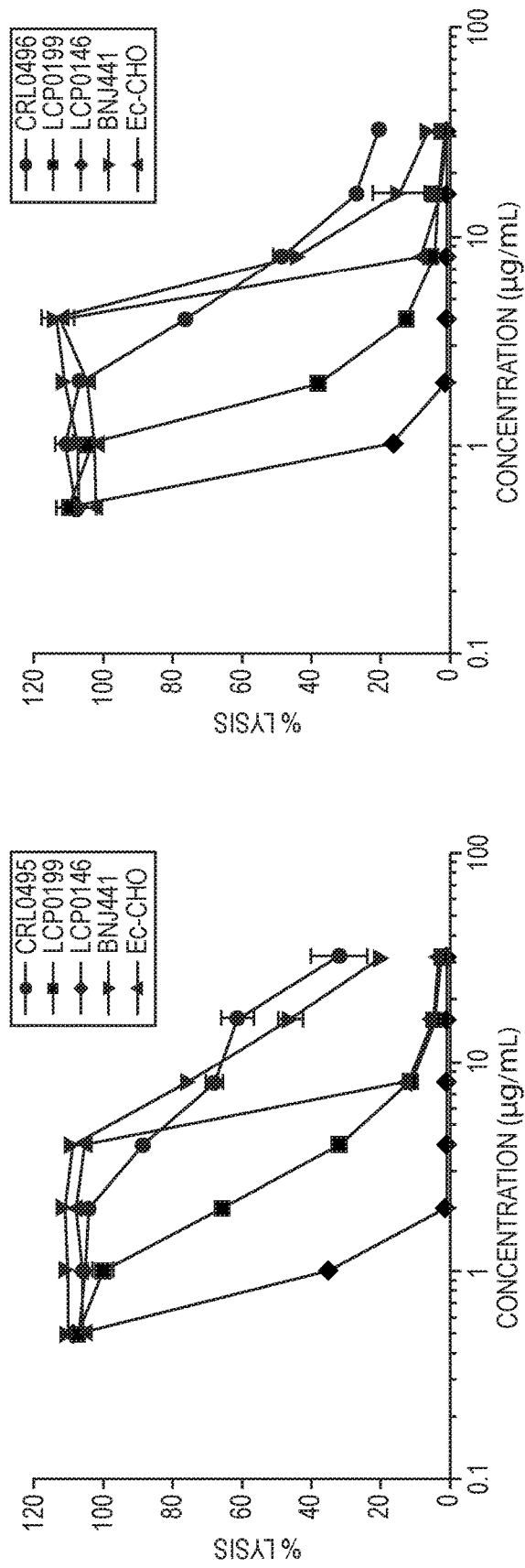
Figure 3D:
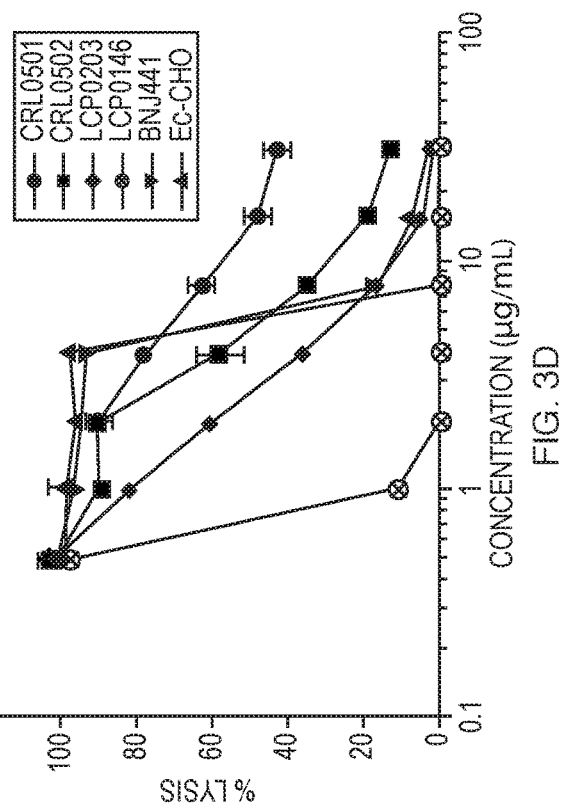

After selecting the optimal linker length, a series of different bispecific fusion molecules were generated with humanized anti-C5 VHH domains fused to two different anti-albumin domains (shown in Table 8). These constructs were expressed in Expi293 cells and purified using Protein A chromatography. Purified bispecific fusion proteins were tested in hemolysis assays and the results are shown in FIGS. 3A and 3B.

TABLE 9

Anti-C5/Anti-Albumin Fusion Proteins

| Name | Sequence | SEQ ID NO: |
|---|---|---|
| CRL0400 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRHFSDYAMAWFRQAPGQEREFVAGIGWS GGDTLYADSVRGRFTISRDNAKNTLYLQMNSLRAEDTAVYYCAARQ GQYIYSSMRSDSYDYWGQGTLVTVSS | 64 |
| CRL0401 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAHSDYAMAWFRQAPGQEREFVAGIGWS GGDTLYADSVRGRFTISRDNAKNTLYLQMNSLRAEDTAVYYCAARQ GQYIYSSMRSDSYDYWGQGTLVTVSS | 65 |
| CRL0402 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRHHSDYAMAWFRQAPGQEREFVAGIGWS GGDTLYADSVRGRFTISRDNAKNTLYLQMNSLRAEDTAVYYCAARQ GQYIYSSMRSDSYDYWGQGTLVTVSS | 66 |
| CRL0403 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRHFSDYAMAWFRQAPGQEREFVAGIGWS GGDTLYADSVRGRFTISRDNSKNTMYLQMNSLRAEDTAVYYCAARQ GQYIYSSMRSDSYDYWGQGTLVTVSS | 67 |
| CRL0404 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAHSDYAMAWFRQAPGQEREFVAGIGWS GGDTLYADSVRGRFTISRDNSKNTMYLQMNSLRAEDTAVYYCAARQ GQYIYSSMRSDSYDYWGQGTLVTVSS | 68 |
| CRL0405 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRHHSDYAMAWFRQAPGQEREFVAGIGWS GGDTLYADSVRGRFTISRDNSKNTMYLQMNSLRAEDTAVYYCAARQ GQYIYSSMRSDSYDYWGQGTLVTVSS | 69 |

TABLE 9-continued

Anti-C5/Anti-Albumin Fusion Proteins

| Name | Sequence | SEQ ID NO: |
|---|---|---|
| CRL0406 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRHFSDYAMAWFRQAPGQERE FVAGIGWSGGDTLYADSVRGRFTISRDNAKNTLYLQMNSLRAEDTA VYYCAARQGQYIYSSMRSDSYDYWGQGTLVTVSS | 70 |
| CRL0407 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAHSDYAMAWFRQAPGQERE FVAGIGWSGGDTLYADSVRGRFTISRDNAKNTLYLQMNSLRAEDTA VYYCAARQGQYIYSSMRSDSYDYWGQGTLVTVSS | 71 |
| CRL0408 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRHHSDYAMAWFRQAPGQERE FVAGIGWSGGDTLYADSVRGRFTISRDNAKNTLYLQMNSLRAEDTA VYYCAARQGQYIYSSMRSDSYDYWGQGTLVTVSS | 72 |
| CRL0409 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRHFSDYAMAWFRQAPGQERE FVAGIGWSGGDTLYADSVRGRFTISRDNSKNTMYLQMNSLRAEDTA VYYCAARQGQYIYSSMRSDSYDYWGQGTLVTVSS | 73 |
| CRL0410 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAHSDYAMAWFRQAPGQERE FVAGIGWSGGDTLYADSVRGRFTISRDNSKNTMYLQMNSLRAEDTA VYYCAARQGQYIYSSMRSDSYDYWGQGTLVTVSS | 74 |
| CRL0411 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRHHSDYAMAWFRQAPGQERE FVAGIGWSGGDTLYADSVRGRFTISRDNSKNTMYLQMNSLRAEDTA VYYCAARQGQYIYSSMRSDSYDYWGQGTLVTVSS | 75 |
| CRL0483 (C5/HSA) | EVQLVESGGGLVQPGGSLRLSCAASGRTFSGILSPYAVGWFRQAPG KGLEFVSTITSGGSAIYTDSVKGRFTISRDNAKDSLYLQMNSLRAE DTAVYYCAVRTRRYGSNLGEVPQENEYGYWGQGTLVTVSSGGGGSG GGGSGGGGSEVQLLESGGGLVQPGGSLRLSCAASGFTFRSFGMSWV RQAPGKGPEWVSSISGSGSDTLYADSVKGRFTISRDNSKNTLYLQM NSLRPEDTAVYYCTIGGSLSRSSQGTLVTVSS | 76 |
| CRL0484 (C5/HSA) | EVQLVESGGGLVQPGGSLRLSCAASGRTFSGILSPYAVGWFRQAPG KGLEFVSTITSGGSAIYTDSVKGRFTISRDNAKDSLYLQMNSLRAE DTAVYYCAVRTRRYGSNLGEVPQENEYGYWGQGTLVTVSSGGGGSG GGGSGGGGSEVQLVESGGGLVKPGGSLRLSCAASGRPVSNYAAAWF RQAPGKEREFVSAINWQKTATYADSVKGRFTISRDNAKNSLYLQMN SLRAEDTAVYYCAAVFRVVAPKTQYDYDYWGQGTLVTVSS | 77 |
| CRL0485 (C5/HSA) | EVQLVESGGGLVQPGGSLRLSCAASGRTFSGILSPYAVGWFRQAPG KGLEFVSTITSGGSAIYTDSVKGRFTISRDNAKNTLYLQMNSLRAE DTAVYYCAVRTRRYGSNLGEVPQENEYGYWGQGTLVTVSSGGGGSG GGGSGGGGSEVQLLESGGGLVQPGGSLRLSCAASGFTFRSFGMSWV RQAPGKGPEWVSSISGSGSDTLYADSVKGRFTISRDNSKNTLYLQM NSLRPEDTAVYYCTIGGSLSRSSQGTLVTVSS | 78 |
| CRL0486 (C5/HSA) | EVQLVESGGGLVQPGGSLRLSCAASGRTFSGILSPYAVGWFRQAPG KGLEFVSTITSGGSAIYTDSVKGRFTISRDNAKNTLYLQMNSLRAE DTAVYYCAVRTRRYGSNLGEVPQENEYGYWGQGTLVTVSSGGGGSG GGGSGGGGSEVQLVESGGGLVKPGGSLRLSCAASGRPVSNYAAAWF RQAPGKEREFVSAINWQKTATYADSVKGRFTISRDNAKNSLYLQMN SLRAEDTAVYYCAAVFRVVAPKTQYDYDYWGQGTLVTVSS | 79 |
| CRL0487 (C5/HSA) | EVQLVESGGGLVQPGGSLRLSCAASGRTFSGILSPYAVGWFRQAPG KGLEFVSTITSGGSAIYTDSVKGRFTISRDNAKNSVYLQMNSLRAE DTAVYYCAVRTRRYGSNLGEVPQENEYGYWGQGTLVTVSSGGGGSG GGGSGGGGSEVQLLESGGGLVQPGGSLRLSCAASGFTFRSFGMSWV RQAPGKGPEWVSSISGSGSDTLYADSVKGRFTISRDNSKNTLYLQM NSLRPEDTAVYYCTIGGSLSRSSQGTLVTVSS | 80 |

TABLE 9-continued

Anti-C5/Anti-Albumin Fusion Proteins

| Name | Sequence | SEQ ID NO: |
|---|---|---|
| CRL0488 (C5/HSA) | EVQLVESGGGLVQPGGSLRLSCAASGRTFSGILSPYAVGWFRQAPG KGLEFVSTITSGGSAIYTDSVKGRFTISRDNAKNSVYLQMNSLRAE DTAVYYCAVRTRRYGSNLGEVPQENEYGYWGQGTLVTVSSGGGGSG GGGSGGGGSEVQLVESGGGLVKPGGSLRLSCAASGRPVSNYAAAWF RQAPGKEREFVSAINWQKTATYADSVKGRFTISRDNAKNSLYLQMN SLRAEDTAVYYCAAVFRVVAPKTQYDYDYWGQGTLVTVSS | 81 |
| CRL0489 (C5/HSA) | EVQLVESGGGLVQPGGSLRLSCAASGRTFSGILSPYAVGWFRQAPG QGLEFVATITSGGSAIYTDSVKGRFTISRDNSKNTLYLQMNSLRAE DTAVYYCAVRTRRYGSNLGEVPQENEYGYWGQGTLVTVSSGGGGSG GGGSGGGGSEVQLLESGGGLVQPGGSLRLSCAASGFTFRSFGMSWV RQAPGKGPEWVSSISGSGSDTLYADSVKGRFTISRDNSKNTLYLQM NSLRPEDTAVYYCTIGGSLSRSSQGTLVTVSS | 82 |
| CRL0490 (C5/HSA) | EVQLVESGGGLVQPGGSLRLSCAASGRTFSGILSPYAVGWFRQAPG QGLEFVATITSGGSAIYTDSVKGRFTISRDNSKNTLYLQMNSLRAE DTAVYYCAVRTRRYGSNLGEVPQENEYGYWGQGTLVTVSSGGGGSG GGGSGGGGSEVQLVESGGGLVKPGGSLRLSCAASGRPVSNYAAAWF RQAPGKEREFVSAINWQKTATYADSVKGRFTISRDNAKNSLYLQMN SLRAEDTAVYYCAAVFRVVAPKTQYDYDYWGQGTLVTVSS | 83 |
| CRL0491 (C5/HSA) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAFSDYAMAWFRQAPGQEREFVAGIGWS GGDTLYADSVRGRFTNSRDNSKNTLYLQMNSLRAEDTAVYYCAARQ GQYIYSSMRSDSYDYWGQGTLVTVSS | 84 |
| CRL0492 (C5/HSA) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAFSDYAMAWFRQAPGQERE FVAGIGWSGGDTLYADSVRGRFTNSRDNSKNTLYLQMNSLRAEDTA VYYCAARQGQYIYSSMRSDSYDYWGQGTLVTVSS | 85 |
| CRL0493 (C5/HSA) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAFSDYAMAWFRQAPGQEREFVAGIGWS GGDTLYADSVRGRFTISRDNAKNTLYLQMNSLRAEDTAVYYCAARQ GQYIYSSMRSDSYDYWGQGTLVTVSS | 86 |
| CRL0494 (C5/HSA) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAFSDYAMAWFRQAPGQERE FVAGIGWSGGDTLYADSVRGRFTISRDNAKNTLYLQMNSLRAEDTA VYYCAARQGQYIYSSMRSDSYDYWGQGTLVTVSS | 87 |
| CRL0495 (C5/HSA) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAFSDYAMAWFRQAPGQEREFVAGIGWS GGDTLYADSVRGRFTISRDNSKNTMYLQMNSLRAEDTAVYYCAARQ GQYIYSSMRSDSYDYWGQGTLVTVSS | 88 |
| CRL0496 (C5/HSA) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAFSDYAMAWFRQAPGQERE FVAGIGWSGGDTLYADSVRGRFTISRDNSKNTMYLQMNSLRAEDTA VYYCAARQGQYIYSSMRSDSYDYWGQGTLVTVSS | 89 |
| CRL0497 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAFSDYAMAWFRQAPGQGLEFVAGIGWS GGDTLYADSVRGRFTISRDNSKNTLYLQMNSLRAEDTAVYYCAARQ GQYIYSSMRSDSYDYWGQGTLVTVSS | 90 |
| CRL0498 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAFSDYAMAWFRQAPGQGLE FVAGIGWSGGDTLYADSVRGRFTISRDNSKNTLYLQMNSLRAEDTA VYYCAARQGQYIYSSMRSDSYDYWGQGTLVTVSS | 91 |

TABLE 9-continued

Anti-C5/Anti-Albumin Fusion Proteins

| Name | Sequence | SEQ ID NO: |
|---|---|---|
| CRL0499 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAHSDYAMAWFRQAPGQEREFVAGIGWS GGDTLYADSVRGRFTNSRDNSKNTLYLQMNSLRAEDTAVYYCAARQ GQYIYSSMRSDSYDYWGQGTLVTVSS | 92 |
| CRL0500 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAHSDYAMAWFRQAPGQERE FVAGIGWSGGDTLYADSVRGRFTNSRDNSKNTLYLQMNSLRAEDTA VYYCAARQGQYIYSSMRSDSYDYWGQGTLVTVSS | 93 |
| CRL0501 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAHSDYAMAWFRQAPGQGLEFVAGIGWS GGDTLYADSVRGRFTISRDNSKNTLYLQMNSLRAEDTAVYYCAARQ GQYIYSSMRSDSYDYWGQGTLVTVSS | 94 |
| CRL0502 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAHSDYAMAWFRQAPGQGLE FVAGIGWSGGDTLYADSVRGRFTISRDNSKNTLYLQMNSLRAEDTA VYYCAARQGQYIYSSMRSDSYDYWGQGTLVTVSS | 95 |

Figure 4:
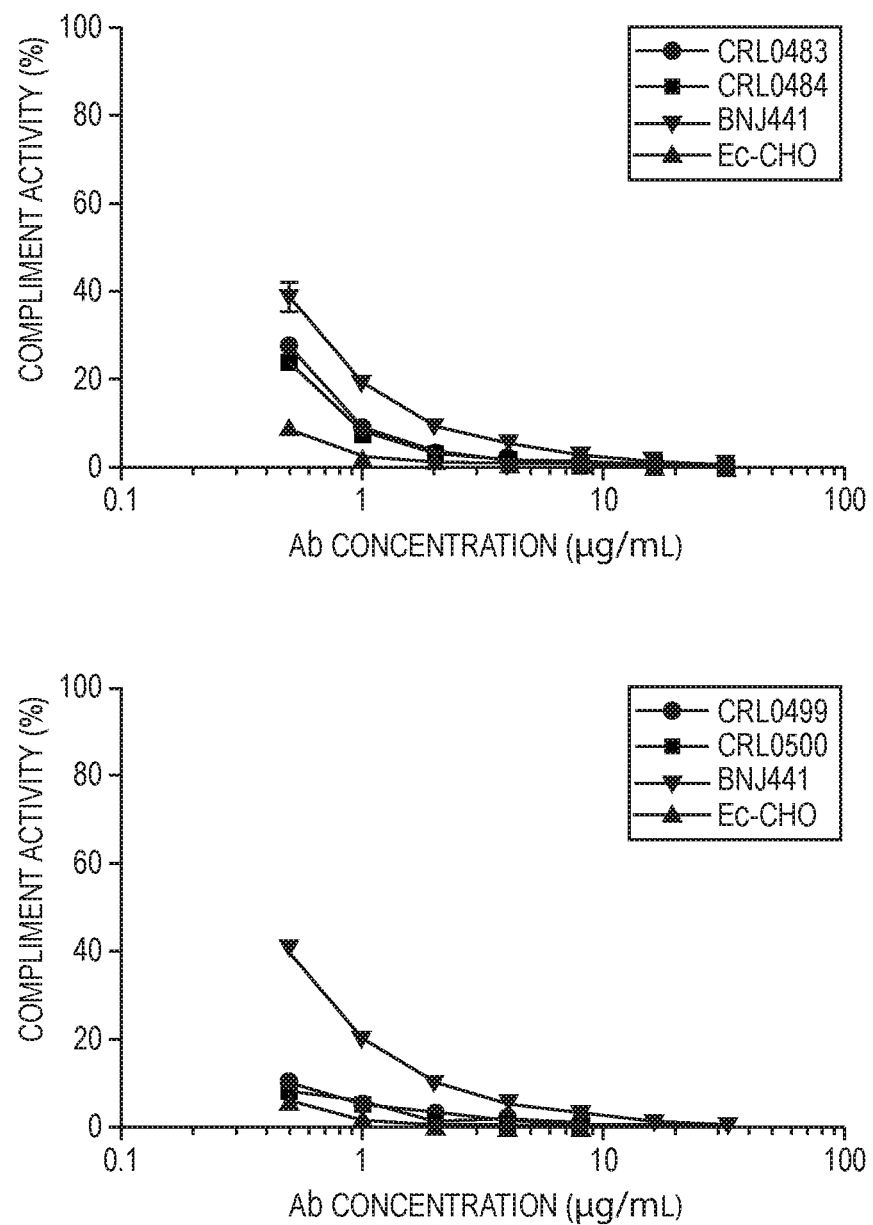
FIG. 4 shows the results of a Wieslab CCP assay for bispecific fusion proteins.
Figure 5:
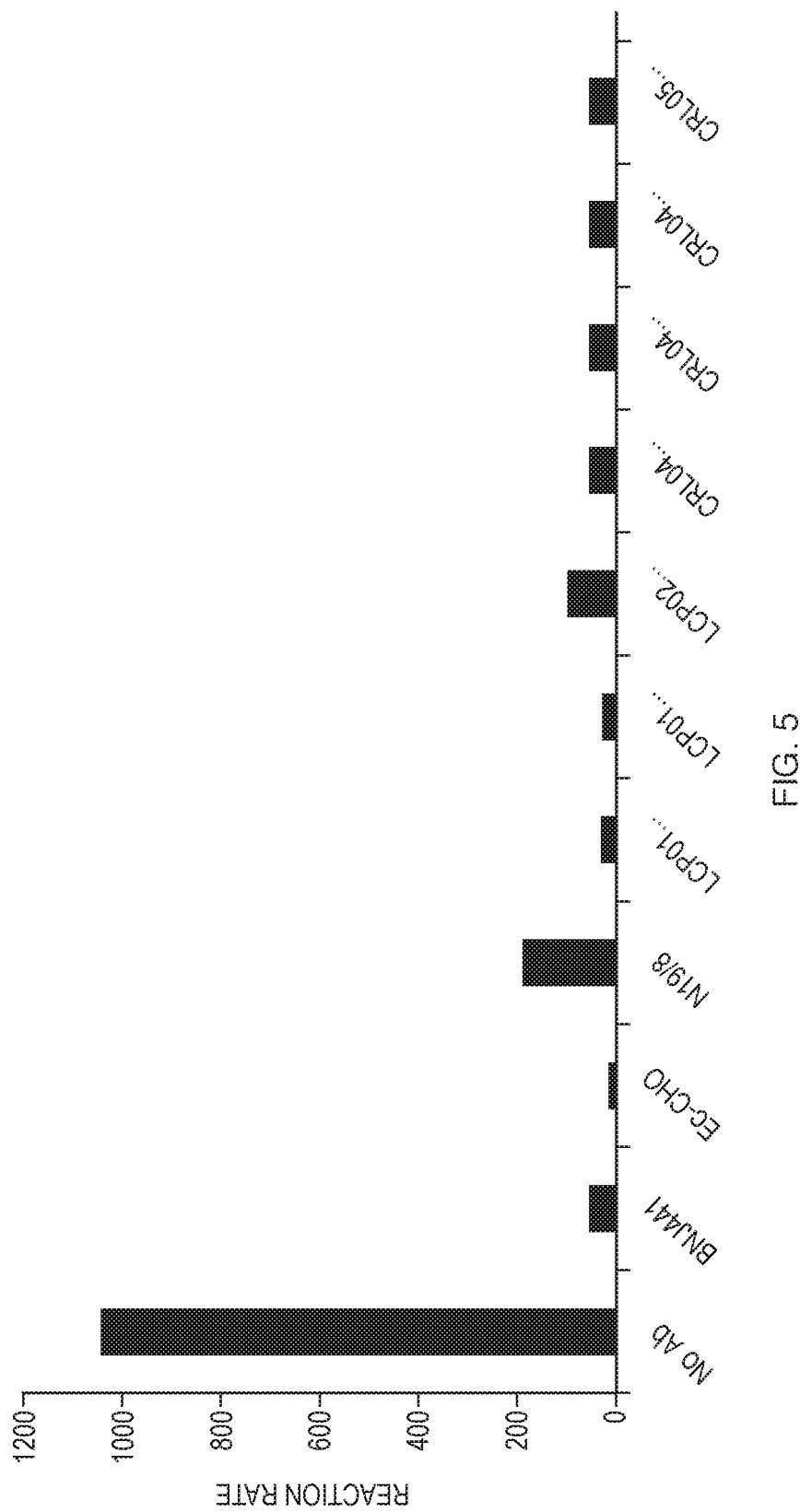
FIG. 5 shows the results of a C5a liberation assay for bispecific fusion proteins.

Four bispecific molecules CRL0483, CRL0484, CRL0499, and CRL0500 were prioritized based on binding and functional assays. Biacore affinity measurements for binding to human C5 for CRL0483, CRL0484, CRL0499, and CRL0500 are shown in Table 10 and functional assessments are shown in in FIGS. 3, 4 and 5. These four bispecific molecules were evaluated in in vivo pharmacokinetic studies in cynomolgus monkeys.

TABLE 10

Biacore measurements of prioritized fusions at pH 7.4 and pH 6.0

| Sample | C5 | pH | $k_a$ (1/Ms) | $k_d$ (1/s) | $K_D$ (M) | Chi$^2$ |
|---|---|---|---|---|---|---|
| CRL0483 | hC5 | 7.4 | 2.25e5 | 2.42e−4 | 1.07e−9 | 0.03 |
|  | cC5 | 7.4 | 9.15e4 | 2.20e−5 | 2.40e−10 | 0.01 |
| CRL0484 | hC5 | 7.4 | 7.01e4 | 7.69e−5 | 1.10e−9 | 0.04 |
|  | cC5 | 7.4 | 9.15e4 | 2.2e−5 | 2.40e−10 | 0.01 |
| CRL0499 | hC5* | 7.4 | 2.22e6 | 3.32e−4 | 1.5e−10 | 3.3 |
|  | cC5 | 7.4 | N.D. | N.D. | N.D. | N.D. |
| CRL0500 | hC5 | 7.4 | 2.88e6 | 6.72e−4 | 2.33e−10 | 0.65 |
|  | cC5 | 7.4 | 2.00e6 | 8.48e−4 | 4.2e−10 | 0.04 |
| CRL0483 | hC5 | 6.0 | 4.00e4 | 2.11e−04 | 5.27e−09 | 0.02 |
|  | cC5 | 6.0 | 3.71e4 | 4.62e−5 | 1.25e−9 | 0.02 |
| CRL0484 | hC5 | 6.0 | 4.25e5 | 2.36e−4 | 5.56e−10 | 0.02 |
|  | cC5 | 6.0 | 4.82e4 | 6.17e−6 | 1.28e−10 | 0.03 |
| CRL0499 | hC5* | 6.0 | 2.51e6 | 1.12e−3 | 4.48e−10 | 0.24 |
|  | cC5 | 6.0 | 1.92e6 | 3.88e−3 | 2.02e−9 | 0.31 |
| CRL0500 | hC5* | 6.0 | 8.02e6 | 1.519e−3 | 1.89e−10 | 1.06 |
|  | cC5* | 6.0 | 3.91e6 | 2.5e−3 | 6.41e−10 | 3.16 |

Example 13. Pharmacokinetic Analysis of Bispecific Fusion Proteins

Purified proteins were dosed at 10 mg/kg either intravenously or subcutaneously in cynomolgus monkeys. Three monkeys per dose group per test article were used. Pharmacokinetics properties of bispecific molecules were measured by LC-MS based quantitation using signature peptides to each construct. The PK profile is shown in FIG. 6, and the parameters are described in Table 11.

TABLE 11

PK parameters after 10 mg/kg of test articles in cynomolgus monkeys

| Test article | $t_{1/2}$ (h) | $t_{max}$ (h) | $C_{max}$ (μg/mL) | AUC (h*μg/mL) | $C_L$ (mL/h/kg) | V (mL/kg) | F (%) |
|---|---|---|---|---|---|---|---|
| CRL0483 IV | 139 | 1.33 | 324 | 47900 | 0.211 | 42.0 |  |
| CRL0484 IV | 125 | 1 | 382 | 43700 | 0.238 | 43.0 |  |
| CRL0483 SC | 103 | 20 | 238 | 46412 | 0.218 | 32.5 | 97 |
| CRL0484 SC | 75.9 | 24 | 161 | 32610 | 0.315 | 34.9 | 75 |
| CRL0499 IV | 170 | 2.11 | 299 | 53773 | 0.184 | 46.9 |  |
| CRL0500 IV | 239 | 0.167 | 351 | 51929 | 0.205 | 62.5 |  |

TABLE 11-continued

Sequences of anti-C5/anti-albumin bi-specifics with different linkers

| Test article | $t_{1/2}$ (h) | $t_{max}$ (h) | $C_{max}$ (μg/mL) | AUC (h*μg/mL) | $C_L$ (mL/h/kg) | V (mL/kg) | F (%) |
|---|---|---|---|---|---|---|---|
| CRL0499 SC | 220 | 32 | 146 | 58666 | 0.173 | 54.2 | 109 |
| CRL0500 SC | 209 | 32 | 161 | 61475 | 0.163 | 49.0 | 118 |

Variant linker sequences were also generated for the bispecific fusion proteins. The sequences including these variant linker sequences are shown in Table 12.

TABLE 12

Sequences of anti-C5/anti-albumin bi-specifics with different linkers

| Name | Sequence | SEQ ID NO |
|---|---|---|
| CRL0952 | EVQLVESGGGLVKPGGSLRLSCAASGRPVSNYAAAWFRQAPGKEREFVS AINWQKTATYADSVKGRFTISRDNAKNSLYLQMNSLRAEDTAVYYCAAV FRVVAPKTQYDYDYWGQGTLVTVSSGGGGAGGGGAGGGGSEVQLVESGG GLVQPGGSLRLSCAASGRAHSDYAMAWFRQAPGQEREFVAGIGWSGGDT LYADSVRGRFTNSRDNSKNTLYLQMNSLRAEDTAVYYCAARQGQYIYSS MRSDSYDYWGQGTLVTVSS | 96 |
| CRL0953 | EVQLVESGGGLVQPGGSLRLSCAASGRTFSGILSPYAVGWFRQAPGKGL EFVSTITSGGSAIYTDSVKGRFTISRDNAKDSLYLQMNSLRAEDTAVYY CAVRTRRYGSNLGEVPQENEYGYWGQGTLVTVSSGGGGAGGGGAGGGGS EVQLVESGGGLVKPGGSLRLSCAASGRPVSNYAAAWFRQAPGKEREFVS AINWQKTATYADSVKGRFTISRDNAKNSLYLQMNSLRAEDTAVYYCAAV FRVVAPKTQYDYDYWGQGTLVTVSS | 97 |
| CRL0954 | EVQLVESGGGVVQAGDSLTLTCTAPVGTISDYGMGWFRQAPGKEREFVA SISWGGMWTDYADSVKGRFTISRDNDKNAVYLRMNSLNAEDTAVYYCGR GRMYRGIGNSLAQPKSYGYWGQGTQVTVSSGGGGAGGGGAGGGGSEVQL VESGGGLVKPGGSLRLSCAASGRPVSNYAAAWFRQAPGKEREFVSAINW QKTATYADSVKGRFTISRDNAKNSLYLQMNSLRAEDTAVYYCAAVFRVV APKTQYDYDYWGQGTLVTVSS | 98 |
| CRL0955 | EVQLVESGGGLVQAGGSLRLSCAASGRTFSGILSAYAVGWFRQAPGKER EFVSTITSGGSTLSADSVKGRFTLSRDNAKDTVYLQMNSLKPEDTAVYY CAVRTWPYGSNRGEVPTENEYGHWGQGTQVTVSSGGGGAGGGGAGGGGS EVQLVESGGGLVKPGGSLRLSCAASGRPVSNYAAAWFRQAPGKEREFVS AINWQKTATYADSVKGRFTISRDNAKNSLYLQMNSLRAEDTAVYYCAAV FRVVAPKTQYDYDYWGQGTLVTVSS | 99 |
| CRL0956 | EVQLVESGGGLVKPGGSLRLSCAASGRPVSNYAAAWFRQAPGKEREFVS AINWQKTATYADSVKGRFTISRDNAKNSLYLQMNSLRAEDTAVYYCAAV FRVVAPKTQYDYDYWGQGTLVTVSSGGGGAGGGGAGGGGSEVQLVESGG GVVQAGDSLTLTCTAPVGTISDYGMGWFRQAPGKEREFVASISWGGMWT DYADSVKGRFTISRDNDKNAVYLRMNSLNAEDTAVYYCGRGRMYRGIGN SLAQPKSYGYWGQGTQVTVSS | 100 |

TABLE 12-continued

Sequences of anti-C5/anti-albumin bi-specifics with different linkers

| Name | Sequence | SEQ ID NO |
|---|---|---|
| CRL0957 | EVQLVESGGGLVKPGGSLRLSCAASGRPVSNYAAAWFRQAPGKEREFVSAINWQKTATYADSVKGRFTISRDNAKNSLYLQMNSLRAEDTAVYYCAAVFRVVAPKTQYDYDYWGQGTLVTVSSGGGGAGGGGAGGGGSEVQLVESGGGLVQAGGSLRLSCAASGRTFSGILSAYAVGWFRQAPGKEREFVSTITSGGSTLSADSVKGRFTLSRDNAKDTVYLQMNSLKPEDTAVYYCAVRTWPYGSNRGEVPTENEYGHWGQGTQVTVSS | 101 |

Example 14. Varying Peptide Linker Sequences

Constructs were generates using the HAS042 (SEQ ID NO:26) albumin binding domain and the CRL0305 (SEQ ID NO:11) humanized anti-C5 VHH. The constructs that were evaluated are listed in Table 13.

TABLE 13

Linkers used for generating fusion proteins.

| Protein | Linker | SEQ ID NO | Octet Binding-Human C5 and HumanAlbumin |
|---|---|---|---|
| TPP-3211 | No anti-albumin domain (only anti-C5) | | no |
| TPP-3212 | No anti-C5 domain (only anti-albumin) | | no |
| TPP-3213 | No linker | | yes |
| TPP-3214 | GGGGS | 104 | yes |
| TPP-3215 | EAAAKEAAAKEAAAK | 110 | yes |
| TPP-3216 | PAPAP | 111 | yes |
| TPP-3217 | GGGGSPAPAP | 112 | yes |
| TPP-3218 | PAPAPGGGGS | 113 | yes |
| TPP-3219 | GSTSGKSSEGKG | 114 | yes |
| TPP-3220 | GGGDSGGGDS | 115 | yes |
| TPP-3221 | GGGESGGGES | 116 | yes |
| TPP-3222 | GGGGSGGGGS | 105 | yes |
| TPP-3223 | GGGDSGGGGS | 117 | yes |
| TPP-3224 | GGGASGGGGS | 118 | yes |
| TPP-3225 | GGGESGGGGS | 119 | yes |
| TPP-3226 | ASTKGP | 120 | yes |
| TPP-3227 | ASTKGPSVFPLAP | 121 | yes |
| TPP-3228 | GGGGGGGP | 123 | yes |
| TPP-3229 | GGGGGGGGP | 321 | yes |
| TPP-3230 | PAPNLLGGP | 124 | yes |
| TPP-3231 | PNLLGGP | 323 | yes |
| TPP-3232 | GGGGGG | 125 | yes |
| TPP-3233 | GGGGGGGGGGGG | 126 | yes |

TABLE 13-continued

Linkers used for generating fusion proteins.

| Protein | Linker | SEQ ID NO | Octet Binding-Human C5 and HumanAlbumin |
|---|---|---|---|
| TPP-3234 | APELPGGP | 127 | yes |
| TPP-3235 | SEPQPQPG | 128 | yes |
| TPP-1252 | GGGGSGGGGSGGGGS | 106 | yes |

The 26 constructs listed in Table 13 were expressed and the fusion proteins were evaluated for binding to human C5 and albumin (Table 13-Octet binding), generation of aggregates, hydrophobicity (HIC HPLC) and glycosylation (electrospray mass spectrometry). For the octet analysis, biotinylated human C5 was captured on a CAP chip followed by an injection of a test bi-specific molecule. Various concentrations of albumin were subsequently injected. Kinetics were determined at pH 7.4 (Biacore 3000). All bi-specific molecules bound to both C5 and albumin, with each having a similar affinity for albumin (5-6 nM).

Figure 9A:
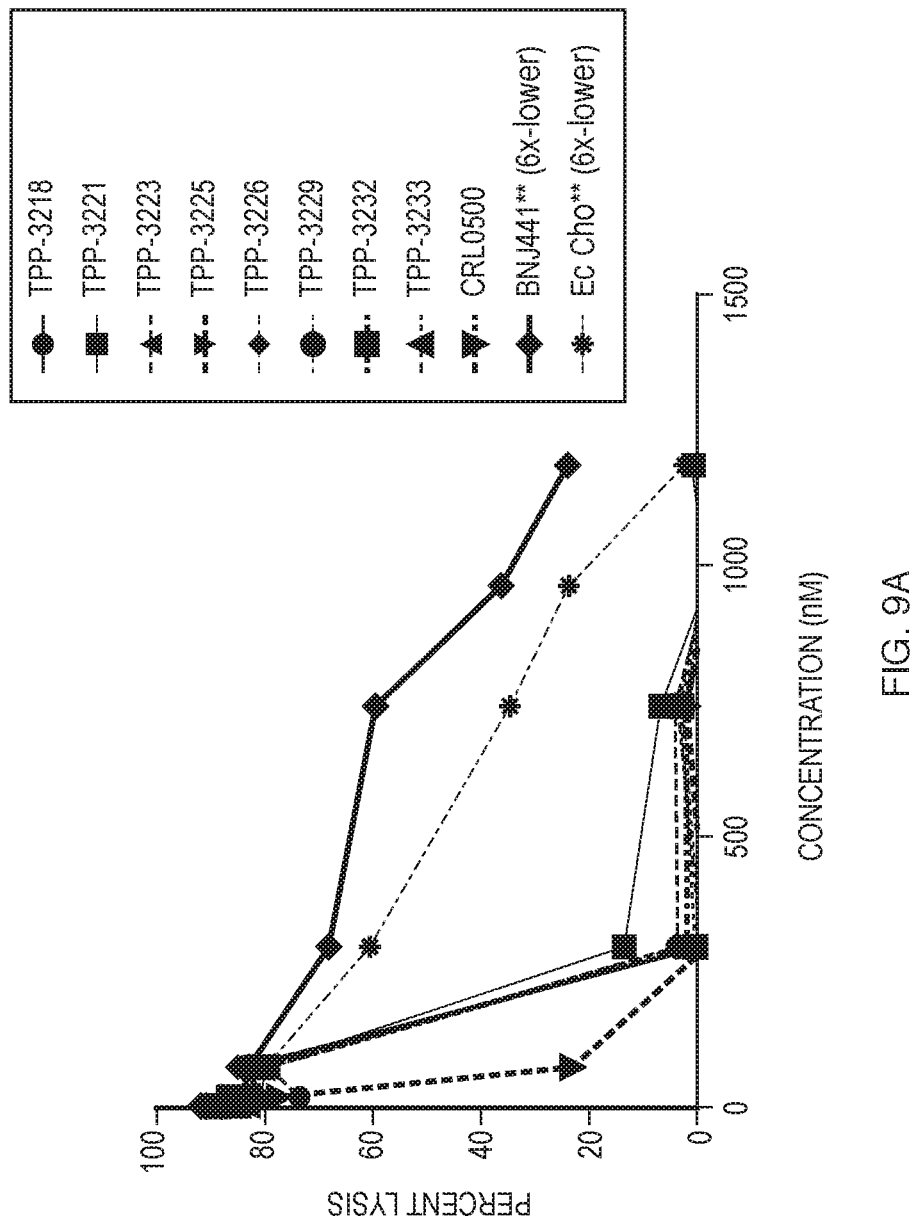
FIGS. 9A and 9B show the ability of various bi-specific fusion proteins to inhibit hemolysis.
Figure 9B:
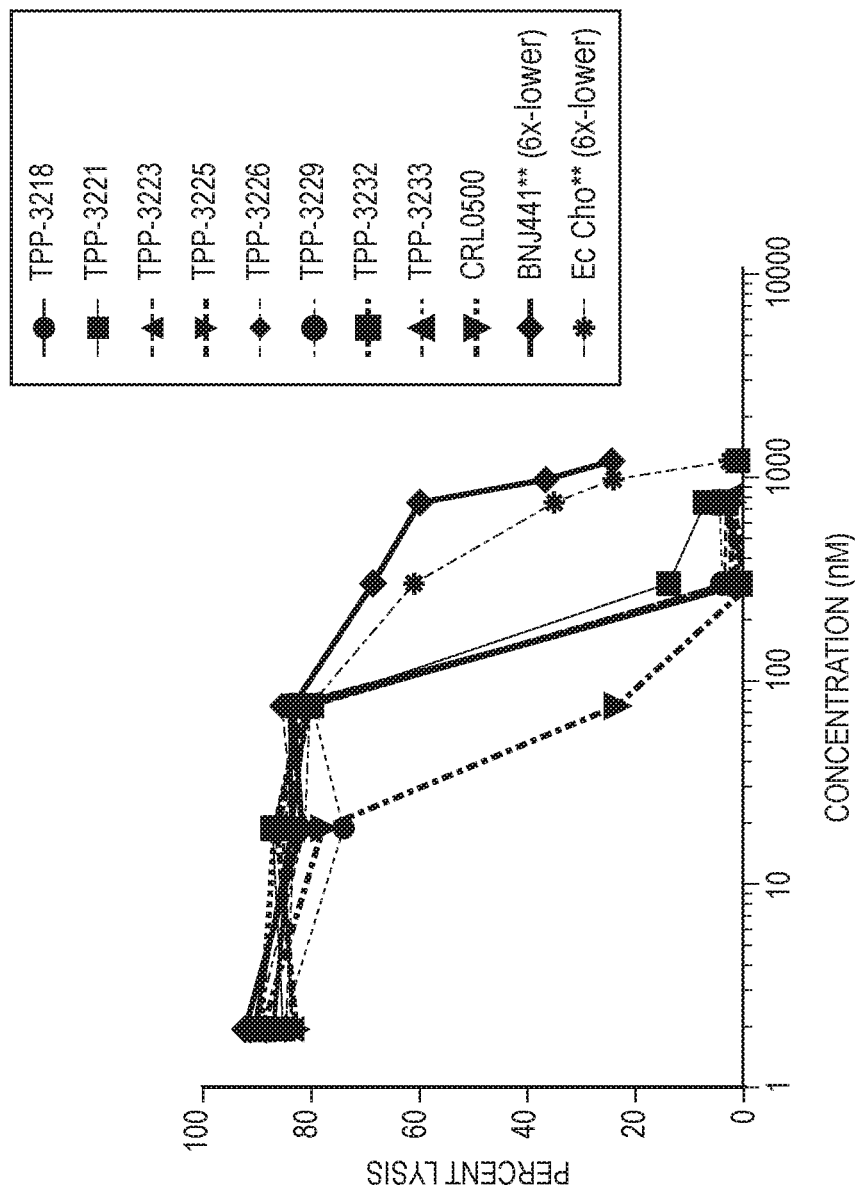
Figure 10:
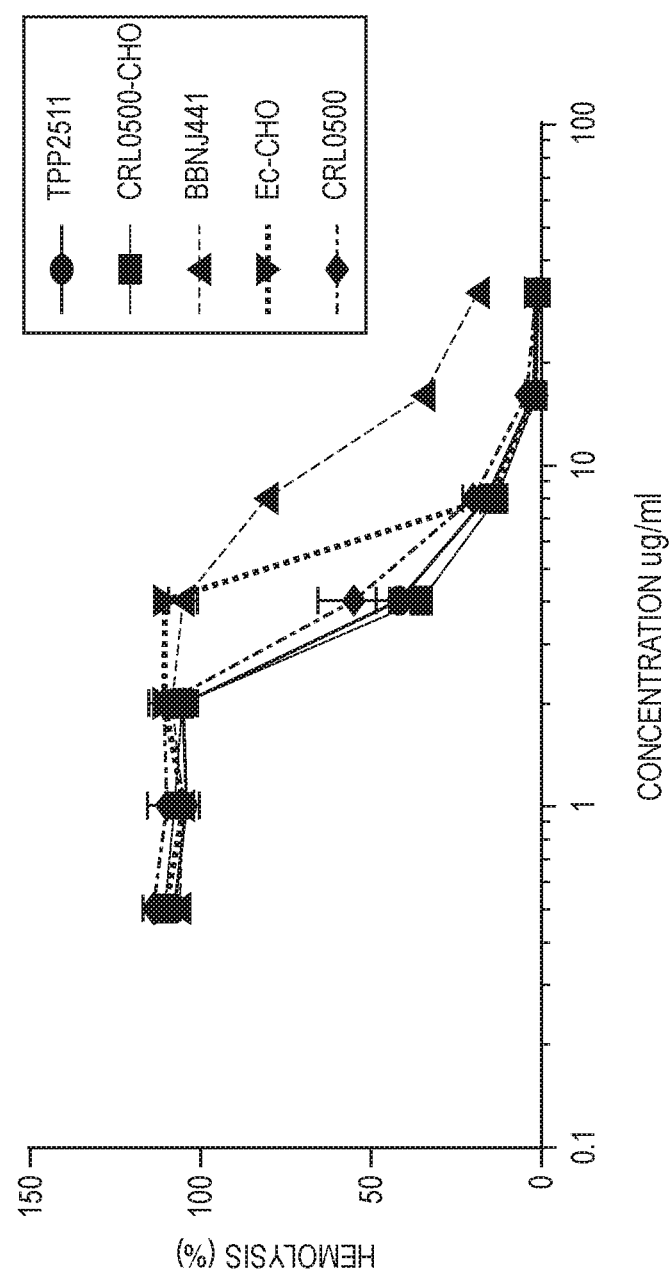
FIG. 10 shows CRL0952 (SEQ ID NO:96) is functionally highly similar to CRL0500 in preventing hemolysis. CRL0500 is a bi-specific C5 and albumin binding fusion protein with a $(G_4S)_3$ (SEQ ID NO:106) linker.
Figure 11A:
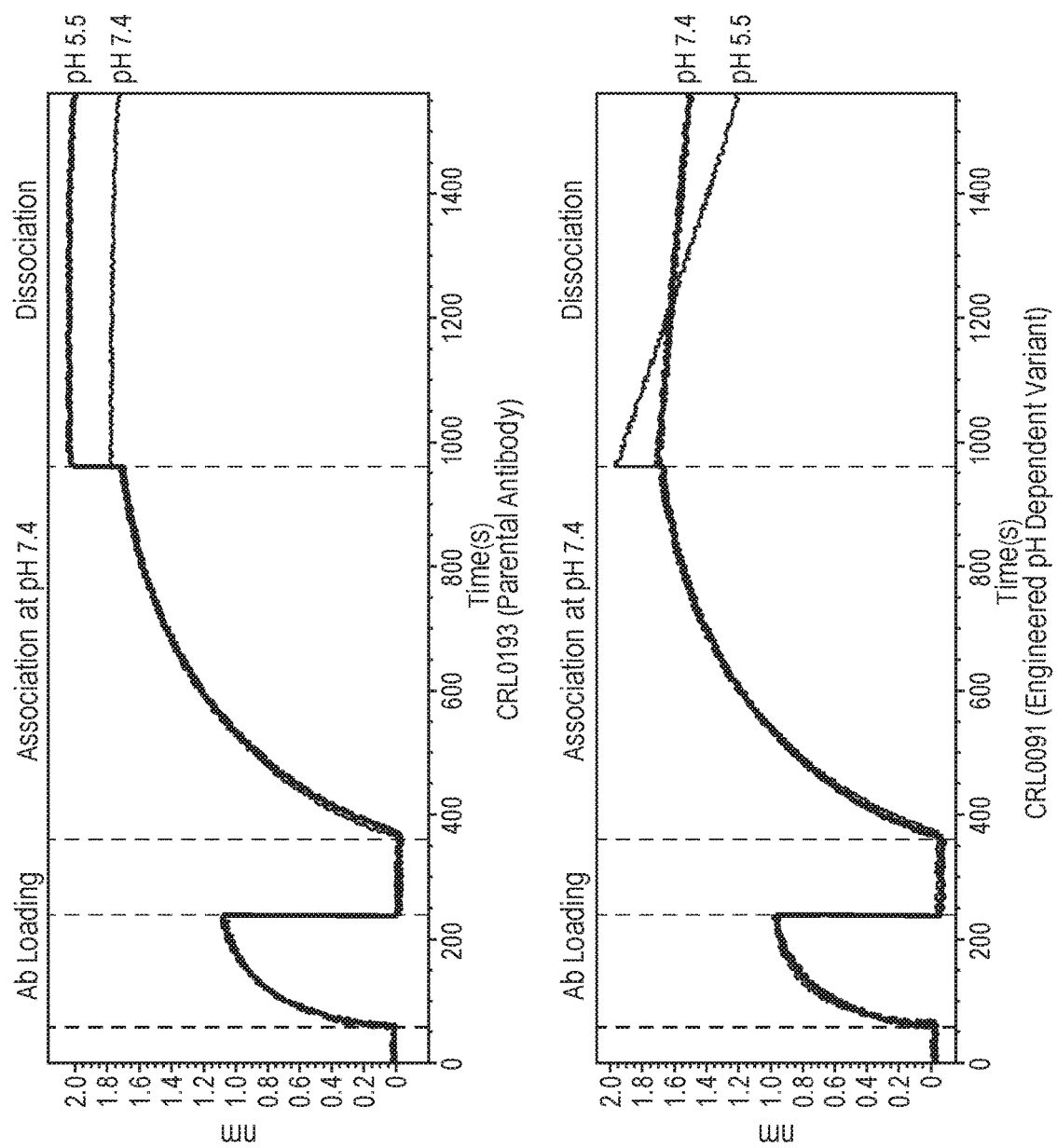
FIGS. 11A-11D show pH-dependent binding of histidine-substituted fusion proteins.
Figure 11B:
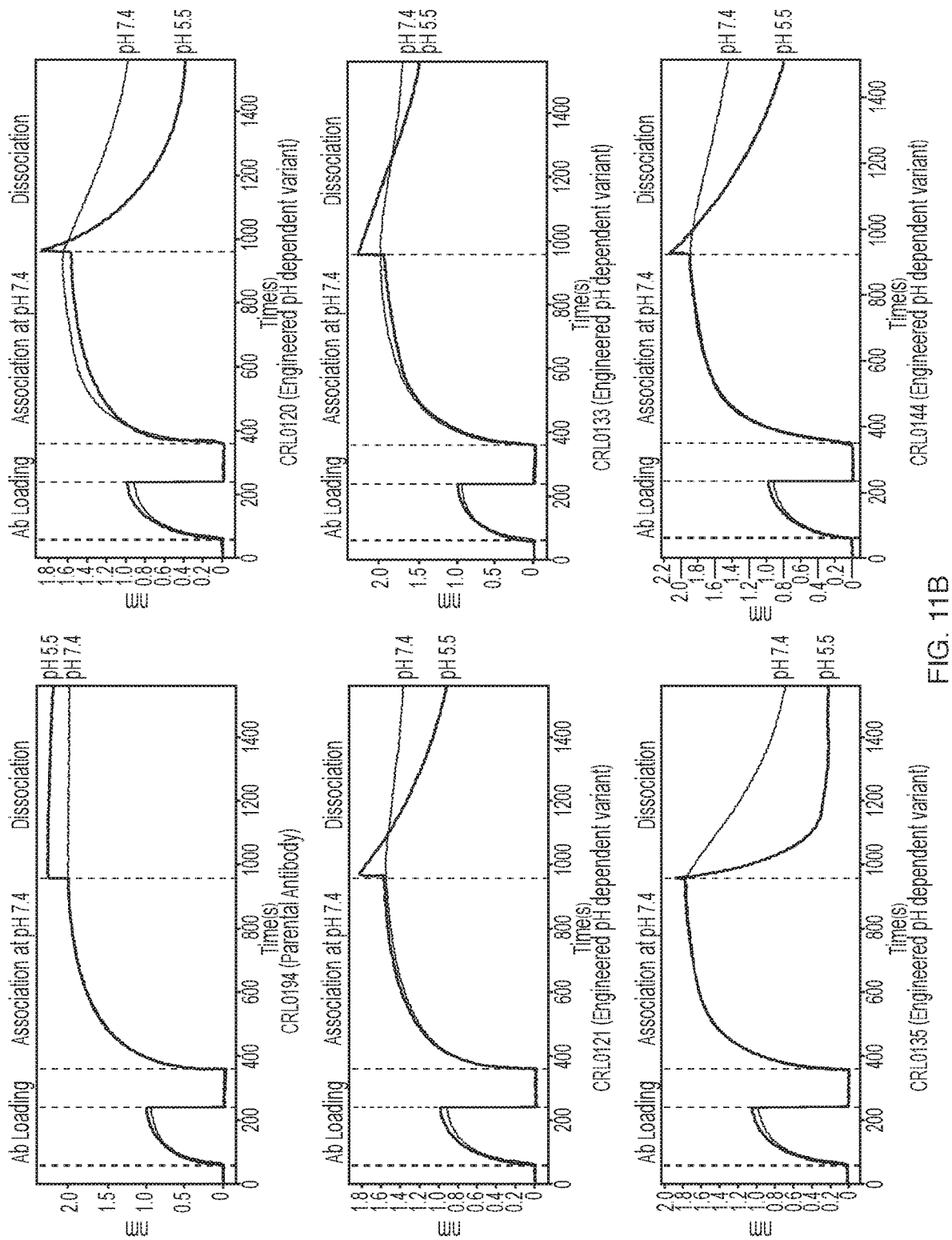
Figure 11C:
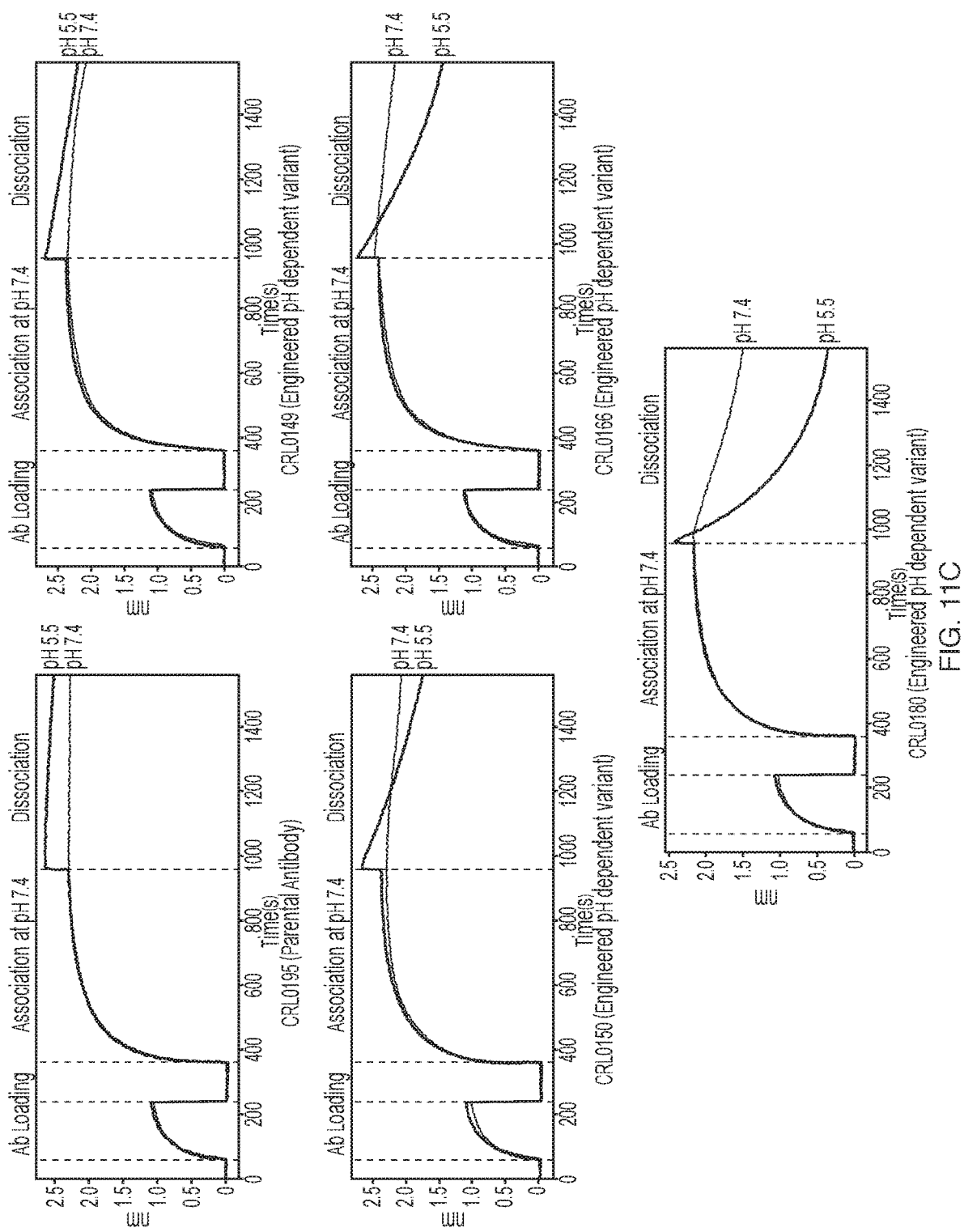
Figure 11D:
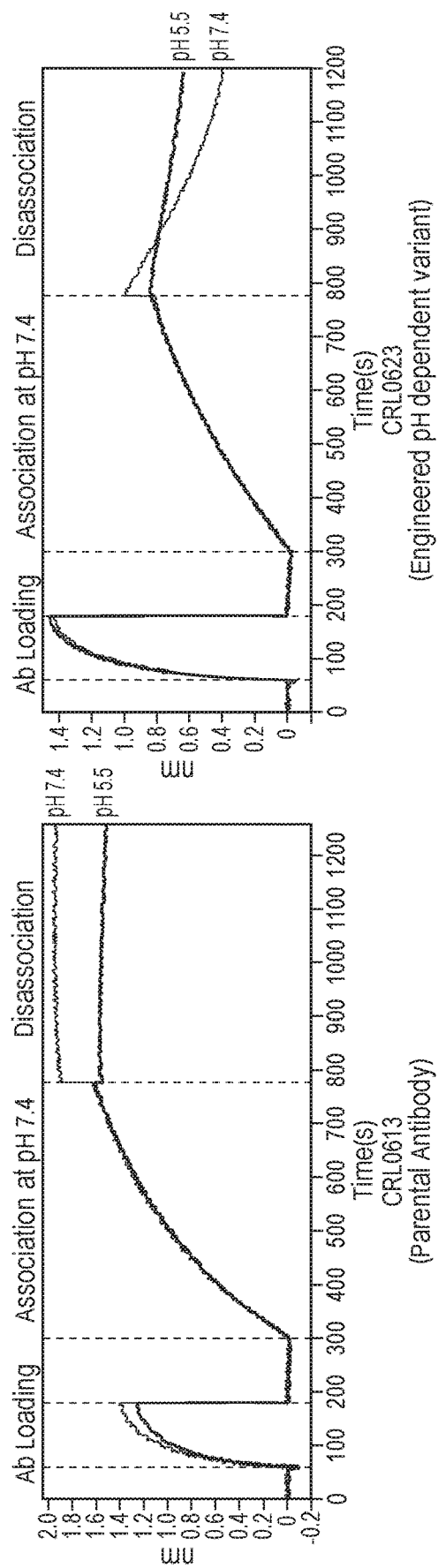

The bi-specific fusion proteins were tested for their ability to inhibit hemolysis in an in vitro hemolysis assay. Data are shown in FIGS. 9A and 9B.

Table 14 shows binding kinetics for CRL0500 and CRL0952 binding to human C5 (hC5) and cynomolgus C5 (cC5).

TABLE 14

Kinetics of bi-specific binding to C5

| Sample | Antigen | pH | $k_a$ (1/Ms) | $k_d$ (1/s) | $K_D$ (M) | Chi$^2$ |
|---|---|---|---|---|---|---|
| CRL0500 | hC5 | 7.4 | 9.60e+06 | 4.91e−04 | 5.12e−11 | 0.24 |
| CRL0500 | cC5 | 7.4 | 3.74e+06 | 8.18e−04 | 2.19e−10 | 0.01 |
| CRL0952 | hC5 | 7.4 | 1.01e+07 | 5.39e−04 | 5.36e−11 | 0.27 |
| CRL0952 | cC5 | 7.4 | 3.53e+06 | 7.86e−04 | 2.23e−10 | 0.01 |
| CRL0500 | hC5 | 6.0 | 7.56e+06 | 1.04e−03 | 1.38e−10 | 0.54 |
| CRL0500 | cC5 | 6.0 | 5.51e+06 | 4.10e−03 | 7.44e−10 | 0.07 |
| CRL0952 | hC5 | 6.0 | 5.84e+06 | 9.07e−04 | 1.55e−10 | 0.58 |
| CRL0952 | cC5 | 6.0 | 5.55e+06 | 3.99e−03 | 7.20e−10 | 0.06 |

Table 15 shows binding kinetics for CRL0500 and CRL0952 binding to Plasbumin® and cynomolgus albumin.

TABLE 15

Albumin bi-specific kinetics

| Sample | Albumin | pH | $k_a$ (1/Ms) | $k_d$ (1/s) | $K_D$ (M) | Chi$^2$ |
|---|---|---|---|---|---|---|
| CRL0500 | Plasbumin | 7.4 | 3.70e06 | 3.46e−03 | 9.36e−10 | 0.30 |
| CRL0500 | Plasbumin | 6.0 | 3.55e06 | 2.0e−03 | 5.63e−10 | 0.17 |
| CRL0952 | Plasbumin | 7.4 | 3.98e06 | 3.59e−03 | 9.01e−10 | 0.21 |
| CRL0952 | Plasbumin | 6.0 | 3.23e06 | 2.10e−03 | 6.49e−10 | 0.10 |
| CRL0500 | cyno | 7.4 | 3.32e06 | 1.26e−02 | 3.78e−09 | 0.42 |
| CRL0500 | cyno | 6.0 | 3.27e06 | 6.93e−03 | 2.12e−09 | 0.43 |
| CRL0952 | cyno | 7.4 | 2.93e06 | 1.52e−02 | 5.19e−09 | 0.17 |
| CRL0952 | cyno | 6.0 | 3.03e06 | 7.55e−03 | 2.49e−09 | 0.22 |

Example 15. pH-Dependent Binding of Anti-C5 VHH Domains

Histidine scanning was performed across all CDRs for anti-C5 VHH domains LCP0115, LCP0143, LCP0146 and LCP0302. Single histidine substitutions were generated at each position in the CDRs (shown in bold, underlined text). Variants were transfected in Expi293 cell culture and evaluated for pH-dependent binding at pH 7.4, 6.0 and 5.5. Several variants from each antibody exhibited pH-dependent binding. These variants are listed in Table 16 and their pH-dependent binding response is illustrated in FIGS. 11A-D.

TABLE 16

Pre-humanized histidine scanned variants of anti-C5 VHH domains.

| Variant name | Histidine variant sequence | SEQ ID NO |
|---|---|---|
| LCP0115 variants | | |
| CRL0085 | EVQLVESGGGLVQAGGSLRLSCAASGRTFSGILSPYAVGWFRQAPGKGREFVSTITSGGSAIYTDSVKGRFTLSRDNAKDTVYLQMNSLKPEDTAVYYCHVRTRRYGSNLGEVPQENEYGYWGQGTQVTVSS | 281 |
| CRL0091 | EVQLVESGGGLVQAGGSLRLSCAASGRTFSGILSPYAVGWFRQAPGKGREFVSTITSGGSAIYTDSVKGRFTLSRDNAKDTVYLQMNSLKPEDTAVYYCAVRTRRHGSNLGEVPQENEYGYWGQGTQVTVSS | 282 |
| LCP0143 variants | | |
| CRL0120 | EVQLVESGGGLVQAGGSLRLSCAAPEMGATINVMAWYRQAPGKQRELVARLPHDNNIDYGDFAKGRFTISRDITRNTVYLQMNNLKPDDTAVYYCNVLLSRQINGAYVHWGQGTQVTVSS | 283 |

TABLE 16-continued

Pre-humanized histidine scanned variants of anti-C5 VHH domains.

| Variant name | Histidine variant sequence | SEQ ID NO |
| --- | --- | --- |
| CRL0121 | EVQLVESGGGLVQAGGSLRLSCAAPEMGATINVMAWYRQAPGK QRELVARLPLHNNIDYGDFAKGRFTISRDITRNTVYLQMNNLK PDDTAVYYCNVLLSRQINGAYVHWGQGTQVTVSS | 284 |
| CRL0133 | EVQLVESGGGLVQAGGSLRLSCAAPEMGATINVMAWYRQAPGK QRELVARLPLDNNIDYGDFAKGRFTISRDITRNTVYLQMNNLK PDDTAVYYHVLLSRQINGAYVHWGQGTQVTVSS | 285 |
| CRL0135 | EVQLVESGGGLVQAGGSLRLSCAAPEMGATINVMAWYRQAPGK QRELVARLPLDNNIDYGDFAKGRFTISRDITRNTVYLQMNNLK PDDTAVYYCNVHLSRQINGAYVHWGQGTQVTVSS | 286 |
| CRL0144 | EVQLVESGGGLVQAGGSLRLSCAAPEMGATINVMAWYRQAPGK QRELVARLPLDNNIDYGDFAKGRFTISRDITRNTVYLQMNNLK PDDTAVYYCNVLLSRQINGAHVHWGQGTQVTVSS | 287 |
| LCP0146 variants | | |
| CRL0149 | EVQLVESGGGLVQAGGSLRLSCAASGRHFSDYAMAWFRQAPGK EREFVAGIGWSGGDTLYADSVRGRFTNSKDNAKNRMSLQMNSL KPEDTAVYYCAARQGQYIYSSMRSDSYDYWGQGTQVTVSS | 288 |
| CRL0150 | EVQLVESGGGLVQAGGSLRLSCAASGRAHSDYAMAWFRQAPGK EREFVAGIGWSGGDTLYADSVRGRFTNSKDNAKNRMSLQMNSL KPEDTAVYYCAARQGQYIYSSMRSDSYDYWGQGTQVTVSS | 289 |
| CRL0166 | EVQLVESGGGLVQAGGSLRLSCAASGRAFSDYAMAWFRQAPGK EREFVAGIGWSGGDTHYADSVRGRFTNSKDNAKNRMSLQMNSL KPEDTAVYYCAARQGQYIYSSMRSDSYDYWGQGTQVTVSS | 290 |
| CRL0180 | EVQLVESGGGLVQAGGSLRLSCAASGRAFSDYAMAWFRQAPGK EREFVAGIGWSGGDTLYADSVRGRFTNSKDNAKNRMSLQMNSL KPEDTAVYYCAARQGQHIYSSMRSDSYDYWGQGTQVTVSS | 291 |
| LCP0302 variants | | |
| CRL0623 | EVQLVESGGGLVQAGGSLRLSCAASGRTFSGILSHYAVGWFRQ APGKEREFVSTITSGGSTLSADSVKGRFTLSRDNAKDTVYLQM NSLKPEDTAVYYCAVRTWPYGSNRGEVPTENEYGHWGQGTQVT VSS | 292 |

Figure 12A:
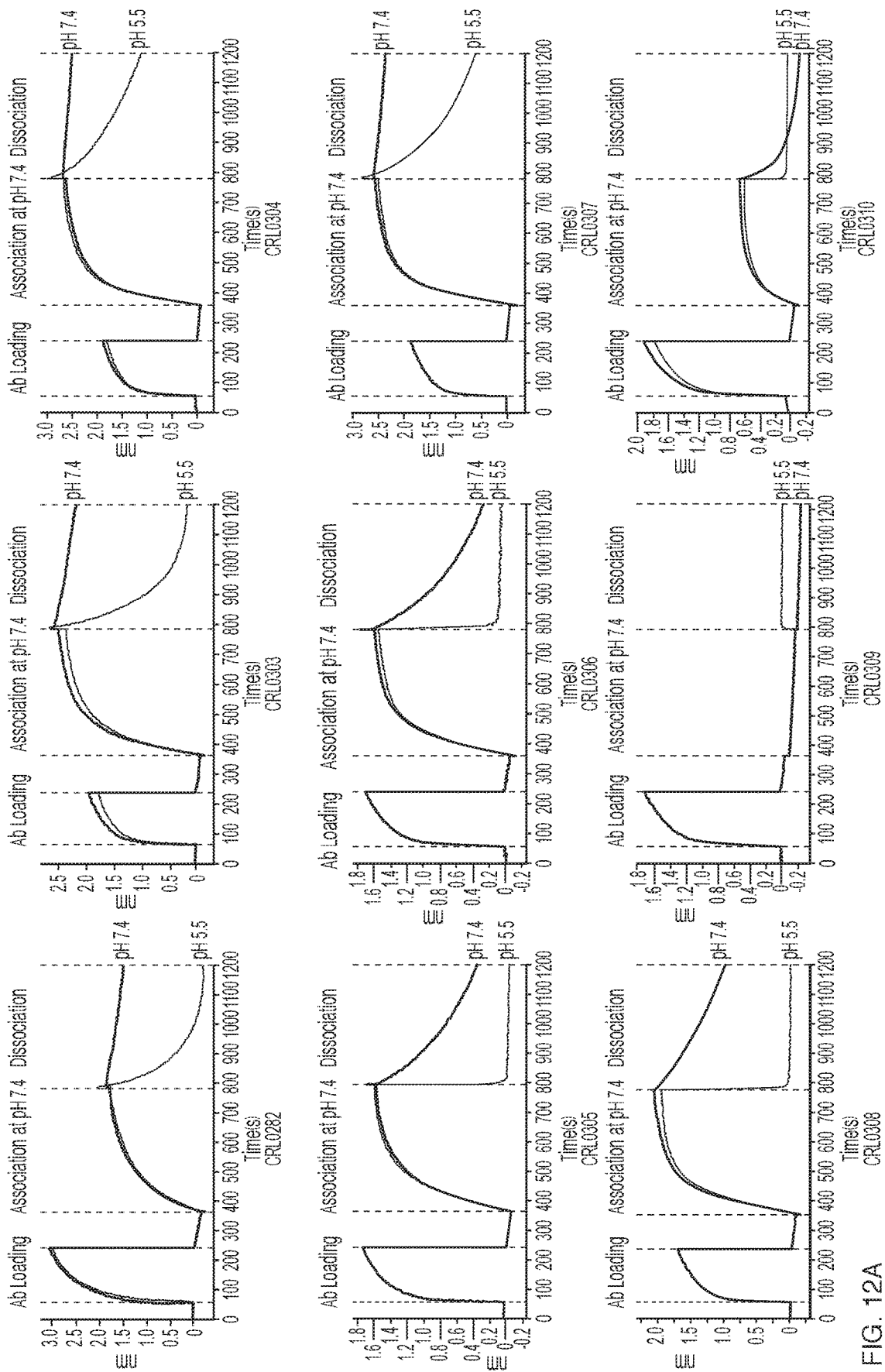
FIGS. 12A and 12B show pH-dependent binding of histidine-substituted fusion proteins.
Figure 12B:
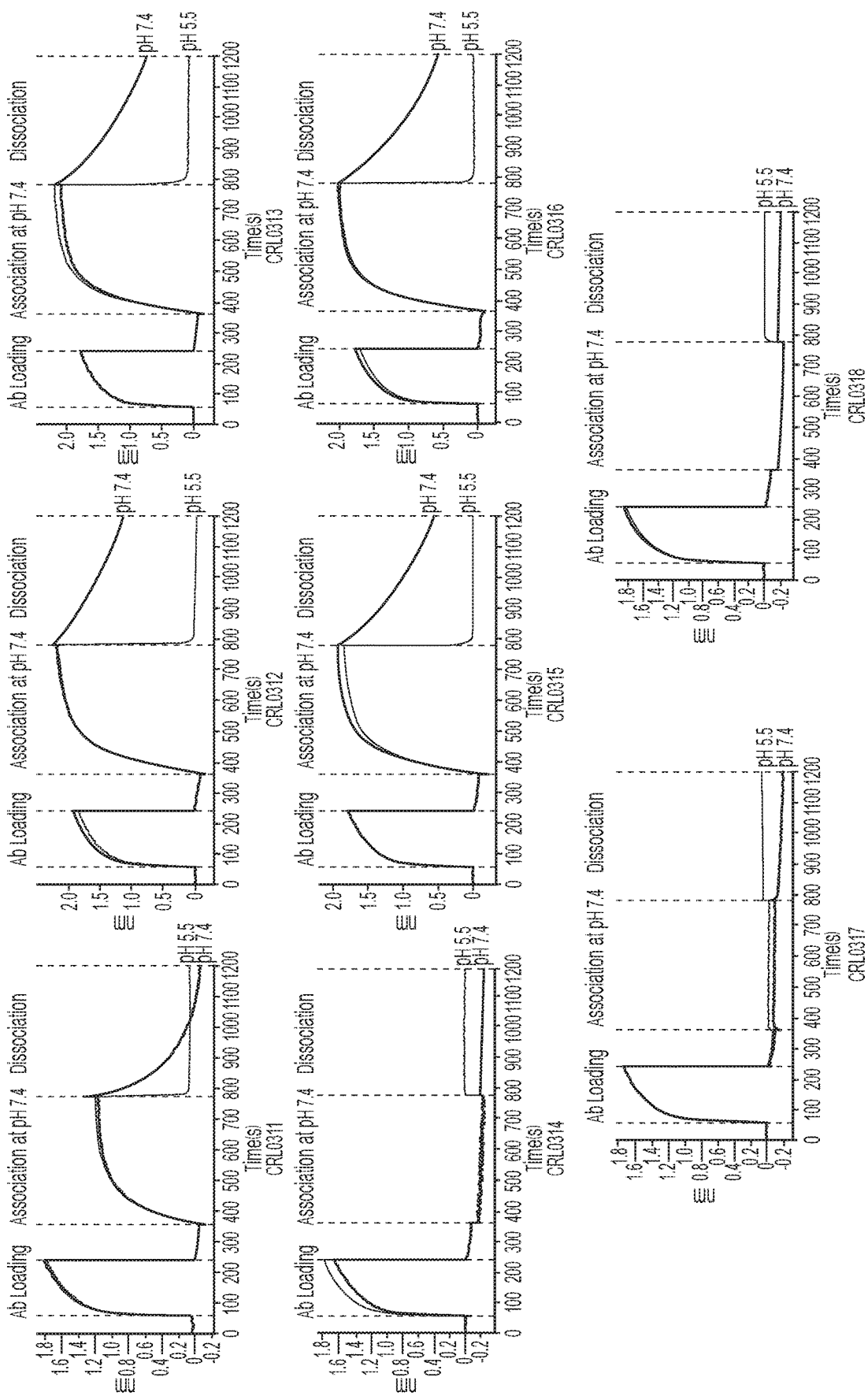

Single histidine mutations identified for pH-dependent binding were combined to enhance pH sensitivity. The sequences of these variants are shown in Table 17. These variants were evaluated in biolayer interferometry for pH-dependent binding and results are shown in FIGS. 12A and 12B.

TABLE 17

Histidine scanning combination variants of humanized anti-C5 VHH domains

| Variant name | Histidine variant sequence | SEQ ID NO |
| --- | --- | --- |
| LCP0115 combination variants | | |
| CRL0282 | EVQLVESGGGLVQPGGSLRLSCAAS<u>GRTFSGILSPYAVGW</u>FRQAPGKG LEFVS<u>TITSGGSAIYTDSVK</u>GRFTISRDNAKNSLYLQMNSLRAEDTAV YYC<u>AVRTRRHGSNLGEVPQENEYGY</u>WGQGTLVTVSS | 293 |
| LCP0146 combination variants | | |
| CRL0303 | EVQLVESGGGLVQPGGSLRLSCAAS<u>GRHFSDYAMA</u>WFRQAPGQEREFV AGIGWSGGDT<u>LYADSVR</u>GRFTISRDNSKNTLYLQMNSLRAEDTAVYYC <u>AARQGQYIYSSMRSDSYDY</u>WGQGTLVTVSS | 9 |
| CRL0304 | EVQLVESGGGLVQPGGSLRLSCAAS<u>GRAHSDYAMA</u>WFRQAPGQEREFV AGIGWSGGDT<u>LYADSVR</u>GRFTISRDNSKNTLYLQMNSLRAEDTAVYYC <u>AARQGQYIYSSMRSDSYDY</u>WGQGTLVTVSS | 10 |
| CRL0305 | EVQLVESGGGLVQPGGSLRLSCAAS<u>GRAFSDYAMA</u>WFRQAPGQEREFV AGIGWSGGDTHYADSVRGRFTISRDNSKNTLYLQMNSLRAEDTAVYYC <u>AARQGQYIYSSMRSDSYDY</u>WGQGTLVTVSS | 294 |
| CRL0306 | EVQLVESGGGLVQPGGSLRLSCAAS<u>GRAFSDYAMA</u>WFRQAPGQEREFV AGIGWSGGDT<u>LYADSVR</u>GRFTISRDNSKNTLYLQMNSLRAEDTAVYYC <u>AARQGQHIYSSMRSDSYDY</u>WGQGTLVTVSS | 295 |

TABLE 17-continued

Histidine scanning combination variants of humanized anti-C5 VHH domains

| Variant name | Histidine variant sequence | SEQ ID NO |
|---|---|---|
| CRL0307 | EVQLVESGGGLVQPGGSLRLSCAASGRHHSDYAMAWFRQAPGQEREFV AGIGWSGGDTLYADSVRGRFTISRDNSKNTLYLQMNSLRAEDTAVYYC AARQGQYIYSSMRSDSYDYWGQGTLVTVSS | 12 |
| CRL0308 | EVQLVESGGGLVQPGGSLRLSCAASGRAHSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 296 |
| CRL0309 | EVQLVESGGGLVQPGGSLRLSCAASGRAFSDYAMAWFRQAPGQEREFV AGIGWSGGDTHYADSVRGRFTISRDNSKNTLYLQMNSLRAEDTAVYYC AARQGQHIYSSMRSDSYDYWGQGTLVTVSS | 297 |
| CRL0310 | EVQLVESGGGLVQPGGSLRLSCAASGRHFSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 298 |
| CRL0311 | EVQLVESGGGLVQPGGSLRLSCAASGRHFSDYAMAWFRQAPGQEREFV AGIGWSGGDTLYADSVRGRFTISRDNSKNTLYLQMNSLRAEDTAVYYC AARQGQHIYSSMRSDSYDYWGQGTLVTVSS | 299 |
| CRL0312 | EVQLVESGGGLVQPGGSLRLSCAASGRAHSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 296 |
| CRL0313 | EVQLVESGGGLVQPGGSLRLSCAASGRAHSDYAMAWFRQAPGQEREFV AGIGWSGGDTLYADSVRGRFTISRDNSKNTLYLQMNSLRAEDTAVYYC AARQGQHIYSSMRSDSYDYWGQGTLVTVSS | 300 |
| CRL0314 | EVQLVESGGGLVQPGGSLRLSCAASGRAFSDYAMAWFRQAPGQEREFV AGIGWSGGDTHYADSVRGRFTISRDNSKNTLYLQMNSLRAEDTAVYYC AARQGQHIYSSMRSDSYDYWGQGTLVTVSS | 297 |
| CRL0315 | EVQLVESGGGLVQPGGSLRLSCAASGRHHSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 301 |
| CRL0316 | EVQLVESGGGLVQPGGSLRLSCAASGRHHSDYAMAWFRQAPGQEREFV AGIGWSGGDTLYADSVRGRFTISRDNSKNTLYLQMNSLRAEDTAVYYC AARQGQHIYSSMRSDSYDYWGQGTLVTVSS | 302 |
| CRL0317 | EVQLVESGGGLVQPGGSLRLSCAASGRAHSDYAMAWFRQAPGQEREFV AGIGWSGGDTHYADSVRGRFTISRDNSKNTLYLQMNSLRAEDTAVYYC AARQGQHIYSSMRSDSYDYWGQGTLVTVSS | 303 |
| CRL0318 | EVQLVESGGGLVQPGGSLRLSCAASGRHFSDYAMAWFRQAPGQEREFV AGIGWSGGDTHYADSVRGRFTISRDNSKNTLYLQMNSLRAEDTAVYYC AARQGQHIYSSMRSDSYDYWGQGTLVTVSS | 304 |

Example 16. Generation of Anti-C5 and Anti-Albumin Bispecific Fusions

Anti-C5 VHH domains were fused to an anti-albumin domain to generate bispecific molecules. Four different linker lengths ($G_4S$)$_3$ (SEQ ID NO: 106), ($G_4S$)$_4$ (SEQ ID NO: 107), ($G_4S$)$_5$ (SEQ ID NO: 108) and ($G_4S$)$_6$ (SEQ ID NO: 109) and two different orientations (N-terminal or C-terminal) of anti-albumin domain were evaluated. The sequences of the generated molecules are shown in Table 18. Constructs were expressed in HEK293F cells and purified using Protein A affinity chromatography. Purified fusion molecules were evaluated in Biacore experiments. Human C5 was biotinylated and immobilized on a biacore chip, purified bispecific molecules were injected to saturate the chip followed by three different concentrations of human serum albumin to obtain kinetics. Measured affinity to human serum albumin was used as a proxy to compare the different linker lengths. ($G_4S$)$_3$ (SEQ ID NO: 106) was chosen as the optimal linker length to generate bispecific fusions. N- or C-terminal anti-albumin fusion was also evaluated in the same experiment. Different orientations were found to be optimal for different anti-C5 VHH domains.

TABLE 8

Sequences of Linker length and Orientation Variants of anti-C5/anti-albumin bi-specifics

| Name | Sequence | SEQ ID NO |
|---|---|---|
| CRL0248 | EVQLVESGGGLVQPGGSLRLSCAASGRTFSGILSPYAVGWFRQAPGKGLEFVST ITSGGSAIYTDSVKGRFTISRDNAKNSLYLQMNSLRAEDTAVYYCAVRTRRYGS NLGEVPQENEYGYWGQGTLVTVSSGGGGSGGGGSGGGGSEVQLLESGGGLVQPG GSLRLSCAASGFTFRSFGMSWVRQAPGKGPEWVSSISGSGSDTLYADSVKGRFT ISRDNSKNTLYLQMNSLRPEDTAVYYCTIGGSLSRSSQGTLVTVSS | 305 |
| CRL0249 | EVQLVESGGGLVQPGGSLRLSCAASGRTFSGILSPYAVGWFRQAPGKGLEFVST ITSGGSAIYTDSVKGRFTISRDNAKNSLYLQMNSLRAEDTAVYYCAVRTRRYGS NLGEVPQENEYGYWGQGTLVTVSSGGGGSGGGGSGGGGSGGGGSEVQLLESGGG LVQPGGSLRLSCAASGFTFRSFGMSWVRQAPGKGPEWVSSISGSGSDTLYADSV KGRFTISRDNSKNTLYLQMNSLRPEDTAVYYCTIGGSLSRSSQGTLVTVSS | 306 |

TABLE 8-continued

Sequences of Linker length and Orientation Variants of
anti-C5/anti-albumin bi-specifics

| Name | Sequence | SEQ ID NO |
|------|----------|-----------|
| CRL0250 | EVQLVESGGGLVQPGGSLRLSCAASGRTFSGILSPYAVGWFRQAPGKGLEFVST ITSGGSAIYTDSVKGRFTISRDNAKNSLYLQMNSLRAEDTAVYYCAVRTRRYGS NLGEVPQENEYGYWGQGTLVTVSSGGGGSGGGGSGGGGSGGGGSGGGGSEVQLL ESGGGLVQPGGSLRLSCAASGFTFRSFGMSWVRQAPGKGPEWVSSISGSGSDTL YADSVKGRFTISRDNSKNTLYLQMNSLRPEDTAVYYCTIGGSLSRSSQGTLVTV SS | 307 |
| CRL0251 | EVQLVESGGGLVQPGGSLRLSCAASGRTFSGILSPYAVGWFRQAPGKGLEFVST ITSGGSAIYTDSVKGRFTISRDNAKNSLYLQMNSLRAEDTAVYYCAVRTRRYGS NLGEVPQENEYGYWGQGTLVTVSSGGGGSGGGGSGGGGSGGGGSGGGGSGGGGS EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSS | 308 |
| CRL0254 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSEVQLVESGGGLVQPGGSLRLSCAASGRTFSGI LSPYAVGWFRQAPGKGLEFVSTITSGGSAIYTDSVKGRFTTSRDNAKNSLYLQM NSLRAEDTAVYYCAVRTRRYGSNLGEVPQENEYGYWGQGTLVTVSS | 309 |
| CRL0255 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSEVQLVESGGGLVQPGGSLRLSCAASGR TFSGILSPYAVGWFRQAPGKGLEFVSTITSGGSAIYTDSVKGRFTISRDNAKNS LYLQMNSLRAEDTAVYYCAVRTRRYGSNLGEVPQENEYGYWGQGTLVTVSS | 310 |
| CRL0256 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSGGGGSEVQLVESGGGLVQPGGSLRLSC AASGRTFSGILSPYAVGWFRQAPGKGLEFVSTITSGGSAIYTDSVKGRFTISRD NAKNSLYLQMNSLRAEDTAVYYCAVRTRRYGSNLGEVPQENEYGYWGQGTLVTV SS | 311 |
| CRL0257 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSGGGGSGGGGSEVQLVESGGGLVQPGGS LRLSCAASGRTFSGILSPYAVGWFRQAPGKGLEFVSTITSGGSAIYTDSVKGRF TISRDNAKNSLYLQMNSLRAEDTAVYYCAVRTRRYGSNLGEVPQENEYGYWGQG TLVTVSS | 312 |
| CRL0272 | EVQLVESGGGLVQPGGSLRLSCAASGRAFSDYAMAWFRQAPGQEREFVAGIGWS GGDTLYADSVRGRFTISRDNSKNTLYLQMNSLRAEDTAVYYCAARQGQYIYSSM RSDSYDYWGQGTLVTVSSGGGGSGGGGSGGGGSEVQLLESGGGLVQPGGSLRLS CAASGFTFRSFGMSWVRQAPGKGPEWVSSISGSGSDTLYADSVKGRFTISRDNS KNTLYLQMNSLRPEDTAVYYCTIGGSLSRSSQGTLVTVSS | 313 |
| CRL0273 | EVQLVESGGGLVQPGGSLRLSCAASGRAFSDYAMAWFRQAPGQEREFVAGIGWS GGDTLYADSVRGRFTISRDNSKNTLYLQMNSLRAEDTAVYYCAARQGQYIYSSM RSDSYDYWGQGTLVTVSSGGGGSGGGGSGGGGSGGGGSEVQLLESGGGLVQPGG SLRLSCAASGFTFRSFGMSWVRQAPGKGPEWVSSISGSGSDTLYADSVKGRFTI SRDNSKNTLYLQMNSLRPEDTAVYYCTIGGSLSRSSQGTLVTVSS | 314 |
| CRL0274 | EVQLVESGGGLVQPGGSLRLSCAASGRAFSDYAMAWFRQAPGQEREFVAGIGWS GGDTLYADSVRGRFTISRDNSKNTLYLQMNSLRAEDTAVYYCAARQGQYIYSSM RSDSYDYWGQGTLVTVSSGGGGSGGGGSGGGGSGGGGSGGGGSEVQLLESGGGL VQPGGSLRLSCAASGFTFRSFGMSWVRQAPGKGPEWVSSISGSGSDTLYADSVK GRFTISRDNSKNTLYLQMNSLRPEDTAVYYCTIGGSLSRSSQGTLVTVSS | 315 |
| CRL0275 | EVQLVESGGGLVQPGGSLRLSCAASGRAFSDYAMAWFRQAPGQEREFVAGIGWS GGDTLYADSVRGRFTISRDNSKNTLYLQMNSLRAEDTAVYYCAARQGQYIYSSM RSDSYDYWGQGTLVTVSSGGGGSGGGGSGGGGSGGGGSGGGGSGGGGSEVQLLE SGGGLVQPGGSLRLSCAASGFTFRSFGMSWVRQAPGKGPEWVSSISGSGSDTLY ADSVKGRFTISRDNSNTLYLQMNSLRPEDTAVYYCTIGGSLSRSSQGTLVTVSS | 316 |
| CRL0278 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSEVQLVESGGGLVQPGGSLRLSCAASGRAFSDY AMAWFRQAPGQEREFVAGIGWSGGDTLYADSVRGRFTISRDNSKNTLYLQMNSL RAEDTAVYYCAARQGQYIYSSMRSDSYDYWGQGTLVTVSS | 317 |
| CRL0279 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSEVQLVESGGGLVQPGGSLRLSCAASGR AFSDYAMAWFRQAPGQEREFVAGIGWSGGDTLYADSVRGRFTISRDNSKNTLYL QMNSLRAEDTAVYYCAARQGQYIYSSMRSDSYDYWGQGTLVTVSS | 318 |

TABLE 8-continued

Sequences of Linker length and Orientation Variants of anti-C5/anti-albumin bi-specifics

| Name | Sequence | SEQ ID NO |
|---|---|---|
| CRL0280 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSGGGGSEVQLVESGGGLVQPGGSLRLSC AASGRAFSDYAMAWFRQAPGQEREFVAGIGWSGGDTLYADSVRGRFTISRDNSK NTLYLQMNSLRAEDTAVYYCAARQGQYIYSSMRSDSYDYWGQGTLVTVSS | 319 |
| CRL0281 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSGGGGSGGGGSEVQLVESGGGLVQPGGS LRLSCAASGRAFSDYAMAWFRQAPGQEREFVAGIGWSGGDTLYADSVRGRFTIS RDNSKNTLYLQMNSLRAEDTAVYYCAARQGQYIYSSMRSDSYDYWGQGTLVTVS S | 320 |

A series of different bi-specific fusion molecules were generated with humanized anti-C5 VHH domains with or without pH-dependent binding. The anti-C5 VHH domains were fused to two different anti-albumin domains to generate bi-specific molecules (shown in Table 9). These constructs were expressed in HEK293F cells and purified using Protein A chromatography. Purified bi-specifics were tested in hemolysis assays and the results are shown in FIGS. 3A-D.

Four bispecific molecules CRL0483, CRL0484, CRL0499 and CRL0500 were prioritized based on binding and functional assays. Biacore affinity measurements for binding to human C5 for CRL0483, CRL0484, CRL0499 and CRL0500 are shown in Table 10 and functional assessments in FIGS. 5, 6 and 7. These four bi-specific molecules were evaluated in in vivo pharmacokinetic studies in cynomolgus monkeys.

Example 17. Pharmacokinetic Analysis of Bispecific Fusion Molecules

Figure 6A:
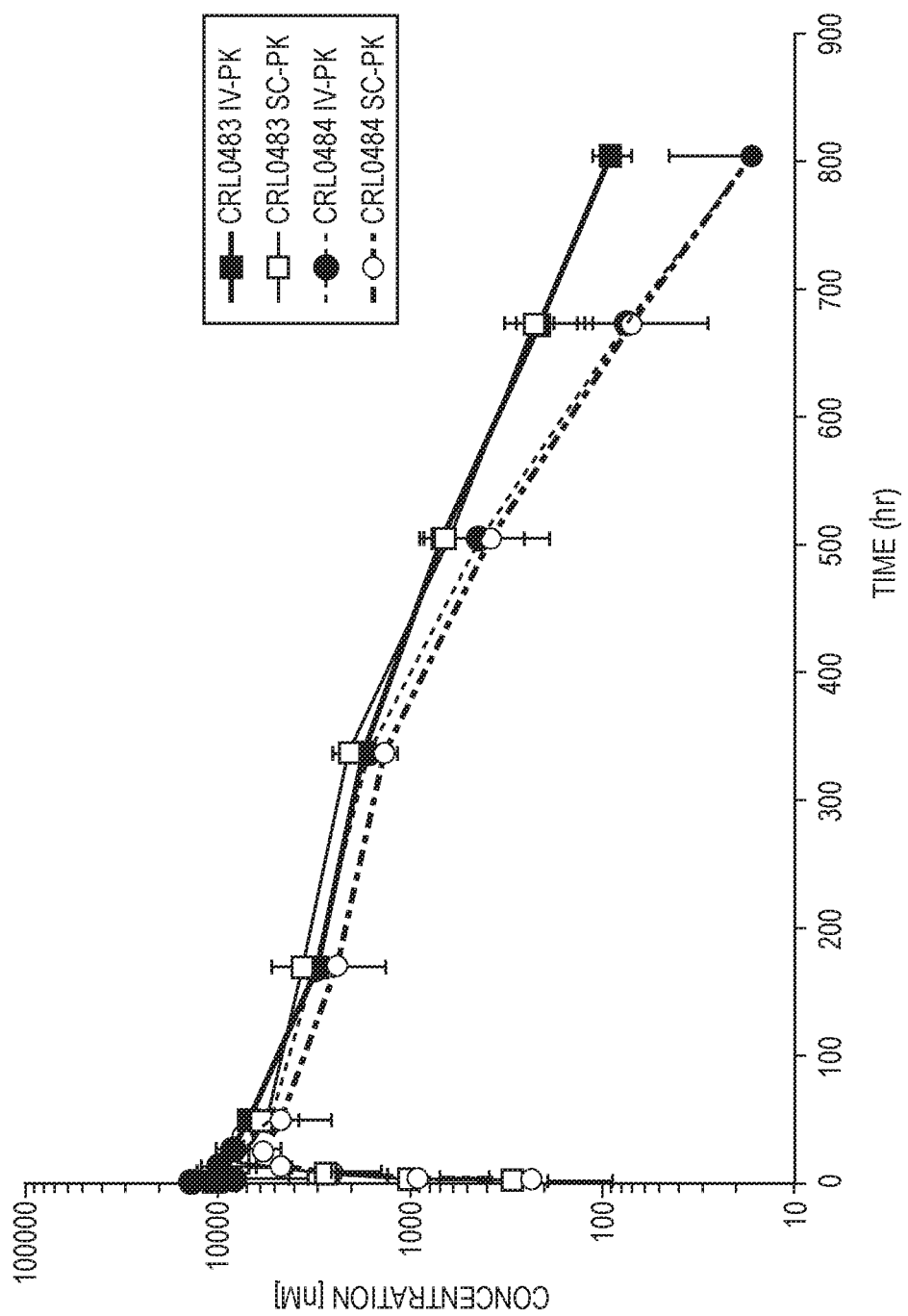
FIGS. 6A and 6B show the results of an LC-MS based quantitation assay demonstrating the pharmacokinetics of bispecific fusion proteins.
Figure 6B:
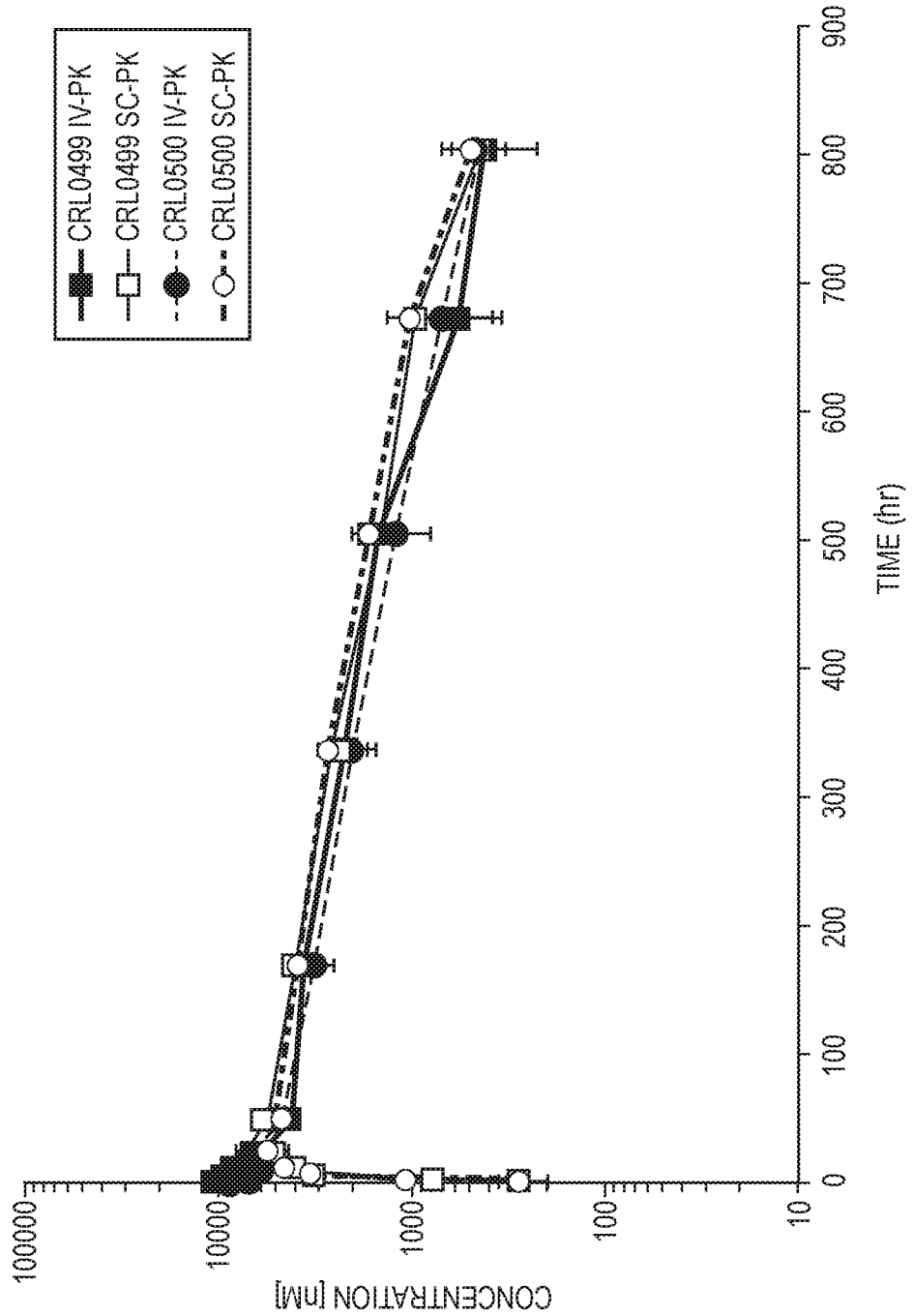
Figure 7B:
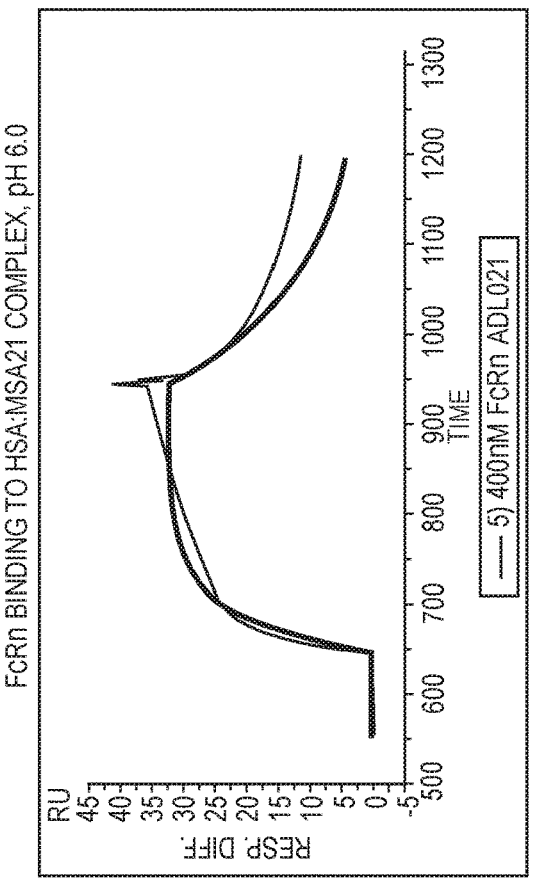
FIGS. 7A-7D show Biacore sensorgrams indicating the binding of FcRn at pH 6.0 in HBS-EP buffer to HSA saturated with no VHH domain (control, FIG. 7A), MSA21 (FIG. 7B), HAS040 (FIG. 7C) or HAS041 (FIG. 7D).
Figure 7D:
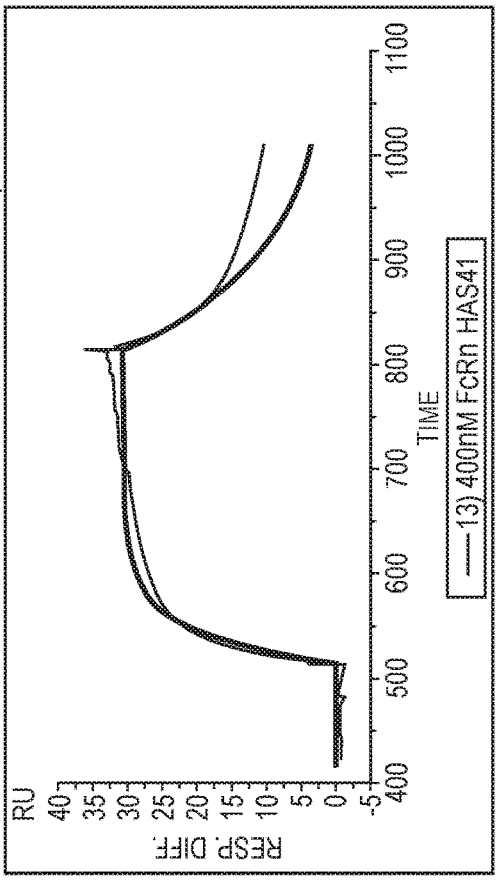
Figure 7A:
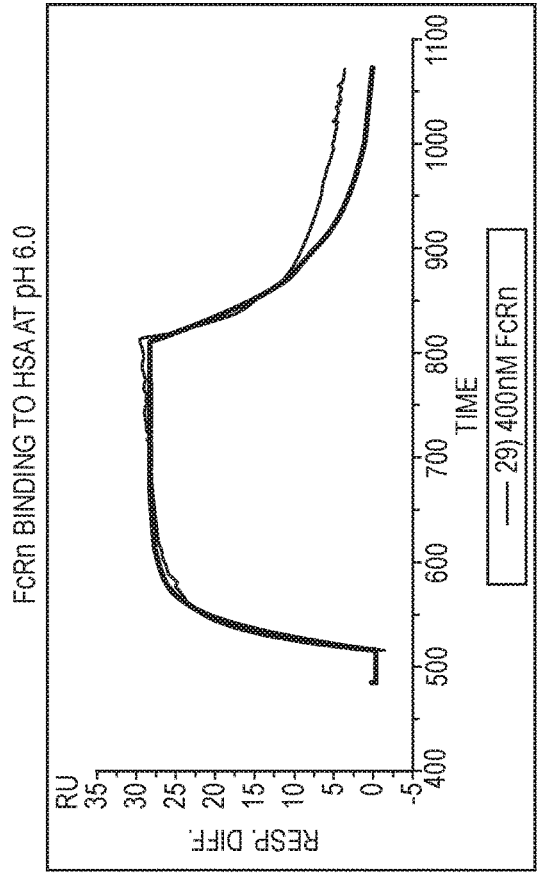
Figure 7C:
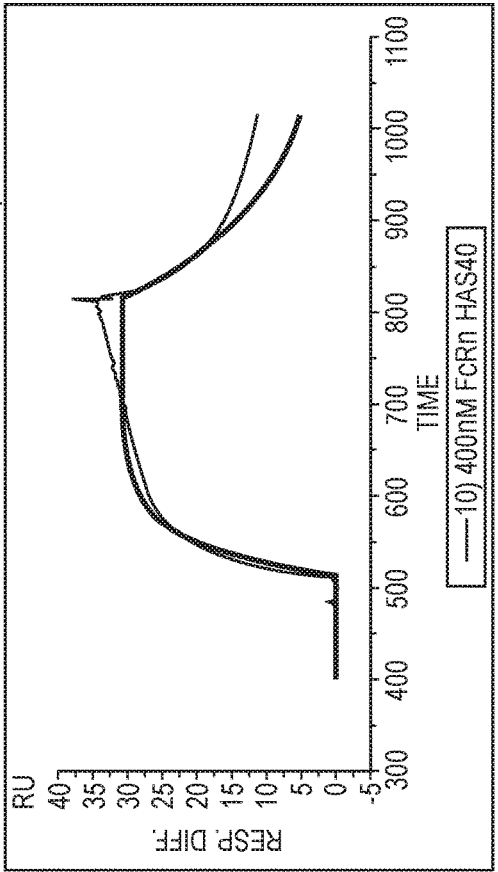
Figure 8A:
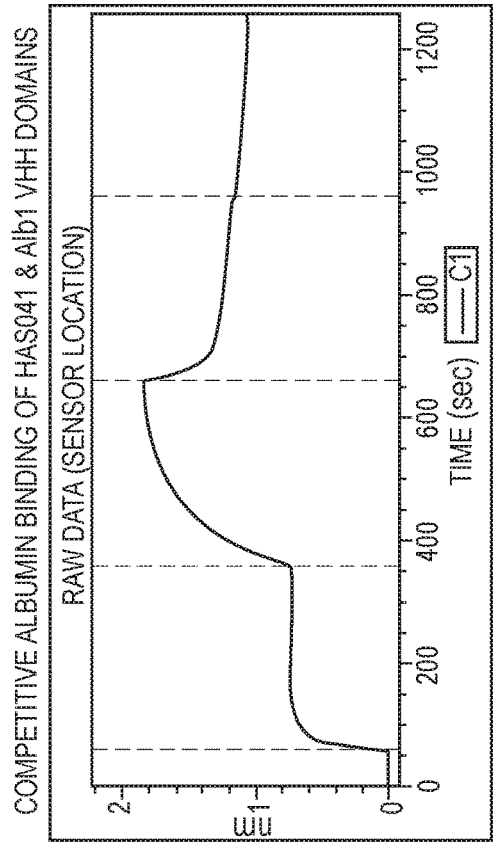
FIGS. 8A-8D show Biacore sensorgrams indicating the binding of albumin by the VHH domains HAS020, HAS040, HAS041 and HAS044 in competition with Alb1 VHH.
Figure 8B:
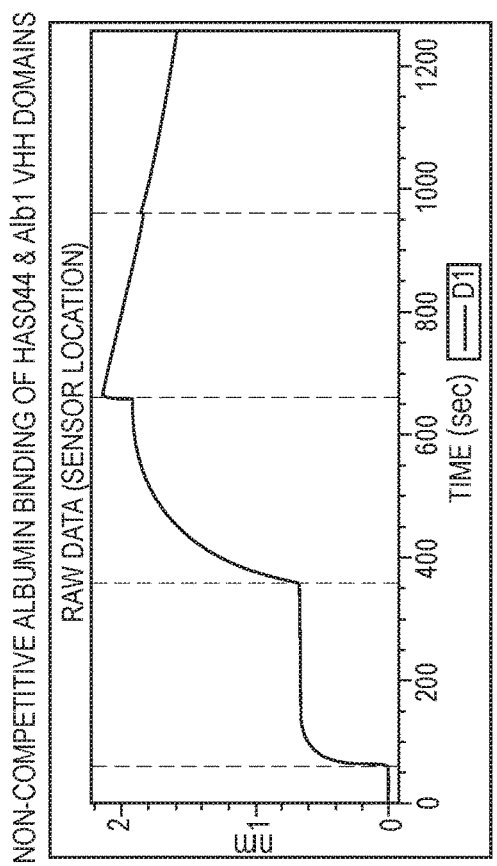
Figure 8C:
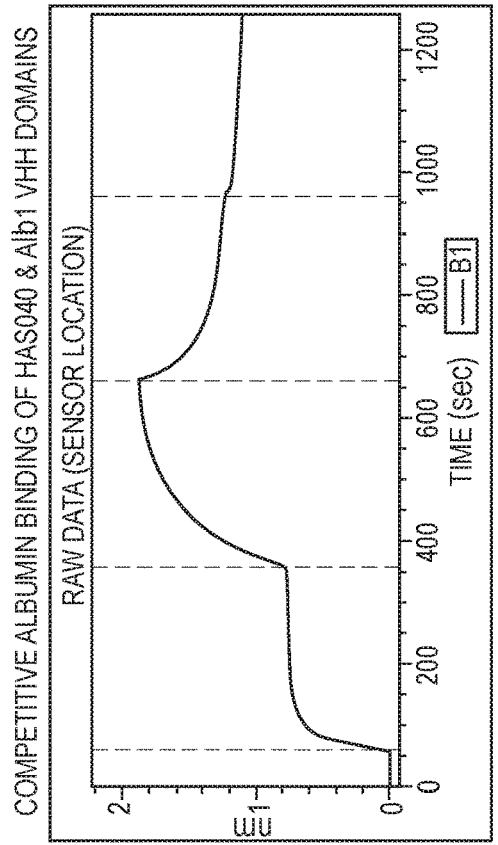
Figure 8D:
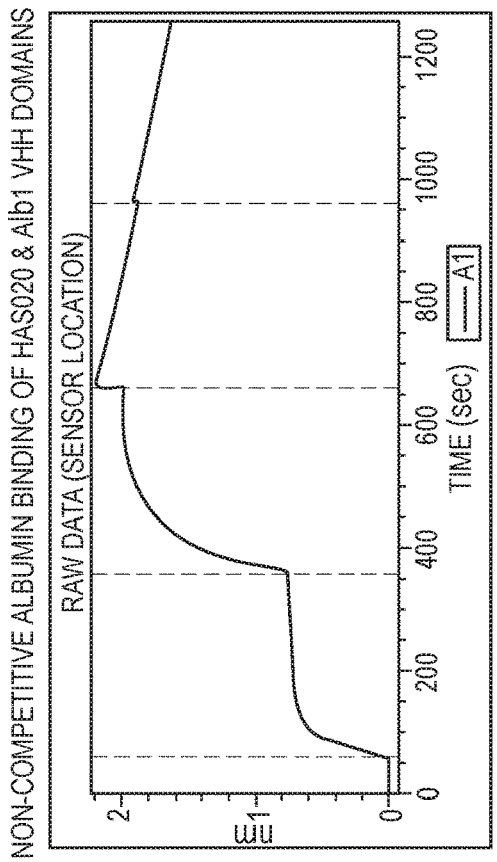

Purified proteins were dosed at 10 mg/kg either intravenously or subcutaneously in cynomolgus monkeys. Three monkeys per dose group per test article were used. Pharmacokinetics of bispecific molecules was measured by a LC-MS based quantitation assay using signature peptides specific to each construct. The PK profiles are shown in FIGS. 6A and 6B and the parameters are described in Table 20.

TABLE 20

PK parameters after 10 mg/kg of test articles in cynomolgus monkeys

| Test article | $t_{1/2}$ h | $t_{max}$ h | $C_{max}$ µg/mL | AUC h*µg/mL | $C_L$ mL/h/kg | V mL/kg | F % |
|---|---|---|---|---|---|---|---|
| CRL0483 IV | 139 | 1.33 | 324 | 47900 | 0.211 | 42.0 | |
| CRL0484 IV | 125 | 1 | 382 | 43700 | 0.238 | 43.0 | |
| CRL0483 SC | 103 | 20 | 238 | 46412 | 0.218 | 32.5 | 97 |
| CRL0484 SC | 75.9 | 24 | 161 | 32610 | 0.315 | 34.9 | 75 |
| CRL0499 IV | 170 | 2.11 | 299 | 53773 | 0.184 | 46.9 | |
| CRL0500 IV | 239 | 0.167 | 351 | 51929 | 0.205 | 62.5 | |
| CRL0499 SC | 220 | 32 | 146 | 58666 | 0.173 | 54.2 | 109 |
| CRL0500 SC | 209 | 32 | 161 | 61475 | 0.163 | 49.0 | 118 |

While the disclosure describes various embodiments, it is understood that variations and modifications will occur to those skilled in the art. Therefore, it is intended that the appended claims cover all such equivalent variations. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

What is claimed is:

1. A fusion protein comprising an engineered polypeptide comprising a VHH domain that specifically binds to human complement component C5 and an engineered polypeptide comprising a VHH domain that specifically binds to human serum albumin, wherein the engineered polypeptide comprising the VHH domain that specifically binds to human complement component C5 is fused to the engineered polypeptide comprising the VHH domain that specifically binds to human serum albumin either directly or via a peptide linker; wherein the VHH domain that specifically binds to human complement component C5 comprises three complementarity determining regions, CDR1, CDR2 and, CDR3, wherein CDR1 comprises the amino acid sequence of SEQ ID NO:16, CDR2 comprises the amino acid sequence of SEQ ID NO:18, and CDR3 comprises the amino acid sequence of SEQ ID NO:20; and wherein the VHH domain that specifically binds to human serum albumin comprises three complementarity determining regions, CDR1, CDR2, and CDR3, wherein CDR1 comprises the amino acid sequence of SEQ ID NO:38, CDR2 comprises the amino acid sequence of SEQ ID NO:48, and CDR3 comprises the amino acid sequence of SEQ ID NO:55.

2. The fusion protein of claim 1, wherein the C-terminal residue of the polypeptide that specifically binds to human serum albumin is fused either directly or via a linker to the N-terminal residue of the polypeptide that specifically binds to human complement component C5.

3. The fusion protein of claim 1, wherein the C-terminal residue of the polypeptide that specifically binds to human complement component C5 is fused either directly or via a linker to the N-terminal residue of the polypeptide that specifically binds to human serum albumin.

4. A fusion protein comprising an engineered polypeptide comprising a VHH domain that specifically binds to human complement component C5 and an engineered polypeptide comprising a VHH domain that specifically binds to human serum albumin, wherein the engineered polypeptide comprising the VHH domain that specifically binds to human complement component C5 is fused to the engineered polypeptide comprising the VHH domain that specifically binds to human serum albumin either directly or via a peptide linker, wherein the polypeptide that specifically binds to human complement component C5 comprises an amino acid sequence selected from the group consisting of SEQ ID NOS:1-12 and fragments thereof; and the polypeptide that specifically binds to human serum albumin comprises an amino acid selected from the group consisting of SEQ ID NOs:22-34 and fragments thereof.

5. The fusion protein of claim 4, wherein the polypeptide that specifically binds to human complement component C5 comprises the amino acid sequence of SEQ ID NO:11 and the polypeptide that specifically binds to human serum albumin comprises the amino acid sequence of SEQ ID NO:26.

6. The fusion protein of claim 5, further comprising a peptide linker having an amino acid sequence of SEQ ID NO:102 or 103.

7. The fusion protein of claim 6, wherein the peptide linker comprises the amino acid sequence of SEQ ID NO:102.

8. The fusion protein of claim 1, wherein the fusion protein comprises a sequence that is at least 95% identical to the sequence of SEQ ID NO:96.

9. The fusion protein of claim 8, wherein the fusion protein consists of the sequence of SEQ ID NO:96.

10. The fusion protein of claim 1, wherein either or both of the polypeptides that bind to human complement component C5 or albumin bind in a pH-dependent manner.

11. A pharmaceutical composition comprising a therapeutically effective amount of a fusion protein of claim 1 and a pharmaceutically acceptable carrier.

12. The pharmaceutical composition of claim 11, further comprising hyaluronidase.

13. An engineered polypeptide comprising a VHH domain that binds to human complement component C5, wherein the engineered polypeptide comprises an amino acid sequence that is at least 90% identical to the sequence of SEQ ID NO:11; wherein the VHH domain that specifically binds to human complement component C5 comprises three complementarity determining regions, CDR1, CDR2 and, CDR3, wherein CDR1 comprises the amino acid sequence of SEQ ID NO:16, CDR2 comprises the amino acid sequence of SEQ ID NO:18, and CDR3 comprises the amino acid sequence of SEQ ID NO:20.

14. An engineered polypeptide comprising a VHH domain that binds to human complement component C5, wherein the engineered polypeptide comprises an amino acid sequence selected from the group consisting of SEQ ID NOS:1-12 and fragments thereof.

* * * * *